US008722910B2

(12) United States Patent
Meyer et al.

(10) Patent No.: US 8,722,910 B2
(45) Date of Patent: May 13, 2014

(54) DIYNE COMPOSITIONS

(75) Inventors: Jean-Philippe Meyer, Mulhouse (FR); Philipp Knechtle, Basel (CH); Katrine Buch Greve, Odense C (DK); Alexandre M P Santana Sørenson, Allschwil (CH)

(73) Assignee: Evolva AG, Reinach (CH)

( * ) Notice: Subject to any disclaimer, the term of this patent is extended or adjusted under 35 U.S.C. 154(b) by 8 days.

(21) Appl. No.: 13/345,300

(22) Filed: Jan. 6, 2012

(65) Prior Publication Data

US 2012/0196822 A1    Aug. 2, 2012

Related U.S. Application Data

(63) Continuation of application No. PCT/EP2010/063161, filed on Sep. 8, 2010, and a continuation-in-part of application No. PCT/US2010/041515, filed on Jul. 9, 2010.

(60) Provisional application No. 61/330,169, filed on Apr. 30, 2010, provisional application No. 61/346,381, filed on May 19, 2010, provisional application No. 61/224,627, filed on Jul. 10, 2009, provisional application No. 61/224,632, filed on Jul. 10, 2009.

(51) Int. Cl.
*C07D 307/54*     (2006.01)
*A01N 43/08*     (2006.01)
*A61K 31/341*     (2006.01)

(52) U.S. Cl.
USPC ............................ 549/499; 549/429; 514/461

(58) Field of Classification Search
None
See application file for complete search history.

(56) References Cited

U.S. PATENT DOCUMENTS

| 3,501,303 | A | * | 3/1970 | Foltz et al. | 430/332 |
|---|---|---|---|---|---|
| 4,432,987 | A | * | 2/1984 | Barth et al. | 514/193 |
| 6,448,055 | B1 | | 9/2002 | Shimizu et al. | |
| 6,541,506 | B1 | | 4/2003 | Cui | |
| 6,873,914 | B2 | | 3/2005 | Winfield et al. | |
| 2002/0016305 | A1 | | 2/2002 | Ahlquist et al. | |
| 2007/0254299 | A1 | | 11/2007 | Yadav et al. | |
| 2008/0076787 | A1 | * | 3/2008 | Paredes et al. | 514/266.23 |

FOREIGN PATENT DOCUMENTS

| EP | 1932921 | 6/2008 |
|---|---|---|
| JP | 10075782 | 3/1998 |
| WO | WO0011012 | 3/2000 |
| WO | WO01/25197 | 4/2001 |
| WO | WO0171045 | 9/2001 |

(Continued)

OTHER PUBLICATIONS

Ernst, Joachim F.; Tielker, Denis. Responses to hypoxia in fungal pathogens. Cellular Microbiology, (Feb. 2009) vol. 11, No. 2, pp. 183-190.

(Continued)

*Primary Examiner* — Kortney L Klinkel
*Assistant Examiner* — John Mauro
(74) *Attorney, Agent, or Firm* — McDonnell Boehnen Hulbert & Berghoff LLP

(57) ABSTRACT

A novel class of diyne compounds and diyne salts provided herein are effective and potent Ole1 protein inhibitors, useful for treating fungal pathogens. Compounds, fungicides and methods are provided as novel, potent and broad spectrum anti-fungal agents for treatment against a wide variety of fungal pathogens in humans and animals, and in the agricultural setting.

16 Claims, 25 Drawing Sheets

(56) References Cited

FOREIGN PATENT DOCUMENTS

| WO | WO0187991 A1 | 11/2001 |
|---|---|---|
| WO | WO 03106385 | 12/2003 |
| WO | WO2004056965 | 7/2004 |
| WO | WO2006076423 | 7/2006 |
| WO | WO2007131720 | 11/2007 |
| WO | WO2011/006061 | 1/2011 |

OTHER PUBLICATIONS

Goldman, Gustavo H.; Marques, Everaldo dos Reis; et al., Expressed sequence tag analysis of the human pathogen *Paracoccidioides brasiliensis* yeast phase: Identification of putative homologues of *Candida albicans* virulence and pathogenicity genes. Eukaryotic Cell (2003), 2(1), 34-48.

Grandjean et al: "First total synthesis of optically pure methyl (2Z,8S,9R)-8,9-epoxydeca-4,6-diyn-2-en-10-hydroxy-1-oate and its acetate, two naturally-occurring antifeedants", Tetrahedron Letters, vol. 33, No. 37, pp. 5355-5358, Sep. 8, 1992.

Krishnamurthy Shankarling; Plaine Armel; Albert Juliane; Prasad Tulika; Prasad Rajendra; Ernst Joachim F. osage-dependent functions of fatty acid desaturase Ole1p in growth and morphogenesis of *Candida albicans*. Microbiology (Reading, England), vol. 150, No. Pt 6, pp. 1991-2003, Jun. 2004.

Moggio I. et al. "Vibrational properties of novel diacetylenic monomers", Journ. of the Chemical Society, Perkin Transactions 2: Physical Organic Chemistry, Royal Society of Chemistry, No. 10, p. 2249-2254, XP002595203, Jan. 1998.

Oh Chan-Seok; Martin Charles E. *Candida albicans* Spt23p controls the expression of the Ole1p Delta9 fatty acid desaturase and regulates unsaturated fatty acid biosynthesis. The Journal of biological chemistry, vol. 281, No. 11, pp. 7030-7039, Mar. 17, 2006.

\* cited by examiner

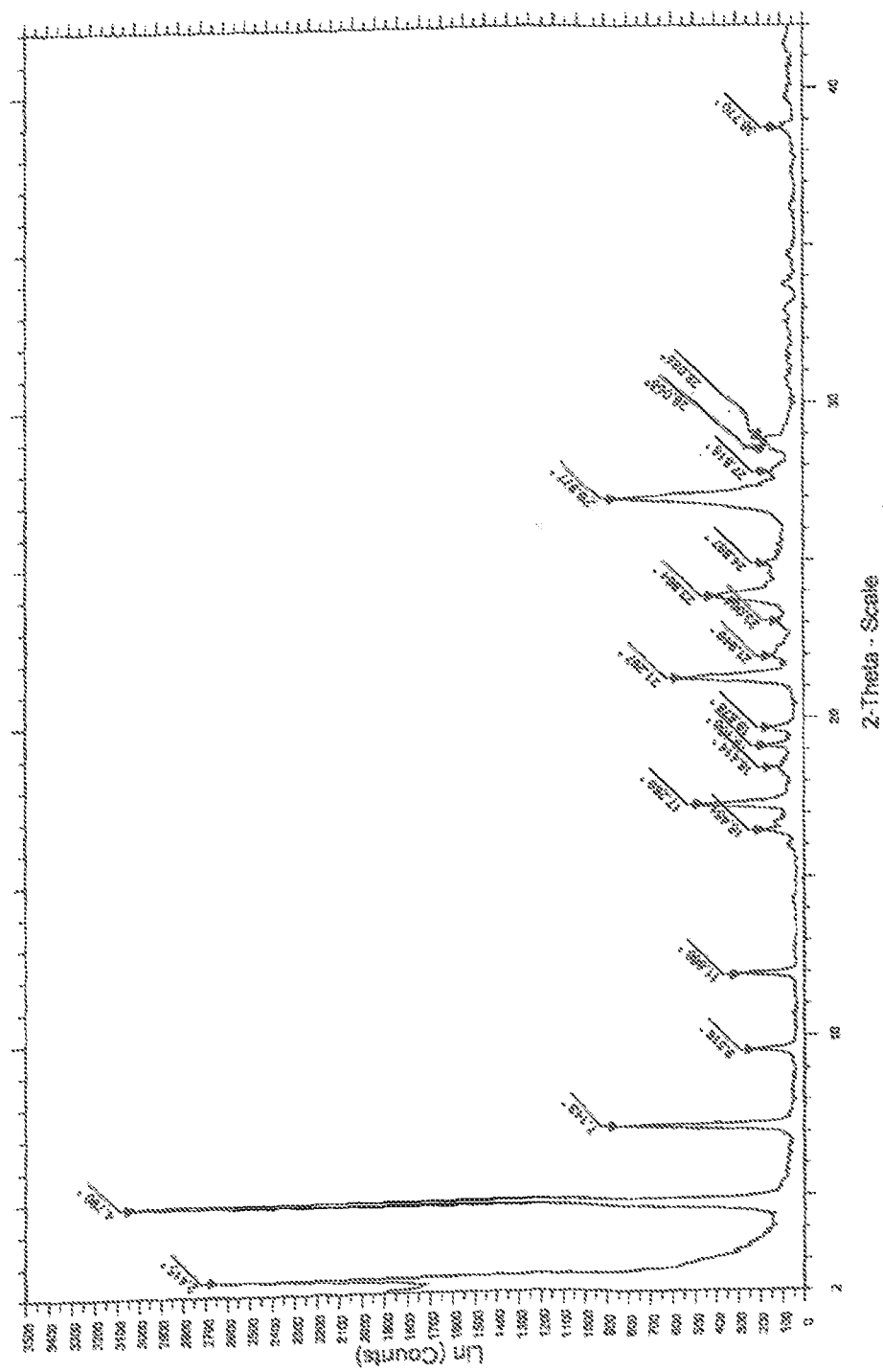

FIG. 5

Candida albicans

| | 5 ng/ml | 2.50 ng/ml | 1.25 ng/ml | 0.63 ng/ml | 0.31 ng/ml | 0.16 ng/ml | 0.08 ng/ml | RPMI/DMSO |
|---|---|---|---|---|---|---|---|---|
| 2,000 ng/ml | 0 | 0 | 0 | 0 | 0 | 0 | 0 | 0 |
| 1,000 ng/ml | 0 | 1 | 1 | 1 | 1 | 1 | 1 | 1 |
| 500 ng/ml | 0 | 1 | 1 | 1 | 1 | 1 | 1 | 1 |
| 250 ng/ml | 0 | 1 | 1 | 2 | 2 | 2 | 2 | 2 |
| 125 ng/ml | 0 | 1 | 1 | 2 | 2 | 3 | 3 | 3 |
| 63 ng/ml | 0 | 1 | 2 | 3 | 3 | 3 | 4 | 4 |
| 31 ng/ml | 0 | 1 | 1 | 2 | 3 | 4 | 4 | 4 |
| RPMI/DMSO | 0 | 0 | 1 | 2 | 3 | 4 | 4 | 4 |

AmphothericinB (rows); (Z)-14-(furan-2-yl)tetradeca-9-en-11,13-diynoic acid, potassium salt (columns)

Candida glabrata

| | 80 ng/ml | 40 ng/ml | 20 ng/ml | 10 ng/ml | 5 ng/ml | 2.50 ng/ml | 1.25 ng/ml | RPMI/DMSO |
|---|---|---|---|---|---|---|---|---|
| 2,000 ng/ml | 0 | 0 | 0 | 0 | 0 | 0 | 0 | 0 |
| 1,000 ng/ml | 0 | 0 | 0 | 0 | 0 | 0 | 0 | 0 |
| 500 ng/ml | 0 | 0 | 0 | 0 | 0 | 0 | 0 | 0 |
| 250 ng/ml | 0 | 0 | 0 | 0 | 0 | 0 | 1 | 4 |
| 125 ng/ml | 0 | 0 | 1 | 1 | 4 | 4 | 4 | 4 |
| 63 ng/ml | 0 | 0 | 1 | 3 | 4 | 4 | 4 | 4 |
| 31 ng/ml | 0 | 0 | 1 | 3 | 4 | 4 | 4 | 4 |
| RPMI/DMSO | 0 | 0 | 1 | 3 | 4 | 4 | 4 | 4 |

AmphothericinB (rows); (Z)-14-(furan-2-yl)tetradeca-9-en-11,13-diynoic acid, potassium salt (columns)

FIG. 5 (continued)

Candida parapsilosis

|  | 10,240 ng/ml | 5,120 ng/ml | 2,560 ng/ml | 1,280 ng/ml | 640 ng/ml | 320 ng/ml | 160 ng/ml | RPMI/DMSO | |
|---|---|---|---|---|---|---|---|---|---|
| 2,000 ng/ml | 0 | 0 | 0 | 0 | 0 | 0 | 0 | 0 | (Z)-14-(furan-2-yl)tetradeca-9-en-11,13-diynoic acid, potassium salt |
| 1,000 ng/ml | 0 | 0 | 0 | 0 | 0 | 0 | 0 | 1 | |
| 500 ng/ml | 0 | 0 | 1 | 2 | 2 | 2 | 3 | 3 | |
| 250 ng/ml | 0 | 0 | 2 | 4 | 4 | 4 | 4 | 4 | |
| 125 ng/ml | 0 | 1 | 2 | 4 | 4 | 4 | 4 | 4 | |
| 63 ng/ml | 0 | 1 | 2 | 4 | 4 | 4 | 4 | 4 | |
| 31 ng/ml | 0 | 0 | 2 | 4 | 4 | 4 | 4 | 4 | |
| RPMI/DMSO | 0 | 1 | 2 | 4 | 4 | 4 | 4 | 4 | |

AmphothericinB

FIG. 6
A)
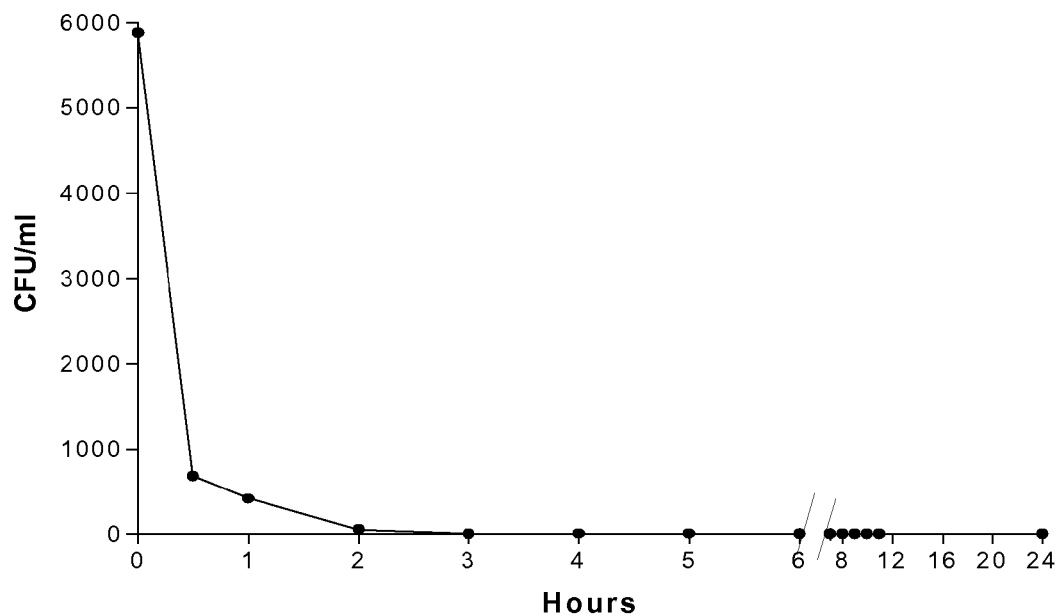
B)
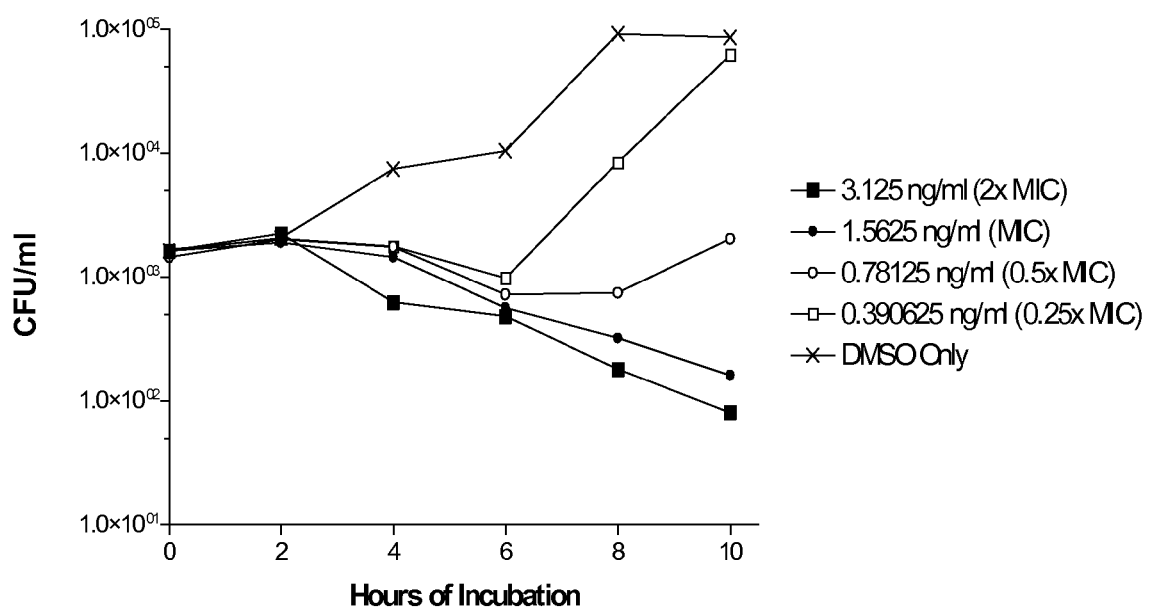

| Na-oleate | Compound IV | 10,240 ng/ml | 2,560 ng/ml | 640 ng/ml | 160 ng/ml | 80 ng/ml | 40 ng/ml | 20 ng/ml | 10 ng/ml | 5 ng/ml | 2.5 ng/ml | 1.25 ng/ml | 0.63 ng/ml | 0.31 ng/ml | 0 ng/ml |
|---|---|---|---|---|---|---|---|---|---|---|---|---|---|---|---|
| 5,120 ng/ml | | 1 | 3 | 3 | 4 | 4 | 4 | 4 | 4 | 4 | 4 | | | | 4 |
| 1,280 ng/ml | | 1 | 1 | 1 | 3 | 3 | 4 | 4 | 4 | 4 | 4 | | | | 4 |
| 320 ng/ml | | 0 | 0 | 0 | 1 | 1 | 1 | 1 | 3 | 4 | 4 | 4 | 4 | 4 | 4 |
| 80 ng/ml | | 0 | 0 | 0 | 0 | 0 | 0 | 0 | 1 | 2 | 4 | 4 | 4 | 4 | 4 |
| 20 ng/ml | | 0 | 0 | 0 | 0 | 0 | 0 | 0 | 0 | 1 | 3 | 4 | 4 | 4 | 4 |
| 5 ng/ml | | 0 | 0 | 0 | 0 | 0 | 0 | 0 | 0 | 0 | 2 | 3 | 4 | 4 | 4 |
| 1.25 ng/ml | | 0 | 0 | 0 | 0 | 0 | 0 | 0 | 0 | 0 | 2 | 4 | 4 | 4 | 4 |
| 0.31 ng/ml | | | | | | 0 | 0 | 0 | 0 | 0 | 2 | 4 | 4 | 4 | 4 |
| 0.08 ng/ml | | | | | | 0 | 0 | 0 | 0 | 0 | 2 | 4 | 4 | 4 | 4 |
| 0.00 ng/ml | | 0 | 0 | 0 | 0 | 0 | 0 | 0 | 0 | 0 | 2 | 4 | 4 | 4 | 4 | c)

| Na-stearate | Compound IV | 160 ng/ml | 80 ng/ml | 40 ng/ml | 20 ng/ml | 10 ng/ml | 5 ng/ml | 2.5 ng/ml | 1.25 ng/ml | 0.63 ng/ml | 0.31 ng/ml | 0 ng/ml |
|---|---|---|---|---|---|---|---|---|---|---|---|---|
| 5,120 ng/ml | | 0 | 0 | 0 | 0 | 0 | 0 | 0 | | | | 4 |
| 1,280 ng/ml | | 0 | 0 | 0 | 0 | 0 | 0 | 0 | | | | 4 |
| 320 ng/ml | | 0 | 0 | 0 | 0 | 0 | 0 | 1 | 2 | 3 | 4 | 4 |
| 80 ng/ml | | 0 | 0 | 0 | 0 | 0 | 0 | 2 | 3 | 4 | 4 | 4 |
| 20 ng/ml | | 0 | 0 | 0 | 0 | 0 | 0 | 2 | 3 | 4 | 4 | 4 |
| 5 ng/ml | | 0 | 0 | 0 | 0 | 0 | 0 | 2 | 3 | 4 | 4 | 4 |
| 1.25 ng/ml | | 0 | 0 | 0 | 0 | 0 | 0 | 2 | 3 | 4 | 4 | 4 |
| 0.31 ng/ml | | | | 0 | 0 | 0 | 1 | 2 | 3 | 4 | 4 | 4 |
| 0.08 ng/ml | | | | 0 | 0 | 0 | 0 | 2 | 3 | 4 | 4 | 4 |
| 0.00 ng/ml | | 0 | 0 | 0 | 0 | 0 | 0 | 2 | 3 | 4 | 4 | 4 |

| |
|---|
| 0 → optically clear |
| 1 → slightly hazy |
| 2 → prominent decrease (50%) in visible growth |
| 3 → slight reduction in visible growth |
| 4 → no reduction in visible growth |
| "blank" → not determined |

FIG. 21

| Na-oleate \ Ev-086-3314K | 10,240 ng/ml | 2,560 ng/ml | 640 ng/ml | 160 ng/ml | 80 ng/ml | 40 ng/ml | 20 ng/ml | 10 ng/ml | 5 ng/ml | 2.5 ng/ml | 1.25 ng/ml | 0.63 ng/ml | 0.31 ng/ml | 0 ng/ml |
|---|---|---|---|---|---|---|---|---|---|---|---|---|---|---|
| 5,120 ng/ml | 1 | 3 | 3 | 4 | 4 | 4 | 4 | 4 | 4 | 4 |   |   |   | 4 |
| 1,280 ng/ml | 1 | 1 | 1 | 3 | 3 | 4 | 4 | 4 | 4 | 4 |   |   |   | 4 |
| 320 ng/ml | 0 | 0 | 0 | 1 | 1 | 1 | 1 | 3 | 4 | 4 | 4 | 4 | 4 | 4 |
| 80 ng/ml | 0 | 0 | 0 | 0 | 0 | 0 | 0 | 0 | 1 | 2 | 4 | 4 | 4 | 4 |
| 20 ng/ml | 0 | 0 | 0 | 0 | 0 | 0 | 0 | 0 | 0 | 1 | 3 | 4 | 4 | 4 |
| 5 ng/ml | 0 | 0 | 0 | 0 | 0 | 0 | 0 | 0 | 0 | 0 | 2 | 3 | 4 | 4 |
| 1.25 ng/ml | 0 | 0 | 0 | 0 | 0 | 0 | 0 | 0 | 0 | 0 | 2 | 4 | 4 | 4 |
| 0.31 ng/ml |   |   |   |   |   |   | 0 | 0 | 0 | 0 | 2 | 4 | 4 | 4 |
| 0.08 ng/ml |   |   |   |   |   |   | 0 | 0 | 0 | 0 | 2 | 4 | 4 | 4 |
| 0.00 ng/ml | 0 | 0 | 0 | 0 | 0 | 0 | 0 | 0 | 0 | 0 | 2 | 4 | 4 | 4 |

| Na-linoleate \ Ev-086-3314K | 10,240 ng/ml | 2,560 ng/ml | 640 ng/ml | 160 ng/ml | 80 ng/ml | 40 ng/ml | 20 ng/ml | 10 ng/ml | 5 ng/ml | 2.5 ng/ml | 1.25 ng/ml | 0.63 ng/ml | 0.31 ng/ml | 0 ng/ml |
|---|---|---|---|---|---|---|---|---|---|---|---|---|---|---|
| 5,120 ng/ml | 2 | 4 | 4 | 4 | 4 | 4 | 4 | 4 | 4 | 4 |   |   |   | 4 |
| 1,280 ng/ml | 0 | 1 | 1 | 1 | 1 | 2 | 4 | 4 | 4 | 4 |   |   |   | 4 |
| 320 ng/ml | 0 | 0 | 1 | 1 | 1 | 1 | 1 | 2 | 4 | 4 | 4 | 4 | 4 | 4 |
| 80 ng/ml | 0 | 0 | 0 | 0 | 0 | 1 | 0 | 1 | 1 | 3 | 4 | 4 | 4 | 4 |
| 20 ng/ml | 0 | 0 | 0 | 0 | 0 | 0 | 0 | 0 | 0 | 0 | 2 | 4 | 4 | 4 |
| 5 ng/ml | 0 | 0 | 0 | 0 | 0 | 0 | 0 | 0 | 0 | 0 | 2 | 4 | 4 | 4 |
| 1.25 ng/ml | 0 | 0 | 0 | 0 | 0 | 0 | 0 | 0 | 0 | 0 | 2 | 4 | 4 | 4 |
| 0.31 ng/ml |   |   |   |   |   |   | 0 | 0 | 0 | 1 | 2 | 4 | 4 | 4 |
| 0.08 ng/ml |   |   |   |   |   |   | 0 | 0 | 0 | 0 | 2 | 4 | 4 | 4 |
| 0.00 ng/ml | 0 | 0 | 0 | 0 | 0 | 0 | 0 | 0 | 0 | 0 | 2 | 4 | 4 | 4 |

| Na-stearate \ Ev-086-3314K | 160 ng/ml | 80 ng/ml | 40 ng/ml | 20 ng/ml | 10 ng/ml | 5 ng/ml | 2.5 ng/ml | 1.25 ng/ml | 0.63 ng/ml | 0.31 ng/ml | 0 ng/ml |
|---|---|---|---|---|---|---|---|---|---|---|---|
| 5,120 ng/ml | 0 | 0 | 0 | 0 | 0 | 0 | 0 |   |   |   | 4 |
| 1,280 ng/ml | 0 | 0 | 0 | 0 | 0 | 0 | 0 |   |   |   | 4 |
| 320 ng/ml | 0 | 0 | 0 | 0 | 0 | 0 | 1 | 2 | 3 | 4 | 4 |
| 80 ng/ml | 0 | 0 | 0 | 0 | 0 | 0 | 0 | 2 | 3 | 4 | 4 |
| 20 ng/ml | 0 | 0 | 0 | 0 | 0 | 0 | 0 | 2 | 3 | 4 | 4 |
| 5 ng/ml | 0 | 0 | 0 | 0 | 0 | 0 | 0 | 2 | 3 | 4 | 4 |
| 1.25 ng/ml | 0 | 0 | 0 | 0 | 0 | 0 | 0 | 2 | 3 | 4 | 4 |
| 0.31 ng/ml |   |   |   | 0 | 0 | 0 | 1 | 2 | 3 | 4 | 4 |
| 0.08 ng/ml |   |   |   | 0 | 0 | 0 | 0 | 2 | 3 | 4 | 4 |
| 0.00 ng/ml | 0 | 0 | 0 | 0 | 0 | 0 | 0 | 2 | 3 | 4 | 4 |

| | |
|---|---|
| 0 -> | optically clear |
| 1 -> | slightly hazy |
| 2 -> | prominent decrease (50%) in visible growth |
| 3 -> | slight reduction in visible growth |
| 4 -> | no reduction in visible growth |
| "blank" -> | not determined |

FIG. 22

Candida albicans — EV-086-3314K

|  | 5120 ng/ml | 1280 ng/ml | 320 ng/ml | 80 ng/ml | 20 ng/ml | 5 ng/ml | 1.25 ng/ml | RPMI/EtOH | Na Oleate |
|---|---|---|---|---|---|---|---|---|---|
| 5120 ng/ml | 3 | 1 | 0 | 0 | 0 | 0 | 0 | 0 | |
| 1280 ng/ml | 4 | 2 | 0 | 0 | 0 | 0 | 0 | 0 | |
| 320 ng/ml | 4 | 2 | 0 | 0 | 0 | 0 | 0 | 0 | |
| 80 ng/ml | 4 | 3 | 1 | 0 | 0 | 0 | 0 | 0 | |
| 20 ng/ml | 4 | 4 | 1 | 0 | 0 | 0 | 0 | 0 | |
| 5 ng/ml | 4 | 4 | 3 | 0 | 0 | 0 | 0 | 0 | |
| 1.25 ng/ml | 4 | 4 | 4 | 4 | 1 | 0 | 0 | 2 | |
| RPMI/EtOH | 4 | 4 | 4 | 4 | 4 | 4 | 4 | 4 | |

Candida albicans — Amphotericin B

|  | 5120 ng/ml | 1280 ng/ml | 320 ng/ml | 80 ng/ml | 20 ng/ml | 5 ng/ml | 1.25 ng/ml | RPMI/EtOH |
|---|---|---|---|---|---|---|---|---|
| 8000 ng/ml | 0 | 0 | 0 | 0 | 0 | 0 | 0 | 0 |
| 4000 ng/ml | 0 | 0 | 0 | 0 | 0 | 0 | 0 | 0 |
| 2000 ng/ml | 0 | 0 | 0 | 0 | 0 | 0 | 0 | 0 |
| 1000 ng/ml | 0 | 0 | 0 | 0 | 0 | 0 | 0 | 0 |
| 500 ng/ml | 0 | 0 | 0 | 0 | 0 | 0 | 0 | 0 |
| 250 ng/ml | 0 | 0 | 2 | 2 | 2 | 2 | 3 | 0 |
| 125 ng/ml | 2 | 4 | 4 | 4 | 4 | 4 | 4 | 2 |
| RPMI/EtOH | 4 | 4 | 4 | 4 | 4 | 4 | 4 | 4 |

Candida albicans — Caspofungin

|  | 5120 ng/ml | 1280 ng/ml | 320 ng/ml | 80 ng/ml | 20 ng/ml | 5 ng/ml | 1.25 ng/ml | RPMI/EtOH | Na Oleate |
|---|---|---|---|---|---|---|---|---|---|
| 2000 ng/ml | 0 | 0 | 0 | 0 | 0 | 0 | 0 | 0 | |
| 1000 ng/ml | 0 | 0 | 0 | 0 | 0 | 0 | 0 | 0 | |
| 500 ng/ml | 0 | 0 | 0 | 0 | 0 | 0 | 0 | 0 | |
| 250 ng/ml | 1 | 1 | 0 | 0 | 0 | 0 | 0 | 1 | |
| 125 ng/ml | 2 | 2 | 2 | 2 | 1 | 1 | 1 | 2 | |
| 63 ng/ml | 2 | 2 | 2 | 2 | 2 | 2 | 2 | 2 | |
| 31 ng/ml | 3 | 3 | 3 | 3 | 3 | 3 | 3 | 3 | |
| RPMI/EtOH | 4 | 4 | 4 | 4 | 4 | 4 | 4 | 4 | |

Candida parapsilosis — Voriconazole

|  | 5120 ng/ml | 1280 ng/ml | 320 ng/ml | 80 ng/ml | 20 ng/ml | 5 ng/ml | 1.25 ng/ml | RPMI/EtOH |
|---|---|---|---|---|---|---|---|---|
| 1280 ng/ml | 0 | 0 | 0 | 0 | 0 | 0 | 0 | 0 |
| 640 ng/ml | 0 | 0 | 0 | 0 | 0 | 0 | 0 | 0 |
| 320 ng/ml | 0 | 0 | 0 | 0 | 0 | 0 | 0 | 0 |
| 160 ng/ml | 1 | 1 | 0 | 0 | 0 | 0 | 0 | 1 |
| 80 ng/ml | 2 | 2 | 2 | 2 | 1 | 1 | 1 | 2 |
| 40 ng/ml | 2 | 2 | 2 | 2 | 2 | 2 | 2 | 2 |
| 20 ng/ml | 3 | 3 | 3 | 3 | 3 | 3 | 3 | 3 |
| RPMI/EtOH | 4 | 4 | 4 | 4 | 4 | 4 | 4 | 4 |

0 -> optically clear
1 -> slightly hazy
2 -> prominent decrease (50%) in visible growth
3 -> slight reduction in visible growth
4 -> no reduction in visible growth

DIYNE COMPOSITIONS

CROSS REFERENCE TO RELATED APPLICATIONS

The present application is continuation of International Patent Application Number PCT/EP2010/063161, filed Sep. 8, 2010, which claims priority to U.S. Provisional Application No. 61/330,169, filed Apr. 30, 2010, and U.S. Provisional Application No. 61/346,381, filed May 19, 2010. The present application is also a continuation-in-part of International Application Number PCT/US2010/041515, filed Jul. 9, 2010, which claims priority to U.S. Provisional Application No. 61/224,627, filed Jul. 10, 2009, U.S. Provisional Application No. 61/224,632, filed Jul. 10, 2009, U.S. Provisional Application No. 61/330,169, filed Apr. 30, 2010, and U.S. Provisional Application No. 61/346,381, filed May 19, 2010.

FIELD OF THE INVENTION

The present invention relates to diyne salt and in particular potassium diyne salts useful as antifungal agents. The diyne salts are useful as active agent in pharmaceutical compositions for treating infection by a fungus in an individual, such as a mammal, but the diyne salts are also useful for reducing the risk of or treating infection by a fungus in plants.

The present invention also relates to diyne compounds useful for treating fungal infections as well as to methods of treating fungal infections in various organisms, such as plants or mammals. The diyne compounds of the invention are in particular useful for treating fungal infections dependent on the activity of stearoyl-CoA desaturase.

This invention further encompasses diynes and diyne salts as Ole1 protein inhibitors, as well as methods for treating fungal infections in humans, animals and plants.

BACKGROUND OF THE INVENTION

The incidence of fungal infections is steadily rising as a consequence of antibiotic treatments, an immunosuppressed or immunocompromised population (mainly caused by cancer treatment, HIV, allergy-treatments, transplantations and general surgery) and an aging population.

Currently, an estimated 15,000 allogenic and 25,000 autologous stem cell transplants are performed worldwide yearly. In addition, from 1998 to 2002, 113,682 solid organ transplants were performed in the United States, which is a 20% increase over the previous 5-year period. Unfortunately, patients undergoing these life-saving procedures are at increased risk for fungal infections for example by *Aspergillus fumigatus* and other *Aspergillus* spp. due to their immuno-compromised condition. Additionally the populations of immuno-compromised patients due to HIV, cancer therapy, surgical non-transplants and general ageing also continue to increase and with it the number of cases of severe fungal infections for example systemic candidiasis. *Candida* species account for 80% of infections in general medicine, 40% in HIV populations and 90% in both cancer therapy and surgical-non transplant cases. *Candida* is now the $4^{th}$ largest cause of nosocomial blood stream infections.

Mortality from systemic fungal infections remains high despite the development of new antifungal agents, and *Candida* bloodstream infections in the United States are associated with a 40% crude mortality rate. Overall, since 1980, the mortality due to *Aspergillus fumigatus* has increased 357% and is continuing to increase.

Furthermore, during the last decade, there have been changes in the epidemiology of these systemic infections, with five species (*C. albicans, C. glabrata, C. parapsilosis, C. tropicalis*, and *C. krusei*) responsible for more than 90% of invasive infections due to *Candida Candida* spp. are the fourth most common cause of nosocomial bloodstream infections, and while *C. albicans* was the predominant cause of *Candida* bloodstream infections in the early 80s, *C. glabrata* has emerged as the second most common cause in various part of the world, including the United States.

In addition to *Aspergillus* and *Candida* infections, other fungal pathogens such as Zygomycetes, *Fusarium* and *Scedosporium* spp. are becoming increasingly important. Their susceptibility to existing antifungals is limited and their mortality rate is ≥70% in patients with hematological malignancies. In other patients the mortality rates vary between 30 and 80%.

Onychomycosis is a fungal infection of the nails which is estimated to affect 2-13% of the general US population and up to 25% of the geriatric and diabetic populations. Common risk factors include age, male gender, diabetes, nail trauma, and chronic Tinea pedis (fungal infection of the foot). Onychomycosis has significant cosmetic, psychological and social implications. In some patient subsets it has serious medical consequences (e.g. foot amputations in diabetics).

Currently the infection is primarily treated with oral drugs, but this is not desirable for what is normally a non life threatening infection, as the currently used antifungal drugs have significant toxicities. It also leads to poor compliance—multiple surveys have shown it is counter intuitive to patients to take a pill for c. 6 months to treat a toe nail infection, especially given there is no visible improvement for the first 2-3 months of treatment. Ideally a fast acting topical approach is desired but existing topical drugs have very poor efficacy due to the difficulty of reaching the fungi that are located under the nail. Ciclopirox nail lacquer is the only FDA-approved topical agent available in the US for the treatment of onychomycosis, while amorolfine is a topical agent available in Japan and in Europe. However, these nail lacquer products have very limited efficacy in part because of their inability to penetrate to the nail bed where the infection resides, but also due to the nature of the compounds. As a result of these limitations, only 14% of onychomycosis patients are currently treated with topical drug and just 7% receive systemic drug therapy. In addition, there is a >25% recurrence rate amongst "cures".

At present there are four major compound classes available for the treatment of fungal infections. They are listed in Table A. The use of these drugs may in some cases of fungal infection deliver reasonable results, however, as outlined above mortality caused by fungal infections is still high. Apart from insufficient efficacy there are furthermore several other problems associated with the existing drugs:

Significant toxicity and/or patient sensitivity to the existing drugs e.g. liver toxicity is associated with many of the existing compounds (a significant problem, in particular due to the extended length of treatments) and Lamisil has cardiac toxicity.

Many pathogenic strains are insensitive or resistant against the anti-fungal drugs and resistance development is also of concern.

High relapse rate

In addition in many cases the efficacy rate is poor.

In relation to treatment of certain fungal infections such as onychomycosis, additional problems are associated with the existing drugs:

Long onset to relief of symptoms

Long treatment and compliance regimes are necessary, leading to problematic compliance Additionally, drug interactions are a common problem. In particular, azoles are cytochromes P-450 inhibitors, which may result in that these compounds cannot be administered to a patient receiving medication, the action of which is dependent on cytochrome P-450 activity.

Antifungals currently available for the treatment of systemic infections include Amphotericin B and its less toxic lipid formulations, e.g. AmBisome, and the echinocandins, which include Anidulafungin, Caspofungin, and Micafungin, all of which must be administered intravenously. Along with fluconazole, the newer triazoles such as Posaconazole (oral) and Voriconazole (oral and intravenous) are FDA approved for the treatment and prevention of systemic *Candida* infections. Despite these new additions to the antifungal armamentarium, treatment failure is still unacceptably high and there is an increase in resistance development to the azole and echinocandin families of drugs.

Caspofungin resistance is still an uncommon occurrence with c. 8% of *C. tropicalis* and c. 2% of *C. glabarata* isolates having been defined as resistant (MIC values of >2 mg/L). Nevertheless, taking into consideration the recent introduction of this drug and the observation that 2001-2004 surveillance studies identified >99.5% of patients as Caspofungin sensitive, it is disconcerting how rapidly echinocandin resistance is spreading. Furthermore, there have recently been reported cases of reduced *C. glabarata* susceptibility developing during Caspofungin therapy. The target of Caspofungin is the enzyme 1,3-β-D-glucan synthase, encoded by one of several FKS genes, depending on the species. It has been shown that in clinical isolates, mutations in the FKS 1 gene resulting in amino acid changes in the protein were necessary and sufficient to confer reduced susceptibility to Caspofungin. Recently *Candida* spp. with reduced susceptibility to the newer members of the echinocandin family have also been reported.

In terms of resistance, for the azoles alone, three different resistance mechanisms have been identified: a) alternative pathways for the synthesis of cell membrane sterols, b) mutations in the target demethylase site and c) increased efflux of drug from the fungal cell.

TABLE A

Summary of existing anti-fungal drug classes and modes of action

| Drug Class | Mode of Action |
|---|---|
| Polyene anti-fungals (e.g. Amphotericin B) | A molecule with a cyclic part, the molecule consisting of a hydrophobic and hydrophilic region. The polyene antimycotics bind with sterols in the fungal cell membrane, principally ergosterol. This changes the transition temperature of the cell membrane from a fluid to a more crystalline state. Animal cells contain cholesterol instead of ergosterol and so they are less susceptible. |
| Imidazole and triazole anti-fungals (e.g. Fluconazole or Itraconazole) | The imidazole and triazole anti-fungal drugs inhibit the enzyme cytochrome P450 14α-demethylase. This enzyme converts lanosterol to ergosterol, and is required in fungal cell membrane homeostasis. These drugs also block steroid synthesis in humans. |
| Allylamines (e.g. Terbinafine) | Allylamines inhibit the enzyme squalene epoxidase, another enzyme required for ergosterol synthesis. |
| Echinocandins (e.g. Caspofungin) | Echinocandins inhibit the synthesis of glucan in the cell wall, probably via the enzyme 1,3-β glucan synthase. |

TABLE A-continued

Summary of existing anti-fungal drug classes and modes of action

Anti-fungals work by exploiting differences between mammalian and fungal cells to selectively inhibit growth or to kill the fungal organism preferably without dangerous effects to the host. Unlike bacteria, both fungi and humans are eukaryotes. The basic structure of fungal cells and human cells is similar. This means it is more difficult to find a target for an anti-fungal drug that does not also exist in the infected organism. Consequently, there are often side-effects to some of these drugs. Some of these side-effects can be life-threatening if the drug is not used properly.

Well established examples of the toxicity problems are the nephrotoxicity of Amphotericin B, the liver damage caused by Terbinafine and the generalized intolerance against azoles. For example, up to 20% of females with vaginal candidiois cannot tolerate Fluconazole.

U.S. Pat. No. 6,541,506 describes methods for the synthesis and use of enediynes (compounds with a double bond and two triple bonds, in a given order.) The patent describes that these compounds may inhibit fungal infections and possibly also inhibit growth of fungal cells.

In agriculture, yield losses caused by various fungal pathogens in crops and other plants (for example, ornamental and amenity grasses) are significant, particularly across the major groups of fungal diseases such as rust, rot (root and fruit), leaf spots, mildews and wilts.

To date however, there has been no discovery of an effective antifungal agent for systemic or topical use, lacking the drawbacks of existing antifungal drugs.

SUMMARY OF THE INVENTION

Accordingly, there is a need for antifungal compounds, which do not have some or all of the above mentioned drawbacks of existing anti-fungal drugs.

Diyne Salts

It is an objective of the present invention to provide antifungal agents with one or more of the following properties, preferably all of the following properties:

Anti-fungal activity, preferably fungicidal activity

Crystalline

High melting point

High solubility in water

Stability in high humidity

Stability upon storage

The present inventors have found that potassium salts of diynes have some and frequently all of above mentioned properties.

Accordingly, it is one objective of the present invention to provide diyne salts of the formula I:

$$K^+Z-[C\equiv C-C\equiv C]-R_3$$

wherein Z is a carbon chain substituted with —COO⁻ or a bioisostere thereof (preferably —COO⁻) and optionally also substituted with one or more additional substituents; and $R_3$ is a heterocyclic ring, which optionally may be substituted at one or more positions.

The invention also provides pharmaceutical compositions comprising such diyne salts and one or more pharmaceutically acceptable excipients. These pharmaceutical compositions are in particular useful for treatment of an infection by a fungus in an individual, such as a mammal in need thereof.

The invention furthermore provides use of the diyne salts for preventing or treating fungal infections of a plant.

Diynes

The present invention provides a new class of compounds with antifungal activity. Thus, diynes compounds disclosed herein generally have a broad spectrum (i.e. activity against a wide range of fungal infections), they generally have potent antifungal activity, including antifungal activity against *A. fumigatus* and other filamentous fungi and they are generally active via the oral and intravenous routes. Importantly, the diynes disclosed herein have a novel mode of action, hence, their activity is generally unaffected by resistance to existing anti-fungal agents.

Fungi comprise enzymes catalysing fatty acid desaturation, for example conversion of saturated fatty acid to Δ9-monounsaturated fatty acid. These stearoyl-CoA desaturases are found in many fungi. In some fungi such as *S. cerevisiae* and *C. albicans* they are referred to as OLE-1. A number of fungi are dependent on stearoyl-CoA desaturases (e.g. OLE-1) for viability. The present invention discloses that for these fungi stearoyl-CoA desaturase is an interesting target for novel antifungal compounds.

The present invention discloses diyne compounds that are capable of specifically inhibiting conversion of a saturated fatty acid to a Δ9-monounsaturated fatty acid in fungi.

Thus it is one aspect of the present invention to provide pharmaceutical compositions comprising a diyne of formula I':

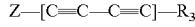

wherein Z is a carbon chain substituted with —COOH or a bioisostere thereof and optionally also substituted with one or more additional substituents; and R$_3$ is a heterocyclic ring, which optionally may be substituted at one or more positions (wherein the diyne may be any of the diynes described herein below in the sections "Diyne" and "Particular diynes")

wherein said diyne is capable of inhibiting conversion of a saturated fatty acid to a Δ9-monounsaturated fatty acid in a fungus, and wherein said pharmaceutical composition is for treatment of an infection by a fungus dependent on activity of stearoyl-CoA desaturase (such as any of the infections described herein below in the section "Fungal infection") in an individual in need thereof (wherein the individual may be any of the individuals described in the section "Individual in need of treatment").

It is also an objective of the present invention to provide methods of treating infections by a fungus dependent on activity of stearoyl-CoA desaturase in an individual in need thereof, said method comprising administering to said individual a pharmaceutical composition comprising a therapeutically effective amount of a diyne of the formula I':

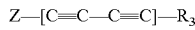

wherein Z is a carbon chain substituted with —COOH or a bioisostere thereof and optionally also substituted with one or more additional substituents; and R$_3$ is a heterocyclic ring, which optionally may be substituted at one or more positions; and wherein said diyne is capable of inhibiting conversion of a saturated fatty acid to a Δ9-monounsaturated fatty acid in a fungus.

It is furthermore an objective of the present invention to provide methods of treating a fungal infection in an individual in need thereof, said method comprising the steps of a) determining whether an individual is infected by a fungus dependent on activity of stearoyl-CoA desaturase and selecting such individual;

b) administering to said selected individual a therapeutically effective amount of a diyne of the formula I':

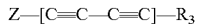

wherein Z is a carbon chain substituted with —COOH or a bioisostere thereof and optionally also substituted with one or more additional substituents; and R$_3$ is a heterocyclic ring, which optionally may be substituted at one or more positions; and or a pharmaceutically acceptable salt of said diyne, wherein said diyne is capable of inhibiting conversion of a saturated fatty acid to a Δ9-monounsaturated fatty acid in a fungus.

It is also an objective of the present invention to provide methods for identifying a fungitoxic compound, said method comprising the steps of, a) providing an indicator composition or cell comprising a gene coding for stearoyl-CoA desaturase and/or a stearoyl-CoA desaturase peptide;

b) contacting the indicator composition or cell with a diyne compound;

c) evaluating the activity of stearoyl-CoA desaturase in the presence and absence of the diyne compound; and d) selecting a diyne compound that down modulates the activity of stearoyl-CoA activity, thereby identifying a fungitoxic compound.

It is furthermore an objective of the invention to provide substantially pure diyne compounds of formula I':

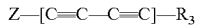

wherein Z is a carbon chain substituted with —COOH or a bioisostere thereof and optionally also substituted with one or more additional substituents; and R$_3$ is a heterocyclic ring, which optionally may be substituted at one or more positions;

wherein the diyne is capable of inhibiting conversion of a saturated fatty acid to a Δ9-monounsaturated fatty acid in a fungus. These diynes compounds are preferably any of the diyne compounds described in the section "Particular diynes" herein below.

It is also an objective of the present invention to provide diynes of the formula I':

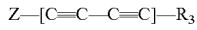

wherein Z is a carbon chain substituted with —COOH or a bioisostere thereof and optionally also substituted with one or more additional substituents; and R$_3$ is a heterocyclic ring, which optionally may be substituted at one or more positions;

wherein said diyne is capable of inhibiting conversion of a saturated fatty acid to a Δ9-monounsaturated fatty acid in a fungus for inhibiting or treating an infection by a fungus dependent on activity of stearoyl-CoA desaturase in a plant.

Ole1 Protein Inhibitors

This invention is also based upon the discovery that a novel class of compounds have been found to inhibit the function of the Ole1 protein in a wide variety of fungal pathogens, and are thus capable of inhibiting fungal growth of fungi dependent on Ole1 protein function. The inventive thus contemplates antifungal compounds for formulations for treating a subject, and also for use in the agricultural setting.

The invention thus provides a novel fungicide comprising an Ole1 protein inhibitor.

The invention also provides novel diyne compounds, their salts, derivatives and analogs.

A preferred embodiment of the invention are novel Ole1 protein inhibitors of structure II″

$$a)(Z)-R_1-C(O)-(C(R_2)_2)_x-C_2H_2-C_4-R_4 \quad \text{II″}$$

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_4$ is a heterocyclic ring, optionally substituted at one or more positions, preferably with one or more substituents selected from the group consisting of a $C_{1-5}$ alkyl, a $C_{1-5}$ alkenyl, a $C_{1-5}$ alkoxy, a $C_{1-5}$ alcohol, a hydroxyl, an amine, a nitrate and a halogen; and x is an integer between 4 and 10, inclusive. In a preferred embodiment, $R_4$ is a pyrrole, furan, or thiophene ring.

In both II″ and IX″ below, specific substituents are contemplated, as set forth in the Description below.

A preferred fungicide is a compound of structure III″,

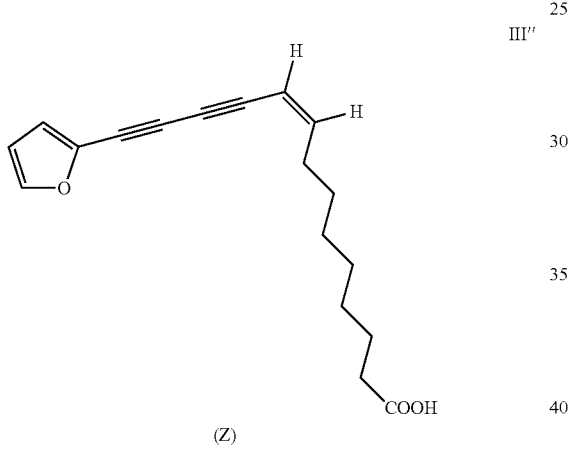

and its potassium (IV″) or sodium salt (V″).

Other preferred compounds are compounds of structure VI″-VIII″.

The invention also contemplates a compound of structure IX″, $$a.R_1-C(O)-(C(R_2)_2)_x-C_2H_4-C_4-R_4 \quad \text{IX″}$$

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_4$ is a heterocyclic ring, optionally substituted at one or more positions, preferably with one or more substituents selected from the group consisting of a $C_{1-5}$ alkyl, a $C_{1-5}$ alkenyl, a $C_{1-5}$ alkoxy, a $C_{1-5}$ alcohol, a hydroxyl, an amine, a nitro group and a halogen; and x is an integer between 4 and 10, inclusive. In a preferred embodiment, $R_4$ is a pyrrole, furan, or thiophene ring.

Preferred compounds include those having the structure of one of X″-XII″.

The invention also contemplates a fungicide comprising an Ole1 protein inhibitor.

Preferred fungicides are provided wherein the Ole1 protein inhibitor is selected from the group consisting of compounds of structures II″-XII″.

More specifically, the Ole1 inhibitor is a compound having the structure of II″, $$a.(Z)-R_1-C(O)-(C(R_2)_2)_x-C_2H_2-C_4-R_4 \quad \text{II″}$$

or is compound having the structure of IX″, $$a.R_1-C(O)-(C(R_2)_2)_x-C_2H_4-C_4-R_4 \quad \text{IX″}$$

One preferred Ole1 inhibitor is compound III″,

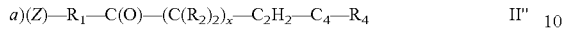

or its potassium salt, IV″, or its sodium salt, compound V″,

Other preferred fungicides comprise an Ole1 inhibitor having the structure of one of VI″, VII″ and VIII″.

Another preferred Ole1 inhibitor is a compound having the structure of one of X"-XII".

The invention further contemplates methods of providing a fungicide comprising an Ole1 protein inhibitor, the inhibitor being a compound having the structure of one of II"-XII".

The invention also contemplates methods of providing a formulation against a fungal pathogen or of enhancing the fungicidal activity of a formulation against a fungal pathogen, comprising adding an Ole1 protein inhibitor to a formulation, wherein the Ole1 inhibitor is a compound having the structure of one of II"-XII".

In preferred embodiments of the inventive fungicides and the inventive methods, the subject is animal, preferably mammal, more preferably human.

The compounds may also be used in co-therapy with one or more other therapeutically used classes of antifungal substances.

The present invention contemplates the use of the inventive compounds and fungicides against any one or more fungal pathogen selected from the group consisting of *Candida* spp. (for example *C. albicans, C. krusei, C. glabrata, C. tropicalis, C. parapsilosis, C. guilliermondii, C. haemulonii, C. lusitaniae, C. lipolytica, C. norvegensis, C. viswanathii, C. kefyr* or *C. dubliniensis*), *Aspergillus* spp. (for example *A. fumigatus, A. flavus, A. niger* or *A. terreus*) *Histoplasma capsulatum, Coccidioides immitis, Coccidioides posadasii, Cryptococcus* spp. (for example *C. neoformans* (for example var. *neoformans* or var. *gattii*), *C. bidus, C. laurentii*, or *C. fusarium*), Zygomycetes (such as *Rhizopus oryzae, R. micropsorus, R. pusillus, Cunninghamelle bertholletiae, Saksenaea vasiformis, Mucor circinelloides, M. ramosissimus, Absidia corymbifera, Apophysomyces elegans, Cokeromyces recurvatus* or *Syncephalastrum racemosum*), *Malassezia* spp. (for example *M. furfur* or *M. globosa*), Hyalohyphomycetes (for example *Fusarium solani* or *Scedosporium* spp., such as *S. prolificans* or *S. apiospermum*), Dermatophytes (for example *Trichophyton* spp. (for example *T. mentagrophytes, T. rubrum* or *T. tonsurans*), *Epidermophyton floccosum, Microsporum* spp (for example *M. cookei, M. canis, M. vanbreuseghemii, M gallinae* or *M. gypseum*) or *Trichosporon terrestre*), *Blastomyces dermatitidis, Sporothrix schenkii*, Chromomycotic fungi (for example *Fonsecaea pedrosoi, F. compacta, Cladophylophora carrionii* or *Phialophora verrucosa*) and *Madurella* spp. (for example *M. mycetomatis* or *M. griseum*), *Pneumocystis jirovecii, Pneumocystis carinii*, Ascomycota *Botrytis cinerea; Magnaporthe grisea; Anamorph; Pyricularia oryzae Colletotrichum gleoesporioides*—Chilli strain; *Colletotrichum gleoesporioides*-mango strain; *Fusarium verticillioides; Fusarium oxysporum; Alternaria solani; Uncinula necator* Syn *Erysiphe necator; Macrophomina phaseolina*; Syn. *Sclerotium bataticola* and *Rizoctonia bataticola; Botryodiplodia theobromae;* Basidiomycota *Sclerotium rolfsii; Rhizoctonia solani; Puccinia arachidis;* Oomycota *Pythium aphanidermatum*; and *Plasmopara viticola* Syn. *Personopora viticola*.

The invention also contemplates methods of providing a fungicidal formulation for use in an agricultural setting or of enhancing the fungicidal activity of a formulation for use in an agricultural setting, comprising adding one or more of the inventive fungicides to a formulation.

In preferred embodiments, the formulation is used to combat a fungal pathogen in a plant, a grass or a field.

The invention also contemplates the use of a fungicide comprising any of compounds II"-VIII" for the preparation of a medicament for treating a mammal suffering from or susceptible to a condition which can be improved or prevented by an Ole1 inhibitor.

The invention also contemplates a kit for treating a fungal pathogen in a subject comprising one or more of the inventive compounds or fungicides of structure II"-VIII".

The invention also contemplates the use of a fungicide comprising any of compounds II"-XII" for the preparation of a treatment for an agricultural condition which can be improved or prevented by treatment of the agricultural condition with an Ole1 protein inhibitor.

A kit for an agricultural fungicide is also contemplated in the present invention, comprising one or more of the inventive compounds or fungicides of structure II"-XII".

Other features and advantages of the invention will be apparent from the following description of the preferred embodiments thereof and from the claims.

BRIEF DESCRIPTION OF DRAWINGS

FIG. 5 shows an assay for synergistic effect between (Z)-14-(furan-2-yl)tetradeca-9-en-11,13-diynoic acid, potassium salt and Amphotericin B.

FIG. 6 shows a time course of the fungicidal effect of (Z)-14-(furan-2-yl)tetradeca-9-en-11,13-diynoic acid

FIG. 17a shows time dependent expressions of the OLE1 gene in response to compound IV'" in *S. cerevisiae*, numbers indicate time intervals in minutes. Expressions of OLE1 are given as multiples of the expression at 10 min, condition a.

FIG. 21 shows antagonistic effects between the potassium salt of (Z)-14-(furan-2-yl)tetradeca-9-en-11,13-diynoic acid and fatty acids as sodium salt in *C. albicans*. Compounds were combined in 96-well plates and inoculated with *C. albicans*. Plates were grown for 48 h and growth determined through visual inspection of growth wells.

FIG. 22 shows antagonistic effects between oleic acid and the potassium salt of (Z)-14-(furan-2-yl)tetradeca-9-en-11, 13-diynoic acid, Amphotericin B, Caspofungin and Voriconauzole on *Candida*. Compounds were combined in 96-well plates and inoculated with *C. albicans* or *C. parapsilosis* for Voriconazole. Plates were grown for 48 h and growth determined through visual inspection of growth wells.

DETAILED DESCRIPTION

A1. Diyne Salt

Figure 1:
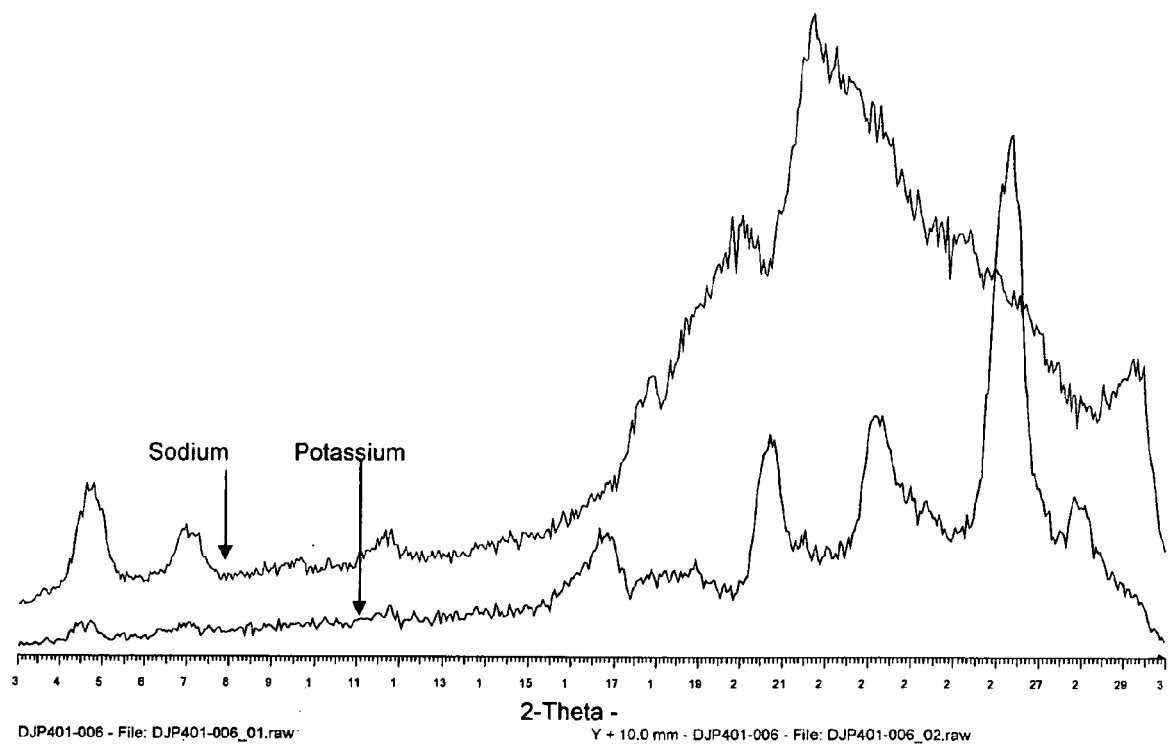
FIG. 1 shows XRPD diffractograms of salts of (Z)-14-(furan-2-yl)tetradeca-9-en-11,13-diynoic acid prepared using potassium ethoxide or sodium ethoxide as indicated in the figure.

The present invention relates to diyne compounds, in particular diyne salts as well as to use of the diyne salts—mainly in the treatment of fungal infections.

The diyne salts according to the present invention are diyne salts of formula I:

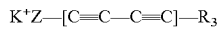

wherein Z is a carbon chain substituted with —COO⁻ or a bioisostere thereof, preferably Z is a carbon chain substituted with —COO⁻ and optionally also substituted with one or more additional substituents, preferably with $R_2$ (wherein $R_2$ is as described in this section below); and $R_3$ is a heterocyclic ring, preferably $R_3$ is any of the $R_3$ groups described in this section below.

Z is preferably a carbon chain, which is substituted with —COO⁻ or a bioisostere thereof (preferably with —COO⁻), preferably said —COO⁻ or bioisostere thereof is positioned at the end of said carbon chain, preferably at the distal end of said carbon chain in relation to the diyne moiety. Thus, Z may preferably be selected from the group consisting of alkyl and alkenyl, which is substituted with $R_4$, wherein $R_4$ is —COO⁻ or a bioisostere thereof, preferably —COO⁻. In addition, said carbon chain (such as said alkyl or alkenyl) may also optionally be substituted with one or more additional groups, preferably with one or more $R_2$ groups, wherein $R_2$ preferably is as defined herein below in relation to diynes of formula II.

Preferably Z is a $C_{6-20}$, preferably a $C_{6-15}$, more preferably $C_{6-12}$, even more preferably a $C_{9-20}$, yet more preferably a $C_{9-15}$, such as a $C_{9-12}$ alkyl or alkenyl substituted with —COO⁻ or a bioisostere thereof (preferably with —COO⁻) and optionally also substituted at one or more positions with $R_2$, preferably substituted with one or more selected from the group consisting of —COO⁻ and $R_2$. More preferably Z is —COO⁻—($C_{6-20}$ alkyl or alkenyl)-, such as —COO⁻—($C_{9-20}$ alkyl or alkenyl)-, for example —COO⁻—($C_{9-15}$ alkyl or alkenyl)-, such as —COO⁻—($C_{6-12}$ alkyl or alkenyl)-.

More preferably, the diyne salt is a diyne salt of the formula II:

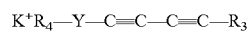

wherein $R_4$ is —COO⁻ or a bioisostere thereof, preferably however $R_4$ is —COO⁻, and Y is preferably a carbon chain of 6 to 20 carbon atoms, more preferably 9 to 20 carbon atoms, even more preferably 9 to 15 carbon atoms, yet more preferably 9 to 12 carbon atoms, even more preferably 9 carbon atoms with up to three double bonds. Depending on whether a carbon atom of said carbon chain is connected to the other carbon atoms of said carbon chain by single bonds and/or double bonds each carbon atom is linked to none, one or two $R_2$ groups. Thus, a carbon atom connected to both its neighbouring carbon atoms in the carbon chain by single bonds will be linked to two $R_2$ groups. A carbon atom connected to both its neighbouring carbon atoms in the carbon chain by double bonds will not be linked to any $R_2$ groups. A carbon atom connected to one neighbouring carbon atom in the carbon chain by a single bond and to the other neighbouring carbon atom in the carbon chain by a double bond will be linked to one $R_2$ group. Y may furthermore be as defined herein below; and $R_3$ is a heterocyclic ring, preferably $R_3$ is any of the $R_3$ groups described in this section below.

More preferably the diyne salt is a diyne salt of the formula III:

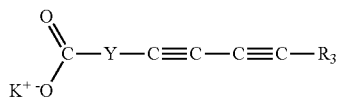

wherein Y is a carbon chain of 6 to 20 carbon atoms and up to three double bonds, wherein each carbon of said alkyl or alkenyl is linked to none, one or two $R_2$ groups, wherein each $R_2$ independently is —H, —OH or a hydrocarbon moiety containing between 1 and 4 carbon atoms, inclusive; $R_3$ is a heterocyclic ring, which optionally may be substituted at one or more positions; or a pharmaceutically acceptable salt of said diyne, wherein said diyne is capable of inhibiting conversion of a saturated fatty acid to a Δ9-monounsaturated fatty acid in a fungus.

Y is preferably a carbon chain of 6 to 20 carbon atoms, more preferably 9 to 20 carbon atoms, even more preferably 9 to 15 carbon atoms, yet more preferably 9 to 12 carbon atoms, even more preferably 9 carbon atoms with up to three double bonds. Depending on whether a carbon atom of said carbon chain is connected to the other carbon atoms of said carbon chain by single bonds and/or double bonds each carbon atom is linked to none, one or two $R_2$ groups. Thus, a carbon atom connected to both its neighbouring carbon atoms in the carbon chain by single bonds will be linked to two $R_2$ groups. A carbon atom connected to both its neighbouring carbon atoms in the carbon chain by double bonds will not be linked to any $R_2$ groups. A carbon atom connected to one neighbouring carbon atom in the carbon chain by a single bond and to the other neighbouring carbon atom in the carbon chain by a double bond will be linked to one $R_2$ group.

Accordingly, Y may be a linear $C_{6-20}$, preferably a $C_{6-15}$, more preferably $C_{6-12}$, even more preferably a $C_{9-20}$, yet more preferably a $C_{9-15}$, such as a $C_{9-12}$ alkyl, preferably a linear $C_{7-11}$ alkyl, yet more preferably a linear $C_{8-10}$ alkyl, even more preferably a linear $C_9$-alkyl.

Y may also be a linear $C_{6-20}$, preferably a $C_{6-15}$, more preferably $C_{6-12}$, even more preferably a $C_{9-20}$, yet more preferably a $C_{9-15}$, such as a $C_{9-12}$ alkenyl, preferably a linear $C_{7-11}$ alkenyl, yet more preferably a linear $C_{8-10}$ alkenyl, even more preferably a linear $C_9$-alkenyl. The alkenyl may comprise 1, 2 or 3 double bonds, preferably 1 or 2 double bonds, even more preferably only 1 double bond. The double bonds may be in the cis or the trans conformation, preferably at least one double bond is in the cis conformation, even more preferably all double bonds are in the cis conformation. Accordingly, Y may be a linear $C_{6-12}$, preferably a linear $C_{7-11}$ alkenyl, yet more preferably a linear $C_{8-10}$ alkenyl preferably a linear $C_9$ alkenyl, wherein all double bonds are cis double bonds. The double bonds may be at any suitable position, however in a preferred embodiment at least one double bond is situated at the $C_8$, $C_9$ or $C_{10}$ position, preferably at the $C_9$ position (the C in the carbonyl group being $C_1$), even more preferably at least one double bond in the cis conformation is situated at the $C_8$, $C_9$ or $C_{10}$ position, preferably at the $C_9$ position (the C in the carbonyl group being $C_1$).

Thus, in a preferred embodiment of the invention the diyne salt is a compound of the formula IV:

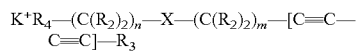

wherein $R_4$ is —COO⁻ or a bioisostere thereof, preferably however $R_4$ is —COO⁻, and
n is an integer, preferably an integer in the range of 4 to 10, inclusive, preferably in the range of 5 to 9, even more preferably in the range of 6 to 8, yet more preferably n is 7; and
m is an integer, preferably an integer in the range of 0 to 10, such as in the range of 0 to 8, for example in the range of 0 to 6, such as in the range of 0 to 4, for example in the range of 0 to 2, such as 0; and
each $R_2$ is, independently, —H, —OH or a hydrocarbon moiety containing between 1 and 6 carbon atoms, inclusive; and
X is —$CH_2$—$CH_2$— or —CH═CH— or phenyl, preferably X is —$CH_2$—$CH_2$— or —CH═CH—; and
$R_3$ is a heterocyclic ring, preferably $R_3$ is any of the $R_3$ groups described in this section below.

In a preferred embodiment of the invention the diyne salt is a compound of formula V:

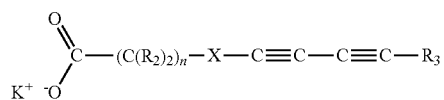

wherein each $R_2$ is, independently, —H, —OH or a hydrocarbon moiety containing between 1 and 6 carbon atoms, inclusive; n is an integer between 4 and 10, inclusive; X is —$CH_2$—$CH_2$— or —CH═CH— or phenyl, preferably X is —$CH_2$—$CH_2$— or —CH═CH—; and $R_3$ is a heterocyclic ring, which optionally may be substituted at one or more positions.

n is an integer in the range of 4 to 10, preferably in the range of 5 to 9, even more preferably in the range of 6 to 8, yet more preferably n is 7.

In one preferred embodiment of the invention, the diyne salt is a compound of formula V, wherein X is —CH═CH—, wherein the double bond is in the trans or cis conformation, preferably in the cis conformation. Also in this embodiment it is preferred that n is as outlined above and $R_2$ is as outlined below.

In another preferred embodiment of the invention, the diyne is a compound of formula V, wherein X is —$CH_2$—$CH_2$—. Also in this embodiment it is preferred that n is as outlined above and $R_2$ is as outlined below.

$R_3$ of the diyne salt of formula I, II, III, IV or V is a heterocyclic ring, which optionally may be substituted at one or more positions. If substituted, the heterocyclic ring is preferably substituted with one or more, preferably one or two selected from the group consisting of lower alkyl, lower alkenyl, lower alkoxy, lower alcohol, hydroxyl, amine, —$NO_2$ and halogen. Lower alkyl is preferably $C_{1-5}$, more preferably $C_{1-3}$, even more preferably $C_1$ alkyl. Lower alkenyl is preferably $C_{1-5}$, more preferably $C_{1-3}$, even more preferably $C_{1-2}$alkenyl. Lower alkoxy is preferably $C_{1-5}$, more preferably $C_{1-3}$, even more preferably $C_1$alkoxy. Lower alcohol is preferably $C_{1-5}$, more preferably $C_{1-3}$, even more preferably $C_1$ alcohol comprising one or more —OH groups, preferably only one —OH group. Halogen may be any halogen, but is preferably —F. It is however preferred that $R_3$ is a heterocyclic ring, which is not substituted or that $R_3$ is a heterocyclic ring substituted with a small substituent, preferably a small substituent selected from the group consisting of methyl, methoxy, hydroxyl, —$CH_2$—OH, amine and halogen, preferably methyl.

$R_3$ of the diyne salt of formula I, II, III, IV or V is preferably an aromatic heterocyclic ring.

$R_3$ of the diyne salt of formula I, II, III, IV or V is preferably a 3 to 7 membered heterocyclic ring, more preferably a 5 to 6 membered heterocyclic ring, even more preferably a 5 membered heterocyclic ring. The heterocyclic ring may be aromatic or non-aromatic. In one embodiment the heterocyclic ring is a 3 to 7 membered aromatic heterocyclic ring, more preferably a 5 to 6 membered aromatic heterocyclic ring, even more preferably a 5 membered aromatic heterocyclic ring.

The heterocyclic ring may comprise one or more heteroatoms, preferably in the range of 1 to 3 heteroatoms, more preferably in the range of 1 to 2 heteroatoms, yet more preferably 1 heteroatom. Said heteroatom(s) are preferably selected from the group consisting of S, N and O.

In a very preferred embodiment of the invention, $R_3$ is selected from the group consisting of pyrrole, furan and thiophene, which may optionally be substituted as outlined above at one or more positions. $R_3$ may also be selected from the group consisting of imidazole, oxazole, cyclopentadiene and triazole. Preferably, $R_3$ is furan, which is not substituted except for being linked to the diyne chain or is substituted at one or more positions as outlined above, even more preferably $R_3$ is furan, which is not substituted except for being linked to the diyne chain or is substituted at one or more positions with a small substituent, preferably a small substituent selected from the group consisting of methyl, methoxy, hydroxyl, amine and halogen, preferably methyl.

In a very preferred embodiment of the invention, $R_3$ is furan.

It is preferred that the heterocyclic ring is 2-substituted with the —[C≡C—C≡C]—Z chain. In particular in embodiments wherein the heterocyclic ring contains only one heteroatom it is preferred that the heterocyclic ring is 2-substituted with the —[C≡C—C≡C]—Z chain. Thus, in embodiments of the invention wherein $R_3$ is pyrrole, furan or thiophene, in particular when $R_3$ is furan, then it is preferred that the heterocyclic ring is 2-substituted with the —[C≡C—C≡C]—Z chain.

Each $R_2$ of a diyne salt of formula IV or V as well as each $R_2$ when contained in diynes of formula I, II or III is preferably, independently, —H, —OH or a hydrocarbon moiety containing between 1 and 6, preferably 1 to 4 carbon atoms, inclusive. The hydrocarbon moiety may be an alkyl, alkenyl or alkynyl, such as $C_{1-4}$ alkyl, $C_{1-4}$ alkenyl or $C_{1-4}$ alkynyl. It is however also possible that two neighbouring $R_2$ groups are connected to form a hydrocarbon ring system. Said ring system may for example be a 3 to 10 membered ring, preferably a 3 to 7 membered ring, more preferably a 5 to 6 membered ring system (numbers include carbon in carbon chain plus $R_2$ carbons). The ring system may be aromatic or none aromatic, for example the ring system may be an 6 membered aromatic ring. However, preferably neighbouring $R_2$ groups are not connected.

Thus, any particular diyne may contain a plurality of different $R_2$ groups. It is preferred that the majority of the $R_2$ groups of a diyne compound of formula I, II, III, IV or V is —H. It is even more preferred that all $R_2$ groups of a diyne compound of formula I, II, III, IV or V except for in the range of 0 to 5 $R_2$ groups, preferably all $R_2$ groups except for in the range of 0 to 3 $R_2$ groups, more preferably all $R_2$ groups except for in the range of 0 to 1 $R_2$ groups are —H. It is even more preferred that each $R_2$ group of a diyne compound of formula I, II, III, IV or V is —H.

In embodiments of the invention where two $R_2$ groups are connected to form a ring system, and in particular if said ring system is aromatic, then it is preferred that said $R_2$ groups are positioned on $C_7$ and $C_8$; or on $C_8$ and $C_9$; or on $C_9$ and C; or on $C_{10}$ and $C_{11}$, preferably on $C_9$ and $C_{10}$ position (the C in the carbonyl group being $C_1$).

A preferred diyne compound according to the invention is potassium (Z)-12-(furan-2-yl)dodeca-7-en-9,11-diynoate.

Another preferred diyne compound according to the invention is potassium (Z)-13-(furan-2-yl)trideca-8-en-10,12-diynoate.

Yet another preferred diyne compound according to the invention is potassium (E)-14-(furan-2-yl)tetradeca-9-en-11,13-diynoate.

Yet another preferred diyne compound according to the invention is the diyne compound potassium (Z)-14-(furan-2-yl)tetradeca-9-en-11,13-diynoate.

Another preferred diyne compound according to the invention is the diyne compound potassium 14-(furan-2-yl)tetradeca-11,13-diynoate.

In yet another embodiment of the invention the diyne compound may be selected from the group consisting of (Z)-14-(furan-2-yl)tetradeca-9-en-11,13-diynoic acid, potassium salt; (Z)-14-(5-methylfuran-2-yl)tetradeca-9-en-11,13-diynoic acid, potassium salt; 8-(2-(4-(furan-2-yl)buta-1,3-diynyl)phenyl)octanoic acid, potassium salt; (Z)-14-(4,5-dimethylfuran-2-yl)tetradeca-9-en-11,13-diynoic acid, potassium salt and 14-(furan-2-yl)tetradeca-11,13-diynoic acid, potassium salt.

A2. Preparation of Diyne Salts

The diyne salts according to the present invention may be prepared using the corresponding carboxylic acids as starting material. Said corresponding diyne carboxylic acids may be prepared essentially as described in U.S. Pat. No. 6,541,506, which is hereby incorporated by reference.

The diyne carboxylic acid is then mixed with a base in a useful solvent. In some embodiments, the diyne carboxylic acid is dissolved in solvent and the base is dissolved in solvent prior to mixing. For preparation of potassium diyne salts, then the base is a base comprising a potassium cation, such as potassium ethoxide.

The solvent may be any useful solvent. In preferred embodiments of the invention the solvent is a water miscible organic solvent, such as a solvent selected from the group consisting of IPA, Dioxane, EtOH and acetone.

The method may also comprise a heating step, for example the step of dissolving the diyne carboxylic acid may comprise a heating step, such as heating to in the range of 40 to 80° C., such as to 50° C. If a heating step is employed, then usually also a cooling step is employed—typically, the heating solution comprising diyne carboxylic acid and base is allowed to cool slowly, for example to a temperature in the range of 0 to 30° C., such as to 15-25° C., for example to 18° C.

Diyne salt may then precipitate as solids. The solvent or part thereof may also be allowed to evaporate.

A useful method for preparing potassium (Z)-14-(furan-2-yl)tetradeca-9-en-11,13-diynoate is described in Example 2 herein below. The skilled person will be able to prepare other potassium diyne salts starting from the corresponding carboxylic acids using a similar approach.

A3. Properties of Diyne Salts

The present invention relates to diyne salts per se as well as to use of the diyne compounds in treatment of fungal infections. The structural properties of the diynes according to the invention are described herein above in the section "Diyne salts". In addition to these structural properties it is preferred that the diyne salts according to the invention also have the functional properties described in detail in this section.

a. Inhibition of Conversion of a Saturated Fatty Acid to Δ9-Monounsaturated Fatty Acid It is very preferred that the diyne salts according to the invention is capable of inhibiting conversion of a saturated fatty acid to a Δ9-monounsaturated fatty acid in a fungus. In particular it is preferred that the diyne compound is capable of inhibiting conversion of stearic acid to oleic acid in a fungus. It is also preferred that the diyne compound is capable of inhibiting conversion of palmitic acid to palmitoleic acid.

Whether a diyne compound is capable of inhibiting conversion of stearic acid to oleic acid in a fungus may be determined in any useful method known to the skilled person. According to the present invention one method for determining whether a diyne compound is capable of inhibiting conversion of stearic acid to oleic acid in a fungus comprises the steps of a) providing a fungus or a fungal extract or an in vitro assembled complex comprising stearoyl-CoA 9 desaturase (such as OLE-1)

b) optionally providing co-factors for stearoyl-CoA 9 desaturase (such as OLE-1)
c) providing a substrate selected from the group consisting of stearic acid and activated forms of stearic acid
d) providing a diyne compound
e) incubating said fungus or fungal extract or in vitro assembled complex with said substrate, optionally co-factors and with a predetermined amount of said diyne compound for a predetermined amount of time
f) detecting the presence of product formed, wherein the product is selected from the group consisting of oleic acid and activated forms of oleic acid.

Said activated form of stearic acid is preferably stearyl-CoA and said activated from of oleic acid is preferably oleoyl-CoA. If stearyl-CoA is provided in step b), then preferably step d) comprises detecting formation of oleoyl-CoA.

Similarly, whether a diyne compound is capable of inhibiting conversion of palmitic acid to palmitoleic acid in a fungus may be determined in any useful method known to the skilled person. According to the present invention one method for determining whether a diyne compound is capable of inhibiting conversion of palmitic acid to palmitoleic acid in a fungus comprises the steps of
a) providing a fungus or a fungal extract or an in vitro assembled complex comprising stearoyl-CoA 9 desaturase (such as OLE-1)
b) optionally providing co-factors for stearoyl-CoA 9 desaturase (such as OLE-1)
c) providing a substrate selected from the group consisting of palmitic acid and activated forms of palmitic acid
d) providing a diyne compound
e) incubating said fungus or fungal extract or in vitro assembled complex with said substrate, optionally cofactors and a predetermined amount of said diyne compound for a predetermined amount of time
f) detecting the presence of product formed, wherein the product is selected from the group consisting of palmitoleic acid and activated forms of palmitoleic acid.

Said activated form of palmitic acid is preferably palmitoyl-CoA and said activated from of palmitoleic acid is preferably palmitoleyl-CoA. If palmitoyl-CoA is provided in step b), then preferably step d) comprises detecting formation of palmitoleyl-CoA.

Said fungus may be provided as an intact viable fungus or as intact fungal cells. The fungal extract may be any extract comprising stearoyl-CoA 9 desaturase (such as OLE-1). In *Saccharomyces cerevisiae* and other fungi the stearoyl-CoA desaturase is mainly located in the membranes of the endoplasmatic reticulum and accordingly it is preferred that said fungal extract comprises endoplasmatic reticulum or parts thereof. For example, the extract may be prepared by lysis of fungal cells, followed by separation of fractions for example by centrifugation. In particular, differential centrifugation may be used to enrich for endoplasmatic reticulum. However, fractions or extracts comprising endoplasmatic reticulum may also be obtained by other useful methods known to the skilled person. Alternatively, stearoyl-CoA desaturase may be obtained by in vitro assembly by methods known to the skilled person.

Preferably, the substrate provided in step c) is labelled allowing easy detection of the product in step f). The substrate may be labelled with any suitable label, such as a radioactive label, a dye, a heavy metal, a fluorescent label or a bioluminescent label. Preferably, the substrate is radioactively labelled. Detecting product formed may then be performed by detecting labelled product. The detection method will dependent on the particular label used.

One non-limiting example of determining inhibition of conversion of stearic acid to oleic acid is described herein below in Example 6. The skilled person will understand that a similar method may be performed for determining inhibition of conversion of palmitic acid to palmitoleic acid, by exchanging the substrate provided.

Preferably, the diyne compounds according to the invention are capable of inhibiting at least 50%, more preferably at least 60%, even more preferably at least 70%, yet more preferably at least 80%, yet more preferably at least 90%, even more preferably at least 95%, yet more preferably essentially 100% of the formation of oleic acid, wherein "essentially 100%" means that no detectable product is formed. Inhibition is determined in relation to a control, wherein said fungus or fungal extract is incubated with said substrate in the absence of said diyne compound for the same predetermined amount of time.

b. Inhibition of stearoyl-CoA 9 desaturase

It is preferred that the diyne salt of the invention is capable of inhibiting the activity of a fungal stearoyl-CoA 9 desaturase, preferably the diyne compound is capable of inhibiting the activity of a fungal OLE-1.

The activity of said fungal stearoyl-CoA 9 desaturase (such as OLE-1) may be inhibited by different means by said diyne compound. Thus, the diyne may directly inhibit the enzymatic activity of said fungal stearoyl-CoA 9 desaturase (such as OLE-1). Thus, the diyne compound may preferably be an inhibitor of the fatty acid desaturase activity of OLE-1 polypeptide.

Whether said diyne salt is capable of directly inhibiting the activity of fungal stearoyl-CoA 9 desaturase (such as OLE-1) may for example be determined using an in vitro assay for fungal stearoyl-CoA 9 desaturase (such as OLE-1) activity. Thus, for example fungal stearoyl-CoA 9 desaturase (such as OLE-1) may be incubated with either stearic acid and/or palmitic acid and/or activated forms thereof (such as stearyl-CoA or palmitoyl-CoA) optionally together with co-factors to form a reaction mixture and the formation of oleic acid and/or palmitoleic acid and/or activated forms thereof may then be determined. Addition of a diyne salt to said reaction mixture preferably significantly inhibits the formation of oleic acid and/or palmitoleic acid or activated forms thereof. Thus, preferably addition of a diyne salt to said reaction mixture reduces the formation of oleic acid and/or palmitoleic acid to less than 30%, preferably less than 20%, more preferably to less than 10%, for example to less than 5%, for example to less than 3%, such as to less than 1%. Said fungal stearoyl-CoA 9 desaturase (such as OLE-1) may be provided to said reaction mixture in a purified form or as part of a crude extract, for example a fungal extract or as prepared in vitro.

Mammalian desaturases are significantly different to fungal stearoyl-CoA 9 desaturases (such as OLE-1), for example mammalian desaturases lacks an integral cytochrome $b_5$ domain (Krishnamurthy et al., 2004, Microbiology, 150, 1991-2003. Accordingly, inhibitors of fungal stearoyl-CoA 9 desaturase (such as OLE-1), may be specific for the fungal enzymes in the sense that they do not inhibit mammalian desaturases to any significant extent.

In a preferred embodiment of the invention the diyne salt according to the invention is a selective inhibitor of a fungal stearoyl-CoA 9-desaturase (such as OLE-1). Thus it is preferred that the diyne compound is capable of inhibiting the activity of at least one fungal stearoyl-CoA 9 desaturase, preferably of more than one fungal stearoyl-CoA 9 desaturase. It is furthermore preferred that the diyne compound of the invention does substantially not inhibit at least one mammalian stearoyl-CoA 9 desaturase, preferably human stearoyl-CoA 9 desaturase. Accordingly, it is preferred that if using the above-described in vitro assay, then the diyne compounds according to the invention are capable of reducing the formation of oleic acid and/or palmitoleic acid to less than 30%, preferably less than 20%, more preferably to less than 10%, for example to less than 5%, for example to less than 3%, such as to less than 1% in the presence of one or more fungal stearoyl-CoA 9 desaturase (such as OLE-1), but in the absence of any mammalian stearoyl-CoA 9 desaturase. In addition it is preferred that in a similar in vitro assay said diyne compound is substantially not capable of reducing the formation of oleic acid and/or palmitoleic acid and thus in the presence of said diyne compound at least 80%, preferably at least 90%, yet more preferably at least 95% oleic acid and/or palmitoleic acid is formed compared to in the absence of said diyne compound, when incubating either stearic acid and/or palmitic acid with one or more mammalian stearoyl-CoA 9 desaturases, preferably in the presence of human stearoyl-CoA 9 desaturase, but in the absence of any fungal stearoyl-CoA 9 desaturase (such as OLE-1).

The diyne salt may also indirectly inhibit the activity of said fungal stearoyl-CoA 9 desaturase (such as OLE-1) by down modulating the level of said fungal stearoyl-CoA 9 desaturase (such as OLE-1) in a fungus. Thus, the diyne compound may decrease the stability or the half life of said fungal stearoyl-CoA 9 desaturase (such as OLE-1), thereby down modulating the level. The diyne compound may also inhibit the expression of said fungal stearoyl-CoA 9 desaturase (such as OLE-1), for example by inhibiting transcription or translation of fungal stearoyl-CoA 9 desaturase (such as OLE-1).

In one embodiment of the invention, the diyne compound may down modulate the expression of the OLE-1 polypeptide by modulating the activity of a transcriptional regulator of the gene encoding the OLE-1 polypeptide. The activity of the transcriptional regulator may for example be down modulated by inhibition of the binding of the transcriptional regulator to an OLE-1 promoter or enhancer region.

Spt23p/Mga2p is a fungal transcriptional regulator that amongst others controls the expression of fungal stearoyl-CoA 9 desaturase (such as OLE-1). Thus, the diyne salt may be capable of inhibiting the activity of Spt23p/Mga2p.

c. Antifungal Activity

The MIC (minimal Inhibitory Concentration) is the minimal concentration of diyne salt required for inhibiting essentially 100%, such as 100% growth of a fungi. Preferably, the MIC of the diyne salts according to the invention is at the most 500 ng/ml, preferably at the most 250 ng/ml, yet more preferably at the most 100 ng/ml, for example at the most 60 ng/ml, such as at the most 40 ng/ml, for example at the most 20 ng/ml, such as at the most 10 ng/ml in relation to at least 3 different fungi.

It is also preferred that the diyne salts according to the invention are capable of killing one or more fungi, preferably capable of killing at least 2, more preferably at least 5, even more preferably at least 10 different fungi. Preferably, the diyne compound has a minimum fungicidal concentration (MFC) of at the most 100 µg/ml, preferably at the most 50 µg/ml, yet more preferably at the most 10 µg/ml, even more preferably at the most 2 µg/ml, against one or more fungi, preferably one or more pathogenic fungi, even more preferably against at least 2, yet more preferably at least 5, even more preferably at least 10 different fungi. Preferably, said MFC for a given fungus is determined in a method comprising the steps of a) cultivating said fungus in vitro
b) contacting said fungus with various concentrations of test diyne compound
c) incubating said fungus with said diyne test compound for a predetermined amount of time
d) transferring said fungus to another in vitro culture medium
e) determining growth of said fungus in said another in vitro culture medium The lowest concentration of diyne test compound resulting in essentially no growth in step e), preferably in no detectable growth in step e) is the MFC.

In addition it is preferred that contacting a fungus with said diyne compound leads to a rapid loss of viability. This may for example be determined by a method comprising the steps of:
a) cultivating one or more fungi in vitro, thereby obtaining a fungal culture
b) determining the CFU/ml in said fungal culture
c) contacting the fungal culture with a test diyne compound
d) incubating said fungal culture with said test diyne compound for a predetermined amount of time
e) determining the CFU/ml in said fungal culture If the CFU/ml determined in step e) is at the most 20%, preferably at the most 15%, yet more preferably at the most 10% of the CFU/ml determined in step b), wherein said predetermined amount of time is in the range of 0.5 to 24 hours, preferably in the range of 0.5 to 12 hours, even more preferably in the range of 0.5 to 6 hours, yet more preferably in the range of 0.5 to 2 hours, such as in the range of 1 to 24 hours, even more preferably in the range of 1 to 12 hours, yet more preferably in the range of 1 to 6 hours, even more preferably in the range of 1 to 2 hours then said diyne compound is said to be capable of leading to rapid loss of viability of said fungus. Thus, it is preferred that at least a 1000 fold reduction in CFU/ml is determined in step e) compared to step b), when said predetermined amount of time is at least 3 hours, such as 3 hours.

As outlined above it is preferred that the diyne compound has fungicidal activity against one or more fungi and in addition it is preferred that said diyne compound is capable of leading to rapid loss of viability of one or more fungi.

It is also preferred that the diyne compounds according to the invention are capable of inhibiting growth of at least 1, preferably of at least 2, such as of at least 3 different fungi, at a concentration of at the most 100 µg/ml, preferably at the most 50 µg/ml, yet more preferably at the most 10 µg/ml, even more preferably at the most 2 µg/ml. Inhibition of growth may for example be determined as described herein below in Example 7.

d. Solubility

In order to obtain a desired antifungal activity in a clinical setting, it is important that the antifungal compound is soluble in water. Thus, it may be challenging to prepare pharmaceutical compositions comprising antifungal compounds, which are not water soluble, and which still may reach the site of disease and be functional there. This is in particular the case with infections by a fungus which involve infection of inner organs or disseminated infections. Also in relation to treatment or reduction of risk of infection by a fungus in a plant, it is preferable that the antifungal compound is soluble in water.

Accordingly, it is one objective of the present invention to provide antifungal compounds, which are not soluble in water. Interestingly, in contrast to for example diyne carboxylic acids, the diyne salts disclosed herein are readily soluble in water.

Thus, the diyne salt of the invention preferably has a solubility in water of at least 50 mg/ml, preferably at least 60 mg/ml, more preferably at least 70 mg/ml, yet more preferably at least 80 mg/ml, even more preferably at least 90 mg/ml.

The solubility in water is preferably determined as described in Example 1 herein below.

e. Crystal

For pharmaceutical applications it is furthermore generally preferred that the active compound is provided in a crystalline form.

Accordingly, it is also an objective to provide antifungal compounds, which are crystalline.

Interestingly, and in contrast to many other diyne salts, the diyne potassium salts provided herein are available in a crystalline form.

Whether a compound is crystalline may be determined by any suitable method known to the skilled person, however, preferably it is determined using X-Ray Powder Diffraction (XRPD). One non-limiting method for performing XRPD is described in Example 1. Crystalline compounds gives rise to a XRPD pattern with distinctive peaks, whereas an amorphous compound gives rise to an XPRD pattern without distinctive peaks. An example of an XPRD pattern for a crystalline compound (potassium (Z)-14-(furan-2-yl)tetradeca-9-en-11,13-diynoate) with distinctive peaks and an amorphous compound (sodium (Z)-14-(furan-2-yl)tetradeca-9-en-11,13-diynoate) without distinctive peaks is shown in FIG. 1.

In a preferred embodiment of the invention, the diyne salt is potassium (Z)-14-(furan-2-yl)tetradeca-9-en-11,13-diynoate. In this particular embodiment it is preferred that said potassium (Z)-14-(furan-2-yl)tetradeca-9-en-11,13-diynoate is in the crystalline form.

More preferably, said potassium (Z)-14-(furan-2-yl)tetradeca-9-en-11,13-diynoate crystals have a high resolution XPRD pattern comprising peaks at the following 2θ angles. Said 2θ angles are wavelength dependent and calculated at Cu—K a, λ=1.54173 Å. Preferably only peaks with an intensity of >3% are included in the pattern. The high resolution XPRD pattern may be obtained using any suitable method known to the skilled person, but in one preferred embodiment it is prepared as described herein below in Example 2.

Preferably, the potassium (Z)-14-(furan-2-yl)tetradeca-9-en-11,13-diynoate crystals have a high resolution XPRD pattern comprising peaks at least at the following 2θ angles: 2.42° and 4.78°.

It is also preferred that the potassium (Z)-14-(furan-2-yl)tetradeca-9-en-11,13-diynoate crystals have a high resolution XPRD pattern comprising peaks at least at the following 2θ angles: 7.14°, 9.52° and 11.89°.

Thus, in a preferred embodiment the potassium (Z)-14-(furan-2-yl)tetradeca-9-en-11,13-diynoate crystals have a high resolution XPRD pattern comprising peaks at least at the following 2θ angles: 2.42° and 4.78°, 7.14°, 9.52° and 11.89°.

In a very preferred embodiment the potassium (Z)-14-(furan-2-yl)tetradeca-9-en-11,13-diynoate crystals have a high resolution XPRD pattern comprising peaks at least at the following 2θ angles: 2.42°, 4.78°, 7.14°, 9.52°, 9.52°, 16.45°, 17.27°, 18.41°, 19.11°, 19.68°, 21.27°, 21.95°, 23.06°, 23.86°, 24.90°, 26.98°, 27.82°, 28.68°, 28.86° and 38.77°. In this embodiment it is preferred that the high resolution XPRD pattern does not comprises any other peaks with an intensity of >5%.

In a very preferred embodiment the potassium (Z)-14-(furan-2-yl)tetradeca-9-en-11,13-diynoate crystals have a high resolution XPRD pattern as shown herein in FIG. 2B f. Moisture Uptake It is also preferred that the diyne salt according to the invention does not take up to much moisture from the surroundings.

Accordingly, it is preferred that the weight change of the compound is less than 5%, preferably less than 4%, more preferably less than 3%, even more preferably less than 2%, for example even less than 1% at a humidity of 60% RH compared to a humidity of 10% RH.

It is also preferred that the weight change of the compound is less than 5%, preferably less than 4% at a humidity of 70% RH compared to a humidity of 10% RH.

In addition, it is preferred that if the diyne salt is exposed to humidity higher than 80%, then upon return to a lower humidity, then moisture is lost and the crystalline form of the diyne salt is kept/regained.

The weight change at various humidity conditions may be determined by any useful method known to the skilled person, however in a preferred embodiment it is determined using GVS, for example as described in Example 2 herein below.

g. Melting Temperature

It is also preferred that the diyne salt has a sufficiently high melting temperature in order to allow handling during manufacture of pharmaceutical compositions and storage at ambient temperature.

Thus, it is preferred that the melting point of said compound is at least 100° C., preferably at least 110° C., more preferably at least 120° C., yet more preferably at least 130° C., even more preferably at least 140° C.

The melting point of a compound may be determined using any suitable method known to the skilled person, however in a preferred embodiment the melting temperature is determined by an DSC analysis, for example as described herein below in Example 1.

h. Stability

It is also preferred that the diyne salt according to the present invention is stable upon storage.

Thus it is preferred that when stored as a solid, the diyne salt is stable for at least 3 months, preferably at least 4 months, more preferably at least 5 months, even more preferably at least 6 months, such as for in the range of 3 to 12 months, for example in the range of 4 to 12 months, such as for in the range of 5 to 12 months, for example in the range of 6 to 12 months, such as for in the range of 3 to 6 months, for example in the range of 4 to 6 months, such as for in the range of 5 to 6 months.

In particular, it is preferred that the content of diyne salt in a diyne salt solid has not decreased significantly as determined by HPLC after storage for at least 3 months, preferably at least 4 months, more preferably at least 5 months, even more preferably at least 6 months, such as for in the range of 3 to 12 months, for example in the range of 4 to 12 months, such as for in the range of 5 to 12 months, for example in the range of 6 to 12 months, such as for in the range of 3 to 6 months, for example in the range of 4 to 6 months, such as for in the range of 5 to 6 months at a temperature in the range of 2 to 25° C., such as at a temperature of 2 to 8° C., for example at a temperature of 25° C. and a humidity of in the range of 10 to 60%, such as 30 to 60%, for example 60%. In this context the term "content of diyne salt in a diyne salt solid has not decreased significantly" preferably means that the content has not decreased to less than 95%, preferably not to less than 96%, more preferably not to less than 97%, yet more preferably not to less than 98%.

It is also preferred that the content of diyne salt in a diyne salt solid has only decreased slightly as determined by HPLC after storage for at least 3 months, preferably at least 4 months, more preferably at least 5 months, even more preferably at least 6 months, such as for in the range of 3 to 12 months, for example in the range of 4 to 12 months, such as for in the range of 5 to 12 months, for example in the range of 6 to 12 months, such as for in the range of 3 to 6 months, for example in the range of 4 to 6 months, such as for in the range of 5 to 6 months at a temperature in the range of 35 to 50° C., such as at a temperature of 35 to 45° C., for example at a temperature of 40° C. and a humidity of in the range of 60 to 75%, such as 70 to 75%, for example 75%. In this context the term "content of diyne salt in a diyne salt solid has only decreased slightly" preferably means that the content has not decreased to less than 90%, preferably not to less than 92%, more preferably not to less than 94%, yet more preferably not to less than 96%.

A4. Pharmaceutical Composition

The pharmaceutical compositions comprising diyne salts according to the present invention are useful for treating fungal infections in an individual in need thereof. The pharmaceutical compositions may be in any suitable form depending on the fungal infection to be treated.

Thus, the pharmaceutical composition may be formulated for topical administration or for systemic administration. Typically, if the fungal infection is a local infection on a body surface, then the pharmaceutical composition is formulated for topical administration. If the fungal infection is a disseminated infection and/or an infection of one or more inner organs, tissues or cells then the pharmaceutical composition is typically formulated for systemic administration, such as parenteral administration or oral administration.

In addition, to said diyne salts the pharmaceutical compositions according to the invention will frequently comprise one or more pharmaceutically acceptable excipients.

For therapeutic uses, the pharmaceutical compositions comprising diyne salts may be administered systemically, for example, formulated in a pharmaceutically acceptable buffer such as physiological saline. Treatment may be accomplished directly, e.g., by treating the individual (such as a human being) with a diyne salt or pharmaceutical composition comprising a diyne salt of the invention. Preferable routes of administration include, for example, inhalation or subcutaneous, intravenous, intraperitoneally, intramuscular, or intradermal injections which provide continuous, sustained levels of the diyne compounds in the patient. Treatment of human beings or other animals is carried out using a therapeutically effective amount of a diyne compound of the invention in a physiologically-acceptable carrier. Suitable carriers and their formulation are described, for example, in *Remington: The Science and Practice of Pharmacy*, (19th ed.) ed. A. R. Gennaro A R., 1995, Mack Publishing Company, Easton, Pa.

In one preferred method, one or more diyne salts of the invention are formulated in combination with a solid or a liquid dermatologically acceptable carrier. Useful solid carriers include finely divided solids such as talc, clay, microcrystalline cellulose, silica, alumina, and the like. Useful liquid carriers include water, alcohols, or glycols (or water-alcohol/glycol blends), in which the present compounds can be dissolved or dispersed at effective levels. Adjuvants (such as flavourings and/or fragrances), surfactants, and additional antimicrobial agents can be added to optimize the properties for a given use. The compositions can be applied from absorbent pads, used to impregnate bandages and other dressings, or sprayed onto the affected area using pump-type or aerosol sprayers. The liquid compositions can also be employed as eye drops, mouth washes, douches, etc.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user, which is mainly relevant for treating fungal infections of the skin.

In other medical applications, diyne salts can be added to materials used to make medical devices such as catheters, including but not limited to intravenous, urinary, intraperitoneal, ventricular, spinal, and surgical drainage catheters, in order to prevent colonization and systemic seeding by potential fungal pathogens. Similarly, an antifungal compound may be added to the materials that constitute various surgical prostheses and to dentures to prevent colonization by fungal pathogens and thereby prevent more serious invasive infection or systemic seeding by these pathogens.

The amount of the diyne salt to be administered may vary depending upon the manner of administration, the age and body weight of the individual, and the type of fungal infection and extensiveness of the infection.

However, preferably the pharmaceutical compositions comprising diyne salts according to the invention are formulated for administration of in the range of 0.001 mg/Kg to 100 mg/kg, preferably in the range of 0.001 mg/Kg to 100 mg/kg daily, in particular when the individual to be treated is a mammal, such as a human being.

The total concentration of one or more diyne salts of the invention in the present compositions can be varied widely, and will depend on factors such as the compatibility of the active ingredient(s) with the vehicle, the potency of the active ingredient(s) and the condition to be treated. Generally, the concentration of the diyne compound(s) in at composition for topical administration, such as a lotion, will be from about 0.01 to 25% by weight, such as from 0.1-25% by weight, preferably from about 0.5-10% by weight, and more preferably from about 0.5% to 5% by weight. In liquid formulations the concentration may be from 0.01 to 90%, preferably from 0.01 to 50%, such as from 0.01 to 25% by weight. The concentration in a semi-solid or solid composition such as a gel or a powder will be about 0.01-99% by weight, such as from 0.01 to 50%, for example from 0.01 to 25% and preferably about 0.5-2.5% by weight.

The pharmaceutical compositions according to the invention may in addition to the diyne salts also comprise one or more additional active agents.

Said additional active agents may for example be antifungal agents.

A5. Individual in Need of Treatment

The present invention relates to pharmaceutical compositions comprising diyne salts for treatment of fungal infections in an individual in need thereof.

Said individual may be any individual suffering from a fungal infection, preferably an animal, more preferably a mammal, even more preferably a human being suffering from a fungal infection. In some preferred embodiments of the invention, the individual is however a non-human mammal suffering from a fungal infection, preferably a mammal selected from the group consisting of horses, cattle, dogs and cats. Said fungal infection may be any of the fungal infections described herein below in the section "Fungal Infections".

In one embodiment, the individual is an individual susceptible to fungal infections, for example an immunocompromised individual, such as an immunocompromised human being. Said immunocompromised individual may be immunocompromised for various reasons, for example the individual may receive immune suppressing medication (for example in connection with transplantation) or the individual may be suffering from an immunocompromising condition, such as HIV infection.

Interestingly, the present invention discloses that the diyne salts of the invention does reduce the activity of cytochromes P450 significantly. Whether a diyne salt is capable of reducing the activity of cytochromes P450 may be determined by any suitable assay known to the skilled person, preferably by an assay comprising the steps of:
a) providing a cytochrome P450
b) providing a substrate for said cytochrome P450
c) incubating said cytochrome P450 with said substrate under conditions allowing for cytochrome P450 activity in the presence and absence of the diyne salt
d) determining a reduction in product formed in the presence of said diyne salt compared to in the absence of said diyne salt A diyne salt is said to not "reduce the activity of cytochromes P450 significantly" if at least 60%, preferably at least 70% product is formed in the presence of 10 µM of the diyne salt compared to in the absence of said diyne salt. Preferably, said diyne salt does not significantly reduce the activity of at least 3, preferably at least 4, more preferably at least 5, even more preferably at least 6, such as in the range of 3 to 10, for example in the range of 5 to 10, such as 7 different cytochromes P450. Said substrate may be labelled, and the product formed may then be detected by detecting labelled product. However, frequently the detection may also be direct using for example chromatographic methods, for example HPLC-UV/VIS or HPLC-MS/MS. A preferred method for determining whether a compound reduces the activity of cytochromes P450 is described in Example 9 herein below, The substrate used is dependent on the particular cytochrome P450. Substrates useful for individual cytochromes P450 are well known to the skilled person. For example the catalogue of Cerep, France (as of 10 Jul. 2009) describes suitable substrates for various cytochromes P450. Useful substrates for some cytochrome P450s are also described in Example 9 herein below.

Accordingly, the pharmaceutical compositions according to the invention are particularly useful for treating individuals receiving one or more other active agents, in particular such active agents wherein the activity of said active agents is increased or even depending on the activity of cytochromes P450. Typically, immunocompromised individuals will receive such active agents, and the pharmaceutical compositions of invention are accordingly in particular useful for treatment of immunocompromised individuals.

Thus, in a preferred embodiment, the pharmaceutical compositions comprising diynes are in particular useful for treating fungal infections in individuals to whom one or more active agents selected from the following group is being administered, has been or is foreseen to be administered, preferably is being administered, has been administered within the past 48 hours or is foreseen to be administered within the next 48 hours.

Said active agents, wherein the activity is increased or even depending on the activity of cytochromes P450 is preferably one or more selected from the group consisting of acetaminophen, alfentanil, alprazolam, alprenolol, aminophyllin, amiodarone, amitriptyline, amlodipine, amphetamine, amprenavir, aniline, artemisinin, astemizole, atorvastatin, azelastine, azithromycin, barnidepine, benzene, bufuralol, bupropion, buspirone, bezafibrate, caffeine, carbamazepine, carisoprodol, carvedilol, celecoxib, cerivastatin, chlorpheniramine, chlorpromazine, chlorzoxazone, cimetidine, ciprofloxacin, cisapride, citalopram, clarithromycin, clemastine, clomipramine, clopidogrel, clozapine, cocaine, codeine, cyclobenzaprine, cyclophosphamide, cyclosporine, dapsone, debrisoquine, delavirdine, desipramine, dexamethasone, dexfenfluramine, dextromethorphan, dextropropoxyphene, diclofenac, diazepam, diltiazem, N, N-dimethyl formamide, diphenhydramine, disulfuram, docetaxel, dofetilide, dolasetron, econazole, efavirenz, encamide, enflurane, enoxacin, ergotamine, estradiol, erythromycin, ethanol, ethinylestradiol, etomidate, etoposide, felbamate, felodipine, fenofibrate, fentanyl, finasteride, flecamide, fluconazole, fluorouracil, fluoxetine, flurbiprofen, fluvastatin, fluvoxamine, gemfibrozil, glibenclamide, glipizide, glyburide, granisetron, growth hormone, halofantrine, haloperidol, halothane, hexobarbital, hydrocortisone, hydroxyzine, ibuprofen, ifosfamide, imipramine, indinavir, indoramine, insulin, indomethacin, irbesartan, irinotecan, isoflurane, isoniazid, isradipine, itraconazole, ketoconazole, lansoprazole, lercanidipine, levomepromazine, lidocaine, lignocaine, loratadine, lornoxicam, losartan, lovastatin, meloxicam, mephenyloin, mephobarbital, mequitazine, mestranol, methadone, methoxsalen, methoxyamphetamine, methoxyflurane, metoclopramide, metoprolol, metronidazole, mianserin, mibefradil, miconazole, midazolam, mifepristone, mirtazapine, mepyramine, methoxyamphetamine, metoclopramide, metyrapone, mexiletine, midazolam, minaprine, moclobemide, montelukast, naproxen, nefazodone, nelfinavir, nicardipine, nifedipine, nilutamide, nisoldipine, nitrendipine, norethindrone, norfloxacin, nortriptyline, omeprazole, ondansetron, orphenadrine, oxcarbazepine, pantoprazole, paracetamol, paroxetine, pefloxacin, perhexyline, perphenazine, pethidine, pentobarbitone, phenacetin, phenformin, phenobarbitone, phenyloin, pimozide, piroxicam, prednisone, primidone, procainamide, progesterone, proguanil, promethazine, propafenone, propofol, propranolol, quanoxan, quinidine, quinine, ranitidine, rifabutin, rifampicin, riluzole, risperidone, ritonavir, ropinirole, ropivacaine, rosiglitazone, salmeterol, saquinavir, secobarbital, selegiline, sildenafil, simvastatin, sertraline, sevoflurane, Snaproxen, sparteine, sufentanil, suprofen, sulphamethoxazole, sulphonamides (sulfonamides), tamoxifen, tacrine, tacrolimus, taxol, teniposide, terbinafine, terfenadine, terfenidine, testosterone, theophylline, thiopental, thioridazine, ticlopidine, timolol, tirilazad, tobacco, tolbutamide, tolterodine, topiramate, torsemide, tramadol, tranylcypromine, trazodone, triazolam, trofosfamide, troglitazone, troleandromycin, tropisetron, valsartan, venlafaxine, verapamil, vesnarinone, vigabatrin, vinblastine, vincristine, warfarin, zafirlukast, zaleplon, zanamivir, zileuton, zolmitriptan, zolpidem, zonisamide, zotepine and zuclopenthixol.

A6. Fungal Infection

The present invention in one aspect relates to pharmaceutical compositions comprising diyne salts (such as any of the diyne salts described herein above in the section "Diyne salt") for treatment of infections by a fungus. The invention also relates to methods of treating an infection by a fungus by administering to an individual in need thereof a therapeutically effective amount of a diyne salt (such as any of the diyne salts described herein above in the section "Diyne salts").

In general said fungus is a fungus dependent on the activity of stearoyl-CoA desaturase (such as OLE-1). The fungus may also be a fungus dependent on the activity of Spt23p/Mga2p, preferably a fungus dependent on both the activity of stearoyl-CoA desaturase (such as OLE-1) and Spt23p/Mga2p.

In general, the diyne salts according to the present invention are capable of killing fungi, i.e. they have fungicidal activity. Accordingly, the pharmaceutical compositions comprising diyne compounds according to the invention are in particular suitable for treating infections by fungus, wherein it is desirable to kill the fungus, rather than just to inhibit growth of the fungus. Thus, the pharmaceutical compositions comprising diyne salts according to the invention are particularly useful for treating recurrent infections by fungus, such as an infection by a fungus, which is expected to be recurrent or an infection by fungus, which has re-occurred at least once, for example at least twice, such as at least 3 times.

Preferably, the pharmaceutical compositions comprising diyne compounds according to the invention are prepared for killing at least 50%, preferably at least 80%, more preferably at least 95% of the infecting fungus.

Another very interesting aspect of the present invention is that the pharmaceutical compositions comprising diyne salts according to the invention are particularly useful for treating infection by a fungus under hypoxic conditions. Without being bound by theory it is believed that this is based on OLE-1 being particularly important for fungal growth under hypoxia. Thus, OLE-1 transcript levels are upregulated in fungi under hypoxia (for example in *C. albicans*).

Accordingly, the infection by a fungus may preferably be an infection involving at least partly infection of tissue, organs or cells with hypoxic conditions, preferably the infection may be infection of tissues, organs or cells with hypoxic conditions. Thus, said infection may at least partly involve infection of one or more inner organs, tissues or cells of a mammal, preferably a human being. More preferably, said infection may be infection of one or more inner organs, tissues or cells of a mammal, preferably a human being.

Said hypoxic condition is preferably an oxygen partial pressure ($pO_2$) of at the most 140 mmHg, preferably at the most 110 mmHg, such as at the most 80 mmHg. Such conditions may in general be found in inner organs, for example in the liver, pancreas, gut, duodenum, skeletal muscles, brain, kidney or peritoneal cavity.

It is also comprised within the present invention that the pharmaceutical compositions comprising diyne salts according to the invention may be for treatment of a disseminated infection or a local infection.

The infection by said fungus may also involve at least partly infection of a body surface, for example infection of skin, nails or mucosal membranes of body surfaces. Thus, said infection may be infection of a body surface, for example infection of skin, nails or mucosal membranes of body surfaces. Body surfaces may include the oral cavity, the genital organs, nose or eyes.

Accordingly, the fungal infection may be one or more selected from the group consisting of oropharyngeal fungal infections (such as thrush, glossitis, stomatitis or angular cheilitis), cutaneous fungal infections (such as intertrigo, diaper candidiasis, paronychia or onychomycosis), paronychia, onychomycosis, vulvovaginal fungal infection, balanitis, mucocutaneous fungal infection, neonatal fungal infection, congenital fungal infection, oesophageal fungal infection, gastrointestinal fungal infection, pulmonary fungal infection, peritonitis, urinary tract fungal infections, renal fungal infection, meningitis associated with fungi, hepatic fungal infection, hepatosplenic fungal infection, endocarditis, myocarditis, pericarditis, ocular fungal infection, endophthalmitis and osteoarticular fungal infection.

Interestingly, the diyne compounds according to the present invention are even useful for treating onychomycosis, i.e. fungal infection of the nails.

The infection by a fungus may be infection by one species of fungus or infection by more than one fungal species, such as two, for example 3, such as 4, for example 5, such as more than 5 different fungal species.

The fungus may be any fungus, but usually it is a pathogenic fungus, such as a fungus pathogenic in the individual to be treated. In one preferred embodiment of the invention, the individual to be treated is a mammal, preferably a human being, and then the fungus is a fungus pathogenic in mammals, preferably in human beings.

The fungus may preferably be selected from the group consisting of wherein one or more fungus is selected from the group consisting of *Candida* spp., *Aspergillus* spp., *Histoplasma capsulatum*, *Coccidioides immitis*, *Coccidioides posadasii*, *Cryptococcus* spp., Zygomycetes, *Malassezia* spp., Hyalohyphomycetes, Dermatophytes, *Epidermophyton floccosum*, *Microsporum* spp, *Blastomyces dermatitidis*, *Sporothrix schenkii*, Chromomycotic fungi and *Madurella* spp.

Thus the fungus may be selected from the group consisting of *Candida* spp., preferably from the group consisting of *C. albicans, C. krusei, C. glabrata, C. tropicalis, C. parapsilosis, C. guilliermondii, C. haemulonii, C. lusitaniae, C. lipolytica, C. norvegensis, C. viswanathii, C. kefyr* and *C. dubliniensis*.

The fungus may also be selected from the group consisting of *Aspergillus* spp., preferably from the group consisting of *A. fumigatus, A. flavus, A. niger* and *A. terreus*.

The fungus may also be selected from the group consisting of *Cryptococcus* spp., Preferably from the group consisting of *C. neoformans, C. bidus, C. laurentii*, and *C. fusarium*. Said *C. neoformans* is preferably selected from the group consisting of var. *neoformans* and var. *gattii*.

The fungus may also be selected from the group consisting of zygomycetes, preferably from the group consisting of *Rhizopus oryzae, R. micropsorus, R. pusillus, Cunninghamelle bertholletiae, Saksenaea vasiformis, Mucor circinelloides, M. ramosissimus, Absidia corymbifera, Apophysomyces elegans, Cokeromyces recurvatus* and *Syncephalastrum racemosum*.

The fungus may also be selected from the group consisting of *Malassezia* spp., preferably from the group consisting of *M. furfur* and *M. globosa*.

The fungus may also be selected from the group consisting of Hyalohyphomycetes, preferably from the group consisting of *Fusarium solani* and *Scedosporium* spp., wherein said *Scedosporium* spp. preferably is selected from the group consisting of *S. prolificans* and *S. apiospermum*.

The fungus may also be selected from the group consisting of Dermatophytes. This is in particular the case when the infection is partly or entirely an infection of the skin. Said Dermatophyte may preferably be selected from the group consisting of *Trichophyton* spp., *Epidermophyton floccosum, Microsporum* spp and *Trichosporon terrestre*. Said *Trichophyton* spp. may preferably be selected from the group consisting of *T. mentagrophytes, T. rubrum* and *T. tonsurans*. Said *Microsporum* spp may preferably be selected from the group consisting of *M. cookei, M. canis, M vanbreuseghemii, M gallinae* and *M. gypseum*.

The fungus may also be selected from the group consisting of Chromomycotic fungi, preferably from the group consisting of *Fonsecaea pedrosoi, F. compacta, Cladophylophora carrionii* and *Phialophora verrucosa*.

The fungus may also be selected from the group consisting of *Madurella* spp., preferably from the group consisting of *M. mycetomatis* and *M. griseum*.

In embodiments of the invention wherein the individual is a non-human animal, preferably a mammal, more preferably a mammal selected from the group consisting of horses, cattle, dogs and cats then the fungus may for example be selected from the group consisting of *Aspergillus* spp., *Batrachochytrium dendrobatidis*, *Blastomyces* spp., *Branchiomyces* spp., *Candida* spp., *Cladosporium* spp., *Coccidioides* spp., *Cryptococcus neoformans*, *Entomophthora* spp., *Epidermophyton* spp., *Fonsecaea* spp., *Geotrichum* spp., *Histoplasma* spp., *Ichthyophonus hoferi*, *Lacazia loboi*, *Malassezia* spp., *Metarhizium* spp., *Microsporum* spp., *Mucor* spp., *Ochroconis* spp., *Paecilomyces* spp., *Penicillium* spp., *Phialophora* spp., *Saprolegnia* spp., *Sporothrix schenckii*, *Trichophyton* spp. and *Wangiella* spp.

A7. Resistant Fungus

Another very interesting aspect of the present invention is that the diyne salts according to the present invention are capable of treating infections by fungi which are resistant to one or more conventional antifungal agents, in particular antifungal agents, which are not capable of inhibiting conversion of a saturated fatty acid to a Δ9-monounsaturated fatty acid in a fungus.

Said fungi may be resistant for any reason. Thus, for example that particular species of fungus may be resistant to treatment with that particular antifungal agent. Alternatively, the fungus may have acquired resistance, i.e. in general said fungal species is not resistant to treatment with the particular antifungal agent, but this particular fungus has become resistant. In a preferred embodiment of the invention, the fungus has acquired resistance to one or more conventional antifungal agents.

Thus, the pharmaceutical compositions comprising diyne salts according to the invention are useful for treating infection by a fungus, which is resistant to one or more antifungal agents, which are not of formula I. In particular, the pharmaceutical compositions comprising diyne salts according to the invention are useful for treating infection by a fungus, which is resistant to one or more antifungal agents capable of at least one of
  a) inhibiting ergosterol biosynthesis;
  b) binding to ergosterol;
  c) inhibiting 1,3-β-glucan synthase;
  d) inhibiting epoxidase;
  e) inhibiting Leucyl-tRNA synthetase; and/or
  f) inhibition of elongation factor 2.

In particular, the pharmaceutical compositions comprising diyne salts according to the invention are useful for treating infection by a fungus, which is resistant to one or more antifungal agents selected from the group consisting of polyene antifungal agents, azole antifungal agents, allylamine antifungal agents and echinocandins.

Polyene antifungal agents are antifungal agents with multiple conjugated double bonds. Typically, polyene antifungal agents also comprise a heavily hydroxylated region. Non-limiting examples of polyenes include Natamycin, Rimocidin, Filipin, Nystatin, Amphotericin B or Candicin.

Azole antifungal agents may for example be imidazole or triazole or thiazole antifungal agents. Non-limiting examples of imidazole antifungal agents include miconazole, ketoconazole, clotrimazole, econazole, bifonazole, butoconazole, fenticonazole, isoconazole, oxiconazole, seraconazole, sulconazole or tioconazole. Non-limiting examples of triazole antifungal agents include fluconazole, itraconazole, isavuconazole, ravuconazole, posaconazole, voriconazole or terconazole. A non-limiting example of a thiazole antifungal is abafungin.

Non-limiting examples of allylamine antifungals include Terbinafine, Amorolfine, Naftifine or Butenafine.

Non-limiting examples of echinocandins include Anidulafungin, Caspofungin or Micafungin.

The pharmaceutical compositions comprising diynes according to the invention may also be useful for treating infection by a fungus, which is resistant to one or more antifungal agents selected from the group consisting of benzoic acid, ciclopirox, tolnaftate, undecylenic acid, flucytosine, griseofulvin, haloprogin and sodium bicarbonate.

By the term "resistant to an antifungal agent", it is meant that said infection by fungus in said individual cannot be treated in a curable manner with said antifungal agent.

The pharmaceutical compositions for treating fungal infections according to the invention may in addition to one or more diyne salts also comprise additional active agents, preferably one or more antifungal agents.

Thus said pharmaceutical compositions may in addition to one or more diynes also comprise one or more antifungal agents capable of at least one of
  a) inhibiting ergosterol biosynthesis;
  b) binding to ergosterol;
  c) inhibiting 1,3-β-glucan synthase;
  d) inhibiting epoxidase;
  e) inhibiting Leucyl-tRNA synthetase; and/or
  f) inhibition of elongation factor 2.

Thus, the additional antifungal agent may be for example be selected from the group consisting of polyene antifungal agents (such as any of the polyene antifungal agents described herein above in the section), azole antifungal agents (such as any of the azole antifungal agents described herein above in the section), allylamine antifungal agents (such as any of the allylamine antifungal agents described herein above in the section) and echinocandins (such as any of the echinocandins described herein above in the section).

In particular, due to the synergistic effect the pharmaceutical compositions of the invention may preferably comprise a diyne compound as described herein above and a polyene antifungal agent.

Said polyene antifungal agent may preferably be Amphotericin B.

A8. Fungal Infection of Plants

The present invention also relates to methods of reducing the risk of an infection by a fungus or to methods of treating an infection by a fungus in a plant by contacting said plant with a diyne salt.

Thus, in one aspect the invention relates to use of a diyne salt of the formula I:

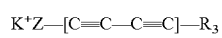

wherein Z and R$_3$ are as defined herein above in the section "Diyne salts"
such as any of the diyne salts described herein above in the section "Diyne salts", for inhibiting or treating an infection by a fungus in a plant, preferably by a plant pathogenic fungus. Said infection by a fungus is preferably an infection by a fungus dependent on activity of stearoyl-CoA desaturase, more preferably an infection by a plant pathogenic fungus dependent on the activity of stearoyl-CoA desaturase.

Said diyne salt may in particular be a diyne salt of formula II,

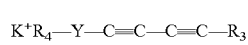

wherein $R_4$, Y and $R_3$ are as described herein above in the section "Diyne salt".

The diyne compound for treating or reducing the risk of infection by a fungus in a plant (preferably a fungus dependent on activity of stearoyl-CoA desaturase) may also be a diyne of formula III:

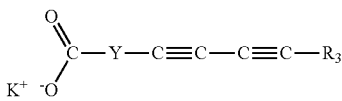

wherein Y and $R_3$ is as described herein above in the section "Diyne salts",

The diyne compound for treating or reducing the risk of infection by a fungus in a plant (preferably a fungus dependent on activity of stearoyl-CoA desaturase) may also be a diyne salt of formula IV,

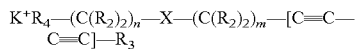

wherein $R_4$, $R_2$, n, m and $R_3$ are as described herein above in the section "Diyne salts" in relation to formula IV.

The diyne salt for treating or reducing the risk of infection by a fungus in a plant (preferably a fungus dependent on activity of stearoyl-CoA desaturase) may also be a diyne salt of formula V,

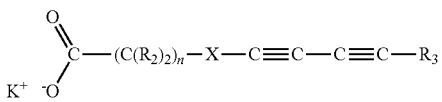

wherein $R_1$, $R_2$, n, X and $R_3$ are as described herein above in the section "Diyne salt" in relation to formula V.

The diyne salt for treating or reducing the risk of infection by a fungus in a plant (preferably a fungus dependent on activity of stearoyl-CoA desaturase) may preferably be selected from the group consisting of potassium (Z)-14-(furan-2-yl)tetradeca-9-en-11,13-diynoate and potassium 14-(furan-2-yl)tetradeca-11,13-diyne-diynoate.

Thus, for example the plant pathogenic fungus may be selected from the group consisting of *Albugo* spp., *Alternaria* spp., *Anisogramma anomala, Apiosporina morbosa, Ascochyta* spp., *Aureobasidium zeae, Bipolaris* spp., *Blumeria* spp., *Blumeriella jaapii, Botritis* spp., *Botryosphaeria dothidea, Ceratocystic paradoxa, Cercospora* spp., *Cercosporidium* spp., *Cladosporium* spp., *Cochiliobolus* spp., *Colletotrichum* spp., *Corynespora cassiicola, Cristulariella moricola, Diaporthe phaseolorum, Didymella bryoniae, Drechslera tritici, Entyloma oryzai, Erysiphe* spp., *Fluvia fluva, Fusarium* spp., *Gaeumannomyces graminis, Gnomonia* spp., *Gremmeniella abietina, Helminthosporium* spp., *Leptosphaerulina crassiasca, Leveillula taurica, Lophodermium hypophyllum, Macrophomina phaseoli, Magnaporthe* spp., *Microdochium* spp., *Microsphaera* spp., *Monilinia* spp., *Mycosphaerella* spp., *Myrothedium roridum, Oidiopsis sicula, Passalora puncta, Penicillium* spp., *Peronospora* spp., *Phaeocryptopus gaeumannii, Phakopsora* spp., *Phoma arachidicola, Phragmidium potentillae, Phytophtora* spp., *Plasmopara* spp., *Plectosporium tabacinum, Pleospora herbarum, Podosphaera* spp., *Pseudocercosporella* spp., *Pseudoperonospora cubensis, Puccinia* spp., *Pucciniastrum vaccinii, Pyrenophora* spp., *Pythium* spp., *Ramularia cynarae, Rhizoctonia* spp., *Rhizosphaera* spp., *Rhynchosporium secalis, Sclerotinia* spp., *Sclerotium* spp., *Selenophoma* spp., *Septoria* spp., *Setosphaeria turcica, Sirococcus conigenus, Sphaerotheca* spp., *Stagonospora nordorum, Stemphyllium botryosum, Taphrina deformans, Thielaviopsis* spp., *Tilletia barclayana, Tranzschelia discolor, Uncinula necator, Uromyces appendiculatus, Ustilaginoidea virens, Ustilago* spp., *Venturia* spp., *Verticillium* spp. and *Wilsonomyces carpophilus*.

Treatment of infections by a fungus in a plant may be done by any suitable means, for example the diyne salts may be applied as sprays or dusts on the foliage of plants, or in irrigation systems. Typically, the diyne salts according to the invention are administered on the surface of the plant in advance of the pathogen in order to prevent or reduced the risk of infection. Seeds, bulbs, roots, tubers, and/or corms may also be treated to prevent pathogenic attack after planting or reducing the risk of infection and for example thereby controlling pathogens carried on them or existing in the soil at the planting site. However, plants, may also be treated once an infection is already present in order to eliminate or reduce the infection, preferably eliminate the infection. Similarly, seeds, bulbs, roots, tubers and/or corms may also be treated once an infection is already present in order to eliminate or reduce the infection, preferably eliminate the infection.

Soil to be planted with vegetables, ormementals, shrubs, or trees can also be treated with the diyne salts of the invention for control of a variety of fungal pathogens. Treatment is preferably done several days or weeks before planting. The diyne salts can be applied by either a mechanized route, e.g., a tractor, or with hand applications.

In most applications said diyne salts are used with an agronomically acceptable carrier. An "agronomically acceptable carrier" is a solid or liquid which is biologically, chemically and physically compatible with the diyne salts of the present invention, and which may be used in agricultural applications. Agronomically acceptable carriers suitable for use in the method of the present invention include organic solvents, and finely divided solids, and aqueous solutions or suspensions. For example, the diyne salts for use in treatment or prevention of an infection by a fungus in a plant can be formulated as wettable powders, emulsifiable concentrates, dusts, granular formulations, aerosols, or flowable emulsion concentrates. In such formulations, the diyne compounds may be extended with a liquid or solid carrier and, when desired, suitable surfactants may be incorporated.

Optionally added components or additives, not required for fungicidal activity but useful or required for other properties, include, but are not limited to, adjuvants such as wetting agents, spreading agents, dispersing agents, stickers, adhesive and the like. Such adjuvants are well known in the art.

In general, the diyne salts of this invention may be dissolved in solvents such as water or other aqueous solutions, acetone, methanol, ethanol, dimethylformamide, pyridine or dimethyl sulfoxide and such solutions can further be diluted with water. The concentrations of the solution after dilution may vary from 1% to 90% by weight, with a preferred range being from 5% to 50%.

For the preparation of emulsifiable formulations and concentrates of the diyne compounds of the present invention, the diyne compound can be dissolved in suitable organic solvents, or a mixture of solvents, together with an emulsifying agent to enhance dispersion of the diyne compound in water. The concentration of the diyne compound in emulsifiable concentrates is usually from 10% to 90%, and in flowable emulsion concentrates, can be as high as 75%.

Wettable, powdered formulations suitable for spraying can be prepared by admixing the diyne salt with a finely divided solid, such as clays, inorganic silicates and carbonates, and silicas and incorporating wetting agents, sticking agents, and/or dispersing agents in such mixtures. The concentration of total active ingredients in such formulations is usually in the range of from 20% to 99% by weight, preferably from 40% to 75%. A typical wettable powder is made by blending 50 parts of a diyne salt, 45 parts of a synthetic precipitated hydrated silicon dioxide, such as that sold under the trademark Hi-SilR, and 5 parts of sodium lignosulfonate. In another preparation a kaolin type (Barden) clay is used in place of the Hi-Sil in the above wettable powder, and in another such preparation part of the Hi-Sil is replaced with a synthetic sodium silicoaluminate sold under the trademark Zeolex® 7 (J. M. Huber Corporation).

Dusting formulations may be prepared by mixing the diyne salts with finely divided inert solids which can be organic or inorganic in nature.

Materials useful for this purpose include botanical flours, silicas, silicates, carbonates and clays. One convenient method of preparing a dust is to dilute a wettable powder with a finely divided carrier. Dust formulations or concentrates containing from 20% to 80% of the active ingredient are commonly made and are subsequently diluted to from 1% to 10% use concentration.

The diyne salt and formulations may be applied as fungicidal sprays by methods commonly employed, such as conventional high-gallonage hydraulic sprays, low-gallonage sprays, air-blast spray, aerial sprays and dusts.

The dilution and rate of application will depend upon the type of equipment employed, the method of application, plants to be treated and diseases to be controlled. Generally, the diyne compounds of this invention will be applied in an amount of from 0.06 to 60 kilograms (kg) per hectare and preferably from 1 to 28 kg per hectare of the active ingredient.

As a seed protectant, the diyne salt formulation may be coated on the seed. The dosage rate may for example be from 3 g of diyne salt per hundred kg of seed, to 1000 g per hundred kg of seed. As a soil fungicide the fungicidal formulation may be incorporated in the soil or applied to the surface for example at a rate of from 0.02 to 20 kg per hectare. As a foliar fungicide, the diyne compounds may be applied to growing plants for example at a rate of from 0.01 to 10 kg per hectare.

The diyne salts of the present invention may be combined with other known fungicides.

B1. Diyne

The present invention relates to diyne compounds per se as well as to the use of the diyne compounds.

Thus, the present invention relates to pharmaceutical compositions comprising a diyne, to methods of treatment of fungal infections with diynes in an individual in need thereof as well as to uses of diynes for inhibiting or treating an infection of a plant by a fungus. The diyne may be any of the diynes described in this section. Fungal infections which may be treated with the diynes described in this section are disclosed in more detail in the section "Fungal Infections" herein below.

The diynes according to the present invention are diynes of formula I':

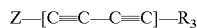

wherein said diyne is capable of inhibiting conversion of a saturated fatty acid to a Δ9-monounsaturated fatty acid in a fungus, and Z is a carbon chain substituted with —COOH or a bioisostere thereof and optionally also substituted with one or more additional substituents, preferably with $R_2$; and $R_3$ is a heterocyclic ring, preferably $R_3$ is any of the $R_3$ groups described in this section below.

Z is preferably a carbon chain, which is substituted with —COOH or a bioisostere thereof, preferably said —COOH or bioisostere thereof is positioned at the end of said carbon chain, preferably at the distal end of said carbon chain in relation to the diyne moiety. Thus, Z may preferably be selected from the group consisting of alkyl and alkenyl, which is substituted with $R_4$, wherein $R_4$ is —COOH or a bioisostere thereof.

In addition, said carbon chain (such as said alkyl or alkenyl) may also optionally be substituted with one or more additional groups, preferably with one or more $R_2$ groups, wherein $R_2$ preferably is as defined herein below in relation to diynes of formula II'.

Said bioisostere of —COOH may for example be —CO—$R_1$, wherein $R_1$ preferably is as defined herein below in relation to diynes of formula II'.

The bioisostere of —COOH may also preferably be selected from the group consisting of tetrazoles, preferably from the group consisting of tetrazoles, tetrazolates and salts thereof.

It is also comprised in the present invention that the bioisostere of —COOH may be selected from the group of azoles, preferably the bioisostere may be a 1,2,4-oxadiazole heterocycle.

Preferably Z is a $C_{6-20}$, preferably a $C_{6-15}$, more preferably $C_{6-12}$, even more preferably a $C_{9-20}$, yet more preferably a $C_{9-15}$, such as a $C_{9-12}$ alkyl or alkenyl substituted with —COOH or a bioisostere thereof and optionally also substituted at one or more positions with $R_2$, preferably substituted with one or more selected from the group consisting of —CO—$R_1$ and $R_2$. More preferably Z is $R_1$—CO—($C_{6-20}$ alkyl or alkenyl)-, such as $R_1$—CO—($C_{9-20}$ alkyl or alkenyl)-, for example $R_1$—CO—($C_{9-15}$ alkyl or alkenyl)-, such as $R_1$—CO—($C_{6-12}$ alkyl or alkenyl)-.

More preferably, the diyne is a diyne of the formula II':

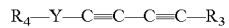

wherein $R_4$ is —COOH or a bioistere thereof, wherein said bioisostere of —COOH may be any bioisostere of —COOH, preferably any of the bioisosteres of —COOH mentioned herein above in relation to compounds of formula I', and Y is preferably a carbon chain of 6 to 20 carbon atoms, more preferably 9 to 20 carbon atoms, even more preferably 9 to 15 carbon atoms, yet more preferably 9 to 12 carbon atoms, even more preferably 9 carbon atoms with up to three double bonds. Depending on whether a carbon atom of said carbon chain is connected to the other carbon atoms of said carbon chain by single bonds and/or double bonds each carbon atom is linked to none, one or two $R_2$ groups. Thus, a carbon atom connected to both its neighbouring carbon atoms in the carbon chain by single bonds will be linked to two $R_2$ groups. A carbon atom connected to both its neighbouring carbon atoms in the carbon chain by double bonds will not be linked to any $R_2$ groups. A carbon atom connected to one neighbouring carbon atom in the carbon chain by a single bond and to the other neighbouring carbon atom in the carbon chain by a double bond will be linked to one $R_2$ group. Y may furthermore be as defined herein below; AND $R_3$ is a heterocyclic ring, preferably $R_3$ is any of the $R_3$ groups described in this section below.

More preferably the diyne is a diyne of the formula III':

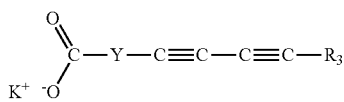

wherein $R_1$ is a hydroxyl group or a moiety that can be replaced by a hydroxyl group in a hydrolysis reaction; Y is a carbon chain of 6 to 20 carbon atoms and up to three double bonds, wherein each carbon of said alkyl or alkenyl is linked to none, one or two $R_2$ groups, wherein each $R_2$ independently is —H, —OH or a hydrocarbon moiety containing between 1 and 4 carbon atoms, inclusive; $R_3$ is a heterocyclic ring, which optionally may be substituted at one or more positions; or a pharmaceutically acceptable salt of said diyne, wherein said diyne is capable of inhibiting conversion of a saturated fatty acid to a Δ9-monounsaturated fatty acid in a fungus.

Y is preferably a carbon chain of 6 to 20 carbon atoms, more preferably 9 to 20 carbon atoms, even more preferably 9 to 15 carbon atoms, yet more preferably 9 to 12 carbon atoms, even more preferably 9 carbon atoms with up to three double bonds. Depending on whether a carbon atom of said carbon chain is connected to the other carbon atoms of said carbon chain by single bonds and/or double bonds each carbon atom is linked to none, one or two $R_2$ groups. Thus, a carbon atom connected to both its neighbouring carbon atoms in the carbon chain by single bonds will be linked to two $R_2$ groups. A carbon atom connected to both its neighbouring carbon atoms in the carbon chain by double bonds will not be linked to any $R_2$ groups. A carbon atom connected to one neighbouring carbon atom in the carbon chain by a single bond and to the other neighbouring carbon atom in the carbon chain by a double bond will be linked to one $R_2$ group.

Accordingly, Y may be a linear $C_{6-20}$, preferably a $C_{6-15}$, more preferably $C_{6-12}$, even more preferably a $C_{9-20}$, yet more preferably a $C_{9-15}$, such as a $C_{9-12}$ alkyl, preferably a linear $C_{7-11}$ alkyl, yet more preferably a linear $C_{8-10}$ alkyl, even more preferably a linear $C_9$-alkyl.

Y may also be a linear $C_{6-20}$, preferably a $C_{6-15}$, more preferably $C_{6-12}$, even more preferably a $C_{9-20}$, yet more preferably a $C_{9-15}$, such as a $C_{9-12}$ alkenyl, preferably a linear $C_{7-11}$ alkenyl, yet more preferably a linear $C_{8-19}$ alkenyl, even more preferably a linear $C_9$-alkenyl. The alkenyl may comprise 1, 2 or 3 double bonds, preferably 1 or 2 double bonds, even more preferably only 1 double bond. The double bonds may be in the cis or the trans conformation, preferably at least one double bond is in the cis conformation, even more preferably all double bonds are in the cis conformation. Accordingly, Y may be a linear $C_{6-12}$, preferably a linear $C_{7-11}$ alkenyl, yet more preferably a linear $C_{8-10}$ alkenyl preferably a linear $C_9$ alkenyl, wherein all double bonds are cis double bonds. The double bonds may be at any suitable position, however in a preferred embodiment at least one double bond is situated at the $C_8$, $C_9$ $_{or}$ $C_{10}$ position, preferably at the $C_9$ position (the C in the carbonyl group being $C_1$), even more preferably at least one double bond in the cis conformation is situated at the $C_8$, $C_9$ $_{or}$ $C_{10}$ position, preferably at the $C_9$ position (the C in the carbonyl group being $C_1$).

Thus, in a preferred embodiment of the invention the diyne compound is a compound of the formula IV':

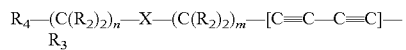

wherein $R_4$ is —COOH or a bioistere thereof, wherein said bioisostere of —COOH may be any bioisostere of —COOH, preferably any of the bioisosteres of —COOH mentioned herein above in relation to compounds of formula I', and n is an integer, preferably an integer in the range of 4 to 10, inclusive, preferably in the range of 5 to 9, even more preferably in the range of 6 to 8, yet more preferably n is 7; and m is an integer, preferably an integer in the range of 0 to 10, such as in the range of 0 to 8, for example in the range of 0 to 6, such as in the range of 0 to 4, for example in the range of 0 to 2, such as 0; and each $R_2$ is, independently, —H, —OH or a hydrocarbon moiety containing between 1 and 6 carbon atoms, inclusive; and X is —CH$_2$—CH$_2$— or —CH=CH— or phenyl, preferably X is —CH$_2$—CH$_2$— or —CH=CH—; and $R_3$ is a heterocyclic ring, preferably $R_3$ is any of the $R_3$ groups described in this section below.

In a preferred embodiment of the invention the diyne is a compound of formula V':

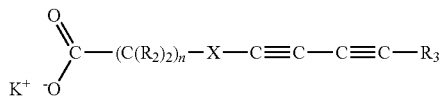

wherein, $R_1$ is a hydroxyl group or a moiety that can be replaced by a hydroxyl group in a hydrolysis reaction; each $R_2$ is, independently, —H, —OH or a hydrocarbon moiety containing between 1 and 6 carbon atoms, inclusive; n is an integer between 4 and 10, inclusive; X is —CH$_2$—CH$_2$— or —CH=CH— or phenyl, preferably X is —CH$_2$—CH$_2$— or —CH=CH—; and $R_3$ is a heterocyclic ring, which optionally may be substituted at one or more positions.

n is an integer in the range of 4 to 10, preferably in the range of 5 to 9, even more preferably in the range of 6 to 8, yet more preferably n is 7.

In one preferred embodiment of the invention, the diyne is a compound of formula III', wherein X is —CH=CH—, wherein the double bond is in the trans or cis conformation, preferably in the cis conformation. Also in this embodiment it is preferred that n is as outlined above and $R_2$ is as outlined below.

In another preferred embodiment of the invention, the diyne is a compound of formula III', wherein X is —CH$_2$—CH$_2$—. Also in this embodiment it is preferred that n is as outlined above and $R_2$ is as outlined below.

$R_1$ of the diyne either of formula II', III' or V' or of formula I', or IV' when comprised therein is a hydroxyl group or a moiety that can be replaced by a hydroxyl group in a hydrolysis reaction. Preferred moieties that can be replaced by a hydroxyl group in a hydrolysis reaction may for example be selected from the group consisting of amines and lower linear or branched alkoxy groups. Lower alkoxy are preferably $C_{1-6}$, more preferably $C_{1-3}$, even more preferably $C_{1-2}$ alkoxy, preferably linear alkoxy. Thus, preferably $R_1$ of the diyne either of formula II' or formula III' may be selected from the group consisting of —OH, —NH$_2$, —OCH$_3$ and —OC$_2$H$_5$, preferably $R_1$ is —OH.

$R_3$ of the diyne of formula I', II', III', IV' or V' is a heterocyclic ring, which optionally may be substituted at one or more positions. If substituted, the heterocyclic ring is preferably substituted with one or more, preferably one or two selected from the group consisting of lower alkyl, lower alkenyl, lower alkoxy, lower alcohol, hydroxyl, amine, —NO$_2$ and halogen. Lower alkyl is preferably $C_{1-5}$, more preferably $C_{1-3}$, even more preferably $C_1$ alkyl. Lower alkenyl is preferably $C_{1-5}$, more preferably $C_{1-3}$, even more preferably $C_{1-2}$ alkenyl. Lower alkoxy is preferably $C_{1-5}$, more preferably $C_{1-3}$, even more preferably $C_1$ alkoxy. Lower alcohol is preferably $C_{1-5}$, more preferably $C_{1-3}$, even more preferably $C_1$ alcohol comprising one or more —OH groups, preferably only one —OH group. Halogen may be any halogen, but is preferably —F. It is however preferred that $R_3$ is a heterocyclic ring, which is not substituted or that $R_3$ is a heterocyclic ring substituted with a small substituent, preferably a small substituent selected from the group consisting of methyl, methoxy, hydroxyl, —CH$_2$—OH, amine and halogen, preferably methyl.

$R_3$ of the diyne of formula I', II', III', IV' or V' is preferably an aromatic heterocyclic ring.

$R_3$ of the diyne of formula I', II', III', IV' or V' is preferably a 3 to 7 membered heterocyclic ring, more preferably a 5 to 6 membered heterocyclic ring, even more preferably a 5 membered heterocyclic ring. The heterocyclic ring may be aromatic or non-aromatic. In one embodiment the heterocyclic ring is a 3 to 7 membered aromatic heterocyclic ring, more preferably a 5 to 6 membered aromatic heterocyclic ring, even more preferably a 5 membered aromatic heterocyclic ring.

The heterocyclic ring may comprise one or more heteroatoms, preferably in the range of 1 to 3 heteroatoms, more preferably in the range of 1 to 2 heteroatoms, yet more preferably 1 heteroatom. Said heteroatom(s) are preferably selected from the group consisting of S, N and O.

In a very preferred embodiment of the invention, $R_3$ is selected from the group consisting of pyrrole, furan and thiophene, which may optionally be substituted as outlined above at one or more positions. $R_3$ may also be selected from the group consisting of imidazole, oxazole, cyclopentadiene and triazole. Preferably, $R_3$ is furan, which is not substituted except for being linked to the diyne chain or is substituted at one or more positions as outlined above, even more preferably $R_3$ is furan, which is not substituted except for being linked to the diyne chain or is substituted at one or more positions with a small substituent, preferably a small substituent selected from the group consisting of methyl, methoxy, hydroxyl, amine and halogen, preferably methyl.

In a very preferred embodiment of the invention, $R_3$ is furan.

It is preferred that heterocyclic ring is 2-substituted with the —[C≡C—C≡C]—Z chain. In particular in embodiments wherein the heterocyclic ring contains only one heteroatom it is preferred that the heterocyclic ring is 2-substituted with the —[C≡C—C≡C]—Z chain. Thus, in embodiments of the invention wherein $R_3$ is pyrrole, furan or thiophene, in particular when $R_3$ is furan, then it is preferred that the heterocyclic ring is 2-substituted with the —[C≡C—C≡C]—Z chain.

Each $R_2$ of a diyne of formula IV' or V' as well as each $R_2$ when contained in diynes of formula I', II' or III' is preferably, independently, —H, —OH or a hydrocarbon moiety containing between 1 and 6, preferably 1 to 4 carbon atoms, inclusive. The hydrocarbon moiety may be an alkyl, alkenyl or alkynyl, such as $C_{1-4}$ alkyl, $C_{1-4}$ alkenyl or $C_{1-4}$ alkynyl. It is however also possible that two neighbouring $R_2$ groups are connected to form a hydrocarbon ring system. Said ring system may for example be a 3 to 10 membered ring, preferably a 3 to 7 membered ring, more preferably a 5 to 6 membered ring system (numbers include carbon in carbon chain plus $R_2$ carbons). The ring system may be aromatic or none aromatic, for example the ring system may be an 6 membered aromatic ring. Thus, any particular diyne may contain a plurality of different $R_2$ groups. It is preferred that the majority of the $R_2$ groups of a diyne compound of formula I', II', III', IV' or V' is —H. It is even more preferred that all $R_2$ groups of a diyne compound of formula I', II', III', IV' or V' except for in the range of 0 to 5 $R_2$ groups, preferably all $R_2$ groups except for in the range of 0 to 3 $R_2$ groups, more preferably all $R_2$ groups except for in the range of 0 to 1 $R_2$ groups are —H. It is even more preferred that each $R_2$ group of a diyne compound of formula I', II', III', IV' or V' is —H.

In embodiments of the invention where two $R_2$ groups are connected to form a ring system, and in particular if said ring system is aromatic, then it is preferred that said $R_2$ groups are positioned on $C_7$ and $C_8$; or on $C_8$ and $C_9$; or on $C_9$ and $C_{10}$ or on $C_{10}$ and $C_{11}$, preferably on $C_9$ and $C_{10}$ position (the C in the carbonyl group being $C_1$).

A preferred diyne compound according to the invention is (Z)-12-(furan-2-yl)dodeca-7-en-9,11-diynoic acid or a salt thereof, preferably a pharmaceutically acceptable salt thereof.

Another preferred diyne compound according to the invention is (Z)-13-(furan-2-yl)trideca-8-en-10,12-diynoic acid or a salt thereof, preferably a pharmaceutically acceptable salt thereof.

Yet another preferred diyne compound according to the invention is (E)-14-(furan-2-yl)tetradeca-9-en-11,13-diynoic acid or a salt thereof, preferably a pharmaceutically acceptable salt thereof.

Yet another preferred diyne compound according to the invention is the diyne compound (Z)-14-(furan-2-yl)tetradeca-9-en-11,13-diynoic acid or a salt thereof, preferably a pharmaceutically acceptable salt thereof.

Another preferred diyne compound according to the invention is the diyne compound (Z)-14-(furan-2-yl)tetradeca-9-en-11,13-diynoic acid or a salt thereof, preferably a pharmaceutically acceptable salt thereof.

Yet another preferred diyne compound according to the invention is (Z)-methyl 14-(furan-2-yl)tetradeca-9-en-11,13-diynoate or a salt thereof, preferably a pharmaceutically acceptable salt thereof.

Another preferred diyne compound according to the (Z)-ethyl 14-(furan-2-yl)tetradeca-9-en-11,13-diynoate or a salt thereof, preferably a pharmaceutically acceptable salt thereof.

In yet another embodiment of the invention the diyne compound may be selected from the group consisting of (Z)-14-(furan-2-yl)tetradeca-9-en-11,13-diynoic acid, (Z)-14-(5-methylfuran-2-yl)tetradeca-9-en-11,13-diynoic acid, 8-(2-(4-(furan-2-yl)buta-1,3-diynyl)phenyl)octanoic acid, (Z)-14-(4,5-dimethylfuran-2-yl)tetradeca-9-en-11,13-diynoic acid and 14-(furan-2-yl)tetradeca-11,13-diynoic acid.

Pharmaceutically acceptable salts of the diyne compounds of the invention and in particular diyne compounds selected from the group consisting of (Z)-12-(furan-2-yl)dodeca-7-en-9,11-diynoic acid, (Z)-13-(furan-2-yl)trideca-8-en-10,12-diynoic acid, (E)-14-(furan-2-yl)tetradeca-9-en-11,13-diynoic acid, (Z)-14-(furan-2-yl)tetradeca-9-en-11,13-diynoic acid, (Z)-14-(furan-2-yl)tetradeca-9-en-11,13-diynoic acid, Z)-14-(furan-2-yl)tetradeca-9-en-11,13-diynoic acid, (Z)-14-(5-methylfuran-2-yl)tetradeca-9-en-11,13-diynoic acid, 8-(2-(4-(furan-2-yl)buta-1,3-diynyl)phenyl)octanoic acid, (Z)-14-(4,5-dimethylfuran-2-yl)tetradeca-9-en-11,13-diynoic acid and 14-(furan-2-yl)tetradeca-11,13-diynoic acid may be any pharmaceutically acceptable salt. Preferably, said pharmaceutically acceptable salt is an alkali metal salt, such as a potassium salt or a sodium salt, preferably a potassium salt.

The diyne compounds according to the invention may be prepared essentially as described in U.S. Pat. No. 6,541,506, which is hereby incorporated by reference.

B2. Particular Diynes

The following section relates to diynes according to the invention which are suitable for being contained within the pharmaceutical compositions according to the invention, as well as for use in methods of treatment of fungal infections according to the invention. However, in some embodiments the invention also relates to substantially pure diyne compounds, such as pure diyne compounds, and the diyne compounds described in this section are in particular useful in these embodiments.

Thus, in certain embodiments of the invention, and in particular in such embodiments of the invention relating to the diyne compounds per se it is preferred that the diyne compound is a diyne compound of formula I':

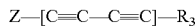

wherein Z is a carbon chain substituted with —COOH or a bioisostere thereof and optionally also substituted with one or more additional substituents; and $R_3$ is a heterocyclic ring, which optionally is substituted and wherein the diyne is capable of inhibiting conversion of a saturated fatty acid to a Δ9-monounsaturated fatty acid in a fungus, with the proviso that the diyne is not a compound selected from the group consisting of (Z)-14-(furan-2-yl)tetradeca-9-en-11,13-diynoic acid, (E)-14-(furan-2-yl)tetradeca-9-en-11,13-diynoic acid, (Z)-13-(furan-2-yl)trideca-8-en-10,12-diynoic acid, (Z)-12-(furan-2-yl)dodeca-7-en-9,11-diynoic acid, (9Z,16Z)-octadeca-9,16-dien-12,14-diynoic acid, (Z)-methyl 14-(furan-2-yl)tetradeca-9-en-11,13-diynoate and (10E,16Z)-9-hydroxyoctadeca-10,16-dien-12,14-diynoic acid In these embodiments it is also preferred that the diyne compound is not a compound selected from the group consisting of (Z)-14-(furan-2-yl)tetradeca-9-en-11,13-diynoic acid, (Z)-13-(furan-2-yl)trideca-8-en-10,12-diynoic acid and (Z)-12-(furan-2-yl)dodeca-7-en-9,11-diynoic acid.

In these embodiments it is even more preferred that the diyne compound is not a compound according to formula VII',

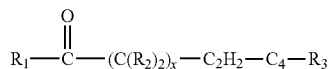

wherein $R_1$ is a hydroxyl group or a moiety that can be replaced by e hydroxyl group in a hydrolysis reaction, each $R_2$ is independently H or a hydrocarbon moiety containing between 1 and 6 carbon atoms, inclusive, $R_3$ is a pyrrole, furan or thiophene ring and X is an integer between 4 and 10, inclusive.

In these embodiments it may also be preferred that $R_3$ of said diyne compound is a heterocyclic ring, which optionally may be substituted at one or more positions with the proviso that $R_3$ is not pyrrole, furan or thiophene.

The diyne compound of these embodiments may also be a diyne of formula VIII',

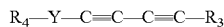

wherein $R_4$, Y and $R_3$ are as described herein above in the section "Diyne",
with the proviso that the diyne compound is not any of the above mentioned compounds, which are preferably excluded.

The diyne compound of these embodiments may be a diyne of formula IX':

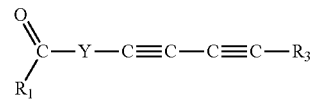

wherein $R_1$ is a hydroxyl group or a moiety that can be replaced by a hydroxyl group in a hydrolysis reaction; Y is a carbon chain of 6 to 12 carbon atoms and up to three double bonds, wherein each carbon of said alkyl or alkenyl is linked to one or two $R_2$ groups, wherein each $R_2$ independently is —H, —OH or a hydrocarbon moiety containing between 1 and 6 carbon atoms, inclusive; $R_3$ is a heterocyclic ring, which optionally may be substituted at one or more positions, with the proviso that the diyne compound is not any of the above mentioned compounds, which are preferably excluded.

The diyne compound of these embodiments may also be a diyne of formula IV',

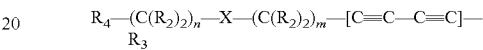

wherein $R_4$, $R_2$, n, m and $R_3$ are as described herein above in the section "Diyne" in relation to formula IV',
with the proviso that the diyne compound is not any of the above mentioned compounds, which are preferably excluded.

The diyne compound of these embodiments may also be a diyne of formula V',

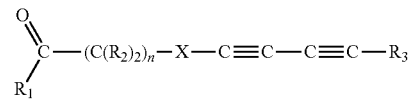

wherein $R_1$, $R_2$, n, X and $R_3$ are as described herein above in the section "Diyne" in relation to formula V',
with the proviso that the diyne compound is not any of the above mentioned compounds, which are preferably excluded.

In one of these particular embodiments it is preferred that the diyne is a diyne of the formula I', wherein Z is alkyl, which optionally may be substituted. Z may for example be substituted with one or more selected from the group consisting of —CO—$R_1$ and $R_2$, wherein $R_1$ and $R_2$ preferably are as defined herein above in relation to diynes of formula II'.

Thus, preferably Z may be a $C_{6-20}$ alkyl, preferably a $C_{6-15}$, more preferably $C_{6-12}$, even more preferably a $C_{9-20}$, yet more preferably a $C_{9-15}$, such as a $C_{9-12}$ alkyl, optionally substituted, preferably substituted with one or more selected from the group consisting of —COOH, bioisosters of —COOH and $R_2$, more preferably from the group consisting of —CO—$R_1$ and $R_2$, yet more preferably substituted with one group selected from the group consisting of —COOH and bioisosters of —COOH and with one or more selected from the group consisting of $R_2$. In this context bioisosters of —COOH may be any of the bioisosters of —COOH described herein above in the section "Diynes" and $R_2$ is as described herein above in the section "Diynes" in relation to formula IV' and V'. More preferably Z is $R_4$—($C_{6-20}$ alkyl)-, for example $R_4$—($C_{6-15}$-alkyl), such as $R_4$—($C_{6-12}$-alkyl), for example $R_4$—($C_{9-20}$-alkyl), such as $R_4$—($C_{9-15}$-alkyl), for example $R_4$—($C_{9-12}$-alkyl), wherein $R_4$ is as described herein above in the section "Diynes" in relation to formula II'.

B3. Properties of Diyne Compounds

The present invention relates to diyne compounds per se as well as to use of the diyne compounds in treatment of fungal infections. The structural properties of the diynes according to the invention are described herein above particularly in the section "Diynes", but also in the section "Particular diynes". In addition to these structural properties it is preferred that the diynes according to the invention, in particular the diyne compounds contained in the pharmaceutical compositions of the invention also have the functional properties described in detail in this section.

It is very preferred that the diyne compound according to the invention is capable of inhibiting conversion of a saturated fatty acid to a Δ9-monounsaturated fatty acid in a fungus. In particular it is preferred that the diyne compound is capable of inhibiting conversion of stearic acid to oleic acid in a fungus. It is also preferred that the diyne compound is capable of inhibiting conversion of palmitic acid to palmitoleic acid.

Whether a diyne compound is capable of inhibiting conversion of stearic acid to oleic acid in a fungus may be determined in any useful method known to the skilled person. According to the present invention one method for determining whether a diyne compound is capable of inhibiting conversion of stearic acid to oleic acid in a fungus comprises the steps of
 a) providing a fungus, a fungal extract or an in vitro assembled complex comprising stearoyl-CoA 9 desaturase (such as OLE-1)
 b) optionally providing co-factors for stearoyl-CoA 9 desaturase (such as OLE-1)
 c) providing a substrate selected from the group consisting of stearic acid and activated forms of stearic acid
 d) providing a diyne compound
 e) incubating said fungus, fungal extract or in vitro assembled complex with said substrate, co-factors and with a predetermined amount of said diyne compound for a predetermined amount of time
 f) detecting the presence of product formed, wherein the product is selected from the group consisting of oleic acid and activated forms of oleic acid.

Said activated form of stearic acid is preferably stearyl-CoA and said activated from of oleic acid is preferably oleoyl-CoA. If stearyl-CoA is provided in step b), then preferably step d) comprises detecting formation of oleoyl-CoA.

Similarly, whether a diyne compound is capable of inhibiting conversion of palmitic acid to palmitoleic acid in a fungus may be determined in any useful method known to the skilled person. According to the present invention one method for determining whether a diyne compound is capable of inhibiting conversion of palmitic acid to palmitoleic acid in a fungus comprises the steps of
 a) providing a fungus, a fungal extract or an in vitro assembled complex comprising stearoyl-CoA 9 desaturase (such as OLE-1)
 b) optionally providing co-factors for stearoyl-CoA 9 desaturase (such as OLE-1)
 c) providing a substrate selected from the group consisting of palmitic acid and activated forms of palmitic acid
 d) providing a diyne compound
 e) incubating said fungus, fungal extract or in vitro assembled complex with said substrate, co-factors and a predetermined amount of said diyne compound for a predetermined amount of time
 f) detecting the presence of product formed, wherein the product is selected from the group consisting of palmitoleic acid and activated forms of palmitoleic acid.

Said activated form of palmitic acid is preferably palmitoyl-CoA and said activated from of palmitoleic acid is preferably palmitoleyl-CoA. If palmitoyl-CoA is provided in step b), then preferably step d) comprises detecting formation of palmitoleyl-CoA.

Said fungus may be provided as an intact viable fungus or as intact fungal cells. The fungal extract may be any extract comprising stearoyl-CoA 9 desaturase (such as OLE-1). In *Saccharomyces cerevisiae* and other fungi the stearoyl-CoA desaturase is mainly located in the membranes of the endoplasmatic reticulum and accordingly it is preferred that said fungal extract comprises endoplasmatic reticulum or parts thereof. For example, the extract may be prepared by lysis of fungal cells, followed by separation of fractions for example by centrifugation. In particular, differential centrifugation may be used to enrich for endoplasmatic reticulum. However, fractions or extracts comprising endoplasmatic reticulum may also be obtained by other useful methods known to the skilled person. Alternatively, stearoyl-CoA desaturase may be obtained by in vitro assembly by methods known to the skilled person.

Preferably, the substrate provided in step c) is labelled allowing easy detection of the product in step f). The substrate may be labelled with any suitable label, such as a radioactive label, a dye, a heavy metal, a fluorescent label or a bioluminescent label. Preferably, the substrate is radioactively labelled. Detecting product formed may then be performed by detecting labelled product. The detection method will dependent on the particular label used.

One non-limiting example of determining inhibition of conversion of stearic acid to oleic acid is described herein below in Example 12B. The skilled person will understand that a similar method may be performed for determining inhibition of conversion of palmitic acid to palmitoleic acid, by exchanging the substrate provided.

Preferably, the diyne compounds according to the invention are capable of inhibiting at least 50%, more preferably at least 60%, even more preferably at least 70%, yet more preferably at least 80%, yet more preferably at least 90%, even more preferably at least 95%, yet more preferably essentially 100% of the formation of oleic acid, wherein "essentially 100%" means that no detectable product is formed. Inhibition is determined in relation to a control, wherein said fungus or fungal extract is incubated with said substrate in the absence of said diyne compound for the same predetermined amount of time.

It is preferred that the diyne compound of the invention is capable of inhibiting the activity of a fungal steraroyl-CoA 9 desaturase, preferably the diyne compound is capable of inhibiting the activity of a fungal OLE-1.

The activity of said fungal stearoyl-CoA 9 desaturase (such as OLE-1) may be inhibited by different means by said diyne compound. Thus, the diyne may directly inhibit the enzymatic activity of said fungal stearoyl-CoA 9 desaturase (such as OLE-1). Thus, the diyne compound may preferably be an inhibitor of the fatty acid desaturase activity of OLE-1 polypeptide.

Whether said diyne is capable of directly inhibiting the activity of fungal stearoyl-CoA 9 desaturase (such as OLE-1) may for example be determined using an in vitro assay for fungal stearoyl-CoA 9 desaturase (such as OLE-1) activity. Thus, for example fungal stearoyl-CoA 9 desaturase (such as OLE-1) may be incubated with either stearic acid and/or palmitic acid and/or activated forms thereof (such as stearyl-CoA or palmitoyl-CoA) optionally together with co-factors to form a reaction mixture and the formation of oleic acid and/or palmitoleic acid and/or activated forms thereof may then be determined. Addition of a diyne compound to said reaction mixture preferably significantly inhibits the formation of oleic acid and/or palmitoleic acid or activated forms thereof. Thus, preferably addition of a diyne compound to said reaction mixture reduces the formation of oleic acid and/or palmitoleic acid to less than 30%, preferably less than 20%, more preferably to less than 10%, for example to less than 5%, for example to less than 3%, such as to less than 1%. Said fungal stearoyl-CoA 9 desaturase (such as OLE-1) may be provided to said reaction mixture in a purified form or as part of a crude extract, for example a fungal extract or as prepared in vitro.

Mammalian desaturases are significantly different to fungal stearoyl-CoA 9 desaturases (such as OLE-1), for example mammalian desaturases lacks an integral cytochrome $b_5$ domain (Krishnamurthy et al., 2004, Microbiology, 150, 1991-2003. Accordingly, inhibitors of fungal stearoyl-CoA 9 desaturase (such as OLE-1), may be specific for the fungal enzymes in the sense that they do not inhibit mammalian desaturases to any significant extent.

In a preferred embodiment of the invention the diyne compound according to the invention is a selective inhibitor of a fungal stearoyl-CoA 9-desaturase (such as OLE-1). Thus it is preferred that the diyne compound is capable of inhibiting the activity of at least one fungal stearoyl-CoA 9 desaturase, preferably of more than one fungal stearoyl-CoA 9 desaturase. It is furthermore preferred that the diyne compound of the invention does substantially not inhibit at least one mammalian stearoyl-CoA 9 desaturase, preferably human stearoyl-CoA 9 desaturase. Accordingly, it is preferred that if using the above-described in vitro assay, then the diyne compounds according to the invention are capable of reducing the formation of oleic acid and/or palmitoleic acid to less than 30%, preferably less than 20%, more preferably to less than 10%, for example to less than 5%, for example to less than 3%, such as to less than 1% in the presence of one or more fungal stearoyl-CoA 9 desaturase (such as OLE-1), but in the absence of any mammalian stearoyl-CoA 9 desaturase. In addition it is preferred that in a similar in vitro assay said diyne compound is substantially not capable of reducing the formation of oleic acid and/or palmitoleic acid and thus in the presence of said diyne compound at least 80%, preferably at least 90%, yet more preferably at least 95% oleic acid and/or palmitoleic acid is formed compared to in the absence of said diyne compound, when incubating either stearic acid and/or palmitic acid with one or more mammalian stearoyl-CoA 9 desaturases, preferably in the presence of human stearoyl-CoA 9 desaturase, but in the absence of any fungal stearoyl-CoA 9 desaturase (such as OLE-1).

The diyne may also indirectly inhibit the activity of said fungal stearoyl-CoA 9 desaturase (such as OLE-1) by down modulating the level of said fungal stearoyl-CoA 9 desaturase (such as OLE-1) in a fungus. Thus, the diyne compound may decrease the stability or the half life of said fungal stearoyl-CoA 9 desaturase (such as OLE-1), thereby down modulating the level. The diyne compound may also inhibit the expression of said fungal stearoyl-CoA 9 desaturase (such as OLE-1), for example by inhibiting transcription or translation of fungal stearoyl-CoA 9 desaturase (such as OLE-1).

In one embodiment of the invention, the diyne compound may down modulate the expression of the OLE-1 polypeptide by modulating the activity of a transcriptional regulator of the gene encoding the OLE-1 polypeptide. The activity of the transcriptional regulator may for example be down modulated by inhibition of the binding of the transcriptional regulator to an OLE-1 promoter or enhancer region.

Spt23p/Mga2p is a fungal transcriptional regulator that amongst others controls the expression of fungal stearoyl-CoA 9 desaturase (such as OLE-1). Thus, the diyne compound may be capable of inhibiting the activity of Spt23p/Mga2p.

It is very preferred that the diyne compounds according to the present invention are capable of reducing or preferably inhibiting formation and/or growth of hyphal filaments and/or formation of germ tubes from blastospores. Formation and/or growth of hyphal filaments may be determined by a method comprising the steps of:
  a) cultivating one or more fungi in vitro under conditions allowing hyphal filament formation and/or growth
  b) contacting said fungi with a test diyne compound
  c) visually inspecting whether hyphal filaments form and/or elongate.

Induction of germ tube formation from blastospores may be determined by a method comprising the steps of
  a) providing one or more fungi in the form of blastospores
  b) cultivating said blastospores in vitro under conditions allowing induction of germ tube formation
  c) contacting said blastospores with a test diyne compound
  d) visually inspecting whether germ tubes are formed Preferably, these methods involve also cultivating one or more fungi under conditions allowing hyphal filament growth or germ tube formation but in the absence of the test diyne compound as control.

If the visual inspection reveals significantly reduced hyphal filament or germ tube formation of said one or more fungi cultivated in the presence of said diyne compared to in the absence of said diyne compound, then the diyne compound is said to be capable of reducing formation and/or growth of hyphal filaments or formation of germ tubes.

If the visual inspection reveals essentially no hyphal tube formation, preferably no hyphal tube formation in the presence of said diyne compound, then the diyne compound is said to be capable of inhibiting formation of hyphal filaments or to be capable of inhibiting hyphal growth.

It is also very preferred that the diyne compounds according to the present invention are capable of reducing or preferably inhibiting clamydospore formation. This may be determined by a method comprising the steps of:
  a) cultivating one or more fungi in vitro under conditions allowing clamydospore formation
  b) contacting said fungi with a test diyne compound
  c) visually inspecting whether clamydospores are formed Preferably, the method involves also cultivating one or more fungi under conditions allowing clamydospore formation but in the absence of the test diyne compound as control.

If the visual inspection reveals significantly reduced clamydospore formation of said one or more fungi cultivated in the presence of said diyne compared to in the absence of said diyne compound, then the diyne compound is said to be capable of reducing formation of clamydospores.

If the visual inspection reveals essentially no clamydospore formation, preferably no clamydospore formation in the presence of said diyne compound, then the diyne compound is said to be capable of inhibiting formation of clamydospores.

The MIC (minimal Inhibitory Concentration) is the minimal concentration of diyne compound required for inhibiting essentially 100%, such as 100% growth of a fungi. Preferably, the MIC of the diyne compounds according to the invention is at the most 500 ng/ml, preferably at the most 250 ng/ml, yet more preferably at the most 100 ng/ml, for example at the most 60 ng/ml, such as at the most 40 ng/ml, for example at the most 20 ng/ml, such as at the most 10 ng/ml in relation to at least 3 different fungi.

It is also preferred that the diyne compounds according to the invention are capable of killing one or more fungi, preferably capable of killing at least 2, more preferably at least 5, even more preferably at least 10 different fungi. Preferably, the diyne compound has a minimum fungicidal concentration (MFC) of at the most 100 µg/ml, preferably at the most 50 µg/ml, yet more preferably at the most 10 µg/ml, even more preferably at the most 1 µg/ml, against one or more fungi, preferably one or more pathogenic fungi, even more preferably against at least 2, yet more preferably at least 5, even more preferably at least 10 different fungi. Preferably, said MFC for a given fungus is determined in a method comprising the steps of a) cultivating said fungus in vitro
b) contacting said fungus with various concentrations of test diyne compound
c) incubating said fungus with said diyne test compound for a predetermined amount of time
d) transferring said fungus to another in vitro culture medium
e) determining growth of said fungus in said another in vitro culture medium The lowest concentration of diyne test compound resulting in essentially no growth in step e), preferably in no detectable growth in step e) is the MFC. The MFC may preferably be determined using the assay described herein below in Example 10.

In addition it is preferred that contacting a fungus with said diyne compound leads to a rapid loss of viability. This may for example be determined by a method comprising the steps of:

a) cultivating one or more fungi in vitro, thereby obtaining a fungal culture
b) determining the CFU/ml in said fungal culture
c) contacting the fungal culture with a test diyne compound
d) incubating said fungal culture with said test diyne compound for a predetermined amount of time
e) determining the CFU/ml in said fungal culture If the CFU/ml determined in step e) is at the most 20%, preferably at the most 15%, yet more preferably at the most 10% of the CFU/ml determined in step b), wherein said predetermined amount of time is in the range of 0.5 to 24 hours, preferably in the range of 0.5 to 12 hours, even more preferably in the range of 0.5 to 6 hours, yet more preferably in the range of 0.5 to 2 hours, such as in the range of 1 to 24 hours, even more preferably in the range of 1 to 12 hours, yet more preferably in the range of 1 to 6 hours, even more preferably in the range of 1 to 2 hours then said diyne compound is said to be capable of leading to rapid loss of viability of said fungus. Thus, it is preferred that at least a 1000 fold reduction in CFU/ml is determined in step e) compared to step b), when said predetermined amount of time is at least 3 hours, such as 3 hours. One example of how rapid loss of viability may be determined is described in Example 11.

As outlined above it is preferred that the diyne compound has fungicidal activity against one or more fungi and in addition it is preferred that said diyne compound is capable of leading to rapid loss of viability of one or more fungi.

It is also preferred that the diyne compounds according to the invention are capable of inhibiting growth of fungi. The IC50 indicates the concentration where 50% growth inhibition is obtained. Preferably, the IC50 of the diyne compounds according to the present invention is at the most 100 ng/ml, preferably at the most 50 ng/ml, even more preferably at the most 25 ng/ml, yet more preferably at the most 10 ng/ml, for example at the most 5 ng/ml, such as at the most 1 ng/ml in respect of at least 1, preferably at least 3 different fungi.

Said one or more fungi are preferably one or more fungi selected from the group consisting of Ascomycete, Basidiomycete, Deuteromycete, Oomycete, and combinations thereof. More preferably said one or more fungi are fungal pathogens of mammals.

Thus said one or more fungi may be selected from the group consisting of *Candida* spp. (for example *C. albicans, C. krusei, C. glabrata, C. tropicalis, C. parapsilosis, C. guilliermondii, C. haemulonii, C. lusitaniae, C. lipolytica, C. norvegensis, C. viswanathii, C. kefyr* or *C. dubliniensis*), *Aspergillus* spp. (for example *A. fumigatus, A. flavus, A. niger* or *A. terreus*), *Histoplasma capsulatum, Coccidioides immitis, Coccidioides posadasii, Cryptococcus* spp. (for example *C. neoformans* (for example var. *neoformans* or var. *gattii*), *C. bidus, C. laurentii*, or *C. fusarium*), Zygomycetes (such as *Rhizopus oryzae, R. micropsorus, R. pusillus, Cunninghamelle bertholletiae, Saksenaea vasiformis, Mucor circinelloides, M. ramosissimus, Absidia corymbifera, Apophysomyces elegans, Cokeromyces recurvatus* or *Syncephalastrum racemosum*), *Malassezia* spp. (for example *M. furfur* or *M. globosa*), Hyalohyphomycetes (for example *Fusarium solani* or *Scedosporium* spp., such as *S. prolificans* or *S. apiospermum*), Dermatophytes (for example *Trichophyton* spp. (for example *T. mentagrophytes, T. rubrum* or *T. tonsurans*), *Epidermophyton floccosum, Microsporum* spp (for example *M. cookei, M. canis, M. vanbreuseghemii, M. gallinae* or *M. gypseum*) or *Trichosporon terrestre*), *Blastomyces dermatitidis, Sporothrix schenkii, Chromomycotic fungi* (for example *Fonsecaea pedrosoi, F. compacta, Cladophylophora carrionii* or *Phialophora verrucosa*) and *Madurella* spp. (for example *M. mycetomatis* or *M. griseum*).

In some embodiments of the invention the diyne compound substantially does not significantly inhibit ergosterol synthesis; however in other embodiments of the invention it is possible that the diyne compounds in addition to above mentioned functions also are capable of inhibiting ergosterol synthesis. In these embodiments, then upon addition of said diyne compound to a fungus cultivated in vitro, then ergosterol is produced at substantially the same level as in the absence of said diyne, i.e. that at least 80%, preferably at least 85%, more preferably at least 90% of the ergosterol produced in the absence of said diyne compound is produced in the presence of said diyne compound. Within the present context "does not significantly inhibit" means that at concentrations similar to the MFC, such as at a concentration of at the most 2 times MFC, more preferably at a concentration of at the most 1.5 time MFC, such as at a concentration of at the most MFC of said particular diyne against a given fungus, then said diyne does not inhibit ergosterol synthesis in said fungus (i.e. ergosterol is produced at substantially the same level as in the absence of said diyne as described above). Ergosterol synthesis may be determined by any suitable method known to the skilled person, for example by incubating fungal cells with $^{13}$C labelled acetate and determining the ratio of $^{13}$C labelled to unlabelled ergosterol. Preferably ergosterol synthesis may be determined as described herein in Example 16.

In some embodiments of the invention the diyne compound does not significantly inhibit chitin synthase and/or β-glucan synthase; however in other embodiments of the invention it is possible that the diyne compounds in addition to above mentioned functions also are capable of inhibiting chitin synthase and/or β-glucan synthase. Within the present context "does not significantly inhibit" means that at concentrations similar to the MFC, such as at a concentration of at the most 2 times MFC, more preferably at a concentration of at the most 1.5 time MFC, such as at a concentration of at the most MFC of said particular diyne against a specific fungus, then chitin synthase and/or β-glucan synthase activity of said fungus is inhibited by no more than 30%, preferably no more than 20%. Inhibition of chitin synthase and/or β-glucan synthase may for example be determined as described herein in Example 15.

B4. Pharmaceutical Composition

The pharmaceutical compositions comprising diyne compound according to the present invention may be in any suitable form depending on the fungal infection to be treated.

Thus, the pharmaceutical composition may be formulated for topical administration or for systemic administration. Typically, if the fungal infection is a local infection on a body surface, then the pharmaceutical composition is typically formulated for topical administration. If the fungal infection is a disseminated infection and/or an infection of one or more inner organs, tissues or cells then the pharmaceutical composition is typically formulated for systemic administration.

In addition, to said diyne compounds the pharmaceutical compositions according to the invention will frequently comprise one or more pharmaceutically acceptable excipients.

For therapeutic uses, the pharmaceutical compositions comprising diynes may be administered systemically, for example, formulated in a pharmaceutically acceptable buffer such as physiological saline. Treatment may be accomplished directly, e.g., by treating the individual (such as a human being) with a diyne compound or pharmaceutical composition comprising a diyne compound of the invention. Preferable routes of administration include, for example, inhalation or subcutaneous, intravenous, intraperitoneally, intramuscular, or intradermal injections which provide continuous, sustained levels of the diyne compounds in the patient. Treatment of human beings or other animals is carried out using a therapeutically effective amount of a diyne compound of the invention in a physiologically-acceptable carrier. Suitable carriers and their formulation are described, for example, in Remington: The Science and Practice of Pharmacy, (19th ed.) ed. A. R. Gennaro A R., 1995, Mack Publishing Company, Easton, Pa.

In one preferred method, one or more diyne compounds of the invention are formulated in combination with a solid or a liquid dermatologically acceptable carrier. Useful solid carriers include finely divided solids such as talc, clay, microcrystalline cellulose, silica, alumina, and the like. Useful liquid carriers include water, alcohols, or glycols (or water-alcohol/glycol blends), in which the present compounds can be dissolved or dispersed at effective levels. Adjuvants (such as flavourings and/or fragrances), surfactants, and additional antimicrobial agents can be added to optimize the properties for a given use. The compositions can be applied from absorbent pads, used to impregnate bandages and other dressings, or sprayed onto the affected area using pump-type or aerosol sprayers. The liquid compositions can also be employed as eye drops, mouth washes, douches, etc.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user, which is mainly relevant for treating fungal infections of the skin.

In other medical applications, an antifungal compound can be added to materials used to make medical devices such as catheters, including but not limited to intravenous, urinary, intraperitoneal, ventricular, spinal, and surgical drainage catheters, in order to prevent colonization and systemic seeding by potential fungal pathogens. Similarly, an antifungal compound may be added to the materials that constitute various surgical prostheses and to dentures to prevent colonization by fungal pathogens and thereby prevent more serious invasive infection or systemic seeding by these pathogens.

The amount of the diyne compound to be administered may vary depending upon the manner of administration, the age and body weight of the individual, and the type of fungal infection and extensiveness of the infection.

However, preferably the pharmaceutical compositions comprising diyne compounds according to the invention are formulated for administration of in the range of 0.001 mg/Kg to 100 mg/kg, preferably in the range of 0.001 mg/Kg to 100 mg/kg daily, in particular when the individual to be treated is a mammal, such as a human being.

The total concentration of one or more diyne compounds of the invention in the present compositions can be varied widely, and will depend on factors such as the compatibility of the active ingredient(s) with the vehicle, the potency of the active ingredient(s) and the condition to be treated. Generally, the concentration of the diyne compound(s) in a composition for topical administration, such as a lotion, will be from about 0.01 to 25% by weight, such as from 0.1-25% by weight, preferably from about 0.5-10% by weight, and more preferably from about 0.5% to 5% by weight. In liquid formulations the concentration may be from 0.01 to 90%, preferably from 0.01 to 50%, such as from 0.01 to 25% by weight. The concentration in a semi-solid or solid composition such as a gel or a powder will be about 0.01-99% by weight, such as from 0.01 to 50%, for example from 0.01 to 25% and preferably about 0.5-2.5% by weight.

The pharmaceutical compositions according to the invention may in addition to the diyne compounds also comprise one or more additional active agents.

Said additional active agents may for example be antifungal agents.

B5. Individual in Need of Treatment

The present invention relates to pharmaceutical compositions comprising diyne compounds for treatment of fungal infections in an individual in need thereof.

Said individual may be any individual suffering from a fungal infection, preferably an animal, more preferably a mammal, even more preferably a human being suffering from a fungal infection. In some preferred embodiments of the invention, the individual is however a non-human mammal suffering from a fungal infection, preferably a mammal selected from the group consisting of horses, cattle, dogs and cats. Said fungal infection may be any of the fungal infections described herein below in the section "Fungal Infections".

In one embodiment, the individual is an individual susceptible to fungal infections, for example an immunocompromised individual, such as an immunocompromised human being. Said immunocompromised individual may be immunocompromised for various reasons, for example the individual may receive immune suppressing medication (for example in connection with transplantation) or the individual may be suffering from an immunocompromising condition, such as HIV infection.

Interestingly, the present invention discloses that the diyne compounds of the invention does not reduce the activity of cytochromes P450 significantly. Whether a diyne compound is capable of reducing the activity of cytochromes P450 may be determined by any suitable assay known to the skilled person, preferably by an assay comprising the steps of
  a) providing a cytochrome P450
  b) providing a substrate for said cytochrome P450 c) incubating said cytochrome P450 with said substrate under conditions allowing for cytochrome P450 activity in the presence and absence of the diyne compound d) determining a reduction in product formed in the presence of said diyne compared to in the absence of said diyne compound A diyne compound is said to not "reduce the activity of cytochromes P450 significantly" if at least 60%, preferably at least 70% product is formed in the presence of 10 µM of the diyne compound compared to in the absence of said diyne compound. Preferably, said diyne compound does not significantly reduce the activity of at least 3, preferably at least 4, more preferably at least 5, even more preferably at least 6, such as in the range of 3 to 10, for example in the range of 5 to 10, such as 7 different cytochromes P450. Said substrate may be labelled, and the product formed may then be detected by detecting labelled product. However, frequently the detection may also be direct using for example chromatographic methods, for example HPLC-UV/VIS or HPLC-MS/MS. A preferred method for determining whether a compound reduces the activity of cytochromes P450 is described in Example 9 herein below, The substrate used is dependent on the particular cytochrome P450. Substrates useful for individual cytochromes P450 are well known to the skilled person. For example the catalogue of Cerep, France (as of 10 Jul. 2009) describes suitable substrates for various cytochromes P450. Useful substrates for some cytochrome P450s are also described in Example 9 herein below.

Accordingly, the pharmaceutical compositions according to the invention are particularly useful for treating individuals receiving one or more other active agents, in particular such active agents wherein the activity of said active agents is increased or even depending on the activity of cytochromes P450. Typically, immunocompromised individuals will receive such active agents, and the pharmaceutical compositions of invention are accordingly in particular useful for treatment of immunocompromised individuals.

Thus, in a preferred embodiment, the pharmaceutical compositions comprising diynes are in particular useful for treating fungal infections in individuals to whom one or more active agents selected from the following group is being administered, has been or is foreseen to be administered, preferably is being administered, has been administered within the past 48 hours or is foreseen to be administered within the next 48 hours.

Said active agents, wherein the activity is increased or even depending on the activity of cytochromes P450 is preferably one or more selected from the group consisting of acetaminophen, alfentanil, alprazolam, alprenolol, aminophyllin, amiodarone, amitriptyline, amlodipine, amphetamine, amprenavir, aniline, artemisinin, astemizole, atorvastatin, azelastine, azithromycin, barnidepine, benzene, bufuralol, bupropion, buspirone, bezafibrate, caffeine, carbamazepine, carisoprodol, carvedilol, celecoxib, cerivastatin, chlorpheniramine, chlorpromazine, chlorzoxazone, cimetidine, ciprofloxacin, cisapride, citalopram, clarithromycin, clemastine, clomipramine, clopidogrel, clozapine, cocaine, codeine, cyclobenzaprine, cyclophosphamide, cyclosporine, dapsone, debrisoquine, delavirdine, desipramine, dexamethasone, dexfenfluramine, dextromethorphan, dextropropoxyphene, diclofenac, diazepam, diltiazem, N,N-dimethyl formamide, diphenhydramine, disulfuram, docetaxel, dofetilide, dolasetron, econazole, efavirenz, encamide, enflurane, enoxacin, ergotamine, estradiol, erythromycin, ethanol, ethinylestradiol, etomidate, etoposide, felbamate, felodipine, fenofibrate, fentanyl, finasteride, flecamide, fluconazole, fluorouracil, fluoxetine, flurbiprofen, fluvastatin, fluvoxamine, gemfibrozil, glibenclamide, glipizide, glyburide, granisetron, growth hormone, halofantrine, haloperidol, halothane, hexobarbital, hydrocortisone, hydroxyzine, ibuprofen, ifosfamide, imipramine, indinavir, indoramine, insulin, indomethacin, irbesartan, irinotecan, isoflurane, isoniazid, isradipine, itraconazole, ketoconazole, lansoprazole, lercanidipine, levomepromazine, lidocaine, lignocaine, loratadine, lornoxicam, losartan, lovastatin, meloxicam, mephenyloin, mephobarbital, mequitazine, mestranol, methadone, methoxsalen, methoxyamphetamine, methoxyflurane, metoclopramide, metoprolol, metronidazole, mianserin, mibefradil, miconazole, midazolam, mifepristone, mirtazapine, mepyramine, methoxyamphetamine, metoclopramide, metyrapone, mexiletine, midazolam, minaprine, moclobemide, montelukast, naproxen, nefazodone, nelfinavir, nicardipine, nifedipine, nilutamide, nisoldipine, nitrendipine, norethindrone, norfloxacin, nortriptyline, omeprazole, ondansetron, orphenadrine, oxcarbazepine, pantoprazole, paracetamol, paroxetine, pefloxacin, perhexyline, perphenazine, pethidine, pentobarbitone, phenacetin, phenformin, phenobarbitone, phenyloin, pimozide, piroxicam, prednisone, primidone, procainamide, progesterone, proguanil, promethazine, propafenone, propofol, propranolol, quanoxan, quinidine, quinine, ranitidine, rifabutin, rifampicin, riluzole, risperidone, ritonavir, ropinirole, ropivacaine, rosiglitazone, salmeterol, saquinavir, secobarbital, selegiline, sildenafil, simvastatin, sertraline, sevoflurane, Snaproxen, sparteine, sufentanil, suprofen, sulphamethoxazole, sulphonamides (sulfonamides), tamoxifen, tacrine, tacrolimus, taxol, teniposide, terbinafine, terfenadine, terfenidine, testosterone, theophylline, thiopental, thioridazine, ticlopidine, timolol, tirilazad, tobacco, tolbutamide, tolterodine, topiramate, torsemide, tramadol, tranylcypromine, trazodone, triazolam, trofosfamide, troglitazone, troleandromycin, tropisetron, valsartan, venlafaxine, verapamil, vesnarinone, vigabatrin, vinblastine, vincristine, warfarin, zafirlukast, zaleplon, zanamivir, zileuton, zolmitriptan, zolpidem, zonisamide, zotepine and zuclopenthixol.

B6. Fungal Infection

The present invention relates to pharmaceutical compositions comprising diynes (such as any of the diynes described herein above in the section "Diynes") for treatment of infections by a fungus. The invention also relates to methods of treating an infection by a fungus by administering to an individual in need thereof a therapeutically effective amount of a diyne (such as any of the diynes described herein above in the section "Diynes").

In general said fungus is a fungus dependent on the activity of stearoyl-CoA desaturase (such as OLE-1). The fungus may also be a fungus dependent on the activity of Spt23p/Mga2p, preferably a fungus dependent on both the activity of stearoyl-CoA desaturase (such as OLE-1) and Spt23p/Mga2p.

In one embodiment of the invention it is preferred that the infection by said fungus is associated with formation of hyphae in said fungus, preferably the infection is dependent on formation of hyphae in said fungus. Fungi may form hyphae during infections, a process also referred to as hyphal morphogenesis. The hyphae may be any kind of hyphae, for example hyphae selected from the group consisting of septate hyphae, pseudohyphae, aseptate or coenocytic hyphae, generative hyphae, skeletal hyphae and fusiform skeletal hyphae, for example from the group consisting of septate hyphae and pseudohyphae. Interestingly, the diyne compounds according to the present invention are capable of inhibiting formation of hyphae. Hyphae are long, filamentous cell(s) of fungi, which may be identified by visual inspection, such as by visual inspection with the aid of a microscope. Example 13 herein below describes how inhibition of hyphal formation for example can be assessed in vitro. Because the diyne compounds of the invention are capable of inhibiting formation of hyphae, they are in particular useful for treating infections by a fungus associated with or dependent on formation of hyphae.

Thus, in one embodiment, the pharmaceutical composition comprising diyne compounds according to the invention may be prepared for inducing growth of small, rounded, compact hyphal forms rather than the hyphal growth seen in the absence of pharmaceutical composition.

In one embodiment of the invention it is preferred that the infection by said fungus is associated with clamydospores, for example the infection by said fungus may be associated with formation of clamydospores of said fungus, preferably the infection may be dependent on formation of clamydospores of said fungus. The infection may also be initiated by germination of clamydospores or associated with germination of clamydospores, preferably the infection by said fungus may be dependent on germination of clamydospores. The infection by said fungus may also be associated with conidia, for example the infection by said fungus may be associated with formation of conidia of said fungus, preferably the infection may be dependent on formation of conidia of said fungus. The infection may also be initiated by conidia, such as by germination of conidia or associated with germination of conidia, preferably the infection by said fungus may be dependent on germination of conidia.

Clamydospores are fungal spores, which may be formed asexually or sexually. They are usually essentially spherical (or spherical), and have a smooth surface. They may be multicellular and the cells may be connected by pores in septae between cells. Conidia may also be referred to as conidiospores or mitospores. Conidia are generally asexual, non-motile spores of a fungus.

Interestingly, the diyne compounds according to the present invention are capable of inhibiting formation of clamydospores and/or conidia. Furthermore, the diyne compounds of the invention may be capable of inhibiting germination of clamydospores and/or conidia. Formation and germination of clamydospores and/or conidia may be detected by visual inspection, preferably by visual inspection with the aid of a microscope. Because the diyne compounds of the invention are capable of inhibiting formation of clamydospores and/or conidia, and/or capable of inhibiting germination of clamydospores and/or conidia, the compounds are in particular useful for treating infections by a fungus associated with or dependent on formation and/or germination of clamydospores and/or conidia.

Accordingly, the pharmaceutical composition comprising diyne compounds according to the invention may be prepared for inhibition of condition and/or for inhibition of sporulation.

In one embodiment of the invention the infection is associated with formation of a biofilm of said fungus (i.e. a fungal biofilm) and/or the infection causes formation of a biofilm of said fungus (i.e. a fungal biofilm). A fungal biofilm is a layer of fungus, which is phenotypically different from suspended fungal cells. In general, biofilms have a significantly decreased susceptibility to antifungal agents, including Amphotericin B and Fluconazole. However, interestingly the present invention discloses that infections by fungus associated with biofilm formation may be treated using the diyne compounds disclosed herein. Biofilms may be formed by a mixture of unicellular fungi, hyphae and/or pseudohyphae arranged in a layer structure, for example in a bilayer structure. Frequently, biofilms are formed on a solid surface, for example on indwelling medical devices (e.g. dental implants, catheters, heart valves, vascular bypass grafts, ocular lenses, artificial joints or central nervous system shunts). The biofilm bilayer may consist of a dense, basal fungus layer that anchors the biofilm to a surface an overlying but more open, hyphal layer. An extracellular matrix typically surrounds the cells within a biofilm.

Examples of fungi, which may form biofilms include *Candida* species, such as any of the *Candida* species mentioned herein below, for example *Candida albicans*.

In some embodiments of the invention the infection by fungus is associated with formation of macronodules, for example the infection may cause formation of macronodules of said fungus, preferably macronodules surrounded by a perimeter of ground-glass opacity. Such macronodules and in particular macronodules surrounded by a perimeter of ground-glass opacity (also referred to as a "halo") may for example be identified using computed tomography (CT) scanning Examples of fungi, which may form such macronodules include *Aspergillus* species, such as any of the *Aspergillus* species mentioned herein below. Macronodules may in particularly be associated with invasive pulmonary infections by fungus, such as invasive pulmonary aspergillosis. Interestingly the present invention discloses that infections by fungus associated with macronodule formation may be treated using the diyne compounds disclosed herein.

In one embodiment of the invention the pharmaceutical compositions comprising diyne compounds according to the invention are prepared for induction of nuclear membrane collapse in one or more fungi.

In one embodiment the pharmaceutical composition is prepared for inhibition of white-opaque switching.

In one embodiment, the pharmaceutical composition is prepared for inhibition of the morphogenetic switch between the hyphal growth form, the pseudo-hyphal growth form and the budding growth form.

Another interesting feature of the diyne compounds according to the present invention is that they are capable of killing fungi, i.e. they have fungicidal activity as described in more detail herein above in the section "Properties of diyne compounds". Accordingly, the pharmaceutical compositions comprising diyne compounds according to the invention are in particular suitable for treating infections by fungus, wherein it is desirable to kill the fungus, rather than just to inhibit growth of the fungus. Thus, the pharmaceutical compositions comprising diyne compounds according to the invention are particularly useful for treating recurrent infections by fungus, such as an infection by a fungus, which is expected to be recurrent or an infection by fungus, which has re-occurred at least once, for example at least twice, such as at least 3 times.

Preferably, the pharmaceutical compositions comprising diyne compounds according to the invention are prepared for killing at least 50%, preferably at least 80%, more preferably at least 95% of the infecting fungus.

Another very interesting aspect of the present invention is that the pharmaceutical compositions comprising diynes according to the invention are particularly useful for treating infection by a fungus under hypoxic conditions. Without being bound by theory it is believed that this is based on OLE-1 being particularly important for fungal growth under hypoxia. Thus, OLE-1 transcript levels are upregulated in fungi under hypoxia (for example in *C. albicans*).

Accordingly, the infection by a fungus may preferably be an infection involving at least partly infection of tissue, organs or cells with hypoxic conditions, preferably the infection may be infection of tissues, organs or cells with hypoxic conditions. Thus, said infection may at least partly involve infection of one or more inner organs, tissues or cells of a mammal, preferably a human being. More preferably, said infection may be infection of one or more inner organs, tissues or cells of a mammal, preferably a human being.

Said hypoxic condition is preferably an oxygen partial pressure ($pO_2$) of at the most 140 mmHg, preferably at the most 110 mmHg, such as at the most 80 mmHg. Such conditions may in general be found in inner organs, for example in the liver, pancreas, gut, duodenum, skeletal muscles, brain, kidney or peritoneal cavity.

It is also comprised within the present invention that the pharmaceutical compositions comprising diynes according to the invention may be for treatment of a disseminated infection or a local infection.

The infection by said fungus may also involve at least partly infection of a body surface, for example infection of skin, nails or mucosal membranes of body surfaces. Thus, said infection may be infection of a body surface, for example infection of skin, nails or mucosal membranes of body surfaces. Body surfaces may include the oral cavity, the genital organs, nose or eyes.

Accordingly, the fungal infection may be one or more selected from the group consisting of oropharyngeal fungal infections (such as thrush, glossitis, stomatitis or angular cheilitis), cutaneous fungal infections (such as intertrigo, diaper candidiasis, paronychia or onychomycosis), paronychia, onychomycosis, vulvovaginal fungal infection, balanitis, mucocutaneous fungal infection, neonatal fungal infection, congenital fungal infection, oesophageal fungal infection, gastrointestinal fungal infection, pulmonary fungal infection, peritonitis, urinary tract fungal infections, renal fungal infection, meningitis associated with fungi, hepatic fungal infection, hepatosplenic fungal infection, endocarditis, myocarditis, pericarditis, ocular fungal infection, endophthalmitis and osteoarticular fungal infection.

Interestingly, the diyne compounds according to the present invention are even useful for treating onychomycosis, i.e. fungal infection of the nails.

The infection by a fungus may be infection by one species of fungus or infection by more than one fungal species, such as two, for example 3, such as 4, for example 5, such as more than 5 different fungal species.

The fungus may be any fungus, but usually it is a pathogenic fungus, such as a fungus pathogenic in the individual to be treated. In one preferred embodiment of the invention, the individual to be treated is a mammal, preferably a human being, and then the fungus is a fungus pathogenic in mammals, preferably in human beings.

The fungus may preferably be selected from the group consisting of wherein one or more fungus is selected from the group consisting of *Candida* spp., *Aspergillus* spp., *Histoplasma capsulatum*, *Coccidioides immitis*, *Coccidioides posadasii*, *Cryptococcus* spp., Zygomycetes, *Malassezia* spp., Hyalohyphomycetes, Dermatophytes, *Epidermophyton floccosum*, *Microsporum* spp, *Blastomyces dermatitidis*, *Sporothrix schenkii*, Chromomycotic fungi and *Madurella* spp.

Thus the fungus may be selected from the group consisting of *Candida* spp., preferably from the group consisting of *C. albicans*, *C. krusei*, *C. glabrata*, *C. tropicalis*, *C. parapsilosis*, *C. guilliermondii*, *C. haemulonii*, *C. lusitaniae*, *C. lipolytica*, *C. norvegensis*, *C. viswanathii*, *C. kefyr* and *C. dubliniensis*.

The fungus may also be selected from the group consisting of *Aspergillus* spp., preferably from the group consisting of *A. fumigatus*, *A. flavus*, *A. niger* and *A. terreus*.

The fungus may also be selected from the group consisting of *Cryptococcus* spp., Preferably from the group consisting of *C. neoformans*, *C. bidus*, *C. laurentii*, and *C. fusarium*. Said *C. neoformans* is preferably selected from the group consisting of var. *neoformans* and var. *gattii*.

The fungus may also be selected from the group consisting of zygomycetes, preferably from the group consisting of *Rhizopus oryzae*, *R. micropsorus*, *R. pusillus*, *Cunninghamelle bertholletiae*, *Saksenaea vasiformis*, *Mucor circinelloides*, *M. ramosissimus*, *Absidia corymbifera*, *Apophysomyces elegans*, *Cokeromyces recurvatus* and *Syncephalastrum racemosum*.

The fungus may also be selected from the group consisting of *Malassezia* spp., preferably from the group consisting of *M. furfur* and *M. globosa*.

The fungus may also be selected from the group consisting of Hyalohyphomycetes, preferably from the group consisting of *Fusarium solani* and *Scedosporium* spp., wherein said *Scedosporium* spp. preferably is selected from the group consisting of *S. prolificans* and *S. apiospermum*.

The fungus may also be selected from the group consisting of Dermatophytes. This is in particular the case when the infection is partly or entirely an infection of the skin. Said Dermatophyte may preferably be selected from the group consisting of *Trichophyton* spp., *Epidermophyton floccosum*, *Microsporum* spp and *Trichosporon terrestre*. Said *Trichophyton* spp. may preferably be selected from the group consisting of *T. mentagrophytes*, *T. rubrum* and *T. tonsurans*. Said *Microsporum* spp may preferably be selected from the group consisting of *M. cookei*, *M. canis*, *M vanbreuseghemii*, *M gallinae* and *M. gypseum*.

The fungus may also be selected from the group consisting of Chromomycotic fungi, preferably from the group consisting of *Fonsecaea pedrosoi*, *F. compacta*, *Cladophylophora carrionii* and *Phialophora verrucosa*.

The fungus may also be selected from the group consisting of *Madurella* spp., preferably from the group consisting of *M. mycetomatis* and *M. griseum*.

In embodiments of the invention wherein the individual is a non-human animal, preferably a mammal, more preferably a mammal selected from the group consisting of horses, cattle, dogs and cats then the fungus may for example be selected from the group consisting of *Aspergillus* spp., *Batrachochytrium dendrobatidis*, *Blastomyces* spp., *Branchiomyces* spp., *Candida* spp., *Cladosporium* spp., *Coccidioides* spp., *Cryptococcus neoformans*, *Entomophthora* spp., *Epidermophyton* spp., *Fonsecaea* spp., *Geotrichum* spp., *Histoplasma* spp., *Ichthyophonus hoferi*, *Lacazia loboi*, *Malassezia* spp., *Metarhizium* spp., *Microsporum* spp., *Mucor* spp., *Ochroconis* spp., *Paecilomyces* spp., *Penicillium* spp., *Phialophora* spp., *Saprolegnia* spp., *Sporothrix schenckii*, *Trichophyton* spp. and *Wangiella* spp.

B7. Resistant Fungus

Another very interesting aspect of the present invention is that the diyne compounds and diyne salts according to the present invention are capable of treating infections by fungi which are resistant to one or more conventional antifungal agents, in particular antifungal agents, which are not capable of inhibiting conversion of a saturated fatty acid to a Δ9-monounsaturated fatty acid in a fungus.

Said fungi may be resistant for any reason. Thus, for example that particular species of fungus may be resistant to treatment with that particular antifungal agent. Alternatively, the fungus may have acquired resistance, i.e. in general said fungal species is not resistant to treatment with the particular antifungal agent, but this particular fungus has become resistant. In a preferred embodiment of the invention, the fungus has acquired resistance to one or more conventional antifungal agents.

Thus, the pharmaceutical compositions comprising diynes or diyne salts according to the invention are useful for treating infection by a fungus, which is resistant to one or more antifungal agents, which are not of formula I'. In particular, the pharmaceutical compositions comprising diynes or diyne salts according to the invention are useful for treating infection by a fungus, which is resistant to one or more antifungal agents capable of at least one of a) inhibiting ergosterol biosynthesis;
b) binding to ergosterol;
c) inhibiting 1,3-β-glucan synthase;
d) inhibiting epoxidase;
e) inhibiting Leucyl-tRNA synthetase; and/or
f) inhibition of elongation factor 2.

In particular, the pharmaceutical compositions comprising diynes according to the invention are useful for treating infection by a fungus, which is resistant to one or more antifungal agents selected from the group consisting of polyene antifungal agents, azole antifungal agents, allylamine antifungal agents and echinocandins.

Polyene antifungal agents are antifungal agents with multiple conjugated double bonds. Typically, polyene antifungal agents also comprise a heavily hydroxylated region. Non-limiting examples of polyenes include Natamycin, Rimocidin, Filipin, Nystatin, Amphotericin B or Candicin.

Azole antifungal agents may for example be imidazole or triazole or thiazole antifungal agents. Non-limiting examples of imidazole antifungal agents include miconazole, ketoconazole, clotromazole, econazole, bifonazole, butoconazole, fenticonazole, isoconazole, oxiconazole, seraconazole, sulconazole or tioconazole. Non-limiting examples of triazole antifungal agents include fluconazole, itraconazole, isavuconazole, ravuconazole, posaconazole, voriconazole or terconazole. A non-limiting example of a thiazole antifungal is abafungin.

Non-limiting examples of allylamine antifungals include Terbinafine, Amorolfine, Naftifine or Butenafine.

Non-limiting examples of echinocandins include Anidulafungin, Caspofungin or Micafungin.

The pharmaceutical compositions comprising diynes according to the invention may also be useful for treating infection by a fungus, which is resistant to one or more antifungal agents selected from the group consisting of benzoic acid, ciclopirox, tolnaftate, undecylenic acid, flucytosine, griseofulvin, haloprogin and sodium bicarbonate.

By the term "resistant to an antifungal agent", it is meant that said infection by fungus in said individual cannot be treated in a curable manner with said antifungal agent.

The pharmaceutical compositions for treating fungal infections according to the invention may in addition to one or more diyne compounds also comprise additional active agents, preferably one or more antifungal agents.

Thus said pharmaceutical compositions may in addition to one or more diynes also comprise one or more antifungal agents capable of at least one of a) inhibiting ergosterol biosynthesis;
b) binding to ergosterol;
c) inhibiting 1,3-β-glucan synthase;
d) inhibiting epoxidase;
e) inhibiting Leucyl-tRNA synthetase; and/or
f) inhibition of elongation factor 2.

Thus, the additional antifungal agent may be for example be selected from the group consisting of polyene antifungal agents (such as any of the polyene antifungal agents described herein above in the section), azole antifungal agents (such as any of the azole antifungal agents described herein above in the section), allylamine antifungal agents (such as any of the allylamine antifungal agents described herein above in the section) and echinocandins (such as any of the echinocandins described herein above in the section).

In particular, due to the synergistic effect the pharmaceutical compositions of the invention may preferably comprise a diyne compound as described herein above and a polyene antifungal agent.

Said polyene antifungal agent may preferably be Amphotericin B.

Due to the synergistic effect such pharmaceutical compositions be formulated for administration of very low levels of said polyene antifungal agent (such as Amphotericin B). Thus, such pharmaceutical compositions may be prepared for administration of less than 0.2 mg/kg, preferably less than 0.1 mg/kg, even more preferably less than 0.05 mg/kg of said polyene antifungal agent, preferably Amphotericin B.

Administration of low levels of polyene antifungal agent (such as Amphotericin B) is preferable, due to reduced toxicity compared to higher levels. As described in more details in the "Back ground" section, then polyene antifungal agent (such as Amphotericin B) may have many adverse effects.

B8. Fungal Infection of Plants

The present invention also relates to methods of reducing the risk of an infection or to methods of treating an infection in a plant by contacting said plant with a diyne compound according to the invention.

Thus, in one aspect the invention relates to use of a diyne of the formula I':

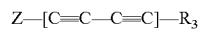

$$Z-[C\equiv C-C\equiv C]-R_3$$

wherein Z and $R_3$ are as defined herein above in the section "Diynes" such as any of the diyne compounds described herein above in the section "Diynes", for inhibiting or treating an infection by a fungus in a plant, preferably by a plant pathogenic fungus. Said infection by a fungus is preferably an infection by a fungus dependent on activity of stearoyl-CoA desaturase, more preferably an infection by a plant pathogenic fungus dependent on the activity of stearoyl-CoA desaturase.

Said diyne compound may in particular be a diyne of formula II',

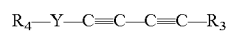

$$R_4-Y-C\equiv C-C\equiv C-R_3$$

wherein $R_4$, Y and $R_3$ are as described herein above in the section "Diyne".

The diyne compound for treating or reducing the risk of infection by a fungus in a plant (preferably a fungus dependent on activity of stearoyl-CoA desaturase) may also be a diyne of formula III':

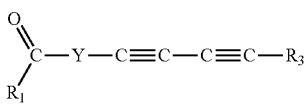

wherein $R_1$, Y and $R_3$ is as described herein above in the section "Diynes", The diyne compound for treating or reducing the risk of infection by a fungus in a plant (preferably a fungus dependent on activity of stearoyl-CoA desaturase) may also be a diyne of formula IV',

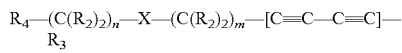

wherein $R_4$, $R_2$, n, m and $R_3$ are as described herein above in the section "Diyne" in relation to formula IV'.

The diyne compound for treating or reducing the risk of infection by a fungus in a plant (preferably a fungus dependent on activity of stearoyl-CoA desaturase) may also be a diyne of formula V',

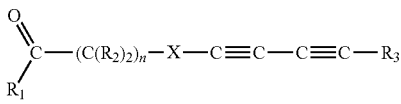

wherein $R_1$, $R_2$, n, X and $R_3$ are as described herein above in the section "Diyne" in relation to formula V'.

The diyne compound for treating or reducing the risk of infection by a fungus in a plant (preferably a fungus dependent on activity of stearoyl-CoA desaturase) may preferably be selected from the group consisting of (Z)-14-(furan-2-yl) tetradeca-9-en-11,13-diynoic acid and 14-(furan-2-yl)tetradeca-11,13-diynoic acid, and salts thereof. The salts thereof are preferably the salts described herein above in the section diynes.

Thus, for example the plant pathogenic fungus may be selected from the group consisting of *Albugo* spp., *Alternaria* spp., *Anisogramma anomala*, *Apiosporina morbosa*, *Ascochyta* spp., *Aureobasidium zeae*, *Bipolaris* spp., *Blumeria* spp., *Blumeriella jaapii*, *Botritis* spp., *Botryosphaeria dothidea*, *Ceratocystic paradoxa*, *Cercospora* spp., *Cercosporidium* spp., *Cladosporium* spp., *Cochiliobolus* spp., *Colletotrichum* spp., *Corynespora cassiicola*, *Cristulariella moricola*, *Diaporthe phaseolorum*, *Didymella bryoniae*, *Drechslera tritici*, *Entyloma oryzai*, *Erysiphe* spp., *Fluvia fluva*, *Fusarium* spp., *Gaeumannomyces graminis*, *Gnomonia* spp., *Gremmeniella abietina*, *Helminthosporium* spp., *Leptosphaerulina crassiasca*, *Leveillula taurica*, *Lophodermium hypophyllum*, *Macrophomina phaseoli*, *Magnaporthe* spp., *Microdochium* spp., *Microsphaera* spp., *Monilinia* spp., *Mycosphaerella* spp., *Myrothedium roridum*, *Oidiopsis sicula*, *Passalora puncta*, *Penicillium* spp., *Peronospora* spp., *Phaeocryptopus gaeumannii*, *Phakopsora* spp., *Phoma arachidicola*, *Phragmidium potentillae*, *Phytophtora* spp., *Plasmopara* spp., *Plectosporium tabacinum*, *Pleospora herbarum*, *Podosphaera* spp., *Pseudocercosporella* spp., *Pseudoperonospora cubensis*, *Puccinia* spp., *Pucciniastrum vaccinii*, *Pyrenophora* spp., *Pythium* spp., *Ramularia cynarae*, *Rhizoctonia* spp., *Rhizosphaera* spp., *Rhynchosporium secalis*, *Sclerotinia* spp., *Sclerotium* spp., *Selenophoma* spp., *Septoria* spp., *Setosphaeria turcica*, *Sirococcus conigenus*, *Sphaerotheca* spp., *Stagonospora nordorum*, *Stemphyllium botryosum*, *Taphrina deformans*, *Thielaviopsis* spp., *Tilletia barclayana*, *Tranzschelia discolor*, *Uncinula necator*, *Uromyces appendiculatus*, *Ustilaginoidea virens*, *Ustilago* spp., *Venturia* spp., *Verticillium* spp. and *Wilsonomyces carpophilus*.

Treatment of infections by a fungus in a plant may be done by any suitable means, for example the diyne compounds may be applied as sprays or dusts on the foliage of plants, or in irrigation systems. Typically, the diyne compounds according to the invention are administered on the surface of the plant in advance of the pathogen in order to prevent infection. Seeds, bulbs, roots, tubers, and/or corms may also be treated to prevent pathogenic attack after planting and for example thereby controlling pathogens carried on them or existing in the soil at the planting site. However, plants may also be treated once an infection is already present in order to eliminate or reduce the infection, preferably eliminate the infection. Similarly, seeds, bulbs, roots, tubers and/or corms may also be treated once an infection is already present in order to eliminate or reduce the infection, preferably eliminate the infection.

Soil to be planted with vegetables, ormementals, shrubs, or trees can also be treated with the diyne compounds of the invention for control of a variety of fungal pathogens. Treatment is preferably done several days or weeks before planting. The diyne compounds can be applied by either a mechanized route, e.g., a tractor, or with hand applications.

In most applications said diyne compounds are used with an agronomically acceptable carrier. An "agronomically acceptable carrier" is a solid or liquid which is biologically, chemically and physically compatible with the diyne compounds of the present invention, and which may be used in agricultural applications. Agronomically acceptable carriers suitable for use in the method of the present invention include organic solvents, and finely divided solids, and aqueous solutions or suspensions. For example, the diyne compounds for use in treatment or prevention of an infection by a fungus in a plant can be formulated as wettable powders, emulsifiable concentrates, dusts, granular formulations, aerosols, or flowable emulsion concentrates. In such formulations, the diyne compounds may be extended with a liquid or solid carrier and, when desired, suitable surfactants may be incorporated.

Optionally added components or additives, not required for fungicidal activity but useful or required for other properties, include, but are not limited to, adjuvants such as wetting agents, spreading agents, dispersing agents, stickers, adhesive and the like. Such adjuvants are well known in the art.

In general, the diyne compounds of this invention may be dissolved in solvents such as water or other aqueous solutions, acetone, methanol, ethanol, dimethylformamide, pyridine or dimethyl sulfoxide and such solutions can further be diluted with water. The concentrations of the solution after dilution may vary from 1% to 90% by weight, with a preferred range being from 5% to 50%.

For the preparation of emulsifiable formulations and concentrates of the diyne compounds of the present invention, the diyne compound can be dissolved in suitable organic solvents, or a mixture of solvents, together with an emulsifying agent to enhance dispersion of the diyne compound in water. The concentration of the diyne compound in emulsifiable concentrates is usually from 10% to 90%, and in flowable emulsion concentrates, can be as high as 75%.

Wettable, powdered formulations suitable for spraying can be prepared by admixing the diyne compound with a finely divided solid, such as clays, inorganic silicates and carbonates, and silicas and incorporating wetting agents, sticking agents, and/or dispersing agents in such mixtures. The concentration of total active ingredients in such formulations is usually in the range of from 20% to 99% by weight, preferably from 40% to 75%. A typical wettable powder is made by blending 50 parts of a diyne compound, 45 parts of a synthetic precipitated hydrated silicon dioxide, such as that sold under the trademark Hi-Sil®, and 5 parts of sodium lignosulfonate. In another preparation a kaolin type (Barden) clay is used in place of the Hi-Sil in the above wettable powder, and in another such preparation part of the Hi-Sil is replaced with a synthetic sodium silicoaluminate sold under the trademark Zeolex® 7 (J. M. Huber Corporation).

Dusting formulations may be prepared by mixing the diyne compounds with finely divided inert solids which can be organic or inorganic in nature.

Materials useful for this purpose include botanical flours, silicas, silicates, carbonates and clays. One convenient method of preparing a dust is to dilute a wettable powder with a finely divided carrier. Dust formulations or concentrates containing from 20% to 80% of the active ingredient are commonly made and are subsequently diluted to from 1% to 10% use concentration.

The fungicidal compound and formulations may be applied as fungicidal sprays by methods commonly employed, such as conventional high-gallonage hydraulic sprays, low-gallonage sprays, air-blast spray, aerial sprays and dusts.

The dilution and rate of application will depend upon the type of equipment employed, the method of application, plants to be treated and diseases to be controlled. Generally, the diyne compounds of this invention will be applied in an amount of from 0.06 to 60 kilograms (kg) per hectare and preferably from 1 to 28 kg per hectare of the active ingredient.

As a seed protectant, the diyne formulation may be coated on the seed. The dosage rate may for example be from 3 g of diyne compound per hundred kg of seed, to 1000 g per hundred kg of seed. As a soil fungicide the fungicidal formulation may be incorporated in the soil or applied to the surface for example at a rate of from 0.02 to 20 kg per hectare. As a foliar fungicide, the diyne compounds may be applied to growing plants for example at a rate of from 0.01 to 10 kg per hectare.

The diyne compounds of the present invention may be combined with other known fungicides.

B9. Method for Identification of Fungitoxic Compound

In one aspect the invention relates to methods for identifying a fungitoxic compound. Preferably, said method comprising the steps of,
a) providing an indicator composition or cell comprising a gene encoding stearoyl-CoA desaturase and/or a stearoyl-CoA desaturase peptide (preferably a wild type fungal stearoyl-CoA desaturase);
b) contacting the indicator composition or cell with a test compound, wherein the test compound comprises a —COOH group or a bioisostere thereof;
c) evaluating the activity of stearoyl-CoA desaturase in the presence and absence of the diyne compound; and
d) selecting a diyne compound that down modulates the activity of stearoyl-CoA activity,
thereby identifying a fungitoxic compound.

Interestingly, the present invention discloses that fungitoxic compounds capable of down modulating fungal stearoyl-CoA desaturase are superior to other classes of antifungal agents. Several diyne compounds capable of downmodulating the activity of stearoyl-CoA desaturase are described in more detail herein above and several advantages connected with this class of compounds are also described.

The present invention discloses that in particular compounds comprising a —COOH group or a bioisostere thereof may be useful for down modulating fungal stearoyl-CoA desaturase activity. Thus, the invention provides methods for testing whether a test compound comprising a —COOH group or a bioisostere thereof may be useful for down modulating fungal stearoyl-CoA desaturase activity.

The biostere of —COOH may be any of the bioisosteres of —COOH described herein above in the section "Diynes". Preferably, the bioisostere is selected from the group consisting of —CO—$R_1$, wherein $R_1$ is —OH or a moiety that can be replaced by a hydroxyl group in a hydrolysis reaction, tetrazoles, tetrazolates and salts thereof.

In one embodiment the test compound may be any of the diynes compounds described herein above in the section "Diynes".

However, the test compound may also be any other compound comprising a —COOH group or a bioisostere thereof. Thus, the test compound may in addition to the —COOH group or a bioisostere thereof comprise one or more carbon chains, which may be linear or branched and which may comprise one or more double bonds and one or more triple bonds. The carbon chain may also be a saturated carbon chain. Said carbon chain may be substituted for example with one or more substituents selected from the group consisting of amines, alkoxy, carbonyl, alcohols, halogens, carboxylic acids, esters, ethers or combinations thereof. The test compound may in addition to the —COOH group or a bioisostere thereof also comprise one or more cyclic groups, which may be heterocyclic groups. The heterocyclic groups may be any of the R3 groups described herein above in the section "Diynes". The cyclic group may however also be a cycle only with carbon atoms, such as a 3 to 10 membered ring, for example a 3 to 7 membered ring. The cyclic group may also consist of several cycles, i.e. it may be ring system. The cyclic group may be substituted for example with one or more substituents selected from the group consisting of amines, alkoxy, carbonyl, alcohols, halogens, carboxylic acids, esters, ethers or combinations thereof. If the test compound comprises several cyclic groups these may be directly connected or connected via linkers, which typically may be carbon chains.

The invention also relates to methods for treating a fungal infection in an individual in need thereof, said method comprising administering a therapeutically effective amount of a fungitoxic compound identified according to the method described in this section.

C1. Ole1 Protein Inhibitors

The present invention provides new class of fungicides that comprise an Ole1 protein inhibitor.

As such the novel fungicides of the invention act as potent antifungals against a wide variety of fungal pathogens that include novel diynes and their salts, derivatives and analogs. The inventive Ole1 protein inhibitors provide potent broad spectrum antifungal agents for the treatment of humans and animals against a wide variety of fungal pathogens. In addition, the compounds provide effective fungicides against agricultural fungal pathogens.

Their mode of action make the inventive compounds highly attractive alternatives to currently available treatment regimes where the treatment drugs have undesirable side effects due to their mode of action.

The inventors have shown that the inventive compounds inhibit oleic acid biosynthesis by inhibition of the Ole1 protein, a process that appears to be conserved across the entire fungal kingdom. Moreover, the instant compounds were tested against the mode of action of existing antifungal drugs and were shown not to act via the targets of existing drugs. Thus, the inventive compounds provide a new mechanism of action with great promise for broad spectrum antifungal treatments.

The inventive compounds exploit a mechanism of action that has so far not been exploited in the development of fungicides to date, the inhibition of the Ole1 protein. The Ole1 protein is essential for the survival of the fungal organism.

Provided herein therefore, are two new classes of antifungal compounds, both derived from a compound of general formula I″, $$a. R_1-C(O)-(C(R_2)_2)_x-R_3-C_4-R_4 \qquad \text{I″}$$

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is $C_2H_2$ or $C_2H_4$; $R_4$ is a pyrrole, furan, or thiophene ring; and x is an integer between 4 and 10, inclusive.

Provided in the invention therefore are new antifungal compounds based on the cis-isomer (Z) of structure II″:

$$a. (Z)-R_1-C(O)-(C(R_2)_2)_x-C_2H_2-C_4-R_4 \qquad \text{II″}$$

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; R4 is a heterocyclic ring, optionally substituted at one or more positions, preferably with one or more substituents selected from the group consisting of a $C_{1-5}$ alkyl, a $C_{1-5}$ alkenyl, a $C_{1-5}$ alkoxy, a $C_{1-5}$ alcohol, a hydroxyl, an amine, a nitro group and a halogen; and x is an integer between 4 and 10, inclusive.

In one embodiment, $R_4$ is a pyrrole, furan, or thiophene ring. In other embodiments, $R_4$ may be an imidazole, oxazole, and cyclopentadiene.

In other preferred embodiments, $R_4$ is a heterocyclic ring substituted at one or more positions with one or more, preferably one or two selected from the group consisting of lower alkyl, lower alkenyl, lower alkoxy, lower alcohol, hydroxyl, amine, $NO_2$ and halogen. A lower alkyl is preferably $C_{1-5}$, more preferably $C_{1-3}$, even more preferably $C_1$ alkyl. A lower alkenyl is preferably $C_{1-5}$, more preferably $C_{1-3}$, even more preferably $C_{1-2}$ alkenyl. A lower alkoxy is preferably $C_{1-5}$, more preferably $C_{1-3}$, even more preferably $C_1$ alkoxy. A lower alcohol is preferably $C_{1-5}$, more preferably $C_{1-3}$, even more preferably $C_1$ alcohol comprising one or more OH groups, preferably only one OH group. Halogen may be any halogen, but is preferably F. It is however preferred that $R_4$ is a heterocyclic ring, which is not substituted or that $R_4$ is a heterocyclic ring substituted with a small substituent, preferably a small substituent selected from the group consisting of methyl, methoxy, hydroxyl, $CH_2$—OH, amine and halogen, and preferably methyl.

In other embodiments, $R_4$ is preferably a 3 to 7-membered heterocyclic ring, more preferably a 5 to 6-membered heterocyclic ring, even more preferably a 5-membered heterocyclic ring. The heterocyclic ring may be aromatic or non-aromatic. In one embodiment the heterocyclic ring is a 3 to 7-membered aromatic heterocyclic ring, more preferably a 5 to 6-membered aromatic heterocyclic ring, even more preferably a 5-membered aromatic heterocyclic ring.

The heterocyclic ring may comprise one or more heteroatoms, preferably in the range of 1 to 3 heteroatoms, more preferably in the range of 1 to 2 heteroatoms, yet more preferably 1 heteroatom, preferably selected from the group consisting of S, N and O.

For example, preferred compounds of the invention are of structure (Z)-14-(furan-2-yl)tetradeca-9-en-11,13-diynoic acid, III″, and its potassium and sodium salts. The substantially pure cis-isomer, (Z)-14-(furan-2-yl)tetradeca-9-en-11, 13-diynoic acid:

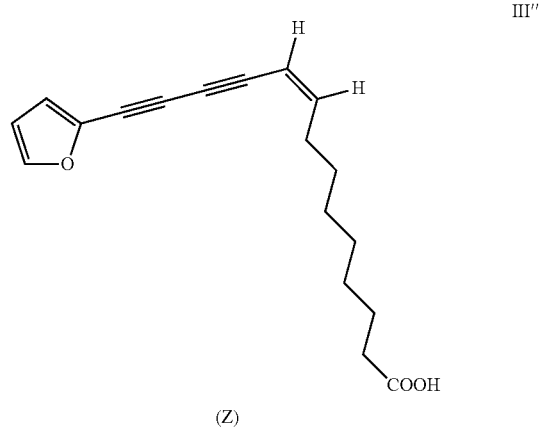 [SMILES: O=C(O)CCCCCCC/C=C\C#CC#Cc1ccco1]

as well as its potassium salt, are preferred embodiments of the present invention. Production of the cis, or Z, isomer compounds is a regioselective Wittig reaction stage which determines the cis/trans structure and produces predominantly the cis-isomer in a 98:2 cis:trans ratio (see Example 21 below). Equally, a preferred salt compound is the sodium salt of (Z)-14-(furan-2-yl)tetradeca-9-en-11,13-diynoic acid, V″:

These preferred cis (or Z) isomer compounds are highly water soluble salts, chemically distinct from any known class of antifungal agents.

Also provided are chemical analogs of III", such as (Z)-14-(4,5-dimethylfuran-2-yl)tetradeca-9-en-11,13-diynoic acid (VI"),

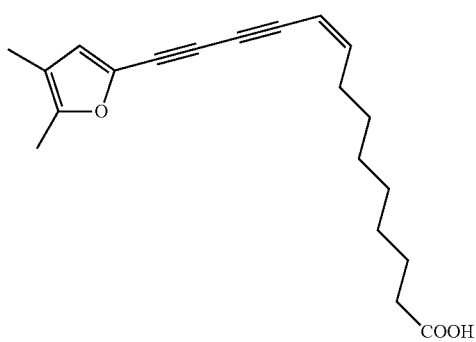

8-(2-(4-(furan-2-yl)buta-1,3-diynyl)phenyl)octanoic acid (VII")

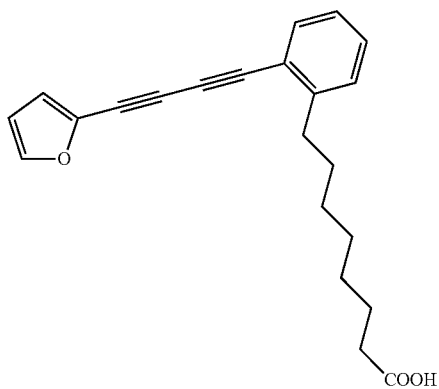

A trans analog of genetic formula I" is (E)-14-(furan-2-yl) tetradeca-9-en-11,13-diynoic acid (VIII"), unsubstituted or substituted as outlined for compound II".

a)

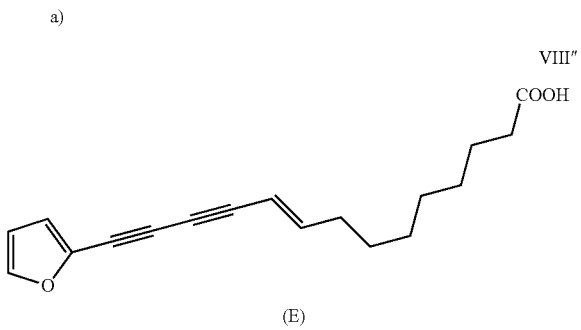

This novel compound class is related to the enediyne compounds general structure $R_1-C(O)-(C(R_2)_2)_x-C_2H_2-C_4-R_3$ and disclosed in U.S. Pat. No. 6,541,506, incorporated herein in entirety. That patent disclosed a structure $R_1-C(O)-(C(R_2)_2)_x-C_2H_2-C_4-R_3$ as a mixture of isomers and which the disclosed synthesis described as being predominantly the trans isomer. That patent did not disclose nor suggest isolating a substantially pure cis-compound. Although the patent stated that antifungal properties attended the disclosed compounds, poor solubility led them to be unsuitable for formulation. Nor did that patent disclose any compound in which the $C_2H_2$ group is an alkyl moiety.

Also provided in the invention is another new class of compounds similar to the compound of structure I" above, but in which the group $R_3$ is an alkyl moiety, having a single bond instead of a double bond at the position of $R_3$. This class has also been shown to also provide potent antifungal activity.

Thus, preferred compounds of the instant invention include analogs, IX",

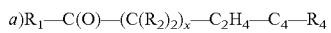

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_4$ is a heterocyclic ring, optionally substituted at one or more positions, preferably with one or more substituents selected from the group consisting of a $C_{1-5}$ alkyl, a $C_{1-5}$ alkenyl, a $C_{1-5}$ alkoxy, a $C_{1-5}$ alcohol, a hydroxyl, an amine, a nitro group and a halogen; and x is an integer between 4 and 10, inclusive.

In one embodiment, $R_4$ is a pyrrole, furan, or thiophene ring. In other embodiments, $R_4$ may be an imidazole, oxazole, and cyclopentadiene.

In other preferred embodiments, R4 is a heterocyclic ring substituted at one or more positions with one or more, preferably one or two selected from the group consisting of lower alkyl, lower alkenyl, lower alkoxy, lower alcohol, hydroxyl, amine, $-NO_2$ and halogen. A lower alkyl is preferably $C_{1-5}$, more preferably $C_{1-3}$, even more preferably $C_1$ alkyl. A lower alkenyl is preferably $C_{1-5}$, more preferably $C_{1-3}$, even more preferably $C_{1-2}$ alkenyl. A lower alkoxy is preferably $C_{1-5}$, more preferably $C_{1-3}$, even more preferably $C_1$ alkoxy. A lower alcohol is preferably $C_{1-5}$, more preferably $C_{1-3}$, even more preferably $C_1$ alcohol comprising one or more OH groups, preferably only one OH group. Halogen may be any halogen, but is preferably F. It is however preferred that $R_4$ is a heterocyclic ring, which is not substituted or that $R_4$ is a heterocyclic ring substituted with a small substituent, preferably a small substituent selected from the group consisting of methyl, methoxy, hydroxyl, $CH_2-OH$, amine and halogen, and preferably methyl.

In other embodiments, $R_4$ is preferably a 3 to 7-membered heterocyclic ring, more preferably a 5 to 6-membered heterocyclic ring, even more preferably a 5-membered heterocyclic ring. The heterocyclic ring may be aromatic or non-aromatic. In one embodiment the heterocyclic ring is a 3 to 7-membered aromatic heterocyclic ring, more preferably a 5 to 6-membered aromatic heterocyclic ring, even more preferably a 5-membered aromatic heterocyclic ring.

The heterocyclic ring may comprise one or more heteroatoms, preferably in the range of 1 to 3 heteroatoms, more preferably in the range of 1 to 2 heteroatoms, yet more preferably 1 heteroatom, preferably selected from the group consisting of S, N and O.

Thus, contemplated in the present invention is the unknown undisclosed acid, single-bonded analog of compound III" above, the compound 14-(furan-2-yl)tetradeca-11,13-diynoic acid, X",

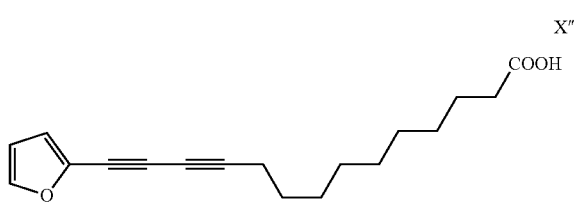 [SMILES: O=C(O)CCCCCCCCCC#CC#Cc1ccco1]

Both 14-(furan-2-yl)tetradeca-11,13-diynoic acid, and its salts, for example the sodium salt, XI″,

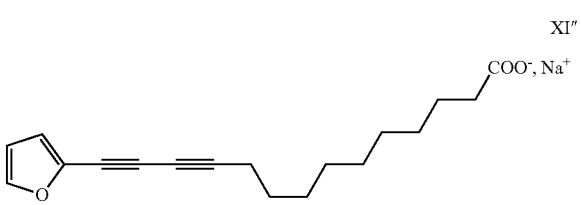

and potassium salt XII″, are effective and potent Ole1 protein inhibitors, and show potency and effectiveness in defeating or lessening agricultural fungal pathogens, providing effective and potent fungicides for use in the agricultural setting.

In preferred embodiments, the inventive compounds and salts, being highly soluble and suitable for formulation, provide highly effective components for formulations as fungicides for a variety of fungal pathogens in humans and animals.

Thus, methods are described herein that use the inventive compounds derived from or based on compound II″, such as salts, acids and analogs, as effective and potent antifungal agents for use in formations and other forms of the compounds suitable for a wide variety of recipients and delivery modes. Their potent antifungal capability, through the mechanism of Ole1 protein inhibition, offers a superior alternative to current antifungal drug treatments and fungicides.

A preferred diyne compound according to the invention is potassium (Z)-12-(furan-2-yl)dodeca-7-en-9,11-diynoate.

Another preferred diyne compound according to the invention is potassium (Z)-13-(furan-2-yl)trideca-8-en-10,12-diynoate.

Yet another preferred diyne compound according to the invention is potassium (E)-14-(furan-2-yl)tetradeca-9-en-11,13-diynoate.

Yet another preferred diyne compound according to the invention is the diyne compound potassium (Z)-14-(furan-2-yl)tetradeca-9-en-11,13-diynoate.

Another preferred diyne compound according to the invention is the diyne compound potassium 14-(furan-2-yl)tetradeca-11,13-diynoate.

In yet another embodiment of the invention the diyne compound may be selected from the group consisting of (Z)-14-(furan-2-yl)tetradeca-9-en-11,13-diynoic acid, potassium salt; (Z)-14-(5-methylfuran-2-yl)tetradeca-9-en-11,13-diynoic acid, potassium salt; 8-(2-(4-(furan-2-yl)buta-1,3-diynyl)phenyl)octanoic acid, potassium salt; (Z)-14-(4,5-dimethylfuran-2-yl)tetradeca-9-en-11,13-diynoic acid, potassium salt and 14-(furan-2-yl)tetradeca-11,13-diynoic acid, potassium salt.

C2. Mechanism of Inhibition of Ole1 Protein

An Ole1 protein inhibitor is inherently fungicidal because the Ole1 protein is an essential protein to the fungal organism. In the biosynthesis of lipids, the Ole1 protein converts stearic acid to oleic acid. Oleic acid is an essential component of lipids and thus essential to the fungal organism—without oleic acid the organism fails to survive due to collapse of the nuclear membrane.

The inventors tested yeast knock-out strains, the results of which indicated that the Ole1 protein might be the target of the inventive compounds in *Saccharomyces cerevisiae*. See Example 17 below. "Competition" experiments showed that in both *Saccharomyces cerevisiae* and *Candida albicans* oleic acid is an antagonist of the inventive compounds, but that stearic acid was not, indicating that the inventive compounds were most likely inhibitors of the biosynthesis of oleic acid from stearic acid. See Example 18 below. The conclusion that the inventive compounds are inhibitors of the biosynthesis of oleic acid from stearic acid in both *Saccharomyces cerevisiae* and *Candida albicans* meant that the inventive compounds either inhibited the Ole1 protein itself, or inhibited the transcriptional activators of the OLE1 gene, the Mga2 and Spt23 proteins. The inventors subsequently determined that the addition of the inventive compounds to a culture of both *Saccharomyces cerevisiae* and *Candida albicans*, increased the expression of the OLE1 gene, indicating that the inventive compounds targeted the Ole1 protein and not the Mga2 and Spt23 proteins (because otherwise a transcriptional down-regulation of the OLE1 gene would have been seen). See Example 19 below.

An Ole1 protein inhibitor is a broad spectrum fungicidal. The inventive diyne compounds are found to inhibit the Ole1 protein in many species. The Ole1 protein is conserved across the fungal kingdom, sequence homologs to the *Candida albicans* OLE1 gene were identified in the following organisms: *Candida glabrata, Candida tropicalis, Candida parapsilosis, Candida guillermondii, Candida lusitaniae, Aspergillus fumigatus, Aspergillus terreus, Aspergillus nidulans, Coccidioides immitis, Histoplasma capsulatum* and in *Cryptococcus neoformans*. Wilson, R. A. et al., 2004 and Kraus, P. R. et al., 2004, have shown that the OLE1 gene is essential to pathogenic fungal species such as *Aspergillus* and *Cryptococcus*, and in vitro susceptibility data for compound III″ and compound IV″ on a set of clinical isolates of human fungal pathogens are provided as follows.

C3. Antifungal Efficacy In Vitro

The efficacy of compound IV″ was investigated on 563 clinical isolates of 33 human fungal pathogens. The efficacy was determined according by broth micro and macro dilution. For species with n≥10, the $MIC_{90}$ (MIC, minimal inhibitory concentration) is given as ng/ml. For species with n≤10, the MIC range is given as ng/ml. 24 h and 48 h reads are indicated (Table 1).

TABLE 1

Susceptibility of human fungal pathogens to compound IV″ and compound III″.

| Strain (# of isolates) | Test Compound | $MIC_{90}$/MIC range | |
|---|---|---|---|
| | | 24 h | 48 h |
| C. albicans (n = 20) | IV″ | — | 2.5 |
| C. glabrata (n = 25) | IV″ | — | 20 |
| C. tropicalis (n = 35) | IV″ | — | 5 |
| C. dubliniensis (n = 25) | IV″ | — | 2.5 |
| C. krusei (n = 27) | IV″ | — | 20 |
| C. lusitaniae (n = 24) | IV″ | — | 128 |
| C. parapsilosis (n = 37) | IV″ | — | 1024 |

TABLE 1-continued

Susceptibility of human fungal pathogens to
compound IV''' and compound III'''.

| Strain (# of isolates) | Test Compound | MIC$_{90}$/MIC range | |
|---|---|---|---|
| | | 24 h | 48 h |
| C. albicans, Fluconazole, Voriconazole, Itraconazole and/or Caspofungin resistant isolates (n = 20) | IV''' | — | 2.5 |
| C. glabrata, Fluconazole, Voriconazole, Itraconazole and/or Caspofungin resistant isolates(n = 21) | IV''' | — | 20 |
| A. fumigatus (n = 40) | IV''' | 160 | 1280 |
| A. terreus (n = 5) | IV''' | 10-20 | 10->5120 |
| A. niger (n = 6) | IV''' | 40->5120 | 80->5120 |
| A. flavus (n = 5) | IV''' | 640->5120 | >5120 |
| A. versicolor (n = 4) | IV''' | 80-2560 | 160-5120 |
| A. nidulans (n = 5) | IV''' | 320->5120 | 1280->5120 |
| Coccidioides spp. (n = 30) | IV''' | — | 30 |
| B. dermatitidis (n = 30) | IV''' | — | 30 |
| H. capsulatum (n = 20) | IV''' | — | 30 |
| C. neoformans (n = 18) | IV''' | — | 2000 |
| Zygomycetes (n = 20) | IV''' | — | 16000 |
| Fusarium solani (n = 10) | IV''' | — | >64000 |
| Scedosporium (n = 10) | IV''' | — | 2048->64000 |
| Sporothrix schenckii (n = 10) | IV''' | — | 32-5120 |
| Fonsecaea pedrosi (n = 4) | IV''' | — | 80-2560 |
| Phialophora verrucosa (n = 4) | IV''' | — | 40-640 |
| Trichophyton tonsurans (n = 15) | III''' | — | <0.06 |
| T. mentagrophytes (n = 15) | III''' | — | <0.06 |
| Microsporum canis (n = 15) | III''' | — | <0.06 |
| T. rubrum (n = 15) | III''' | — | <0.06 |
| Epidermophyton floccosum (n = 15) | III''' | — | <0.06 |
| T. rubrum, Terbinafine resistant isolates (n = 9) | III''' | — | <0.06 |
| M. cookie (n = 1) | III''' | — | 1000 |
| M. vanbreuseghemii (n = 1) | III''' | — | 30 |
| M. gypseum (n = 1) | III''' | — | <0.06 |
| T. terrestre (n = 1) | III''' | — | <0.06 |
| M. gallinae (n = 1) | III''' | — | <0.06 |

The in vitro efficacy of compounds III''', IV''', VI''', VII''', VIII''' and XII''' was investigated on 8 *Candida* reference strains. The efficacy was determined according by broth micro dilution and the MIC given as ng/ml (see Table 2).

TABLE 2

Susceptibility of reference *Candida* strains to compounds III''', IV''', VI''', VII''', VIII''' and XII'''.

| Strain name | Compound | | | | | |
|---|---|---|---|---|---|---|
| | III''' | IV''' | VI''' | VII''' | VIII''' | XII''' |
| C. albicans ATCC-24433 | 1.25 | 1.25 | >10240 | >10240 | — | 10 |
| C. albicans ATCC-90028 | 1.25 | 1.25 | >10240 | >10240 | — | 10 |
| C. glabrata ATCC-90030 | 10 | 20 | >10240 | >10240 | — | 320 |
| C. krusei ATCC-6258 | 10 | 20 | >10240 | >10240 | — | 640 |
| C. parapsilosis ATCC-22019 | 2560 | 2560 | >10240 | >10240 | — | >10240 |
| C. parapsilosis ATCC-90018 | 2560 | 2560 | >10240 | >10240 | — | 5120 |
| C. tropicalis ATCC-750 | 2.5 | 5 | >10240 | >10240 | — | 10 |
| C. albicans SC5314 | 0.5 | 1.25 | >10240 | >10240 | 150 | 10 |

C4. Antifungal Efficacy In Vivo

The efficacy of compound V''' and compound IV''' in systemic *C. albicans* infections in small mammals is demonstrated as follows.

Figure 10:
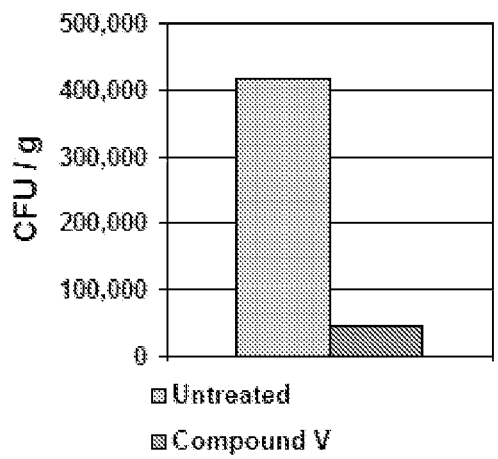
FIG. 10 shows liver fungal burden as determined by colony forming units (CFU) per gram of homogenised tissue.

When compound V''' was administered to rats infected systemically with *C. albicans* as a single intravenous infusion at 12 mg/kg, liver fungal burden decreased 93% after 24 h (see FIG. 10 showing liver fungal burden as determined by colony forming units (CFU) per gram of homogenised tissue).

Figure 11:
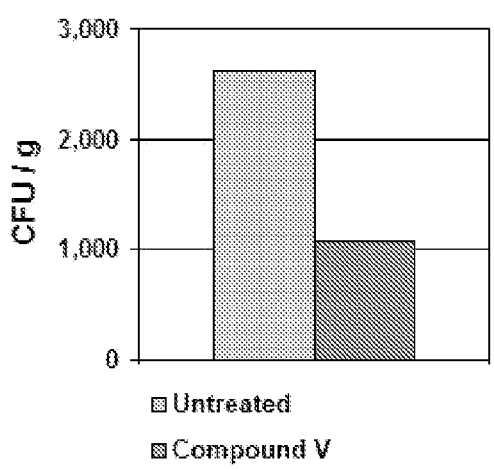
FIG. 11 shows kidney fungal burden as determined by colony forming units (CFU) per gram of homogenised tissue.

When compound V''' was administered to rats infected systemically with *C. albicans* as a single oral dose at 17 mg/kg, kidney fungal burden decreased by 57% after 6 h (see FIG. 11 showing kidney fungal burden as determined by colony forming units (CFU) per gram of homogenised tissue).

Figure 12:
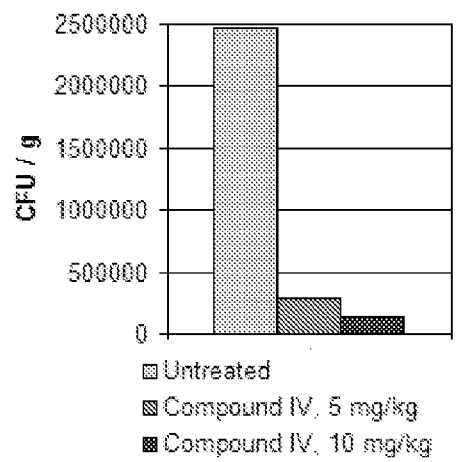
FIG. 12 show kidney fungal burden as determined by colony forming units (CFU) per gram of homogenised tissue.

Mice were infected systemically with *C. albicans*. Compound IV''' was administered orally twice daily for 3 days at 5 mg/kg or 10 mg/kg per dose. Kidney fungal burden decreased by 88% and 94% respectively, compared to the untreated control (as shown in FIG. 12 showing kidney fungal burden as determined by colony forming units (CFU) per gram of homogenised tissue).

Figure 13:
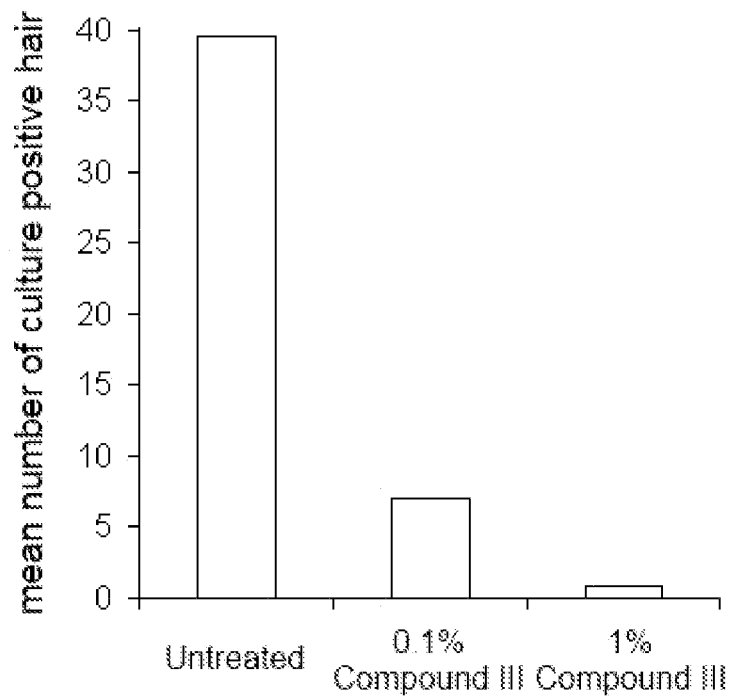
FIG. 13 shows topical fungal burden as determined by culture positive hair removed from the site of infection.

The efficacy of compound III''' in skin infections of small mammals was shown in guinea pigs infected with *Trichophyton mentagrophytes* on abrased skin. Compound III''' was administered topically at 0.1% or 1% once daily for seven days. Fungal burden decreased by 82% and 98% respectively, compared to the untreated control (see FIG. 13 showing topical fungal burden as determined by culture positive hair removed from the site of infection).

Figure 14:
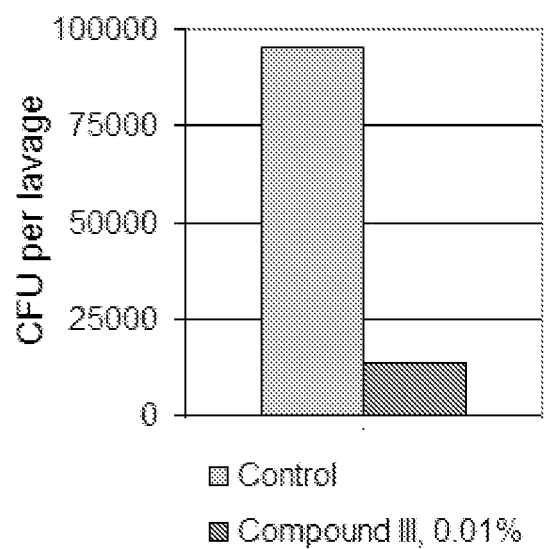
FIG. 14 shows vaginal fungal burden as determined by colony forming units (CFU) from vaginal lavage fluid.

The efficacy of compound III''' in vaginal infections of small mammals has been shown. Mice were vaginally infected with *Candida albicans*. Compound III''' was administered topically at 0.01% daily for five days. Fungal burden decreased 86% compared to the untreated control (see FIG. 14 showing vaginal fungal burden as determined by colony forming units (CFU) from vaginal lavage fluid).

C5. Agricultural Fungal Infection

The Ole1 protein inhibitors of the instant invention provide potent broad spectrum antifungal agents for a wide variety of agricultural purposes. Preferred embodiments comprise any of the inventive compounds disclosed herein based on and/or derived from compound I''', its salts and analogs. The inventive Ole1 protein inhibitors are suitable and efficacious for treating a fungal infection in the agricultural setting, including reducing the risk of a fungal infection, and in particular may be used for methods of treating an infection in a plant, or a grass, by contacting a plant with an Ole1 protein inhibitor according to the invention. Plants include trees, crops, grasses, and flowering plants.

Thus, contemplated in the present invention is a pesticide composition comprising and plant propagation material comprising any of the inventive compounds described herein, its derivatives, salts and analogs.

In a preferred embodiment, a pesticide composition is provided comprising compound X'''. In other preferred embodiments, the pesticide composition is provided comprising 14-(furan-2-yl)tetradeca-11,13-diynoic acid, compound X''' or its derivatives, especially its salts, such as compound XI''', or its analogs, providing effective and potent Ole1 protein inhibitors, in defeating or lessening agricultural fungal pathogens, providing effective and potent compounds for use in the agricultural setting.

In other embodiments are provided, incorporating the same inventive compounds, a plant propagation material, a system for protecting a plant from disease caused by a given susceptible fungus, and methods of controlling or preventing fungal infestation in plants, parts of plants, seeds, or at their locus of growth.

Also contemplated is a system for protecting a plant from disease caused by a given susceptible fungus, comprising inventive compounds X", its derivatives, salts and analogs.

Further, the present invention contemplates methods for preventing or controlling fungal infections in plants, parts of plants, seeds, or at their locus of growth.

C6. Efficacy in Agricultural Species

Compounds based on structure IX", X", XI" and XII" and analogs and derivatives have been tested on various agricultural setting fungal pathogens (see Example 20 below). Conidia/spores are the major source of spreading diseases, and if the sporulation is affected, disease spread in the farming field is contained. Thus, inhibiting sporulation is an indirect way of conducting disease control. Moreover, if sporulation is affected, the emergence of disease resistance is minimised, because the genetic changes which make the pathogen to adopt for the fungicide will not be carried to the next generation. The asexual fruit body of the plant pathogenic fungus *Colletotrichum gloeosporioides* is called acervulus. Acervuli, visible to the naked eye and salmon colour, are produced in concentric circles. When the potassium salt of compound X" was loaded on a sterile paper disc in the path of pathogen growth, the growth of the mycelia is arrested. Although the pathogen continues growth somewhat, there is no sporulation observed in mycelia grown around the region where the disc is loaded with test compound. The mycelia grown in the region diffused with the test compound was weak and did not differentiate into conidiophores—no sporulation observed.

Malformation and inhibition takes place in the spore germination in *M. grisea*.

Spore germination in the *M. grisea* control starts with small beak-like germination, which extends into long germ tube and culminates into an appressorium. The appressorium will be densely melanized to withstand the high turgor pressure created during penetration of infection peg through the plant cell wall. The germ tube starts from one or two terminal cells of a three-celled spore, and the process is completed in 8 hrs. When the spores were incubated in sterile water containing different concentrations of test compound (potassium salt of compound X"), more than 50% of spores did not germinate, and where small beak-like germination started in germinated spores: in some more spores, though the appressorium is formed, they were not melanised enough to withstand the pressure; breakage in the germ tube near the formation of appressoria was observed; some appressoria burst due to turgor pressure; and in some spores germ tubes formed from the middle cell, instead of from the terminal cells.

a. Ole1 Protein Inhibitor Compound Solubility

For desired antifungal activity in a clinical setting it is preferable that the inventive fungacides are soluble in water. In the preparation of pharmaceutical compositions comprising antifungal compounds to reach the site of disease and be functional there, water solubility is important, particularly the case with infections by a fungus which involve infection of inner organs or disseminated infections, but also in relation to treatment or reduction of risk of a fungal infection in agriculture where water solubility is crucial. Accordingly, the inventive compounds preferably have a water solubility of at least 50 mg/ml, preferably at least 60 mg/ml, more preferably at least 70 mg/ml, yet more preferably at least 80 mg/ml, even more preferably at least 90 mg/ml.

b. Crystalline Compound

An exemplary crystalline compound is the potassium (Z)-14-(furan-2-yl)tetradeca-9-en-11,13-diynoate, having a high resolution XPRD pattern comprising peaks at least at the following 2θ angles: 2.42° and 4.78°. In preferred embodiments, the potassium (Z)-14-(furan-2-yl)tetradeca-9-en-11,13-diynoate crystals have a high resolution XPRD pattern comprising peaks at least at the following 2θangles: 7.14°, 9.52° and 11.89°, or at the following 2θ angles: 2.42° and 4.78°, 7.14°, 9.52° and 11.89°, or at the following 2θ angles: 2.42°, 4.78°, 7.14°, 9.52°, 9.52°, 16.45°, 17.27°, 18.41°, 19.11°, 19.68°, 21.27°, 21.95°, 23.06°, 23.86°, 24.90°, 26.98°, 27.82°, 28.68°, 28.86° and 38.77°. Preferably, this high resolution XPRD pattern does not comprises any other peaks with an intensity of >5%.

c. Moisture Uptake

It is preferred that the fungacides according to the invention do not take up much moisture from the surroundings, and that the weight change of a compound is less than 5%, preferably less than 4%, more preferably less than 3%, even more preferably less than 2%, for example even less than 1% at a humidity of 60% RH compared to a humidity of 10% RH, or that the weight change of the compound is less than 5%, preferably less than 4% at a humidity of 70% RH compared to a humidity of 10% RH, or that if a crystalline compound is exposed to humidity higher than 80%, then upon return to a lower humidity, when moisture is lost its crystalline form is kept/regained.

d. Melting Temperature and Stability

It is also preferred that the inventive fungacides have a sufficiently high melting temperature to allow handling during manufacture of pharmaceutical compositions and storage at ambient temperature. Thus, it is preferred that the melting point of the compounds is at least 100° C., preferably at least 110° C., more preferably at least 120° C., yet more preferably at least 130° C., even more preferably at least 140° C., and are stable upon storage.

e. Formulations

The inventive compounds disclosed herein should be understood to include any pharmaceutically acceptable salts encompassing either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methanesulfonic acid, p-toluenesulfonic acid and the like or in case the compound is acidic in nature with an organic base such as, for example, triethylamine, triethanolamine, tert-butylamine, or an inorganic base like an alkali or earth alkali base, e.g. sodium hydroxide, potassium hydroxide, calcium hydroxide etc.

Because of their ability to inhibit a wide variety of fungal pathogens occurring in humans and/or animals, occurring both systemically and topically, the described compounds can be used for the treatment of diseases which are associated with an infection by such type of pathogens. They are valuable antifungal treatments.

The compounds can be administered orally, rectally, parenterally e.g. by intravenous, intramuscular, subcutaneous, intrathecal or transdermal administration or sublingually or as ophthalmic preparation or administered as aerosol. Examples of applications are capsules, tablets, orally administered suspensions or solutions, intravenous solutions, suppositories, injections, eye-drops, ointments or aerosols/nebulizers.

Preferred applications are oral or i.v. systemic formulations and ointment, pellet, liquid or liquid suspension topical formulations. The dosage used depends upon the type of the specific active ingredient, the age and the requirements of the patient and the kind of application. The preparations with the inventive compounds can contain inert or as well pharmacodynamically active excipients. Tablets or granules, for example, could contain a number of binding agents, filling excipients, carrier substances or diluents.

These pharmaceutical compositions may contain the compounds of the invention as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, lipids, liquid or half-liquid polyols etc. may be used. For the preparation of solutions and syrups e.g. water, polyols, saccharose, glucose etc. are used. Injectables are prepared by using e.g. water, polyols, alcohols, glycerin, vegetable oils, lecithin, liposomes etc. Suppositories may be prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, antioxidants etc.

f. Resistant Fungus Infections

Fungal infections may be resistant to treatment for many reasons, resistant to treatment with a particular antifungal agent, or because of acquired resistance. Thus, a further aspect of the invention is the use of the inventive compounds for treating infection by a fungus resistant to one or more alternative treatment and that acts via:
  a) inhibiting ergosterol biosynthesis;
  b) binding to ergosterol;
  c) inhibiting 1,3-β-glucan synthase;
  d) inhibiting epoxidase;
  e) inhibiting Leucyl-tRNA synthetase; and/or
  f) inhibition of elongation factor 2.

Particularly, such resistant antifungal treatments may be benzoic acid, ciclopirox, tolnaftate, undecylenic acid, flucytosine, griseofulvin, haloprogin and sodium bicarbonate or may be polyenes, azoles, allylamines or echinocandins. Polyene antifungal agents have multiple conjugated double bonds, and typically, also comprise a heavily hydroxylated region, exemplified by Natamycin, Rimocidin, Filipin, Nystatin, Amphotericin B or Candicin. Azole antifungal agents may for example be imidazole or triazole or thiazole antifungal agents. Imidazole antifungal agents may for example include miconazole, ketoconazole, clotromazole, econazole, bifonazole, butoconazole, fenticonazole, isoconazole, oxiconazole, seraconazole, sulconazole or tioconazole. Triazole antifungal agents may for example include fluconazole, itraconazole, isavuconazole, ravuconazole, posaconazole, voriconazole, terconazole, and abafungin. Allylamine antifungals include Terbinafine, Amorolfine, Naftifine or Butenafine. Non-limiting examples of echinocandins include Anidulafungin, Caspofungin or Micafungin.

D1. The Mechanism of Action of (Z)-14-(furan-2-yl)tetradeca-9-en-11,13-diynoic acid and its salts The potassium salt of (Z)-14-(furan-2-yl)tetradeca-9-en-11,13-diynoic acid (aka (9Z)-14-(2-furyl)tetradeca-11,13-diynoic acid) is shown as follows:

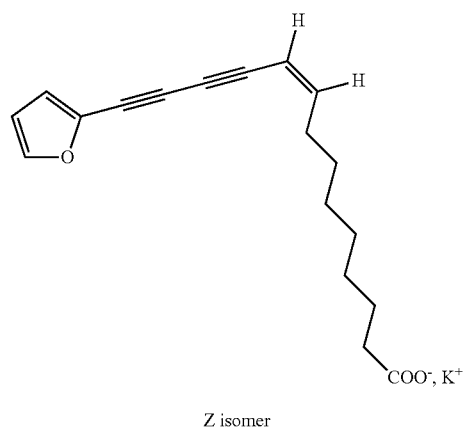

Z isomer

The mechanism of action of the sodium salt was investigated in a chemical-genetic screen in S. cerevisiae. The screen made use of the S. cerevisiae knock-out collection, which consists of 4917 individual strains each deleted for one defined gene. All 4917 strains were tested for increased or decreased susceptibility to this sodium salt. The rationale of the screen was chemical enhancement genetics. In biological systems, pathway redundancies ensure robust signaling of essential processes.

Given that a certain gene deletion strain is more susceptible to this sodium salt, it possible that the sodium salt acts on a redundant pathway. Inhibition of the two redundant pathways, one through the gene deletion, the other through the action of the sodium salt, will lead to cell death if both pathways regulate one common essential function. It is also possible that the sodium salt interferes with a complex that is already destabilized by the absence of the gene product of the deleted gene.

Together, the screen for gene deletion strains with increased or decreased susceptibility to the sodium salt highlights biological processes affected by sodium (Z)-14-(furan-2-yl)tetradeca-9-en-11,13-diyno ate.

From 4917 analyzed strains of the S. cerevisiae knock-out collection, 44 had an increased susceptibility to the sodium salt. No strain with a decreased susceptibility was identified (Knechtle, P. and Greve, K., 2008). The S. cerevisiae GO-Slim vocabulary was used to map the identified genes to higher level biological processes. The GO-Slim vocabulary consists of higher level gene ontology terms used to describe the biology of a gene product. From a total of 39 biological processes available, the 44 genes identified mapped to 29 processes, from which "lipid metabolic process" ($p<0.004$) and "organelle organization and biogenesis" ($p<0.04$) were significantly overrepresented.

Figure 19:
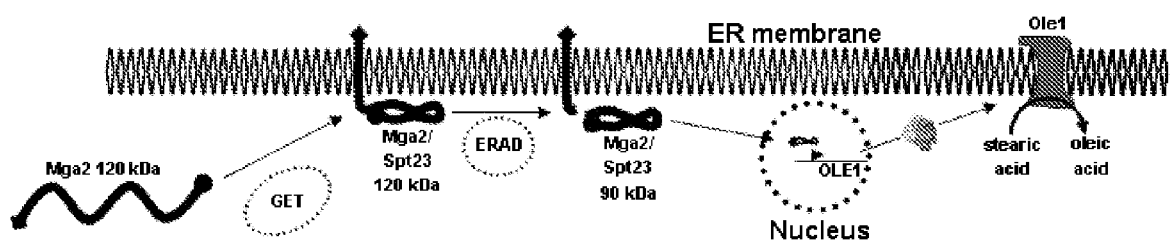
FIG. 19 shows regulation of OLE1 transcriptional activation. Components of the GET complex putatively mediate the insertion of Mga2/Spt23 into the ER membrane. The ERAD complex proteolytically activates Mga2/Spt23, which shuttles to the nucleus where it activates OLE1 transcription.

Among the genes identified was MGA2, which encodes a transcriptional activator of the OLE1 Δ9-fatty acid desaturase. MGA2 is a duplicated gene in S. cerevisiae with SPT23 being its homolog. The Ole1 protein converts stearic to oleic acid and palmitic to palmitoleic acid, respectively, and is an essential gene in S. cerevisiae. Another six genes from the identified set of 44 genes could be assembled together with MGA2 to a pathway likely to regulate OLE1 transcriptional activation. This pathway included components of the ERAD (endoplasmatic reticulum associated protein degradation) complex required for the proteolytic activation of Mga2 and genes coding for GET complex components, which is putatively required to insert Mga2 into the membrane of the endoplasmatic reticulum (see FIG. 19).

Mutations in genes of this three-step pathway most likely decrease the expression of the OLE1 gene. Consequently, less Ole1 protein is available in these mutant cells and thus the levels of oleic acid decreased, suggesting that decreased levels of endogenous oleic acid increases the susceptibility to the sodium salt.

Figure 20:
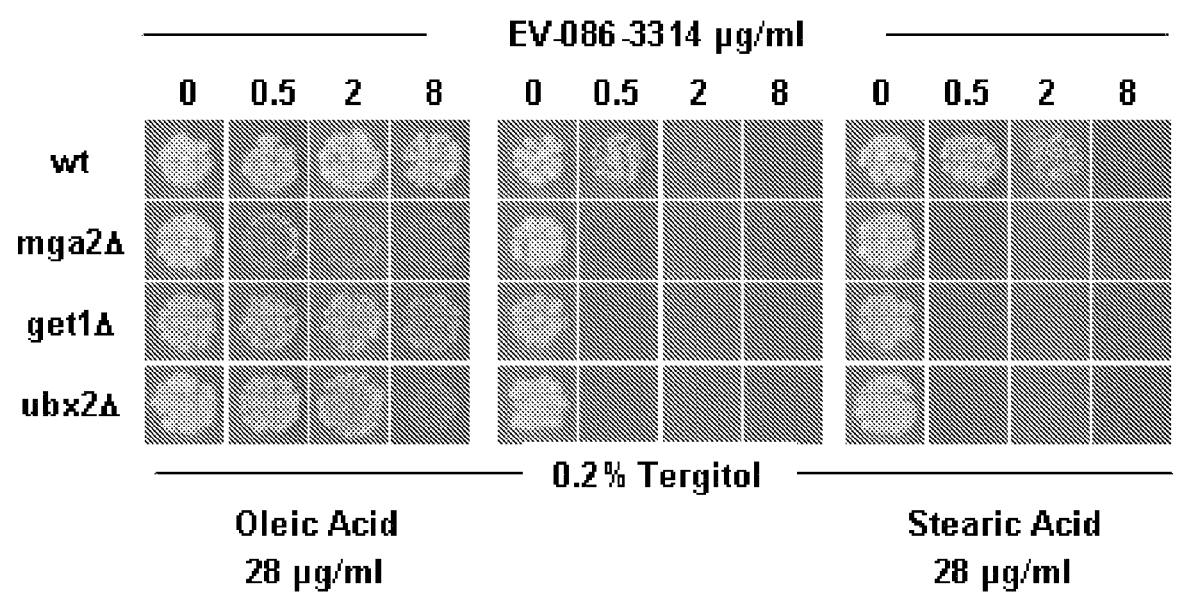
FIG. 20 shows oleic acid antagonizes the sodium salt of (Z)-14-(furan-2-yl)tetradeca-9-en-11,13-diynoic acid. YPD agar plates were prepared containing 0, 0.5, 2 and 8 µg/ml of (Z)-14-(furan-2-yl)tetradeca-9-en-11,13-diynoic acid. The plates were either supplemented with 28 µg/ml oleic acid, 28 µg/ml stearic acid or 0.2% Tergitol alone as control required for solubilisation of the fatty acids. Suspensions of MGA2, GET1 and UBX2 deletion strains and wild-type were spotted and the plates incubated for 2d at 30° C.

Indeed, the addition of exogenous oleic acid counteracted the increased sensitivity to the sodium salt of (Z)-14-(furan-2-yl)tetradeca-9-en-11,13-diynoic acid of the identified mutants (2). In the wild-type, the addition of oleic acid decreased the sensitivity to the sodium salt of (Z)-14-(furan-2-yl)tetradeca-9-en-11,13-diynoic acid. Stearic acid, however, decreased the sensitivity to Na—(Z)-14-(furan-2-yl)tetradeca-9-en-11,13-diynoic acid only marginally (see FIG. 20).

This direct competition between oleic acid and Na—(Z)-14-(furan-2-yl)tetradeca-9-en-11,13-diynoic acid suggests that Na—(Z)-14-(furan-2-yl)tetradeca-9-en-11,13-diynoic acid is an inhibitor of oleic acid biosynthesis. Inhibition is taking place at the conversion of stearic to oleic acid, since stearic acid does not compete with Na—(Z)-14-(furan-2-yl)tetradeca-9-en-11,13-diynoic acid.

Mechanistically, it is likely that Na—(Z)-14-(furan-2-yl)tetradeca-9-en-11,13-diynoic acid inhibits the biosynthesis of oleic acid, either through direct inhibition of the $\Delta 9$ fatty acid desaturase Ole1 or through inhibition of Mga2 dependent transcriptional activation of OLE1, thereby inducing an oleic acid auxotrophy to the cell as it is observed for cells deleted for the OLE1 gene (Stukey, J. E. et al., "Isolation and characterization of OLE1, a gene affecting fatty acid desaturation from *Saccharomyces cerevisiae*", J Biol Chem 264 (28), 16537-16544 (1989)).

OLE1 transcriptional levels were determined to distinguish between these two hypotheses, and to generally confirm the oleic acid biosynthesis inhibitory model.

Assuming that the potassium salt of (Z)-14-(furan-2-yl)tetradeca-9-en-11,13-diynoic acid directly inhibited the Ole1 protein, a compensating up-regulation of the OLE1 transcriptional level for the potassium salt of (Z)-14-(furan-2-yl)tetradeca-9-en-11,13-diynoic acid treated cells would be expected. If the potassium salt of (Z)-14-(furan-2-yl)tetradeca-9-en-11,13-diynoic acid inhibited Mga2 or any other component required for OLE1 transcriptional activation such as the GET complex or the CDC48 proteasome, a down-regulation of OLE1 for the potassium salt treated cells would be expected. potassium salt independent transcription of OLE1 would indicate another mechanism of action and suggested that the antagonistic effect of oleic acid with potassium salt was indirect.

*S. cerevisiae* was cultured in the presence of 1 and 10 μg/ml of the potassium salt, 10 μg/ml oleic acid and 1 μg/ml of the potassium salt combined with 10 μg/ml oleic acid. The calculated doubling times are shown in Table 24 below.

TABLE 24

Doubling times of *S. cerevisiae* in the presence of the potassium salt of (Z)-14-(furan-2-yl) tetradeca-9-en-11,13-diynoic acid and/or oleic acid

| condition | | oleic acid | Doubling time in h |
| --- | --- | --- | --- |
| A | — | — | 2.0 |
| B | 1 μg/ml | — | 2.4 |
| C | 10 μg/ml | — | 4.2 |
| D | — | 10 μg/ml | 2.0 |
| E | 1 μg/ml | 10 μg/ml | 2.1 |

The potassium salt of (Z)-14-(furan-2-yl)tetradeca-9-en-11,13-diynoic acid increased the doubling times in a concentration dependent manner, which was reversed by the addition of oleic acid.

The expression of OLE1 was determined by real time PCR 10, 60, 120 and 240 min after compound addition (Knechtle, P. and Greve, K., 2009). OLE1 transcript levels were calibrated to the expression of the tubulin gene (TUB1) and normalized to the OLE1 expression at 10 min without compound addition (FIG. 17(a)).

Expression levels of OLE1 in cultures without the potassium salt of (Z)-14-(furan-2-yl)tetradeca-9-en-11,13-diynoic acid did not vary significantly over the time scale investigated. The addition of 1 μg/ml of the potassium salt of (Z)-14-(furan-2-yl)tetradeca-9-en-11,13-diynoic acid increased the expression level of OLE1 about 3-5 fold (4.9 fold at 120 min, p<0.023) and 10 μg/ml increased the expression level about 7-19-fold (18.7 fold at 120 min, p<0.018). As reported elsewhere, the addition of 10 μg/ml oleic acid alone decreased the expression level of OLE1 about 6-fold, which was confirmed in the experiment (condition "d"). 10 μg/ml oleic acid compensated for the OLE1 increase caused by 1 μg/ml of the Potassium salt of (Z)-14-(furan-2-yl)tetradeca-9-en-11,13-diynoic acid alone.

The potassium salt (Z)-14-(furan-2-yl)tetradeca-9-en-11,13-diynoic acid dependent up-regulation of OLE1 strongly favours the first hypothesis with the potassium salt of (Z)-14-(furan-2-yl)tetradeca-9-en-11,13-diynoic acid as an inhibitor of the Ole1 protein. The antagonistic effect of oleic acid, which was found in the susceptibility assays, is reflected mechanistically in this experiment by a down-regulation of the target Ole1 through oleic acid.

For all described genes above, a sequence homologue had been identified in *C. albicans*, which indicates that the identified process is conserved in at least these two organisms. For *S. cerevisiae* MGA2/SPT23 and OLE1, even functional homologues have been described in *C. albicans* (Krishnamurthy, S. et al., "Dosage-dependent functions of fatty acid desaturase Ole1p in growth and morphogenesis of *Candida albicans*.", Microbiology 150(Pt 6), 1991-2003 (2004); Martin, C. E. et al., "Regulation of long chain unsaturated fatty acid synthesis in yeast.", Biochim. Biophys. Acta 1771(3), 271-285 (2007); Oh, C. S. et al., "*Candida albicans* Spt23p controls the expression of the Ole1p Delta9 fatty acid desaturase and regulates unsaturated fatty acid biosynthesis.", J. Biol. Chem. 281(11), 7030-7039 (2006)).

Sequence homologues were further identified in *Aspergillus* and *Cryptococcus* (Kraus, P. R. et al., "Identification of *Cryptococcus neoformans* temperature-regulated genes with a genomic-DNA microarray.", Eukaryot. Cell 3(5), 1249-1260 (2004); Wilson, R. A. et al., "Two Delta9-stearic acid desaturases are required for *Aspergillus nidulans* growth and development", Fungal. Genet. Biol. 41(5), 501-509 (2004)).

Competition assays were done in *C. albicans* to investigate the antagonistic effect of oleic acid to the potassium salt of (Z)-14-(furan-2-yl)tetradeca-9-en-11,13-diynoic acid.

As in *S. cerevisiae*, oleic acid but not stearic acid antagonized the effect of the potassium salt of (Z)-14-(furan-2-yl)tetradeca-9-en-11,13-diynoic acid in *C. albicans* (see FIG. 21). We have also identified linoleic acid and palmitoleic (but not palmitic acid) as antagonists of the potassium salt of (Z)-14-(furan-2-yl)tetradeca-9-en-11,13-diynoic acid in *C. albicans*, which are all $\Delta 9$-unsaturated fatty acids. In *S. cerevisiae*, different $\Delta 9$-unsaturated fatty acids including palmitoleic and linoleic acid, but not saturated fatty acids, have been shown to complement the oleic acid auxotrophy of OLE1 deletion strains (1), which further supports our model.

In contrast, oleic acid did not decrease the susceptibility of *C. albicans* to Voriconazole, AmphotericinB or Caspofungin, which represent the relevant classes of clinical antifungal compounds. This corroborates that the oleic acid auxotrophy induced by the potassium salt of (Z)-14-(furan-2-yl)tetradeca-9-en-11,13-diynoic acid is not a general stress response of the cell but specific to the potassium salt of (Z)-14-(furan-2-yl)tetradeca-9-en-11,13-diynoic acid (FIG. 22).

Figure 23:
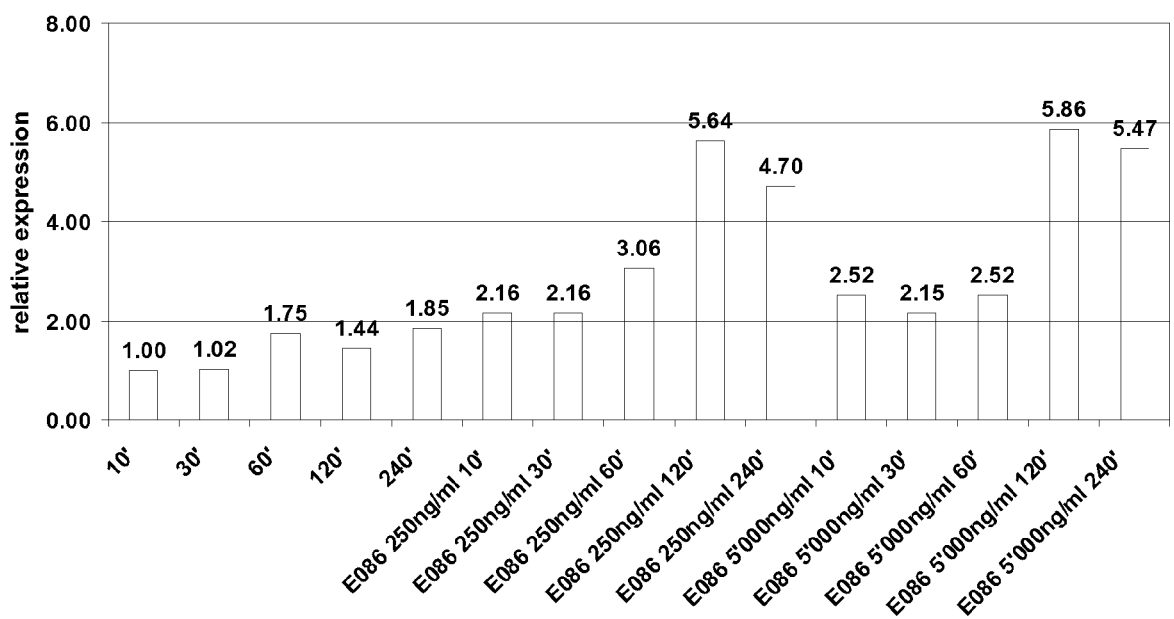
FIG. 23 shows time and concentration dependent expressions of OLE1 in response to the potassium salt of (Z)-14-(furan-2-yl)tetradeca-9-en-11,13-diynoic acid in *Candida albicans*. Numbers indicate time intervals in minutes. Expression values are normalized to TUB1 and given as multiples of OLE1 expression at 10 minutes in ethanol.

Further, the expression of OLE1 in *C. albicans* was investigated in response to the potassium salt of (Z)-14-(furan-2-yl)tetradeca-9-en-11,13-diynoic acid (Knechtle, P. and Greve, K., "EV-086-3314K up-regulates OLE1 expression in *Candida albicans*," in REP-S-EV-086-3314-0092 ed. (Evolva, 2009)). In the presence of 250 ng/ml of the potassium salt of (Z)-14-(furan-2-yl)tetradeca-9-en-11,13-diynoic acid, OLE1 transcript levels were increased 4-fold after 120 min incubation time compared to the drug free control (FIG. 23). These results demonstrate a conservation of the mechanism of action between *S. cerevisiae* and *C. albicans*.

From a structural point of view the potassium salt of (Z)-14-(furan-2-yl)tetradeca-9-en-11,13-diynoic acid is similar to oleic acid. The molecules share a $\Delta$9-monounsaturated decanoic acid group characteristic for unsaturated fatty acids in fungi. (Z)-14-(furan-2-yl)tetradeca-9-en-11,13-diynoic acid might therefore be recognized as a fatty acid and incorporated as an acyl chain into membrane lipids. The rapid incorporation of exogenous non *S. cerevisiae* fatty acids into lipids has previously been shown (8). (Z)-14-(furan-2-yl)tetradeca-9-en-11,13-diynoic acid-oyl lipids might then inhibit the Ole1 protein. Inhibition, however could also take place through free (Z)-14-(furan-2-yl)tetradeca-9-en-11,13-diynoic acid.

Thus, there is strong evidence that the potassium salt of (Z)-14-(furan-2-yl)tetradeca-9-en-11,13-diynoic acid inhibits oleic acid biosynthesis through inhibition of the Ole1 protein. The process is likely to be conserved across the entire fungal kingdom and it represents a novel mechanism of action that has so far not been described for any antimicrobial compound in clinical development or on market.

EXAMPLES

The invention is furthermore illustrated by the following non-limiting examples.

Example 1

This example describes the characterisation of (Z)-14-(furan-2-yl)tetradeca-9-en-11,13-diynoic acid (herein after in this example designated "the material").

An X-Ray Powder Diffraction (XRPD) analysis was performed to determine crystallinity of the material. X-Ray Powder Diffraction patterns were collected on a Siemens D5000 diffractometer using Cu K$\alpha$ radiation (40 kV, 40 mA), $\theta$-$\theta$ goniometer, divergence of V20 and receiving slits, a graphite secondary monochromator and a scintillation counter. The software used for data collection was Diffrac Plus XRD Commander v2.3.1 and the data were analysed and presented using Diffrac Plus EVA v 11.0.0.2 or v 13.0.0.2.

Samples run under ambient conditions were prepared as flat plate specimens using the material. Approximately 35 mg of the sample was gently packed into a cavity cut into polished, zero-background (510) silicon wafer. The sample was rotated in its own plane during analysis. The details of the data collection are:

Angular range: 2 to 42 °2$\theta$
Step size: 0.05 °2$\theta$
Collection time: 4 s.step$^{-1}$ The analysis shows that the material has good crystallinity. Material having the XRPD pattern similar to the material prior to any subsequent treatment is designated "Form 1".

A Differential Scanning calorimetry (DSC) was performed. DSC data were collected on a TA Instruments Q2000 equipped with a 50 position auto-sampler. The instrument was calibrated for energy and temperature calibration using certified indium. Typically 0.5 mg of each sample, in a pin-holed aluminium pan, was heated at 10° C.min$^{-1}$ from 25° C. to 300° C. A nitrogen purge at 50 ml.min$^{-1}$ was maintained over the sample.

The instrument control software was Advantage for Q Series v2.8.0.392 and Thermal Advantage v4.8.3 and the data were analysed using Universal Analysis v4.3A.

The DSC trace shows a melting temperature with an onset of 45° C., then an exotherm of degradation with an onset of 171° C.

Also a Thermo-Gravimetric Analysis (TGA) was performed to determine the melting temperature and heat stability of the material. TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C.min$^{-1}$ from ambient temperature to 350° C. A nitrogen purge at 60 ml.min$^{-1}$ was maintained over the sample.

The instrument control software was Advantage for Q Series v2.8.0.392 and Thermal Advantage v4.8.3

The TGA trace of the material showed no weight loss until the start of the degradation at approximately 160° C.

Solubility in water was determined. This was carried out by transferring 10 mg of the material into 1.5 ml HPLC vials. Then 10 µl (1 vol) of water was added. The sample was then isothermally held at 50° C. with stirring for 30 mins. The process was continued up to 50 µl by 10 µl increments with heating to 50° C. in between. The material however still did not dissolve.

Example 2

Bases used for preparation of salts of (Z)-14-(furan-2-yl)tetradeca-9-en-11,13-diynoic acid are shown in Table 3.

TABLE 3

| Base | Class | pKa | Solution. |
| --- | --- | --- | --- |
| Potassium ethoxide | 1 | 14.00 | 1M EtOH |
| Sodium ethoxide | 1 | 14.00 | 1M EtOH |
| L-Arginine | 1 | 13.20 | 0.5M H2O |
| L-Lysine | 1 | 10.79 | 0.5M H2O |
| Ammonium hydroxide | 1 | 9.27 | 2M EtOH |
| Dimethylaminoethanol | 1 | 8.83 | 1M EtOH |
| N-Methylglucamine | 1 | 8.03 | 1M H2O |

Several of the bases employed were only soluble in water and water miscible solvents were therefore employed. To this end the use of IPA, Dioxane, EtOH and acetone were selected.

(Z)-14-(furan-2-yl)tetradeca-9-en-11,13-diynoic acid (25 mg) was dissolved in solvent (250 µl, 10 volumes) and the mixture warmed to 50° C. The base solution was added (1.1 eq) and the reactions were then allowed to cool. Reactions that did not produce any solid were allowed to cool to 18° C. and if no solid had formed they were then allowed to slowly evaporate.

The results using IPA as solvent are shown in Table 4

TABLE 4

| Experiment | Base | RT | Cool - 18° C. | Evaporation |
|---|---|---|---|---|
| DJP401-006-1 | Potassium ethoxide 1M in EtOH 97 µl | Solid filtered off | n/a | n/a |
| DJP401-006-2 | Sodium ethoxide 1M in EtOH 97 µl | Solid at addition, filtered off | n/a | n/a |

TABLE 4-continued

| Experiment | Base | RT | Cool - 18° C. | Evaporation |
|---|---|---|---|---|
| DJP401-006-3 | L-Arginine 0.5M in H2O 194 µl | Solution | Solution | Gum |
| DJP401-006-4 | L-Lysine 0.5M in H2O 194 µl | Solution | Solution | Gum |
| DJP401-006-5 | Ammonium hydroxide 2M in EtOH 48 µl | Solution | Solution | Gum |
| DJP401-006-6 | Dimethylaminoethanol 1M in EtOH 97 µl | Solution | Solution | Gum |

The results using dioxane, ethanol or acetone as solvents are shown in Table 5.

TABLE 5

| Experiment | Solvent | Base | RT | Cool - 18° C. | Evaporation |
|---|---|---|---|---|---|
| DJP401-009-1 | Dioxane | Potassium ethoxide 1M in EtOH 97 µl | Solid formed upon cooling | n/a | n/a |
| DJP401-009-2 | Dioxane | Sodium ethoxide 1M in EtOH 97 µl | Solid formed upon addition | n/a | n/a |
| DJP401-009-3 | Dioxane | L-Arginine 0.5M in H2O 194 µl | Solution | Frozen solid | Gum |
| DJP401-009-4 | Dioxane | L-Lysine 0.5M in H2O 194 µl | Solution | Frozen solid | Gum |
| DJP401-009-5 | Dioxane | Ammonium hydroxide 2M in EtOH 48 µl | Solution | Frozen solid | Gum |
| DJP401-009-6 | Dioxane | Dimethylaminoethanol 1M in EtOH 97 µl | Solution | Frozen solid | Gum |
| DJP401-009-7 | Dioxane | N-Methylglucamine 1M in H2O 97 µl | Solution | Frozen solid | gum |
| DJP401-009-8 | EtOH | Potassium ethoxide 1M in EtOH 97 µl | Solid formed upon cooling | n/a | n/a |
| DJP401-009-9 | EtOH | Sodium ethoxide 1M in EtOH 97 µl | Solid formed upon addition | n/a | n/a |
| DJP401-009-10 | EtOH | L-Arginine 0.5M in H2O 194 µl | Solution | Solution | Gum |
| DJP401-009-11 | EtOH | L-Lysine 0.5M in H2O 194 µl | Solution | Solution | Gum |
| DJP401-009-12 | EtOH | Ammonium hydroxide 2M in EtOH 48 µl | Solution | Solution | Gum |
| DJP401-009-13 | EtOH | Dimethylaminoethanol 1M in EtOH 97 µl | Solution | Solution | Gum |
| DJP401-009-14 | EtOH | N-Methylglucamine 1M in H2O 97 µl | Solution | Solution | Gum |
| DJP401-009-15 | Acetone | Potassium ethoxide 1M in EtOH 97 µl | Solid formed upon cooling | n/a | n/a |
| DJP401-009-16 | Acetone | Sodium ethoxide 1M in EtOH 97 µl | Solid formed upon addition | n/a | n/a |
| DJP401-009-17 | Acetone | L-Arginine 0.5M in H2O 194 µl | Solution | Solution | Gum |
| DJP401-009-18 | Acetone | L-Lysine 0.5M in H2O 194 µl | Solution | Solution | Gum |
| DJP401-009-19 | Acetone | Ammonium hydroxide 2M in EtOH 48 µl | Solution | Solution | Gum |
| DJP401-009-20 | Acetone | Dimethylaminoethanol 1M in EtOH 97 µl | Solution | Solution | gum |
| DJP401-009-21 | Acetone | N-Methylglucamine 1M in H2O 97 µl | Solution | Solution | Gum |

The reactions only yielded gums for most of the bases tried. The only exception was the reactions with potassium ethoxide and the sodium ethoxide. These solids were analysed by XRPD (XRPD performed as described herein above in Example 1). The potassium salts were all crystalline and appeared to be the same solid form and the sodium salts were all amorphous but there were some hints of crystallinity.

The potassium and sodium salts were scaled up to a 100 mg scale of the free acid to provide more material for characterisation. In an attempt to allow the sodium salt to crystallise the sodium reaction was carried out in a more dilute fashion and also both reactions were carried out at 70° C. The experiments are summarized in Table 6.

TABLE 6

| Experiment | Solvent | Base + amount | Result |
| --- | --- | --- | --- |
| DJP401-007-1 | IPA (1 ml) | KOEt (388 µl, 1M in EtOH) | Solid crystallised while still warm. |
| DJP401-007-1 | IPA (2 ml) | NaOEt (388 µl, 1m IN EtOH) | Solid precipitated upon addition of base. |

The solids from these reactions were analysed by XRPD and the diffractograms are shown in FIG. 1. This X-Ray Powder Diffraction pattern was collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2.

Samples run under ambient conditions were prepared as flat plate specimens using powder. Approximately 1-2 mg of the sample was lightly pressed on a glass slide to obtain a flat surface.

As can be seen in FIG. 1 the potassium salt was crystalline and the sodium salt was amorphous with some hints of crystallinity.

The potassium salt was analysed by various techniques in order to fully understand its solid form behaviour. A high resolution XRPD diffractogram was prepared. These X-Ray Powder Diffraction patterns were collected on a Bruker D8 diffractometer using Cu K radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v 11.0.0.2 or v 13.0.0.2.

Figure 2A:
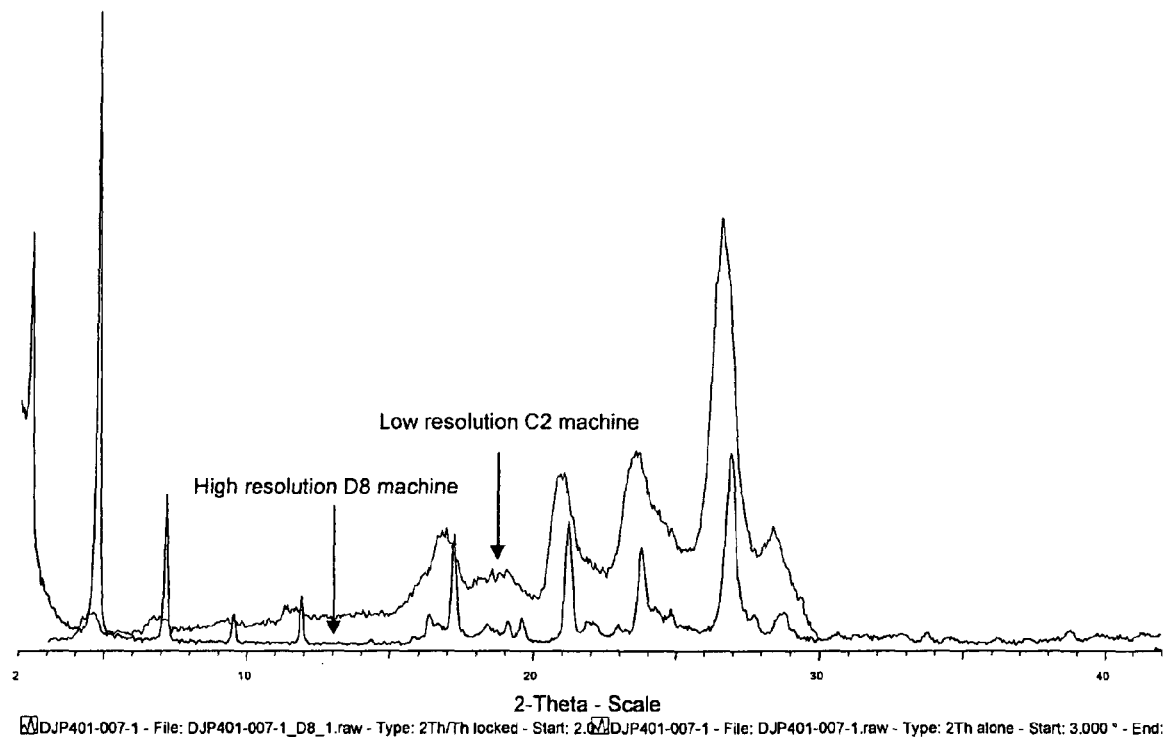
FIG. 2 shows a high resolution XRPD diffractogram and a low resolution XPRD diffractogram as indicated in the figure of the potassium (Z)-14-(furan-2-yl)tetradeca-9-en-11,13-diynoate.

Samples were run under ambient conditions as flat plate specimens. Approximately 20 mg of the sample was gently packed into a cavity cut into polished, zero-background (510) silicon wafer. The sample was rotated in its own plane during analysis. The details of the data collection are:
Angular range: 2 to 42° 2θ
Step size: 0.05° 2θ
Collection time: 0.5 s.step$^{-1}$ The result is shown in FIG. 2A.

The free acid (100 mg) was dissolved in THF (1 ml) and warmed to 50° C. before the addition of potassium ethoxide (388 ml, 1M in EtOH). The reaction was then cooled and the solid produced filtered and dried under suction and then analysed by high resolution XRPD on a Bruker D8 diffractometer as described above. The 2θ angles were calculated at Cu—Kα, λ=1.54173. The diffractogram with the 2θ angles of the peaks with an intensity >5% are shown in FIG. 2B. The 2θ Angle, d value, Å and intensity of peaks are indicated in Table 7.

TABLE 7

| Peak No. | 2θ Angle° | d value, Å | Intensity, % |
| --- | --- | --- | --- |
| 1 | 2.42 | 36.56055 | 87.50 |
| 2 | 4.78 | 18.47136 | 100.00 |
| 3 | 7.14 | 12.36523 | 27.90 |
| 4 | 9.52 | 9.28642 | 7.30 |
| 5 | 11.89 | 7.43965 | 9.50 |
| 6 | 16.45 | 5.38417 | 5.70 |
| 7 | 17.27 | 5.13092 | 15.10 |
| 8 | 18.41 | 4.81433 | 4.30 |
| 9 | 19.11 | 4.64095 | 5.20 |
| 10 | 19.68 | 4.50779 | 4.50 |
| 11 | 21.27 | 4.17455 | 18.30 |
| 12 | 21.95 | 4.04675 | 4.60 |
| 13 | 23.06 | 3.85315 | 3.40 |
| 14 | 23.86 | 3.72571 | 13.10 |
| 15 | 24.90 | 3.57343 | 5.30 |
| 16 | 26.98 | 3.30246 | 27.80 |
| 17 | 27.82 | 3.20449 | 5.10 |
| 18 | 28.68 | 3.10984 | 5.50 |
| 19 | 28.86 | 3.09123 | 6.00 |
| 20 | 38.77 | 2.32077 | 3.50 |

Figure 3:
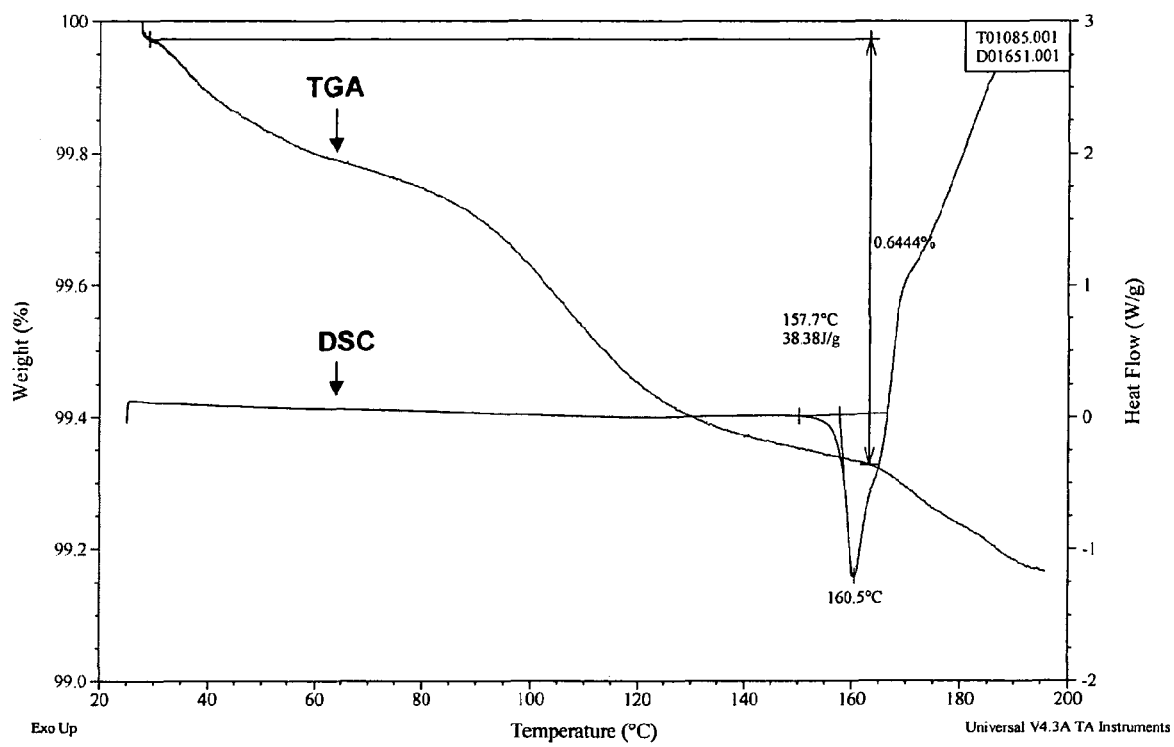
FIG. 3 shows TGA and DSC analysis (as indicated in the figure) of potassium (Z)-14-(furan-2-yl)tetradeca-9-en-11,13-diynoate.

The potassium salt was also analysed by TGA (TGA performed as described herein above in Example 1) and DSC (DSC performed as described herein above in Example 1) and the data is shown in FIG. 3.

The material shows only a small loss in the TGA until decomposition start at approximately 170° C. The DSC shows a melting temperature with an onset of 159° C. followed by gross decomposition peaking at 192.5° C.

The potassium salt was furthermore submitted to a solubility determination. Aqueous solubility was determined by suspending sufficient compound in water to give a maximum final concentration of ≥100 mg.ml-1 of the parent free-form of the compound. The suspension was equilibrated at 25° C. for 24 hours then the pH was measured. The suspension was then filtered through a glass fibre C filter into a 96 well plate. The filtrate was then diluted by a factor of 101. Quantification was by HPLC with reference to a standard solution of approximately 0.1 mg.ml-1. in DMSO. Different volumes of the standard, diluted and undiluted sample solutions were injected. The solubility was calculated using the peak areas determined by integration of the peak found at the same retention time as the principal peak in the standard injection. Analysis was performed on an Agilent HP1100 series system equipped with a diode array detector and using ChemStation software vB.02.01-SR1.

The aqueous solubility of potassium (Z)-14-(furan-2-yl) tetradeca-9-en-11,13-diynoate was >96.5 mg/ml.

The potassium salt was also analysed by GVS.

Sorption isotherms were obtained using a Hiden IGASorp moisture sorption analyser, controlled by CFRSorp software. The sample temperature was maintained at 25° C. by a Huber re-circulating water bath. The humidity was controlled by mixing streams of dry and wet nitrogen, with a total flow rate of 250 ml.min-1. The relative humidity (RH) was measured by a calibrated Vaisala RH probe (dynamic range of 0-95% RH), located near the sample. The weight change, (mass relaxation) of the sample as a function of % RH was constantly monitored by the microbalance (accuracy ±0.001 mg). Typically 10-20 mg of sample was placed in a tared mesh stainless steel basket under ambient conditions. The sample was loaded and unloaded at 40% RH and 25° C. (typical room conditions). A moisture sorption isotherm was performed. The software uses a least squares minimisation procedure together with a model of the mass relaxation, to predict an asymptotic value. The measured mass relaxation value must be within 5% of that predicted by the software, before the next % RH value is selected. The sample was recovered after completion of the isotherm and re-analysed by XRPD.

Figure 4:
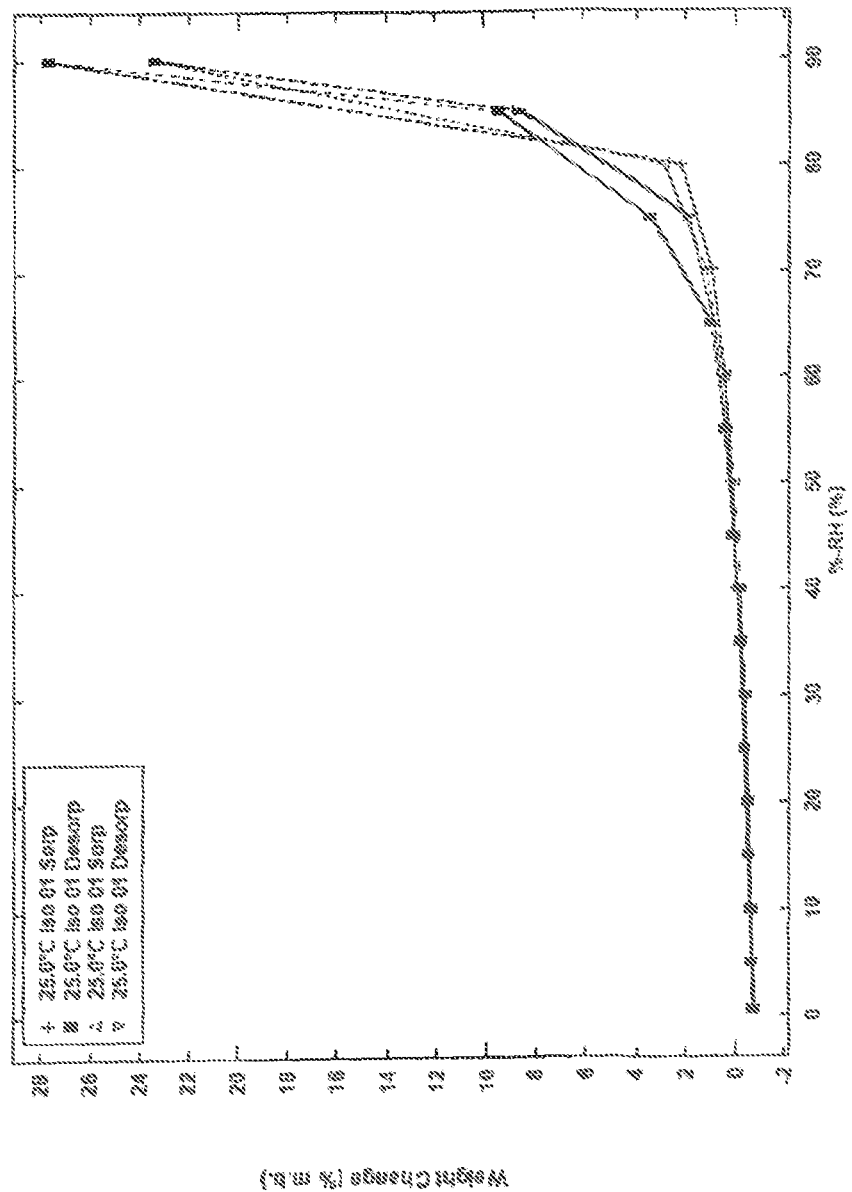
FIG. 4 shows a GVS analysis of the potassium salt of potassium (Z)-14-(furan-2-yl)tetradeca-9-en-11,13-diynoate.

The result of the GVS analysis is shown in FIG. 4. As shown the potassium (Z)-14-(furan-2-yl)tetradeca-9-en-11,13-diynoate takes up very little moisture until it reaches approximately 70-80% RH at which point the sample almost certainly deliquesces due to the massive uptake of 28% in weight at 90% RH. The sample does however loose this moisture upon going to lower RH levels. The sample was analysed by XRPD post GVS and the diffractogram was similar to the diffractogram pre GVS.

Example 3

The example describes attempts to prepare crystalline sodium, arginine or lysine salts of (Z)-14-(furan-2-yl)tetradeca-9-en-11,13-diynoic acid.

Free acid (300 mg) was suspended in water (30 ml) and 1 eq of base was added. After 5 minutes of stirring, a clear solution was obtained. The solution was frozen and dried via lyophilisation. For the maturation of the amorphous sodium, arginine and lysine salts approximately 10 mg of the amorphous salt was treated with 200 µl of solvent and then placed in a maturation chamber that cycled between 50° C. and ambient with four hours spent under each condition. The experiments were maturated for four days and then any solids produced were analyzed by XRPD. The results are shown in Table 8 (sodium salt), Table 9 (arginine salt) and Table 10 (lysine salt).

TABLE 8

| Experiment | Solvent | Observation |
|---|---|---|
| DJP401-022-1 | Ethyl acetate | Amorphous |
| DJP401-022-2 | Isopropyl acetate | Amorphous |
| DJP401-022-3 | Ethanol | Amorphous |
| DJP401-022-4 | Methanol | In solution |
| DJP401-022-5 | IPA | Amorphous |
| DJP401-022-6 | 1-Butanol | Amorphous |
| DJP401-022-7 | Acetone | Amorphous |
| DJP401-022-8 | Butanone | Amorphous |
| DJP401-022-9 | MIBK | Amorphous |
| DJP401-022-10 | Toluene | Amorphous |
| DJP401-022-11 | Dioxane | Amorphous |
| DJP401-022-12 | THF | Amorphous |
| DJP401-022-13 | MeCN | Amorphous |
| DJP401-022-14 | IPA + 5% H2O | Amorphous |
| DJP401-022-15 | MeCN + 5% H2O | Amorphous |
| DJP401-022-16 | Ethanol + 5% H2O | Amorphous |
| DJP401-022-17 | Dioxane + 5% H2O | Amorphous |
| DJP401-022-18 | Acetone + 5% H2O | Gum |
| DJP401-022-19 | THF + 5% H2O | Oiled out |
| DJP401-022-20 | Methanol + 5% H2O | In solution |

TABLE 9

| Experiment | Solvent | Observation |
|---|---|---|
| DJP401-023-1 | Ethyl acetate | Amorphous |
| DJP401-023-2 | Isopropyl acetate | Amorphous |
| DJP401-023-3 | Ethanol | Amorphous |
| DJP401-023-4 | Methanol | In solution |
| DJP401-023-5 | IPA | Oiled out |
| DJP401-023-6 | 1-Butanol | Amorphous |
| DJP401-023-7 | Acetone | Oiled out |
| DJP401-023-8 | Butanone | In solution |
| DJP401-023-9 | MIBK | Amorphous |
| DJP401-023-10 | Toluene | In solution |
| DJP401-023-11 | Dioxane | Amorphous |
| DJP401-023-12 | THF | In solution |
| DJP401-023-13 | MeCN | Amorphous |
| DJP401-023-14 | IPA + 5% H2O | Oiled out |
| DJP401-023-15 | MeCN + 5% H2O | Oiled out |
| DJP401-023-16 | Ethanol + 5% H2O | Oiled out |
| DJP401-023-17 | Dioxane + 5% H2O | In solution |
| DJP401-023-18 | Acetone + 5% H2O | In solution |
| DJP401-023-19 | THF + 5% H2O | Oiled out |
| DJP401-023-20 | Methanol + 5% H2O | In solution |

TABLE 10

| Experiment | Solvent | Observation |
|---|---|---|
| DJP401-024-1 | Ethyl acetate | Amorphous |
| DJP401-024-2 | Isopropyl acetate | Amorphous |
| DJP401-024-3 | Ethanol | Amorphous |
| DJP401-024-4 | Methanol | Solution |
| DJP401-024-5 | IPA | Amorphous |
| DJP401-024-6 | 1-Butanol | Amorphous |
| DJP401-024-7 | Acetone | Amorphous |
| DJP401-024-8 | Butanone | Amorphous |
| DJP401-024-9 | MIBK | Amorphous |
| DJP401-024-10 | Toluene | Amorphous |
| DJP401-024-11 | Dioxane | Amorphous |
| DJP401-024-12 | THF | Amorphous |
| DJP401-024-13 | MeCN | Amorphous |
| DJP401-024-14 | IPA + 5% H2O | Amorphous |
| DJP401-024-15 | MeCN + 5% H2O | Amorphous |
| DJP401-024-16 | Ethanol + 5% H2O | Amorphous |
| DJP401-024-17 | Dioxane + 5% H2O | Oiled out |
| DJP401-024-18 | Acetone + 5% H2O | Oiled out |
| DJP401-024-19 | THF + 5% H2O | Oiled out |
| DJP401-024-20 | Methanol + 5% H2O | Oiled out |

No crystalline sodium, arginine or lysine was obtained.

Example 4

This example describes preparation of a potassium (Z)-14-(furan-2-yl)tetradeca-9-en-11,13-diynoate.

(Z)-14-(furan-2-yl)tetradeca-9-en-11,13-diynoic acid may be prepared by any useful method, for example as described in U.S. Pat. No. 6,541,506.

300 mg of (Z)-14-(furan-2-yl)tetradeca-9-en-11,13-diynoic acid were dissolved in IPA (3 ml) and warmed to 50° C. before the addition of potassium ethoxide (1066 µl of 1M solution in EtOH 1.01 equivalents). The reaction was allowed to cool to room temperature and it was then filtered and dried under suction and then placed in a vacuum oven at 25° C./5 mbar for two and a half days. The yield was 298 mg (88%).

Example 5

Stability of Diyne Salts

Potassium (Z)-14-(furan-2-yl)tetradeca-9-en-11,13-diynoate was kept as a crystalline solid for 6 month at 2-8° C. The content of potassium (Z)-14-(furan-2-yl)tetradeca-9-en-11,13-diynoate was determined by HPLC against a reference sample kept at −20° C. After 6 months of storage characteristics such as colour, water content, XRPD profile, of the solid had not changed and it was still a beige solid. Furthermore, the content of potassium (Z)-14-(furan-2-yl)tetradeca-9-en-11,13-diynoate had not significantly changed. Also no change in the impurity profile was observed after 6 months storage.

Potassium (Z)-14-(furan-2-yl)tetradeca-9-en-11,13-diynoate was also kept as a crystalline solid for 6 month at 25° C., 60% RH. Analysis was performed as described above. After 6 months of storage characteristics of the solid has not changed and it was still a beige solid. Furthermore, the potassium (Z)-14-(furan-2-yl)tetradeca-9-en-11,13-diynoate content had not changed significantly, as analysed by HPLC. Also no change in the impurity profile was observed after 6 months storage.

Potassium (Z)-14-(furan-2-yl)tetradeca-9-en-11,13-diynoate was also kept as a crystalline solid for 6 month at 40° C., 75% RH. Analysis was performed as described above. After 6 months of storage the appearance of the solid had changed to a brown solid. Furthermore, a decrease in the content of potassium (Z)-14-(furan-2-yl)tetradeca-9-en-11,13-diynoate to 96% was observed as analysed by HPLC.

Sodium (Z)-14-(furan-2-yl)tetradeca-9-en-11,13-diynoate was kept as an amorphous solid at room temperature. After short term storage the colour darkened. Furthermore the salt was dissolved in an aqueous solution and already after few days the content of sodium (Z)-14-(furan-2-yl)tetradeca-9-en-11,13-diynoate was reduced by 35%, thus proving strong instability of the amorphous salt form.

Example 6

Biochemical assay for the measurement of OLE-1 inhibition by potassium (Z)-14-(furan-2-yl)tetradeca-9-en-11,13-diynoate Potassium (Z)-14-(furan-2-yl)tetradeca-9-en-11,13-diynoate dependent inhibition of the OLE-1 protein is investigated in a cell free assay. Fungi are grown on oleic acid free medium to enrich for cellular OLE-1 protein. Spheroplasts are generated by enzymatic digestion and lysis through polycarbonate filters. Differential centrifugation is used to enrich for endoplasmatic reticulum fractions.

Fractions are supplemented with radiolabelled stearyl-CoA and co-factors (stearyl-CoA is the activated form of stearic acid). OLE-1 dependent conversion from stearyl-CoA to oleoyl-CoA is determined photoradiographically from chromatographic separations of stearyl-CoA and Oleoyl-CoA or by tandem mass spectrometry.

Potassium (Z)-14-(furan-2-yl)tetradeca-9-en-11,13-diynoate dependent inhibition of OLE-1 is determined by the addition of different amounts of potassium (Z)-14-(furan-2-yl)tetradeca-9-en-11,13-diynoate to the reaction mixture.

Example 7

Anti-Fungal Activity

Potassium (Z)-14-(furan-2-yl)tetradeca-9-en-11,13-diynoate was tested against *Aspergillus fumigatus* and various *Candida* species alone to determine antifungal activity and in various combinations with Amphotericin B to determine if any synergistic or antagonistic interactions may occur. Combinations resulting in significantly decreased MICs of the combined compounds are defined as synergistic; those resulting in increased MICs of one or both compounds are antagonistic.

Amphotericin B and potassium (Z)-14-(furan-2-yl)tetradeca-9-en-11,13-diynoate were added to an in vitro culture of different fungi in various concentrations and the culture was visually inspected. If there is inhibition of growth the culture will remain optically clear, whereas growth results in a hazy culture. The results are shown in FIG. 5, where 0 means optically clear (i.e. no growth), 1 means slightly hazy, 2 means prominent decrease (at least 50%) in visible growth, 3 means slight reduction in visible growth and 4 means no reduction in visible growth.

Potassium (Z)-14-(furan-2-yl)tetradeca-9-en-11,13-diynoate clearly inhibits growth of both *Candida glabrata, Candida parapsilosis* and *Candida albicans* at a concentration of 2 μg/ml and even at lower concentrations (see FIG. 5).

Synergism was observed for potassium (Z)-14-(furan-2-yl)tetradeca-9-en-11,13-diynoate with Amphotericin B on *Candida glabrata* and on *Aspergillus fumigatus* and to a lesser extent on *Candida parapsilosis*. Thus, AmphotericinB/potassium (Z)-14-(furan-2-yl)tetradeca-9-en-11,13-diynoate combinations with the concentrations 250/2.5 ng/ml or 125/10 ng/ml clearly inhibit growth of *Candida glabrata*, whereas the individual compounds at that concentration do not or just slightly.

Example 8

Minimum Inhibitory Concentration (MIC) Testing

MIC determinations of (Z)-14-(furan-2-yl)tetradeca-9-en-11,13-diynoic acid, potassium salt and 14-(furan-2-yl)tetradeca-11,13-diynoic acid against fungi were performed according to the NCCLS M27A standard (NCCLS. *Reference Method for Broth Dilution Antifungal Susceptibility Testing of Yeasts; Approved Standard*. NCCLS document M27-A. NCCLS, 940 West Valley Road, Suite 1400, Wayne, Pa. 19087-1898. 1997). A ten-dilution range of each drug was prepared in RPMI-1640 and dispensed into 96-well microtiter plates.

The inoculum size was $0.5$-$2.5 \times 10^3$ colony-forming units (CFU)/ml. Incubation time and temperature were 35° C. and 24 hrs.

The MIC endpoint was 100% inhibition as compared to the growth control for all strains. The results are shown in Table 11.

TABLE 11

| | MICs (100% inhibition) | |
|---|---|---|
| Organism ID | potassium (Z)-14-(furan-2-yl)tetradeca-9-en-11,13-diynoate | 14-(furan-2-yl)tetradeca-11,13-diynoic acid |
| C. albicans ATCC 24433 | 2.5 | 20 |
| C. albicans ATCC 90028 | 5 | 20 |
| C. glabrata ATCC 90030 | 60 | 2560 |
| C. krusei ATCC 6258 | 60 | 1280 |
| C. parapsilosis ATCC 22019 | 10240 | >10240 |
| C. parapsilosis ATCC 90018 | >10240 | >10240 |
| C. tropicalis ATCC 750 | 7.5 | 80 |

Example 9

The inhibition of CYP450 enzymes by (Z)-14-(furan-2-yl)tetradeca-9-en-11,13-diynoic acid, potassium salt was tested. Peak areas corresponding to the metabolite of each substrate were recorded. The percent of control activity was then calculated by comparing the peak area obtained in the presence of the diyne potassium salt and in the absence. A range of concentrations of (Z)-14-(furan-2-yl)tetradeca-9-en-11,13-diynoic acid, potassium salt (1, 3, 10, 30 and 100 µM) were tested and $IC_{50}$ values were determined

TABLE 12

Inhibition of cytochrome P450 enzymes by (Z)-14-(furan-2-yl)tetradeca-9-en-11,13-diynoic acid, potassium salt

| Cytochrome P450 | Substrate | $IC_{50}$ (µM) | % control at 10 µM |
|---|---|---|---|
| 1A | ethoxyresorufin | 59 | 92 |
| 2B6 | bupropion | 24 | 82 |
| 2C8 | paclitaxel | >100 | 84 |
| 2C9 | diclofenac | 18 | 74 |
| 2C19 | omeprazole | 32 | 84 |
| 2D6 | dextromethorphan | >100 | 88 |
| 3A | midazolam | 45 | 85 |
| 3A | testosterone | 57 | 90 |

ABBREVIATIONS

| | |
|---|---|
| AcN, ACN | acetonitrile, methyl cyanide |
| n-BuOAc | n-butyl acetate |
| s-BuOAc | s-butyl acetate |
| DCE | Dichloroethane |
| DCM | Dichloromethane, methylene chloride |
| DIPE | di-isopropylether |
| DMA | dimethyl acetamide |
| DMF | dimethyl formamide |
| EtOAc | ethyl acetate |
| EtOH | ethanol, ethyl alcohol |
| $H_2O$ | water—distilled or HPLC grade |
| IPA | iso-propyl alcohol, propan-2-ol |
| i-PrOAc | iso-propyl acetate |
| MEK | methyl ethyl ketone, butanone |
| MeOH | methanol, methyl alcohol |
| MTBE | tertiary butyl methyl ether |
| NMP | n-methyl pyrrolidone |
| t-BME/TBME | t-butyl methyl ether |
| THF | Tetrahydrofuran |

Example 10

This example shows the antifungal activity of various diynes according to the invention against various yeast and dermatophyte strains. The inhibition is partly measured by minimum inhibitory and minimum fungicidal concentration (MIC and MFC, respectively) and partly as $IC_{50}$ (i.e. concentration required for 50% inhibition).

The antifungal activity was compared to the activity of for example Fluconazole (FLU) and Terbinafine (TERB) for yeasts and dermatophytes, respectively (herein also named comparators).

a. Test Isolates

The fungal isolates tested in this study to evaluate the antifungal activity of (Z)-14-(furan-2-yl)tetradeca-9-en-11,13-diynoic acid, 14-(furan-2-yl)tetradeca-11,13-diynoic acid, (Z)-14-(furan-2-yl)tetradeca-9-en-11,13-diynoic acid, potassium salt and comparators are clinical isolates collected from patients and deposited at the culture collection of the Center for Medical Mycology. Tested isolates included: *Candida albicans, C. glabrata, C. guilliermondii, C. krusei, C. lipolytica, C. lusitaniae, C. parapsilosis, C. tropicalis* and *Malassezia furfur*. Dermatophyte strains included *Trichophyton rubrum, T. mentagrophytes, T. tonsurans, T. terrestre, Epidermophyton floccosum, Microsporum canis, M. cookie, M. gallinae, M. gypseum*, and *M. vanbreuseghemii*.

b. Minimum Inhibitory Concentration (MIC) Testing

MIC determinations of various diyne compounds against yeasts were performed according to the NCCLS M27A standard (NCCLS. *Reference Method for Broth Dilution Antifungal Susceptibility Testing of Yeasts; Approved Standard*. NCCLS document M27-A. NCCLS, 940 West Valley Road, Suite 1400, Wayne, Pa. 19087-1898. 1997) with dermatophytes tested in a modified microdilution method. (Z)-14-(furan-2-yl)tetradeca-9-en-11,13-diynoic acid and TERB were dissolved in dimethyl sulfoxide (DMSO), while FLU was dissolved in sterile water. A ten-dilution range of each drug was then prepared in RPMI-1640 and dispensed into 96-well microtiter plates.

For yeast strains, the inoculum size was $0.5\text{-}2.5 \times 10^3$ colony-forming units (CFU)/ml. Incubation time and temperature were 35° C. and 24 hrs. (The *Malassezia* strain required a week's incubation with the addition of olive oil to obtain adequate growth for visual reading). For dermatophytes, the inoculum size, temperature, and time were $1\text{-}3 \times 10^3$ CFU/ml, 35° C. and 4 days, respectively. The MIC endpoint was 90% inhibition as compared to the growth control for all strains.

c. Minimum Fungicidal Concentration (MFC) Testing

For MFC testing, 20 µl from each visibly clear well from the MIC assay were subcultured onto the center of potato dextrose agar plates and allowed to dry overnight. The plates were then streaked with an inoculating loop to remove the cells from the drug source. The MFC was defined as the lowest concentration to inhibit 100% of fungal growth upon subculture.

a. Activity of (Z)-14-(furan-2-yl)tetradeca-9-en-11,13-diynoic acid against yeasts Table 13 lists the MIC and MFC data for *Candida* and *Malassezia* strains obtained as described above. As can be seen (Z)-14-(furan-2-yl)tetradeca-9-en-11,13-diynoic acid MIC range for all *Candida* strains was <0.00006-4.0 µg/ml, as compared with 0.125-16 µg/ml for FLU. The MIC of (Z)-14-(furan-2-yl)tetradeca-9-en-11,13-diynoic acid against the *Malassezia* strain was <0.00006 µg/ml, as compared to 0.125 µg/ml for FLU. Importantly, the (Z)-14-(furan-2-yl)tetradeca-9-en-11,13-diynoic acid MIC against *C. krusei*, a strain with known innate resistance to FLU, was 0.0005 µg/ml (corresponding FLU MIC=16 µg/ml). The MFC range for (Z)-14-(furan-2-yl)tetradeca-9-en-11,13-diynoic acid against yeasts was <0.00006-32.0 µg/ml.

b. Activity of (Z)-14-(furan-2-yl)tetradeca-9-en-11,13-diynoic acid against dermatophytes Table 14 is a summary of the activity of (Z)-14-(furan-2-yl)tetradeca-9-en-11,13-diynoic acid against dermatophytes. As can be seen, the MIC range against all dermatophyte strains was <0.00006-1.0 µg/ml, as compared to 0.002-4 µg/ml for TERB. (Z)-14-(furan-2-yl)tetradeca-9-en-11,13-diynoic acid demonstrated potent activity against the nine *T. rubrum* strains with elevated TERB MICs (4.0 µg/ml) tested. The MFC range for (Z)-14-(furan-2-yl)tetradeca-9-en-11,13-diynoic acid against dermatophytes was <0.00006-16 µg/ml.

(Z)-14-(furan-2-yl)tetradeca-9-en-11,13-diynoic acid demonstrated potent activity against all fungal isolates tested.

The MICs for (Z)-14-(furan-2-yl)tetradeca-9-en-11,13-diynoic acid would be within the susceptible range established for FLU vs. *Candida* strains (≤8 μg/ml). Importantly (Z)-14-(furan-2-yl)tetradeca-9-en-11,13-diynoic acid showed activity against the FLU-resistant (MIC=16 μg/ml) *C. krusei* and also against the *T. rubrum* strains with elevated TERB MICs (MIC=4.0 μg/ml).

The data shows (Z)-14-(furan-2-yl)tetradeca-9-en-11,13-diynoic acid possesses potent activity against yeast and dermatophytes. This activity was superior to FLU (against yeast) and TERB (against dermatophytes). The data indicate that (Z)-14-(furan-2-yl)tetradeca-9-en-11,13-diynoic acid have utility in the treatment of yeast and dermatophyte infections.

TABLE 13

In vitro antifungal activity vs. yeasts (in μg/ml).

| Organism | (Z)-14-(furan-2-yl)tetradeca-9-en-11,13-diynoic acid | | FLU |
|---|---|---|---|
| | MIC | MFC | MIC |
| *Candida albicans* (n = 8) | <0.00006 | <0.00006 | 1.0 |
| *C. glabrata* (n = 1) | 0.008 | 0.5 | 2.0 |
| *C. lusitaniae* (n = 1) | <0.00006 | <0.00006 | 0.125 |
| *C. lipolytica* (n = 1) | <0.00006 | <0.00006 | 0.125 |
| *C. guilliermondii* (n = 1) | <0.00006 | 0.0005 | 4.0 |
| *C. parapsilosis* (n = 2) | 4.0 | 32 | 1.0 |
| *C. krusei* (n = 1) | 0.0005 | 0.001 | 16 |
| *Malassezia furfur* (n = 1) | <0.00006 | <0.00006 | 0.125 |

TABLE 14

In vitro antifungal activity vs. dermatophytes (in μg/ml).

| Organism | (Z)-14-(furan-2-yl)tetradeca-9-en-11,13-diynoic acid | | TERB |
|---|---|---|---|
| | MIC | MFC | MIC |
| *Trichophyton tonsurans* (n = 15) | <0.00006 | <0.00006 | 0.008 |
| *T. mentagrophytes* (n = 15) | <0.00006 | 0.0001 | 0.008 |
| *Microsporum canis* (n = 15) | <0.00006 | 0.0005 | 0.015 |
| *T. rubrum* (n = 15) | <0.00006 | <0.00006 | 0.002 |
| *Epidermophyton floccosum* (n = 15) | <0.00006 | 0.015 | 0.015 |
| *T. rubrum* (TERB-resistant) (n = 9) | <0.00006 | <0.00006 | 4.0 |

TABLE 14-continued

In vitro antifungal activity vs. dermatophytes (in μg/ml).

| Organism | (Z)-14-(furan-2-yl)tetradeca-9-en-11,13-diynoic acid | | TERB |
|---|---|---|---|
| | MIC | MFC | MIC |
| *M. cookie* (n = 1) | 1.0 | 2.0 | 0.008 |
| *M. vanbreuseghemii* (n = 1) | 0.03 | 16 | 0.015 |
| *M. gypseum* (n = 1) | <0.00006 | 16 | 0.004 |
| *T. terrestre* (n = 1) | <0.00006 | 16 | 0.008 |
| *M. gallinae* (n = 1) | <0.00006 | 4.0 | 0.008 |

In contrast to its potent anti-fungal activity, (Z)-14-(furan-2-yl)tetradeca-9-en-11,13-diynoic acid has minimal antibacterial (Table 15) or mammalian cytotoxic activities in vitro (Table 16); in many cases, the drug is 10-20.000-fold more toxic to fungal organisms than to bacteria and mammalian cells. These data suggest a very high therapeutic index for treatment of fungal infections in mammals.

TABLE 15

In vitro Antibacterial Activity MIC$_{90}$, μg/ml

| Organism | Strain | (Z)-14-(furan-2-yl)tetradeca-9-en-11,13-diynoic acid | Standard Agent |
|---|---|---|---|
| *Staphylococcus aureus* | 29213 | 50 | Gentamicin—0.78 |
| *Enterobacter faecalis* | 29212 | 12.5 | Ampicillin—0.78 |
| *Escherichia coli* | 700 | >200 | Ampicillin—3.125 |

TABLE 16

In vitro Mammalian Cell Cytotoxicity of (Z)-14-(furan-2-yl)tetradeca-9-en-11,13-diynoic acid

| | CC$_{50}$, μg/ml |
|---|---|
| Vero Cells | 46 |
| HFF Cells | 75 |

IC$_{50}$ against two different *S. cerevisiae* strains and two different *C. albicans* strains by a number of diyne compounds was determined and the results are shown in Table 17.

TABLE 17

| Compound | MW | *S. cerevisiae* IC$_{50}$ (μg/ml) | | *C. albicans* IC$_{50}$ (μg/ml) | |
|---|---|---|---|---|---|
| | | AD1-9 | 2229-5C | DSY1024 | SC5314 |
| (Z)-12-(furan-2-yl)dodeca-7-en-9,11-diynoic acid | 256 | ~6.25 | ~50 | 1.8 | 50 |
| (Z)-13-(furan-2-yl)trideca-8-en-10,12-diynoic acid | 270 | ~50 | >200(25%) | 0.5 | >200 |
| (E)-14-(furan-2-yl)tetradeca-9-en-11,13-diynoic acid | 284 | 0.4 | 2.7 | 0.004 | 3 |
| (Z)-methyl 14-(furan-2-yl)tetradeca-9-en-11,13-diynoate | 298 | >0.4(6%) | >0.4(4%) | 0.19 | 0.4 |
| (Z)-ethyl 14-(furan-2-yl)tetradeca-9-en-11,13-diynoate | 312 | 0.7 | 8.9 | — | 9 |

Table 18 shows the minimal inhibitory concentrations of (Z)-14-(furan-2-yl)tetradeca-9-en-11,13-diynoic acid, potassium salt and (Z)-14-(furan-2-yl)tetradeca-9-en-11,13-diynoic acid versus reference *Candida* strains.

TABLE 18

| Organism ID | (Z)-14-(furan-2-yl)tetradeca-9-en-11,13-diynoic acid, potassium salt | 14-(furan-2-yl)tetradeca-11,13-diynoic acid |
|---|---|---|
| C. albicans ATCC 24433 | 2.5 ng/ml | 20 ng/ml |
| C. albicans ATCC 90028 | 5 ng/ml | 20 ng/ml |
| C. glabrata ATCC 90030 | 60 ng/ml | 2560 ng/ml |
| C. krusei ATCC 6258 | 60 ng/ml | 1280 ng/ml |
| C. parapsilosis ATCC 22019 | 10240 ng/ml | >10240 ng/ml |
| C. parapsilosis ATCC 90018 | >10240 ng/ml | >10240 ng/ml |
| C. tropicalis ATCC 750 | 7.5 ng/ml | 80 ng/ml |

Example 11

In Vitro Fungicidal Activity Vs. *Candida albicans*

The fungicidal activity by (Z)-14-(furan-2-yl)tetradeca-9-en-11,13-diynoic acid was more exhaustively examined with respect to *C. albicans*. $MIC_{90}$s were determined following a 24 hr incubation period. Aliquots of growth-negative samples were both subcultured by dilution into fresh media and filtered and washed extensively to remove remaining drug. The filters were placed on the surface of nutrient agar plates and incubated for 24 hours. (Z)-14-(furan-2-yl)tetradeca-9-en-11,13-diynoic acid gave greater than 99.9% reduction of the original inoculum (<5 cfu/ml) indicating that it had killed the organisms rather than merely retarding growth. Several standard anti-fungal compounds were tested side-by-side with (Z)-14-(furan-2-yl)tetradeca-9-en-11,13-diynoic acid and the results are shown in Table 19.

TABLE 19

| In vitro fungicidal activity vs. *Candida albicans* | | | | | |
|---|---|---|---|---|---|
| (ng/ml) | Diyne* | Amphotericin B | Cycloheximide | Ketoconazole | 5-fluorocytosine |
| $MIC_{90}$  24 h | 0.4 | 200 | 1,600,000 | 50,000 | 98 |
| 48 h | 0.4 | 800 | 12,800,000 | >800,000 | 195 |
| Fungicidal Concentration | 0.4 | 800 | 12,800,000 | >800,000 | 1563 |

* The diyne used in this example is (Z)-14-(furan-2-yl)tetradeca-9-en-11,13-diynoic acid.

The fungicidal effect of (Z)-14-(furan-2-yl)tetradeca-9-en-11,13-diynoic acid is also rapid. As seen in FIG. 6, (Z)-14-(furan-2-yl)tetradeca-9-en-11,13-diynoic acid produced >3-log reduction in *C. albicans* CFUs after 3 hours of incubation.

*C. albicans* at $5 \times 10^3$ cfu/ml was incubated with 200 ng/ml (~100-fold MIC) of (Z)-14-(furan-2-yl)tetradeca-9-en-11,13-diynoic acid (A) or with various concentrations of (Z)-14-(furan-2-yl)tetradeca-9-en-11,13-diynoic acid within 0.25 to 2-fold the MIC (B). Samples were removed periodically, filtered, washed and plated onto nutrient agar.

Example 12A

1 Genes Encoding the Regulation of OLE-1 Expression are Conserved Between *S. cerevisiae* and *C. albicans*

44 *S. cerevisiae* gene deletion strains with increased sensitivity to (Z)-14-(furan-2-yl)tetradeca-9-en-11,13-diynoic acid, sodium salt have been identified. Analysis of the deleted genes allowed the assembly of a putative pathway critical for (Z)-14-(furan-2-yl)tetradeca-9-en-11,13-diynoic acid, sodium salt sensitivity. The pathway regulates the expression of OLE-1, which encodes a Δ9 fatty acid desaturase that converts stearic acid to oleic acid.

Genes encoding components of the assembled pathway in *S. cerevisiae* were searched for homologues in *C. albicans*. For all of the genes, an orthologue was identified in *C. albicans* (Table 20). MGA2 and SPT23 are duplicate genes in *S. cerevisiae* but only one orthologue was identified in *C. albicans*, and OLE-1 is present as single copy gene in *S. cerevisiae* whereas two copies were identified in *C. albicans*.

This suggests that the pathway identified in *S. cerevisiae* is conserved in *C. albicans*.

TABLE 20

| *S. cerevisiae* - *C. albicans* orthologues | | | |
|---|---|---|---|
| *S. cerevisiae* gene | | *Candida* homologue | |
| Standard Name | Systematic Name | Standard Name | Systematic Name |
| MGA2[1] | YIR033W | CaSPT23 | orf19.751 |
| SPT23[1] | YKL020C | | |
| UBX2 | YML013W | | orf19.3135 |
| SSM4 | YIL030C | | orf19.5175 |
| UBC7 | YMR022W | | orf19.7329 |
| GET1 | YGL020C | | orf19.2101 |
| GET2 | YER083C | | orf19.4839 |
| GET3 | YDL100C | | orf19.2965 |
| OLE-1 | YGL055W | CaOLE-1[1] | orf19.5117 |
| | | CaOLE2[1] | orf.19.2264 |

Example 12B

Biochemical assay for the measurement of OLE-1 inhibition by (Z)-14-(furan-2-yl)tetradeca-9-en-11,13-diynoic acid, potassium salt and other diyne compounds (Z)-14-(furan-2-yl)tetradeca-9-en-11,13-diynoic acid, potassium salt dependent inhibition of the OLE-1 protein is investigated in a cell free assay. Fungi are grown on oleic acid free medium to enrich for cellular OLE-1 protein. Spheroplasts are generated by enzymatic digestion and lysis through polycarbonate filters. Differential centrifugation is used to enrich for endoplasmatic reticulum fractions.

Fractions are supplemented with radiolabelled stearyl-CoA and co-factors (stearyl-CoA is the activated form of stearic acid). OLE-1 dependent conversion from stearyl-CoA to oleoyl-CoA is determined photoradiographically from chromatographic separations of stearyl-CoA and Oleoyl-CoA or by tandem mass spectrometry.

by (Z)-14-(furan-2-yl)tetradeca-9-en-11,13-diynoic acid, potassium salt dependent inhibition of OLE-1 is determined by the addition of different amounts of (Z)-14-(furan-2-yl)tetradeca-9-en-11,13-diynoic acid, potassium salt to the reaction mixture.

Example 13

Effect on the Morphology of Growing *Candida albicans* Cultures

Figure 7:
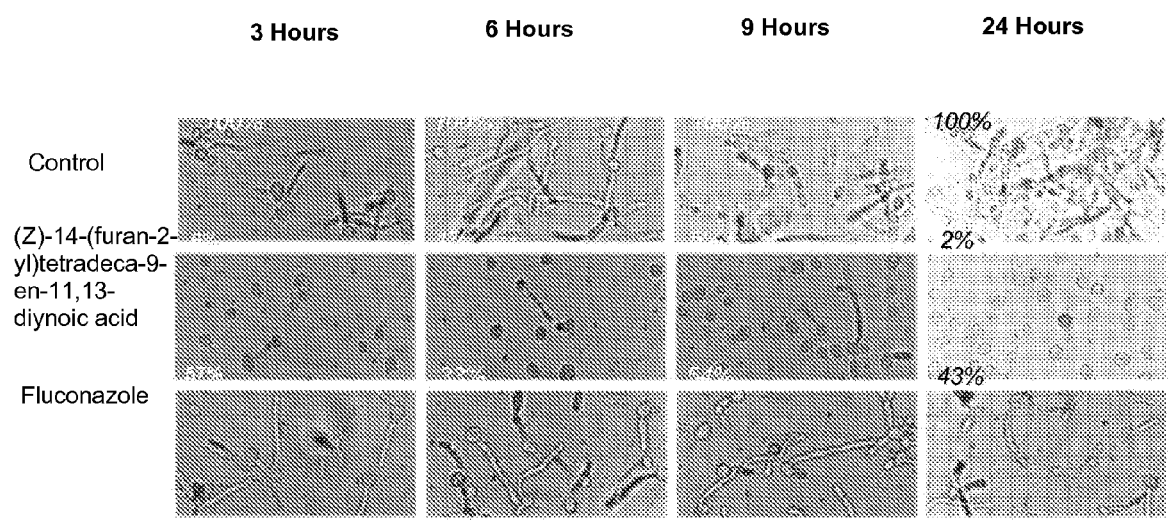
FIG. 7 shows the morphological effect of (Z)-14-(furan-2-yl)tetradeca-9-en-11,13-diynoic acid and Fluconazole on growing *C. albicans*. The % shown in the upper left corners indicates percent cell viability as assessed by MTT (metabolic dye staining).

Cultures of *C. albicans* were grown in the presence and absence of inhibiting concentrations of (Z)-14-(furan-2-yl) tetradeca-9-en-11,13-diynoic acid and Fluconazole, a standard anti-fungal agent. Periodically, the cultures were examined microscopically and photographed and an aliquot was tested for cell viability using the MTT metabolic dye method. FIG. 7 shows the morphology of normal growing yeast and yeast growing in the presence of either anti-fungal agent. (Z)-14-(furan-2-yl)tetradeca-9-en-11,13-diynoic acid was fungicidal, totally preventing cell growth. Furthermore, (Z)-14-(furan-2-yl)tetradeca-9-en-11,13-diynoic acid also prevented hyphal tube formation. By contrast, Fluconazole (a fungistatic agent) permitted fungal growth (albeit at a reduced rate) and did not affect hyphal tube formation.

Example 14

Effect on the Germination of *C. albicans*

Figure 8:
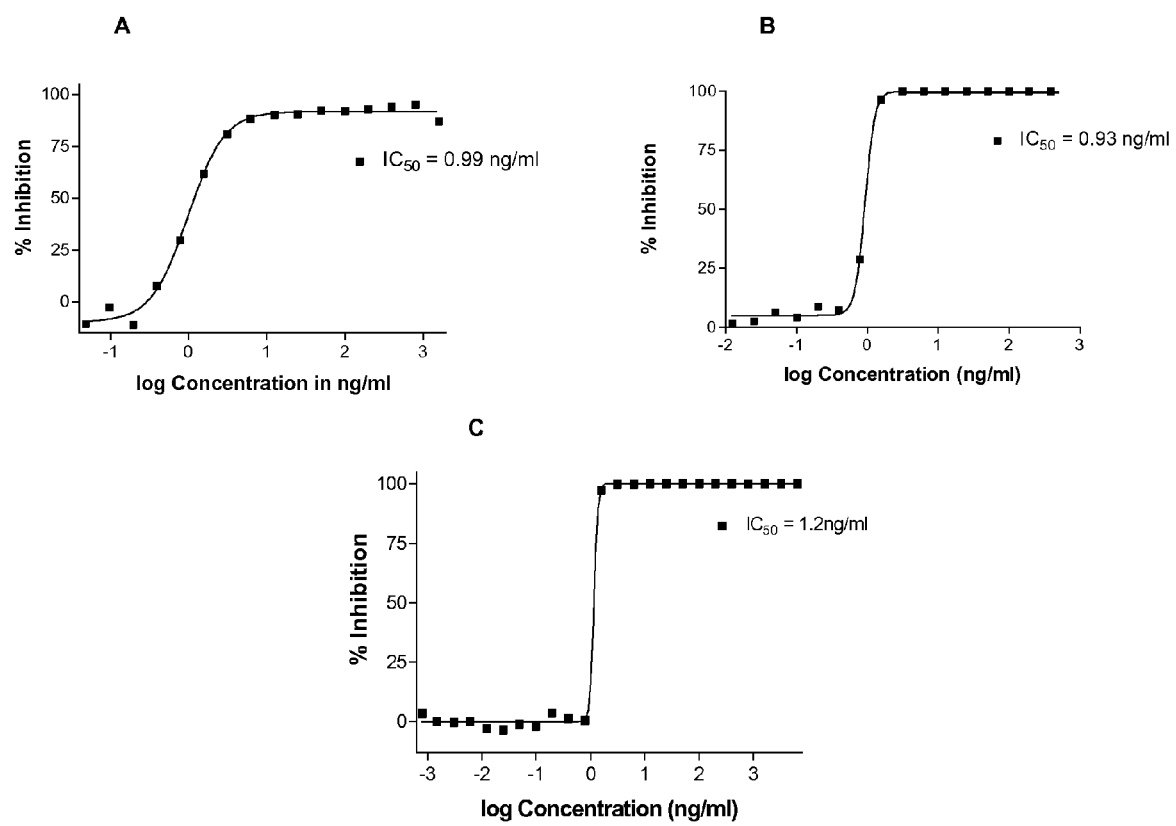
FIG. 8 shows the dose-dependent inhibition of *C. albicans* germination by (Z)-14-(furan-2-yl)tetradeca-9-en-11,13-diynoic acid (A), dose-dependent inhibition of vegetative growth by (Z)-14-(furan-2-yl)tetradeca-9-en-11,13-diynoic acid (B) and dose dependent inhibition of germinated spores by (Z)-14-(furan-2-yl)tetradeca-9-en-11,13-diynoic acid (C)

To assess the effect of (Z)-14-(furan-2-yl)tetradeca-9-en-11,13-diynoic acid on fungal spore germination, *C. albicans* spores were incubated with or without (Z)-14-(furan-2-yl)tetradeca-9-en-11,13-diynoic acid for 5 hours, washed and then incubated with a metabolic dye (MTT) for a further 24 hours to assess cell growth and viability. The $IC_{50}$ of (Z)-14-(furan-2-yl)tetradeca-9-en-11,13-diynoic acid for germination inhibition (FIG. 8 A) was essentially identical to its $IC_{50}$ for inhibition of vegetative growth (FIG. 8 B). In addition, (Z)-14-(furan-2-yl)tetradeca-9-en-11,13-diynoic acid effectively inhibited the subsequent growth of spores that were allowed to germinate in the absence of drug (spores were incubated for 3 hours, a sufficient period to allow germination before the addition of (Z)-14-(furan-2-yl)tetradeca-9-en-11, 13-diynoic acid), (FIG. 8 C). Thus, (Z)-14-(furan-2-yl)tetradeca-9-en-11,13-diynoic acid is capable of acting at multiple stages of the fungal growth cycle.

Example 15

Effect on Fungal Cell Wall Synthetic Enzymes

The inhibitory activity of (Z)-14-(furan-2-yl)tetradeca-9-en-11,13-diynoic acid on two enzymes essential for cell wall biosynthesis was determined. Specific inhibitors of each enzyme served as positive controls (Cilofungin, a β-glucan synthase inhibitor and nikkomycin Z, a chitin synthase inhibitor). As shown in Table 21, (Z)-14-(furan-2-yl)tetradeca-9-en-11,13-diynoic acid only inhibited these enzymes at very high concentrations (>100 μg/ml) which exceed effective anti-fungal concentrations by 5 orders of magnitude. This indicates that inhibition of β-glucan synthase or chitin synthase is not the primary mechanism of anti-fungal activity of (Z)-14-(furan-2-yl)tetradeca-9-en-11,13-diynoic acid.

TABLE 21

Inhibition of fungal cell wall synthesis enzymes

| Compound | Concentration μg/ml | % Inhibition, Chitin Synthase | % Inhibition, (1,3)β-Glucan Synthase |
|---|---|---|---|
| (Z)-14-(furan-2-yl)tetradeca-9-en-11,13-diynoic acid | 500 | 97 | — |
| | 400 | — | 90 |
| | 100 | 85 | 73 |
| | 10 | 16 | 0 |
| Cilofungin | 20.6 | — | 51 |
| Nikkomycin Z | 9.9 | 61 | — |

Example 16

Inhibition of Sterol Biosynthesis

Figure 9:
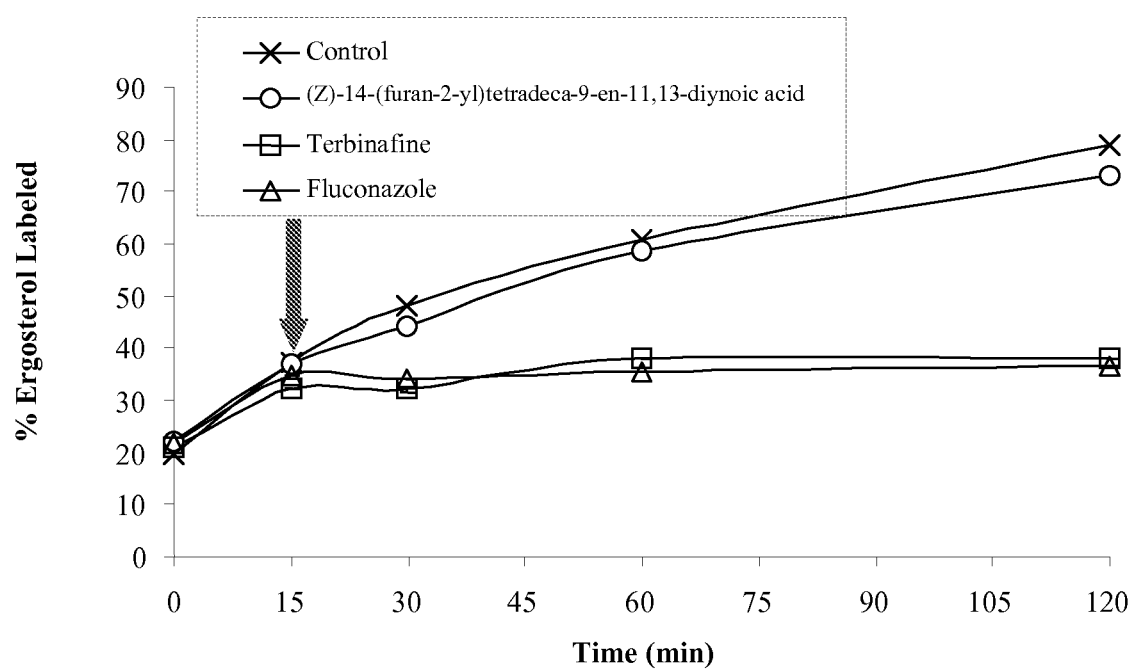
FIG. 9 shows $^{13}$C-Acetate incorporation into Ergosterol in *C. albicans* in the presence (Z)-14-(furan-2-yl)tetradeca-9-en-11,13-diynoic acid, Terbinafine or Fluconazole.

Many therapeutically important anti-fungal agents are known to inhibit the biosynthesis of essential membrane sterols, primarily ergosterol. For instance, azole anti-fungal agents, such as Ketoconazole and Fluconazole, do so principally by inhibition of cytochrome P450 14 α-demethylase (P45014DM). Terbinafine and other allylamines inhibit ergosterol biosynthesis at the penultimate step of lanosterol biosynthesis, squalene epoxidase. A stable-isotopic method was developed to probe the metabolic effects of anti-fungal agents in yeast. Exponentially growing cultures of *Candida albicans* were incubated with $^{13}$C-labeled acetate and the resulting labeled sterols evaluated by API-LC-MS. The ratio of labeled to unlabeled sterol (e.g., ergosterol) was a quantitative indication of the net biosynthesis of the sterol from acetate. Representative results are shown in FIG. 9. After the first 15 minutes, drugs were added to the incubation medium at concentrations approximating their respective MICs; the control contained only DMSO vehicle. As expected, both Terbinafine and Fluconazole inhibited the incorporation of acetate into ergosterol. However, (Z)-14-(furan-2-yl)tetradeca-9-en-11,13-diynoic acid did not significantly inhibit the net biosynthesis of ergosterol (i.e. the level of $^{13}$C incorporation into ergosterol in the presence of (Z)-14-(furan-2-yl)tetradeca-9-en-11,13-diynoic acid was nearly identical to the control level).

Example 17

The mechanism of action of the sodium salt of (Z)-14-(furan-2-yl)tetradeca-9-en-11,13-diynoic acid, V''', was investigated in a chemical-genetic screen in *S. cerevisiae*. The screen made use of the *S. cerevisiae* knock-out collection consisting of 4917 individual strains each deleted for one defined gene. All 4917 strains were tested for increased or decreased susceptibility to compound V'''. From 4917 analyzed strains, 44 had an increased susceptibility to compound V'''. No strain with a decreased susceptibility was identified. The *S. cerevisiae* Gene Ontology Slim vocabulary was used to map the identified genes to higher level biological processes. From a total of 39 biological processes available, the 44 genes identified mapped to 29 processes, from which "lipid metabolic process" (p<0.004) and "organelle organization and biogenesis" (p<0.04) were significantly overrepresented.

Figure 15:
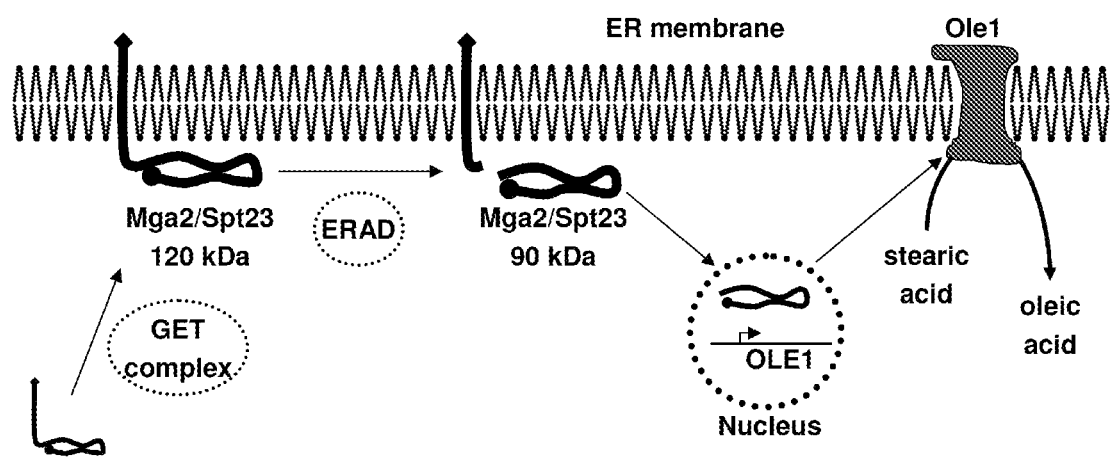
FIG. 15 shows regulation of OLE1 transcriptional activation.

Among the genes identified was MGA2, which encodes a transcriptional activator of the OLE1 Δ9-fatty acid desaturase gene. MGA2 is a duplicated gene in *S. cerevisiae* with SPT23 being its homolog. The Ole1 protein converts stearic acid to oleic acid and is an essential gene in *S. cerevisiae*. Another six genes from the identified set of 44 genes could be assembled together with MGA2 to a pathway likely to regulate OLE1 transcriptional activation. This pathway included components of the ERAD (endoplasmatic reticulum associated protein degradation) complex required for the proteolytic activation of the Mga2 protein and genes coding for GET complex components, which is putatively required to insert Mga2 into the membrane of the endoplasmatic reticulum. FIG. 15 illustrates the regulation of OLE1 transcriptional activation. Components of the GET complex putatively mediate the insertion of the Mga2/Spt23 proteins into the ER membrane. The ERAD complex proteolytically activates Mga2/Spt23, which shuttles to the nucleus where it activates OLE1 transcription). These data indicate that compound V'", interferes with the regulatory pathway for OLE1 gene expression, or the Ole1 protein itself.

Example 18

Figure 16A:
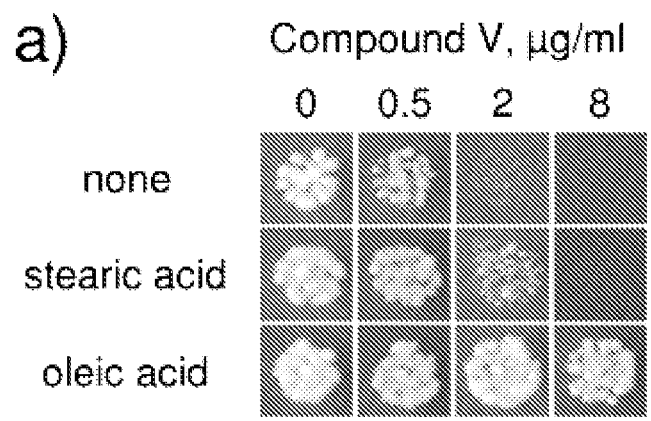
FIG. 16 *a., b.* and *c.* showing that oleic acid, but not stearic acid, is an antagonist of compound V", b. and c. together showing that oleic acid, but not stearic acid, had an antagonistic effect on compound IV".

The Ole1 protein is a Δ9-fatty acid desaturase, which converts stearic acid to oleic acid. Deletion of the OLE1 gene induces an oleic acid auxotrophy, which is lethal to the fungal cell. In *S. cerevisiae*, oleic acid (but not stearic acid) had an antagonistic effect on the activity of compound V'", demonstrating that compound V'" inhibits the conversion from stearic acid to oleic acid. See FIG. 16*a* which shows that when *Saccharomyces cerevisiae* was cultured on nutrient agar supplemented with increasing amounts of compound V'", addition of oleic acid decreased the susceptibility of *S. cerevisiae* to compound V'", whereas stearic acid did not, indicating that oleic acid is an antagonist of compound V'", but not stearic acid. Similarly in *C. albicans*, oleic acid (but not stearic acid) had an antagonistic effect on compound IV'". FIG. 16 *b*. and *c*. show that when *Candida albicans* was cultured in nutrient broth and supplemented with combinations of compound IV'" and b) oleic acid, sodium salt or c) stearic acid, sodium salt, oleic acid, sodium salt, had an antagonistic effect on compound IV'", whereas stearic acid, sodium salt, did not, demonstrating that oleic acid, sodium salt, is an antagonist of compound IV'", but not stearic acid, sodium salt.

Example 19

Compound V'" was thus seen to inhibit the biosynthesis of oleic acid, via a mechanism that is either through direct inhibition of the Δ9 fatty acid desaturase Ole1 protein, or through inhibition of Mga2 protein dependent transcriptional activation of OLE1 gene expression, thereby inducing an oleic acid auxotrophy to the cell. To distinguish between these two hypotheses, OLE1 transcriptional levels were determined. Assuming that compound IV'" directly inhibited the Ole1 protein, a compensating up-regulation of the OLE1 transcriptional level for compound IV'" treated cells would be expected. If compound IV'" inhibited the Mga2 protein or any other component required for OLE1 transcriptional activation such as the GET complex or the CDC48 proteasome, a down-regulation of OLE1 for compound IV'" treated cells would have been expected. Compound IV'" independent transcription of the OLE1 gene would indicate another mechanism of action and suggested that the antagonistic effect of oleic acid with compound IV'" was indirect.

When *S. cerevisiae* was cultured in the presence of 1 and 10 μg/ml compound IV'", the doubling times increased to 2.4 h and 4.2 h, respectively, compared to 2 h for the untreated control. The addition of 10 μg/ml oleic acid, sodium salt, to 1 μg/ml compound IV'" reversed the doubling time to 2 h as observed for the untreated control or 10 μg/ml oleic acid, sodium salt alone.

Doubling times found are shown in Table 22.

TABLE 22

Doubling times of *S. cerevisiae* in the presence of compound IV'" and/or oleic acid

| condition | compound IV'" | oleic acid | doubling time in h |
|---|---|---|---|
| a | — | — | 2.0 |
| b | 1 μg/ml | — | 2.4 |
| c | 10 μg/ml | — | 4.2 |
| d | — | 10 μg/ml | 2.0 |
| e | 1 μg/ml | 10 μg/ml | 2.1 |

Figure 17A:
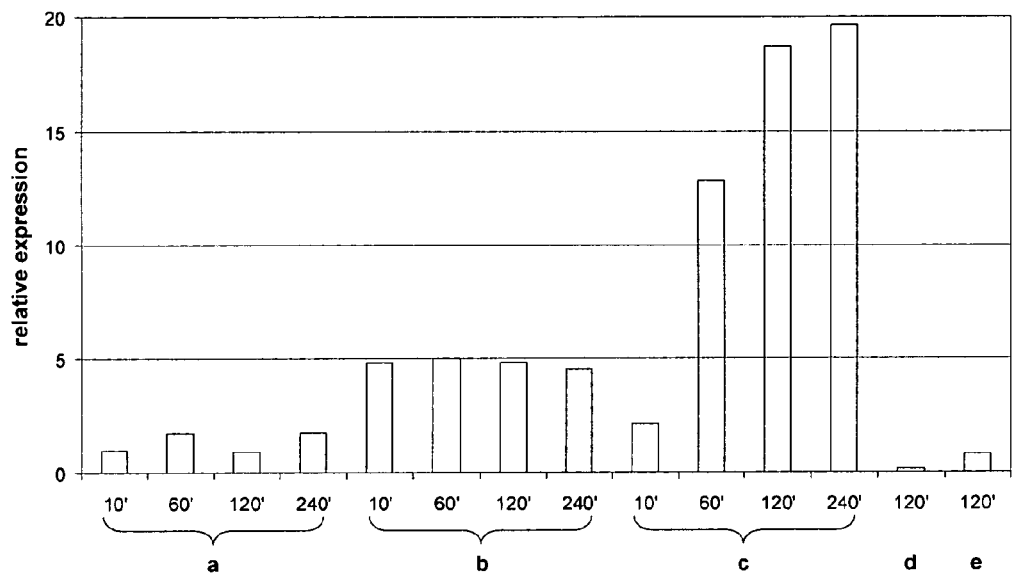

The expression of the OLE1 gene was determined by real time PCR 10, 60, 120 and 240 min for the conditions a.-e., as indicated in Table 3 above. OLE1 transcript levels were calibrated to the expression of the tubulin gene (TUB1) and normalized to the OLE1 expression at 10 min without compound addition. See FIG. 17*a* showing time dependent expressions of OLE1 in response to compound IV'". Conditions a.-e. are listed in Table 3 above, numbers indicate time intervals in minutes. Expressions of OLE1 are given as multiples of the expression at 10 min, condition a. Expression levels of OLE1 in cultures without compound IV'" did not vary significantly over the time scale investigated. The addition of 1 μg/ml compound IV'" increased the expression level of OLE1 about 3-5 fold (4.9 fold at 120 min, p<0.023) and 10 μg/ml increased the expression level about 7-19-fold (18.7 fold at 120 min, p<0.018). 10 μg/ml oleic acid compensated for the OLE1 expression increase caused by 1 μg/ml compound IV alone. Compound IV'" dependent up-regulation of OLE1 expression thus confirms that compound IV'" is acting as an inhibitor of the Ole1 protein. The antagonistic effect of oleic acid found in the susceptibility assays, is reflected mechanistically in this experiment by a down-regulation of the target Ole1 protein through oleic acid.

Figure 17B:
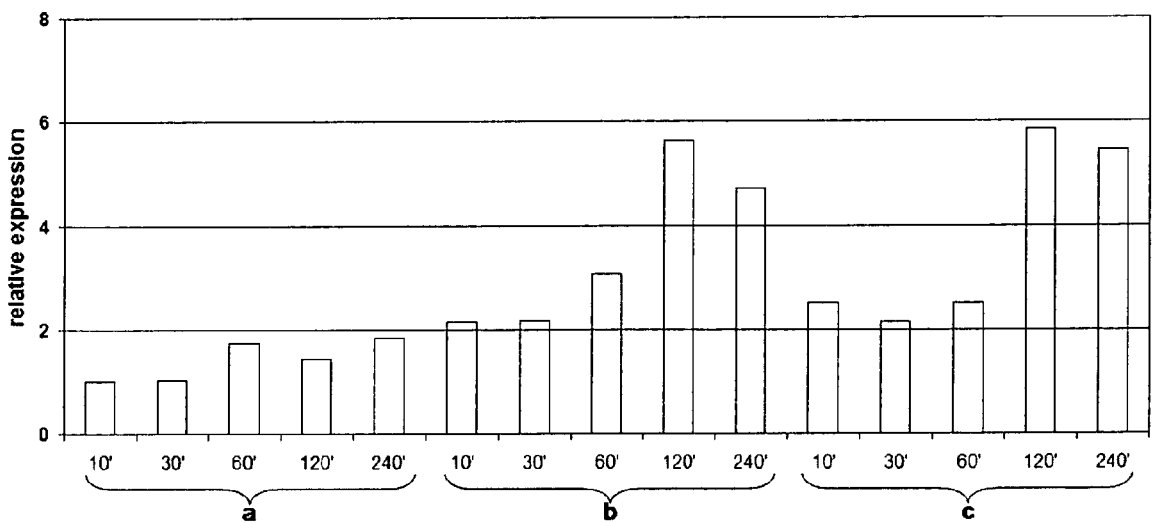
FIG. 17b shows time and concentration dependent expressions of the OLE1 gene in response to compound IV'" in *C. albicans*.

Similarly, the expression of OLE1 in *C. albicans* was investigated in response to compound IV'". In the presence of 250 ng/ml Compound IV, OLE1 transcript levels were increased 4-fold after 120 min incubation time compared to the drug free control. FIG. 17*b* shows time and concentration dependent expressions of OLE1 in response to compound IV'" in *C. albicans*. a: compound free control; b: 250 ng/ml compound IV'"; c: 5000 ng/ml compound IV'"; time intervals in minutes. Expression values are normalised to TUB1 and given as multiples of OLE1 expression at 10 minutes in ethanol.

Example 20

Compounds IX'" and X'" of the invention were screened against the following 15 agricultural pathogens: Ascomycota *Botrytis cinerea*; *Magnaporthe grisea* anamorph; *Pyricularia oryzae*; *Colletotrichum gleoesporioides*—Chilli strain; *Colletotrichum gleoesporioides*—mango strain; *Fusarium verticillioides*; *Fusarium oxysporum*; *Alternaria solani*; *Uncinula necator* Syn *Erysiphe necator*; *Macrophomina phaseolina* Syn. *Sclerotium bataticola* and *Rizoctonia bataticola*; *Botryodiplodia theobromae*; Basidiomycota *Sclerotium rolfsii*; *Rhizoctonia solani*; *Puccinia arachidis*; Oomycota *Pythium aphanidermatum*; *Plasmopara viticola* Syn. *Personopora viticola*, selection being based on i) yield losses and disease severity caused on crops and other plants (for example, ornamental and amenity grasses); ii) host infected by fungi; iii) difficulty in providing control measures with existing fungicides; representation across major classes of pathogenic fungi; and representation across major groups of fungal diseases viz., rust, rot (root and fruit), leaf spots, mildews and wilts.

Agriculture Assays:

In vitro mycelial growth inhibition assays—poisoned plate:

Growth of fungi was carried out in potato dextrose agar media at 40-45° C., and test compound was added at different concentrations and at pH 5.8 for compound X" and at pH 7.0 for its potassium salt, compound XII", with a water control instead of test compound. Radial mycelial growth was measured at regular intervals 4, 8, 12 and 16 days for slow growing fungi and at 3, 6 and 8 days for fast growing fungi. When the mycelia reached the end of the plate, measurements were stopped. Morphological changes in the hyphal growth and sporulation patterns were also observed. For dose response studies a range of concentrations and a range of inhibition obtained falling below and above 50% inhibition (see Table 23 below)

Spore germination studies for plant fungal pathogens-hanging drop method:

Spore/conidial suspension of $5\text{-}10\times10^3$ spores per ml (for larger spores) and $5\text{-}10\times10^5$ for smaller spores, was tested against different concentrations of the potassium salt of compound X". Spore germination was carried out in sterile distilled water, under a moist chamber, in cavity slides. After over night incubation the spores were observed. Where applicable, the solvent dimethyl sulfoxide was added to both test and control. Spore suspensions were prepared from good sporulating field isolates and grown in appropriate media, generally potato dextrose agar, or for *Magnaporthe grisea* oatmeal agar. For specific sporulating structure, spore suspensions were prepared devoid of mycelial bits. Spore number was adjusted using haemocytometer. Final spore concentration of spores was $5\text{-}10\times10^3$ spores per ml. Photographic recordings were made of perfect/good germination; recording of any malformation such as disintegration, shrinking of germ tubes or spores. Inhibition was calculated by comparison with the control germination (inhibition=[(% of spore germination in control with DMSO–% of spore germination in treated with compound)/([(% of spore germination in control with DMSO)].

Leaf Disk Assay:

Leaf disk assay was carried out by the cavity well plate method for powdery mildew disease of grapes. Leaf disks of 14 mm in diameter were cut with a cork borer from the healthy leaves (second and third from the tip) of grapevine plants, and were dipped in 100 µl of each test compound at different concentrations for two minutes, as in treatment details shown below. The control leaf disks were dipped only in sterile water for two minutes. The compound treated leaf disks were placed, abaxial side up, in TC-24 well plates containing water agar medium. The disks were inoculated by placing 20 µl of inoculum ($1\text{-}5\times10^6$ spores/ml) on the centre of the disk. After inoculation, the cavity well plates were incubated at 20° C. for 10 days. After incubation, the powdery mildew lesions on the leaf disks were rated to 0-9 scale, in which, 0 was no visible symptoms and 9 represented more than 50% leaf area with mildew growth/lesion. Percent disease index (PDI) was calculated as follows:

$$PDI = \frac{\text{Sum of individual ratings}}{\text{Total no. of leaf disk grade observed}} \times \frac{100}{\text{maximum disease}} \quad a)$$

After the observation, the conidia were washed from the leaf disks in known volume of a fixative solution of ethanol-formaldehyde-acetic acid (90:5:5, v/v/v) and counted with a hemocytometer.

TABLE 23

Mycelial growth inhibition

| | | Compound XII", potassium salt | |
|---|---|---|---|
| S. No. | Pathogen | Quantity µg/ml | % Mycelial growth Inhibition |
| 1 | *Botrytis cinerea* | 2.5 | 76 |
| 2 | *Magnaporthe grisea* | 5 | 27 |
| 3 | *Colletotrichum gloeosporioides* (mango strain) | 5 | 28 |
| 4 | *Colletotrichum gloeosporioides* (chili strain) | 5 | 10 |
| 5 | *Alternaria solani* | 50 | 42 |

| | | Compound X" | |
|---|---|---|---|
| Serial No | Pathogen | Quantity µg/ml | % Mycelial Growth Inhibition |
| 6 | *Rhizoctonia solani* | 50 | 19 |
| 7 | *Botryodiplodia theobromae* | 50 | 15 |
| 8 | *Sclerotium rolfsii* | 50 | 5 |
| 9 | *Macrophomina phaseolina* | 100 | 15 |
| 10 | *Pythium aphanidermatum* | 50 | No inhibition |
| 11 | *Fusarium verticillioides* | 50 | 14 |
| 12 | *Fusarium oxysporum* | Disc diffusion assay | No inhibition |

| | | Compound XII", potassium salt | |
|---|---|---|---|
| S. No. | Pathogen | Quantity µg/ml | Reduction in % disease index/germination |
| 13 | *Plasmopara viticola* (spore germiantion) | 01 | 93 |
| 14 | *Uncinula necator* (leaf disc assay) | 10 | 65 |
| | | 20 | 100 |
| 15 | *Puccinia arachidis* (leaf disc assay) | 10 | 67 |
| | | 20 | 75 |

Figure 18:
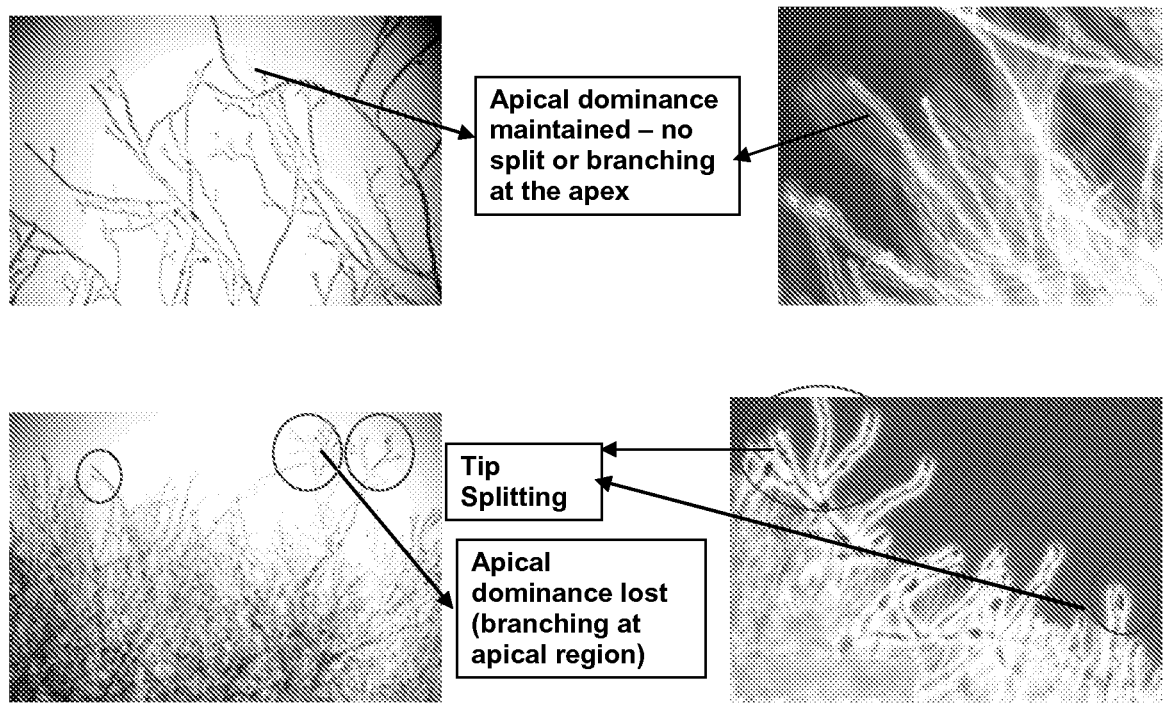
FIG. 18 shows (upper pictures, controls) normal hyphal growth as compared with changes in the plane of hyphal growth and abnormal thickening of the hyphae due to the antifungal effect of the potassium salt, XII", (two lower pictures).

Changes in the hyphal tips of *Botrytis cinerea* using potassium salt of 14-(furan-2-yl)tetradeca-11,13-diynoic acid, XII", were investigated to measure the effect of the Ole1 inhibitor upon growth and thriving. The compound was found to be toxic to the fungus *Botrytis cinerea* as described in the following. Apical dominance is an important criterion for growth of hyphae of fungi: at the apical tip of the mycelia branching is not seen near the growing tip. Apical dominance is maintained but branching of hyphae will start at sub-apical point, a distance away from the growth point. Under abnormal conditions of stress, apical dominance is lost, extensive branching begins, resulting in the growth of the fungal mycelia being arrested. When the test compound is incorporated in the media in which the fungi is present, hyphal tip splitting and branching is seen with loss of apical dominance and polarity. FIG. 18 shows (in the two lower pictures) the changes in the plane of hyphal growth and abnormal thickening of the hyphae when the mycelia are inoculated in the plates with potassium salt of 14-(furan-2-yl)tetradeca-11,13-diynoic acid (XII"), 2 µg/ml). Hyphae from the inoculated disc start growing against gravity and are thicker than the normal hyphae seen in the control (the two upper pictures). Abnormal thickening of the hyphae shows the stress created by the presence of the Ole1 inhibitor.

Example 21

Synthesis of (Z)-14-(furan-2-yl)tetradeca-9-en-11, 13-diynoic acid (III")

(Z)-14-(furan-2-yl)tetradeca-9-en-11,13-diynoic acid was prepared in a required isomeric ratio of at least 95:5 cis:trans, as determined by HPLC and NMR. Additional purification steps were performed in order to increase the purity of the coupling fragments. The route provided involves a convergent synthesis of intermediate 8 from the two fragments 2 and 7. The final product is synthesized by hydrolysis of the methyl ester to provide (Z)-14-(furan-2-yl)tetradeca-9-en-11,13-diynoic acid 9 (compound III″)

Fragment Synthesis:

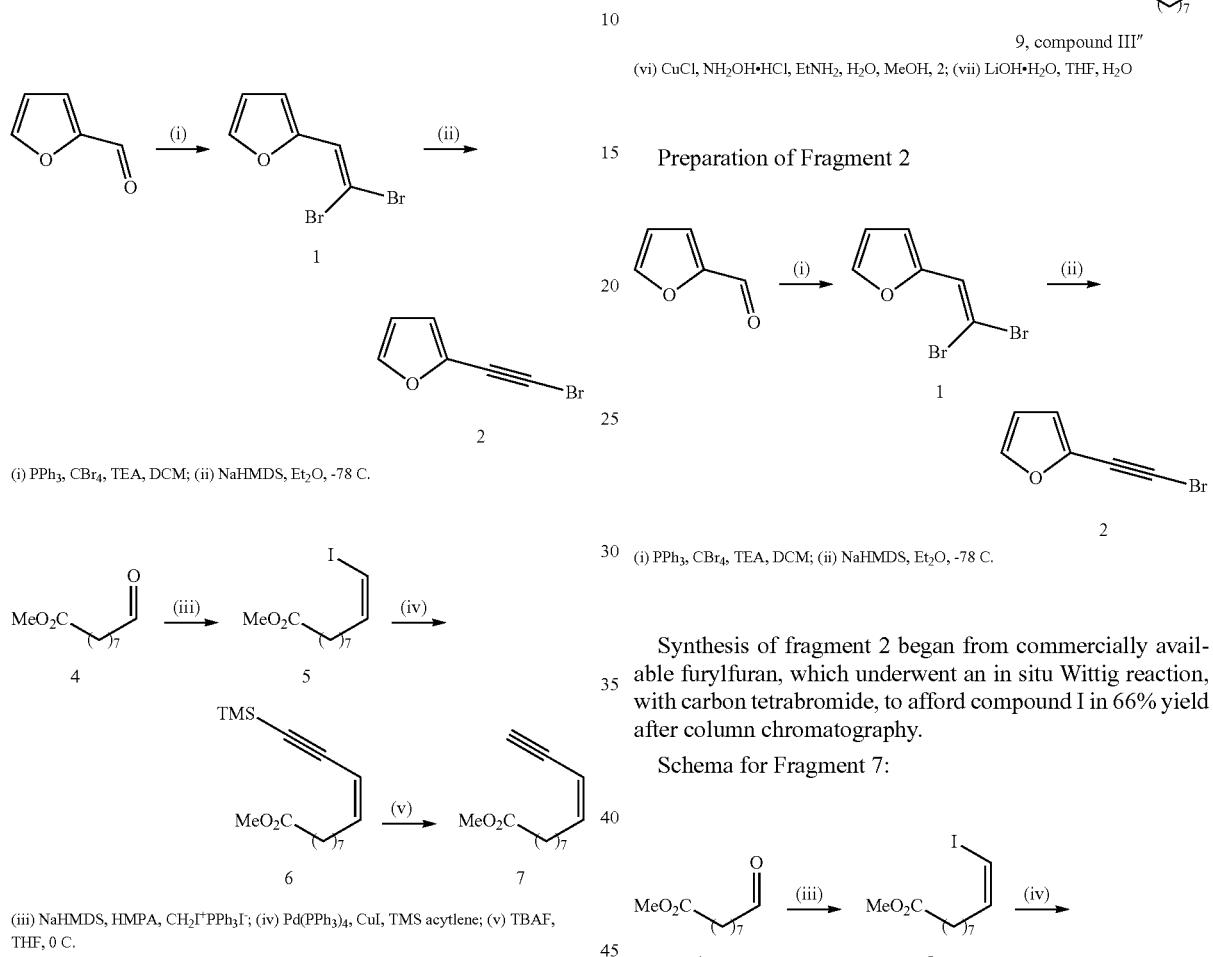

(vi) CuCl, NH$_2$OH·HCl, EtNH$_2$, H$_2$O, MeOH, 2; (vii) LiOH·H$_2$O, THF, H$_2$O Preparation of Fragment 2

(i) PPh$_3$, CBr$_4$, TEA, DCM; (ii) NaHMDS, Et$_2$O, -78 C.

Synthesis of fragment 2 began from commercially available furylfuran, which underwent an in situ Wittig reaction, with carbon tetrabromide, to afford compound I in 66% yield after column chromatography.

Schema for Fragment 7:

(iii) NaHMDS, HMPA, CH$_2$I$^+$PPh$_3$I$^-$; (iv) Pd(PPh$_3$)$_4$, CuI, TMS acytlene; (v) TBAF, THF, 0 C.

Synthesis of intermediate 5 is based on a Wittig olefination and the required salt was prepared from diiodomethane and triphenyl phosphine in 41% yield. The Wittig reaction of 9-oxononanoic acid methyl ester was initially carried out on a 10 g scale to afford the desired product in 88% yield. The column chromatography separated a close running impurity, which has been tentatively identified as triphenylphosphine, which presumably arises from decomposition of the excess phosphonium salt. The $^1$H NMR of the final product also showed the presence of a second impurity (based on a triplet at 6.6 ppm in the ¹H NMR). The cis:trans ratio of the alkene was determined by ¹H NMR, and shown to be 98:2.

Schema for (Z)-14-(furan-2-yl)tetradeca-9-en-11,13-diynoic acid (III")

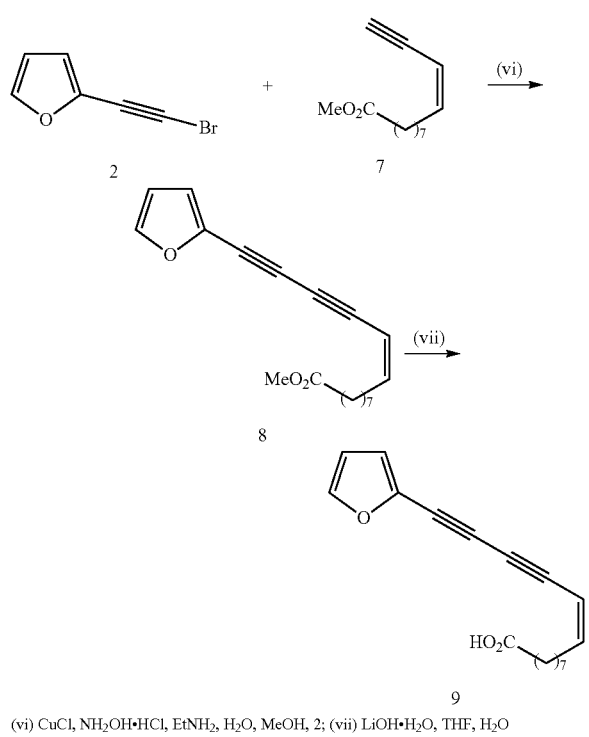

(vi) CuCl, NH₂OH•HCl, EtNH₂, H₂O, MeOH, 2; (vii) LiOH•H₂O, THF, H₂O

The final steps towards (Z)-14-(furan-2-yl)tetradeca-9-en-11,13-diynoic acid involved the coupling of the two key building blocks 2 and 7, followed by the hydrolysis of the ester 8 to yield the final compound. Compound 8 was prepared via a Cadiot-Chodkiewicz coupling of an ether solution of furan 2 to acetylene 7 under standard conditions (CuCl, HONH₂.HCl, EtNH₂, MeOH). The reaction was carried out on a test scale of 0.5 g of compound 7 and gave a recovery of 0.27 g in 37% yield. The final scale up of the coupling reaction was undertaken in two discrete batches and the results are summarized below:

Synthesis of Compound 8":

| Experiment | Scale, 7 (g) | Product (g) | Yield (%) | HPLC Purity (%) |
|---|---|---|---|---|
| CM/291/18 | 0.51 | 0.27 | 37 | 92 |
| CM/291/27 | 10 g | 8.28 | 58 | 92 |
| CM/291/29 | 10 g | 8.24 | 58 | 91 |

The scale up of the coupling reaction proceeded well, presumably due to the high purity of fragment 7. Column chromatography separated the product from several unidentified impurities. Hydrolysis of ester 8 was carried out in a 6:1:1 mixture of THF:water:MeOH with lithium hydroxide monohydrate at room temperature for five hours. The reaction mixture was acidified to pH 2 with 2N HCl and the partially precipitated solid was extracted with ethyl acetate. The reaction was initially carried out on an 0.4 g scale to afford the final product in high purity after dry flash column chromatography followed by precipitation from cold heptanes. The two batches from the coupling reactions were hydrolyzed separately to afford 13.7 g of (Z)-14-(furan-2-yl)tetradeca-9-en-11,13-diynoic acid after purification:

| Experiment | Scale (g) | Product (g) | Yield (%) | HPLC Purity (%) |
|---|---|---|---|---|
| CM/291/15 | 0.38 | 0.3 | 83 | 92 |
| CM/291/31 | 8.28 | 6.5 | 82 | 87 |
| CM/291/32 | 8.24 | 7.2 | 91 | 89 |

HPLC analysis of the crude product showed the presence of an impurity, arising from the coupling step, and although the levels were reduced after purification, they were still high. The two batches were therefore combined and slurried in the minimal amount of heptanes at room temperature for one hour. Cooling to 0° C. before filtration and washing with cold heptanes afforded 10.5 g of (Z)-14-(furan-2-yl)tetradeca-9-en-11,13-diynoic acid with an HPLC purity of 96% by area.

Experimental 2-(2,2-Dibromovinyl)Furan (1)

A solution of carbon tetrabromide (241.6 g, 0.73 mol) in anhydrous DCM (1000 mL) was cooled to −20° C. under nitrogen and triphenylphosphine (191.1 g, 0.73 mol) in anhydrous DCM (1000 mL) was added drop wise. After twenty minutes of stirring, the reaction was cooled to −60° C., and then a mixture of furfural (30 mL, 0.36 mol) and triethylamine (50.5 mL, 0.36 mol) in anhydrous DCM (375 mL) were added drop wise. The mixture was brought to room temperature and diethyl ether (500 mL) was added with stirring. The reaction was filtered and filtrate was concentrated in vacuo. Column chromatography (SiO₂, heptanes) yielded the title compound (58.1 g, 63%) as a brown oil:

¹H-NMR (400 MHz, CDCl₃) δ 6.46 (s, 1H), 6.94 (s, 1H), 7.40 (s, 1H), 7.43 (s, 2H).

2-Bromoethynylfuran (2)

Sodium Hexamethyldisilazane (NaHMDS, 111 mL, 0.22 mol, 2M in THF) was added drop wise to a solution of compound 1 (56 g, 0.22 mol) in anhydrous diethyl ether (1120 mL) at −78° C. and the resulting solution stirred for fifteen minutes. Aqueous ammonium chloride (500 mL, sat.) was added at −78 C and the reaction allowed to warm to room temperature. More aqueous ammonium chloride (200 mL, sat.) was added along with diethyl ether (200 mL). The layers were separated and the aqueous phase was extracted with diethyl ether (2×200 mL). The combined organic layers were washed with brine (500 mL) before being dried (MgSO₄) and filtered. The solvent was removed by atmospheric distillation to afford the title compound (20.8 g, 55%) in a condensed solution.

Iodomethylenetriphenyphosphonium iodide

Diiodomethane (150 mL, 1.86 mmol) and triphenylphosphine (425 g, 1.62 mmol) was dissolved in toluene (500 mL) and the resulting solution heated to 50° C. for eighteen hours. The solution was allowed to cool to room temperature before being filtered. The precipitate was washed with toluene (2×500 mL) before being dried under vacuo to yield the title compound (404 g, 41% yield) as a white solid:

$^1$H NMR (400 MHz, CDCl$_3$) δ 5.05 (m, 2H), 7.79-7.87 (m, 15H).

10-Iodec-9(Z)-enioc acid methyl ester (5)

NaHMDS (285 mL, 0.57 mol, 2M in THF) was added drop wise to a suspension of CH$_2$IP$^+$PPh$_3$I$^-$ (299 g, 0.56 mol) in anhydrous THF (1.5 L) at room temperature. After stirring for five minutes the solution was cooled to −78° C. and HMPA (139 mL, 0.77 mol) was added drop wise. 9-oxononanoic acid methyl ester 4 (75.0 g, 0.40 mol) was dissolved in anhydrous THF (375 mL) and added drop wise at −78° C. The resulting solution was allowed to warm to room temperature and stirred for sixteen hours. Ethyl acetate (1000 mL) and water (500 mL) were added and the layers separated. The aqueous phase was extracted with ethyl acetate (2×500 mL). The combined organic layers were washed with water (2×500 mL) and brine (500 mL) before being dried (MgSO$_4$), filtered and concentrated in vacuo. The resulting brown oil was dry loaded onto silica (~1 volume) and purified by column chromatography (SiO$_2$, 10% diethyl ether in heptanes) to afford the title compound (64.8 g, 52%) as a yellow oil. The mixed fractions were combined and concentrated before being purified by column chromatography (SiO$_2$, 10% DCM in heptanes) to afford compound 5 (18.4 g, 67% combined yield):

$^1$H NMR (400 MHz, Benzene-d6) δ 0.97-1.15 (m, 10H), 1.46-1.49 (m, 2H), 1.93-2.10 (m, 2H), 3.39 (s, 3H), 5.74 (q, 1H, J=7.0, 13.9 Hz), 5.92 (dt, 1H, J=7.3, 1.1 Hz).

12-Trimethylsilanyldodec-9(Z)-en-11-ynoic acid methyl ester (6)

10-Iododec-9-enioc acid methyl ester 5 (64.8 g, 0.21 mmol) and trimethylsilylacetylene (35.4 mL, 0.25 mol) was dissolved in anhydrous DMF (285 mL) and cooled to 0° C. Triethylamine (34.75 mL, 0.25 mol), copper (I) iodide (10.3 g, 0.05 mol) and tetrakis(triphenylphosphine)palladium (14.5 g, 0.01 mol) were added. The resulting solution was stirred at 0° C. for eighteen hours before being allowed to warm to room temperature. Water (200 mL) was added and the mixture was extracted with diethyl ether (2×500 mL). The combined organic layers were washed with brine (500 mL) before being dried (MgSO$_4$), filtered and concentrated in vacuo. The dark brown residue was dissolved in heptanes (500 mL) before being filtered and concentrated in vacuo. The residue was passed through a silica pad (SiO$_2$, 5% ethyl acetate in heptanes) to afford the title compound (45.0 g, 77%) as a yellow oil:

$^1$H NMR (400 MHz, CDCl$_3$) δ 0.20 (s, 9H), 1.50-1.20 (m, 8H), 1.70-1.60 (m, 2H), 2.40-2.20 (m, 4H), 3.65 (s, 3H), 5.9-5.7 (m, 1H), 5.5-5.4 (m, 1H).

9(Z)-Dodecen-11-ynoic acid methyl ester (7)

Tetrabutylammonium fluoride, TBAF (177 mL, 0.18 mol, 1M in THF) was added dropwise to a solution of 12-trimethylsilanyldodec-9-en-11-ynoic acid methyl ester (6) (45.0 g, 0.16 mol) in anhydrous THF (950 mL) at 0° C. The resulting solution was stirred for thirty minutes before being allowed to warm to room temperature. The THF was removed in vacuo and the resulting dark oil was passed through a silica pad (SiO$_2$, 10% ethyl acetate in heptanes) to afford the title compound (20.0 g, 60%) as a yellow oil:

$^1$H NMR (400 MHz, CDCl$_3$) δ 1.31-1.40 (m, 10H), 1.58-1.61 (m, 2H), 2.29-2.32 (m, 2H), 3.06 (s, 1H), 3.66 (s, 3H), 3.44 (m, 1H), 5.99 (m, 1H).

Methyl (9Z)-14-(2-furyl)tetradeca-11,13-diyneoate (8)

Copper (I) chloride (0.52 g, 5.27 mmol), hydroxylamine hydrochloride (1.67 g, 24.00 mmol) and ethylamine (144 mL, 1.78 mol, 70% in H$_2$O) were dissolved in methanol (120 mL) and cooled to 0° C. Dodec-9-en-11-ynoic acid methyl ester 7 (10 g, 0.048 mmol) in methanol (85 mL) was added drop wise to the above solution. 2-Bromoethynylfuran 2 (66 g, 0.06 mol, 16% THF/diethyl ether solution) was added drop wise to the above solution. The resulting solution was stirred at 0° C. for two hours before water (150 mL) and diethyl ether (150 mL) were added and the layers separated. The aqueous phase was extracted with diethyl ether (3×100 mL) and combined organic layers were washed with brine (250 mL) before being dried (MgSO$_4$), filtered and concentrated in vacuo. Column chromatography (SiO$_2$, 2-5% ethyl acetate in heptanes) afforded the title compound (8.28 g, 58% yield) as a yellow oil:

$^1$H NMR (400 MHz, CDCl$_3$) δ 1.50-1.20 (m, 8H), 1.70-1.60 (m, 2H), 2.42-2.30 (m, 4H), 3.60 (s, 3H), 5.59 (d, 1H, J=10.5 Hz), 6.19-6.14 (m, 1H), 6.48-6.38 (m, 1H), 6.70 (d, 2H, J=3.0 Hz), 7.45-7.40 (m, 1H).

(9Z)-14-(2-furyl)tetradeca-11,13-diynoic acid (9)(III)

Lithium hydroxide monohydrate (3.49 g, 0.083 mol) was added to a solution of methyl ester 8 (8.28 g, 0.028 mmol) in THF:water:methanol (160 mL, 6:1:1) at 0° C. The solution was allowed to warm to room temperature and stirred for eighteen hours before water (100 mL) was added. The pH of the solution was adjusted to pH2 with 2N aqueous hydrochloric acid (~45 mL). Ethyl acetate (100 mL) was added and the layers separated. The aqueous phase was extracted with ethyl acetate (2×50 mL) and the combined organic layers were washed with brine (100 mL) before being dried (MgSO$_4$), filtered and concentrated in vacuo. The residue was passed through a silica pad (SiO$_2$, 10% ethyl acetate in heptanes) before being dissolved in heptanes (~15 volumes) and left in the freezer overnight. The yellow precipitate was filtered and washed with cold heptanes before being dried to afford the title compound (7.5 g, 91%) as a pale yellow solid:

$^1$H NMR (400 MHz, CDCl$_3$) δ 1.5-1.2 (m, 8H), 1.7-1.6 (m, 2H), 2.4-2.3 (m, 4H), 5.59 (d, 1H, J=10.5 Hz), 6.19-6.14 (m, 1H), 6.48-6.38 (m, 1H), 6.7 (d, 2H, J=3.0 Hz), 7.45-7.4 (m, 1H).

m.p. 49.8-52.3° C.;

Synthesis of potassium (IV") and sodium (V") salts of (9Z)-14-(2-furyl)tetradeca-11,13-diynoic acid (9)(III")

Compound III" (25 mg) was dissolved in 250 μl of solvent (dioxane, acetone or ethanol) and warmed to 50° C. A solution of potassium or sodium ethoxide (1M in ethanol, 1.1 equivalents) was added and the reactions were then allowed to cool to room temperature. Salts (IV" and V" respectively) precipitated out and were filtered off and dried.

Example 22

Synthesis of 8-(2-(4-(furan-2-yl)buta-1,3-diynyl)phenyl)octanoic acid (VII")

Scheme 1

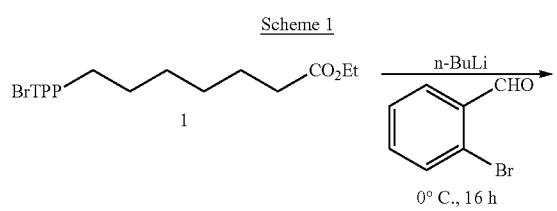

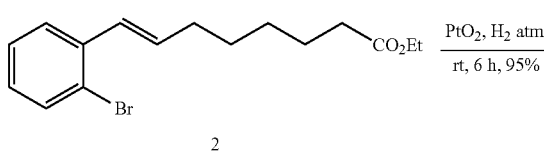

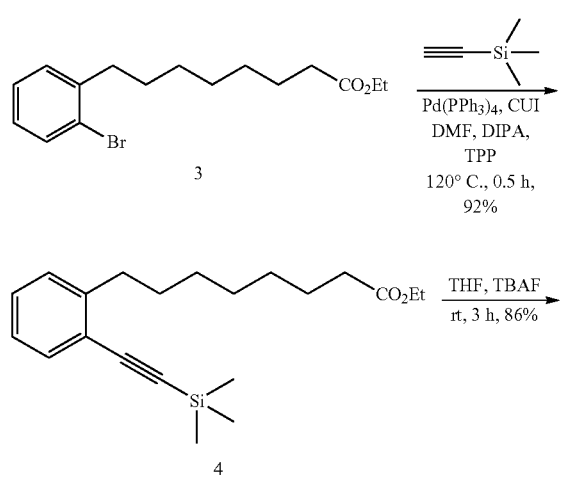

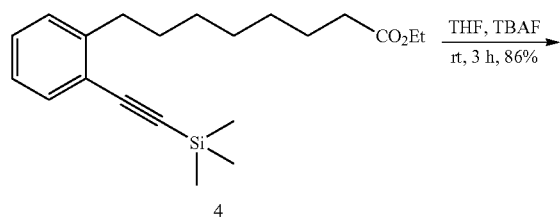

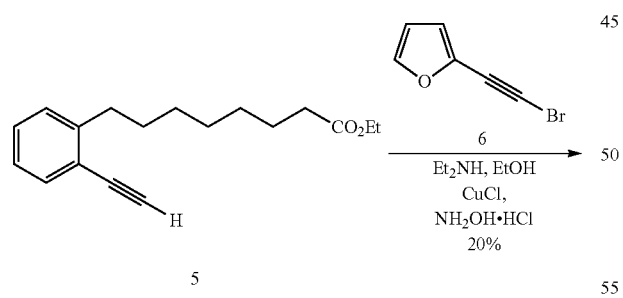

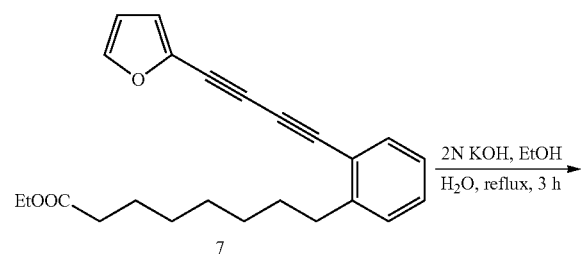

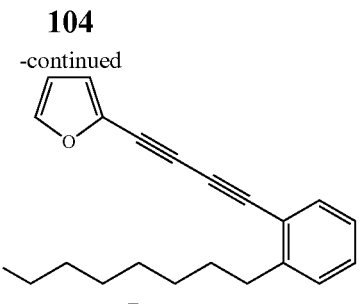

Target

Example 23

Synthesis of 14-(2-furyl)tetradeca-11,13-diynoic acid (X")

Laboratory scale synthesis of approximately 10 g of 14-(2-furyl)tetradeca-11,13-diynoic acid gave good overall yield of high purity from relatively cheap and readily available starting materials. The route involved the synthesis of two building blocks followed by the convergent synthesis of the target molecule.

Fragment Synthesis:

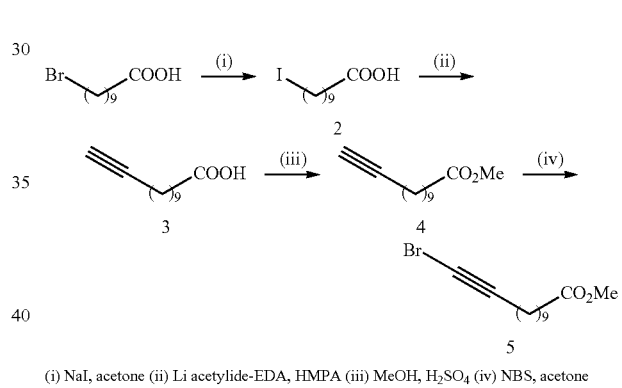

(i) NaI, acetone (ii) Li acetylide-EDA, HMPA (iii) MeOH, $H_2SO_4$ (iv) NBS, acetone

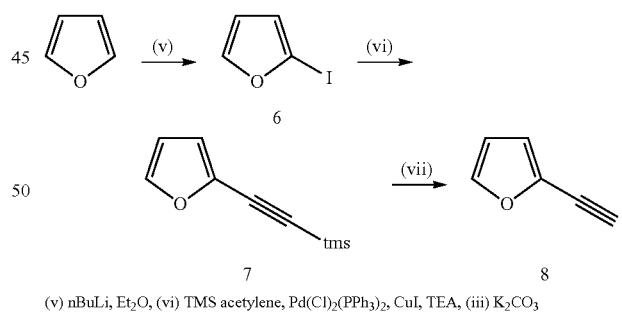

(v) nBuLi, $Et_2O$, (vi) TMS acetylene, $Pd(Cl)_2(PPh_3)_2$, CuI, TEA, (iii) $K_2CO_3$ Coupling Steps:

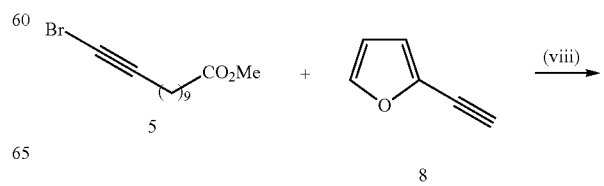

-continued

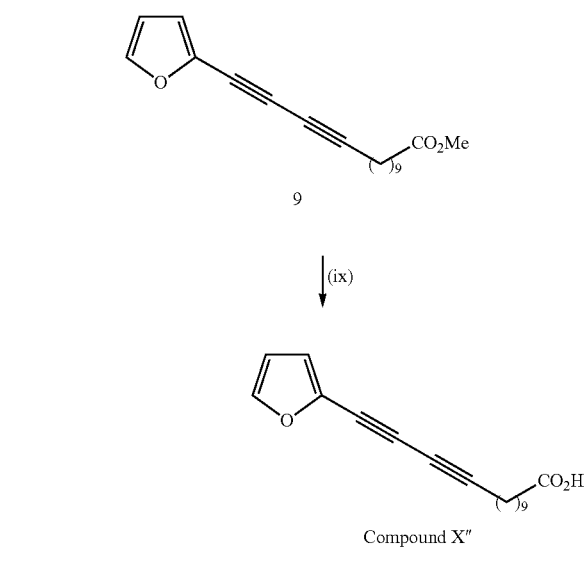

Compound X″

(vii) CuI, pyrrolidine (ix) LiOH•H₂O, THF/MeOH/H₂O

Schema for decanoic acid fragment (5):

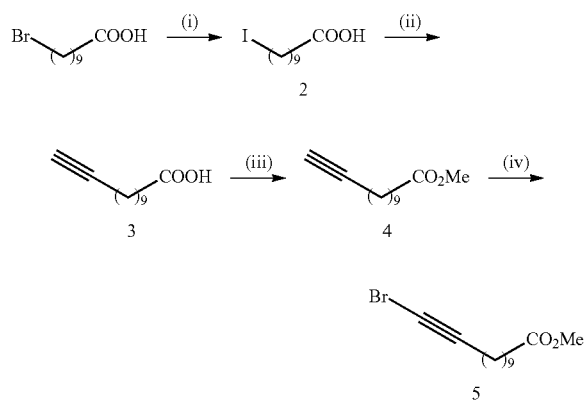

(i) NaI, acetone (ii) Li acetylide-EDA, HMPA (iii) MeOH, H₂SO₄ (iv) NBS, acetone Schema for 2-ethynylfuran building block (8):

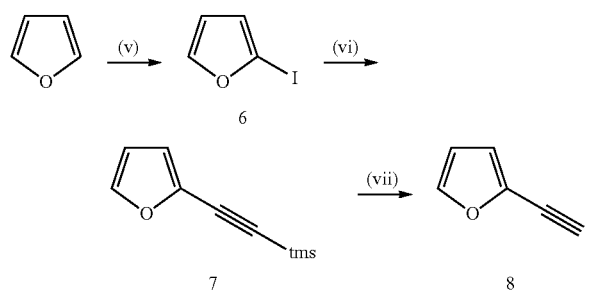

(v) nBuLi, Et₂O, (vi) TMS acetylene, Pd(Cl)₂(PPh₃)₂, CuI, TEA, (iii) K₂CO₃

Schema for 14-(2-furyl)tetradeca-11,13-diynoic acid:

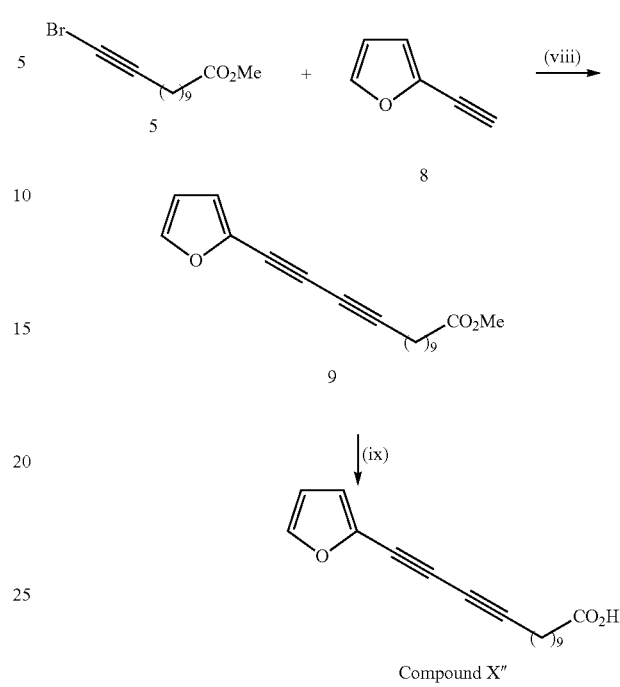

Compound X″

(vii) CuI, pyrrolidine (ix) LiOH•H₂O, THF/MeOH/H₂O

Experimental

10-Iododecanoic acid (2)

To a mechanically stirred solution of 10-bromodecanoic acid (50 g, 0.2 mol) in 1 L of acetone under nitrogen was added sodium iodide (238.7 g, 1.59 mol) and the resulting heterogeneous reaction mixture was allowed to stir at room temperature for 18 h. The thick reaction mixture was filtered through a pad of Celite 521, concentrated in vacuo to one-fifth volume and diluted with 1 L of brine. This was extracted with 4×250 mL of hexanes. The combined organic extracts were washed with 2×250 mL of freshly prepared 10% aqueous sodium thiosulfate, dried over sodium sulfate, concentrated in vacuo and vacuum dried to give iodo acid 2 (57.5 g, 98%) as a white solid:

$^1$H NMR (400 MHz, CDCl$_3$): 1.23-1.41 (m, 10H), 1.60-1.67 (m, 2H), 1.80-1.85 (m, 2H), 2.34 (t, J=7.3 Hz, 2H), 3.17 (t, J=7.32 Hz, 2H), 11.45 (br s, OH).

11-Dodecynoic acid (3) (see De Jarlais, et al., *Synth. Comm.* 1980, 10, 653)

A suspension of lithium acetylide-ethylenediamine complex (90% w/w, 58.7 g, 573 mmol) under nitrogen in 330 mL of HMPA was mechanically stirred at room temperature for 45 min and then cooled to −5 degrees C. A solution of iodo acid 2 (57.00 g, 191 mmol) in 130 mL of HMPA was then added via pressure equalized addition funnel to the cooled acetylide suspension with stirring at such a rate as to maintain the internal temperature between 0 and 5 degrees C. The reaction mixture was allowed to stir an additional 30 min at −3 degrees C. and then was carefully quenched in portions into 2 L of ice. The yellowish ice mixture was acidified to pH 2.5 with 5M aqueous sulfuric acid, divided into two portions and the tan solids in each portion were extracted with 3×250 mL of diethyl ether. The combined ether layers were washed with 4×50 mL of water, dried over sodium sulfate, concentrated in vacuo, and vacuum dried to give omega acetylenic acid 3 (37.6 g, 100%) as an orange solid:

$^1$H NMR (400 MHz, CDCl$_3$): 1.24-1.42 (m, 10H), 1.48-1.66 (m, 4H), 1.92 (t, J=2.56 Hz, 1H), 2.16 (dt, J$^1$=2.56 Hz, J$^2$=7.69 Hz, 2H), 2.39 (t, J=7.69 Hz, 2H).

Methyl 11-dodecynoate (4)

To a stirring solution of acetylenic acid 3 (37 g, 188 mmol) in 1.1 L of methanol was added 2.2 mL of concentrated sulfuric acid, and the resulting reaction mixture was heated under reflux for 16 h. Upon cooling to room temperature, the reaction mixture was concentrated to one third volume in vacuo, diluted with 1 L of 2:1 hexanes/diethyl ether, and washed with 2×50 mL of saturated aqueous sodium bicarbonate. The combined aqueous washes were further extracted with 2×150 mL of diethyl ether, treated with 50 mL of brine, combined with the previous organic extract and dried sodium sulfate. Concentration in vacuo gave a biphasic residue that was partitioned with 500 mL of hexanes and 50 mL of brine. The aqueous layer was further extracted with 2×50 mL of hexanes, the combined organic layers were dried over sodium sulfate, concentrated in vacuo, and vacuum dried to give methyl ester 4 (38.2 g, 96%) a golden-brown oil:

$^1$H NMR (400 MHz, CDCl$_3$): 1.25-1.36 (m, 10H), 1.41-1.65 (m, 4H), 1.92 (t, J=2.56 Hz, 1H), 2.16 (dt, J'=2.56 Hz, J$^2$=7.32 Hz, 2H), 2.31 (t, J=7.32 Hz, 2H), 3.64 (s, 3H).

Methyl 12-bromo-11-dodecynoate (5)

To a mechanically stirred solution of ester 4 (37 g, 176 mmol) in 700 mL of acetone under nitrogen was added N-bromosuccinimide (34.4 g, 194 mmol) followed by silver nitrate (2.7 g, 18 mmol). The reaction mixture was allowed to stir at room temperature in the absence of light for 21 h. The thick, pale yellow reaction mixture was filtered through a sintered glass funnel, concentrated in vacuo to one third volume, and diluted with 500 mL of water. This was extracted with 4×250 mL of hexanes, and the combined organic layers were washed with 100 mL of brine, dried over sodium sulfate, concentrated in vacuo, and vacuum dried to give bromoacetylene 5 (47.81 g, 94%) as a yellow oil:

$^1$H NMR (400 MHz, CDCl$_3$): 1.25-1.40 (m, 10H), 1.46-1.59 (m, 4H), 2.17 (t, J=6.96 Hz, 2H), 2.27 (t, J=7.32 Hz, 2H), 3.64 (s, 3H).

2-Iodofuran (6)

To a mechanically stirred, cooled (−78° C.) solution of furan (60.0 mL, 825 mmol) in 500 mL of dry ether under nitrogen was added a solution of n-butyllithium in cyclohexane (2.0M, 412 mL, 825 mmol) via pressure-equalized addition funnel over 60 min. The metalation was allowed to proceed at −78° C. for 5 h, and at room temperature for 2 h. The thick, yellow reaction mixture was again cooled to −78° C., and iodine (209 g, 825 mmol) was added in two portions with good stirring (a slight exotherm was noted). The reaction mixture was allowed to warm to room temperature overnight. Upon warming to room temperature, the mixture was treated with 2×250 mL of freshly prepared 10% aqueous sodium thiosulfate and 250 mL each of saturated aqueous sodium bicarbonate and brine, and dried over sodium sulfate. The organic layer was concentrated in vacuo at 35 torr to give iodide 6 (382 g, contaminated with cyclohexane, 30% w/w 6, 72% yield) as a red oil:

$^1$H NMR (400 MHz, CDCl$_3$): 6.35 (s, 1H), 6.53 (s, 1H), 7.53 (s, 1H).

2-(Trimethylsilylethynyl)furan (7)

To a stirring solution of 6 (30% w/w, 79 g, 407 mmol) in 600 mL of triethylamine under nitrogen was added trimethylsilylacetylene (44 g, 448 mmol), dichlorobis(triphenylphosphine)palladium(II) (10 g, 14 mmol), and copper (I) iodide (5.1 g, 27 mmol). The reaction mixture was allowed to stir at room temperature in the absence of light for 16 h. The thick reaction mixture was diluted with 100 mL of diethyl ether and passed through a pad of Celite 521. The pad was washed with 2×100 mL of diethyl ether and the combined filtrates were concentrated in vacuo at 50 ton. The residue was purified by flash chromatography on silica gel (hexanes) to give TMS-protected ethynylfuran 7 (56.9 g, 85%) as a yellow oil:

$^1$H NMR (400 MHz, CDCl$_3$): 0.22-0.28 (br(s), 9H), 6.37 (t, 1H), 6.61 (d, 1H), 7.36 (d, 1H).

2-Ethynylfuran (8)

To a mechanically stirred, ice-water bath-cooled solution of 7 (54 g, 329 mmol) in 540 mL of methanol under nitrogen was added potassium carbonate (104.5 g, 756 mmol). The resulting heterogeneous reaction mixture was stirred for 18 h as the vessel came to room temperature. The reaction mixture was diluted with 1500 mL of water and extracted with 4×500 mL of diethyl ether. The combined organic layers were washed with 3×150 mL of water, 200 mL of brine, dried over sodium sulfate and the ether was removed by fractional distillation at atmospheric pressure to give 8 (88.3 g, contaminated with diethyl ether and silanol, 23% w/w 8, 68% yield) as a red oil.

$^1$H NMR (400 MHz, CDCl$_3$): 3.35 (s, 1H), 6.32 (s, 1H), 6.60 (s, 1H), 7.35 (s, 1H).

Methyl 14-(2-furyl)tetradeca-11,13-diynoate (9) (see Ferri, *Tetrahedron Lett.*, 1996, 37, 2763):

A mechanically stirred solution of bromoacetylene 5 (35 g, 121 mmol) and ethynylfuran 8 (23% w/w, 16.7 g, 182 mmol) in 400 mL of pyrrolidine under nitrogen was cooled via ice-water bath. Copper (I) iodide (3.69 g, 19 mmol) was added in one portion and after 5 min the cooling bath was removed and the homogeneous mixture was stirred an additional 1 h. The dark red reaction was quenched by addition of 850 mL of water with stirring. The orange-yellow suspension was extracted with 4×300 ml of diethyl ether. The combined organic layers were washed with 3×100 mL of water and 100 mL of brine, dried over sodium sulfate, and concentrated in vacuo to a dark red oil. The residue was resuspended in 100 mL of 10% ethyl acetate in hexanes and passed through a pad of silica gel in a flitted funnel. The pad was washed with an additional 4×50 mL of solvent and concentrated in vacuo to give 21.0 g of crude 9 as a dark red oil.

$^1$H NMR (400 MHz, CDCl$_3$): 1.26-1.43 (m, 10H), 1.53-1.66 (m, 4H), 2.31 (t, 2H), 2.37 (t, 2H), 3.65 (s, 3H), 6.39 (s, 1H), 6.65 (s, 1H), 7.38 (s, 1H).

14-(furan-2-yl)tetradeca-11,13-diynoic acid (X")

To a solution of crude ester 9 (10 g) in 200 mL of THF:water:methanol (150:25:25) was added with stirring 4.2 g Lithium hydroxide (3 eq). The atmosphere was replaced with nitrogen and the mixture was stirred for 5 h and then cooled via ice-water bath. The golden-brown mixture was slowly acidified with 2N aqueous hydrochloric acid to pH2. The partially precipitated acid was extracted in two portions with 4×250 mL of ethyl acetate. The combined organic layers were washed with 2×75 mL of water and 75 mL of brine, dried over sodium sulfate, and concentrated in vacuo. The dark brown solid was partially purified by suction filtration column chromatography on silica gel (0 to 30% ethyl acetate in heptane) to give a yellow solid. This solid was resuspended in heptane and cooled in an ice bath. The mixture was filtered to yield a fine tan-yellow powder (6.88 g, 72%).

m.p. 62.6-63.5° C.

$^1$H NMR (400 MHz, CDCl$_3$): 1.25-1.45 (m, 10H), 1.53-1.60 (m, 2H), 1.60-1.68 (m, 2H), 2.34-2.40 (m, 4H), 6.37 (d, 1H), 6.65 (d, 1H), 7.36 (s, 1H)

$^{13}$C NMR (100 MHz, CDCl$_3$): 19.72, 24.72, 28.15, 28.87, 29.21, 29.24, 29.39, 29.46, 34.26, 64.30, 64.74, 79.19, 87.80, 111.07, 117.44, 136.77, 144.22, 180.45.

Potassium 14-(furan-2-yl)tetradeca-11,13-diynoate (XII")

To a solution of 1 mmol 14-(furan-2-yl)tetradeca-11,13-diynoic acid in water, 1 m molar aqueous potassium hydroxide was added at room temperature with stirring. After 2-3 hours the reaction mixture was concentrated under reduced pressure. The crude product was dissolved in acetone and heated to 40° C. for 10 min, then the solid product filtered off and washed several times with acetone. The resultant solid product was evaporated under reduced pressure yielding potassium 14-(furan-2-yl)tetradeca-11,13-diynoate. The sodium salt 14-(furan-2-yl)tetradeca-11,13-diynoate (XI") was achieved in like manner from 14-(furan-2-yl)tetradeca-11,13-diynoic acid.

Example 24

Minimum Inhibitory Concentration (MIC) Testing

The in vitro efficacy of antifungal compounds is determined in susceptibility assays, which are indicative for the spectrum and potency of a compound. Susceptibilities are reported as minimal inhibitory concentrations (MIC, as ng/ml or µg/ml) required to inhibit growth to a defined degree compared to the drug free control. The MIC$_{90}$ defines the MIC required to inhibit growth for ≥90% of the strains of a population tested.

MIC of (Z)-14-(furan-2-yl)tetradeca-9-en-11,13-diynoic acid, potassium salt versus reference Candida strains (Z)-14-(furan-2-yl)tetradeca-9-en-11,13-diynoic acid, potassium salt and 14-(furan-2-yl)tetradeca-11,13-diynoic acid were tested against seven clinical Candida reference strains according to the CLSI reference method M27-A3. MIC break points were read at a growth inhibition of 100% compared to the drug free control. The inoculum size was 0.5-2.5×10$^3$ colony-forming units (CFU)/ml. Incubation temperature and time were 35° C. and 24 hrs.

Table 25 lists the MIC breakpoints in ng/ml obtained for the indicated reference strains.

TABLE 25

| Organism ID | (Z)-14-(furan-2-yl)tetradeca-9-en-11,13-diynoic acid, potassium salt | 14-(furan-2-yl)tetradeca-11,13-diynoic acid |
|---|---|---|
| C. albicans ATCC 24433 | 2.5 | 20 |
| C. albicans ATCC 90028 | 5 | 20 |
| C. glabrata ATCC 90030 | 60 | 2560 |
| C. krusei ATCC 6258 | 60 | 1280 |
| C. parapsilosis ATCC 22019 | 10240 | >10240 |
| C. parapsilosis ATCC 90018 | >10240 | >10240 |
| C. tropicalis ATCC 750 | 7.5 | 80 |

MIC$_{90}$ of (Z)-14-(furan-2-yl)tetradeca-9-en-11,13-diynoic acid, potassium salt versus clinical Candida isolates (Z)-14-(furan-2-yl)tetradeca-9-en-11,13-diynoic acid, potassium salt was tested head-to-head against AmphotericinB, Voriconazole and Caspofungin versus 193 clinical Candida isolates according to the CLSI reference method M27-A3. For (Z)-14-(furan-2-yl)tetradeca-9-en-11,13-diynoic acid, potassium salt and Voriconazole, MIC break points were read at a growth inhibition of 50% compared to the drug free control and for Amphotericin, MIC breakpoints were read at a growth inhibition of 100%. For Caspofungin, the minimum effective concentration (MEC) was determined according to the CLSI reference method M27-A3. The inoculum size was 0.5-2.5×10$^3$ colony-forming units (CFU)/ml. Incubation temperature and time were 35° C. and 24 hrs. The MIC$_{90}$ was calculated for the indicated species.

Table 26 lists the MIC$_{90}$ values in ng/ml obtained for the indicated Candida species tested versus (Z)-14-(furan-2-yl)tetradeca-9-en-11,13-diynoic acid, potassium salt, AmphotericinB, Voriconazole and Caspofungin.

TABLE 26

| Organism ID (# of isolates) | (Z)-14-(furan-2-yl)tetradeca-9-en-11,13-diynoic acid, potassium salt | Amphotericin B | Voriconazole | Caspofungin |
|---|---|---|---|---|
| C. albicans (n = 20) | 2.5 | 500 | 30 | n.d. |
| C. glabrata (n = 25) | 20 | 2000 | 125 | 2000 |
| C. tropicalis (n = 35) | 5 | 1000 | 30 | 1000 |
| C. dubliniensis (n = 25) | 2.5 | 1000 | 16 | 1000 |
| C. krusei (n = 27) | 20 | 4000 | 500 | 2000 |
| C. lusitaniae (n = 24) | 128 | 1000 | 30 | 2000 |
| C. parapsilosis (n = 37) | 1024/128* | 500 | 125 | 8000 |

*calculated MIC$_{90}$ and MIC$_{50}$ value, respectively

In parallel, a panel of clinical C. albicans and C. glabrata isolates with resistances versus Fluconazole, Itraconazole, Voriconazole and Caspofungin were tested for susceptibility versus (Z)-14-(furan-2-yl)tetradeca-9-en-11,13-diynoic acid, potassium salt, AmphotericinB, Voriconazole and Caspofungin.

Table 27 lists the $MIC_{90}$ values in ng/ml obtained for the resistant *Candida* species tested versus (Z)-14-(furan-2-yl)tetradeca-9-en-11,13-diynoic acid, potassium salt, AmphotericinB, Voriconazole and Caspofungin.

TABLE 27

| Organism ID (# of isolates) | EV-086-3314K | Amphotericin B | Voriconazole | Caspofungin |
|---|---|---|---|---|
| *C. albicans* resistant[1] (n = 20) | 2.5 | 500 | >500 | n.d. |
| *C. glabrata* resistant[2] (n = 21) | 20 | 2000 | 500 | 2000 |

[1] including clinical isolates with resiscances against Fluconazole, Itraconazole and Caspofungun
[2] including clinical isolates with resiscances against Fluconazole, Itraconazole, Voriconazole and Caspofungin MIC of (Z)-14-(furan-2-yl)tetradeca-9-en-11,13-diynoic acid, potassium salt versus clinical *Aspergillus* isolates (Z)-14-(furan-2-yl)tetradeca-9-en-11,13-diynoic acid, potassium salt was tested head-to-head against AmphotericinB and Voriconazole versus 39 clinical *Aspergillus* isolates. Susceptibilities were determined according to the CLSI reference method M38-A2. MIC break points were read at a growth inhibition of 50% compared to the drug free control. Incubation time was 24 h and $MIC_{50}$ values were calculated.

Table 28 lists the $MIC_{50}$ values in ng/ml obtained for the indicated *Aspergillus* species tested versus (Z)-14-(furan-2-yl)tetradeca-9-en-11,13-diynoic acid, potassium salt, AmphotericinB and Voriconazole.

TABLE 28

| Organism ID (# of isolates) | (Z)-14-(furan-2-yl)tetradeca-9-en-11,13-diynoic acid, potassium salt | Amphotericin B | Voriconazole |
|---|---|---|---|
| *A. fumigatus* (n = 20) | 80 | 500 | 250 |
| *A. terreus* (n = 5) | 10 | 2000 | 250 |
| *A. niger* (n = 6) | 2560 | 1000 | 1000 |
| *A. flavus* (n = 2) | >5120 | 2000 | 500 |
| *A. versicolor* (n = 3) | 1280 | 2000 | 250 |
| *A. nidulans* (n = 3) | 5120 | 2000 | 125 |

MIC of (Z)-14-(furan-2-yl)tetradeca-9-en-11,13-diynoic acid, potassium salt versus clinical dimorphic fungi (Z)-14-(furan-2-yl)tetradeca-9-en-11,13-diynoic acid, potassium salt was tested head-to-head against AmphotericinB, Voriconazole and Caspofungin versus 80 clinical isolates of dimorphic fungi including *Coccidioides* spp., *B. dermatitidis* and *H. capsulatum* according to the CLSI reference method M38-A2. MIC break points were defined as a growth reduction of 50% compared to the drug free control Table 29 lists the $MIC_{90}$ values in ng/ml obtained for the indicated dimorphic fungal species tested versus (Z)-14-(furan-2-yl)tetradeca-9-en-11,13-diynoic acid, potassium salt, AmphotericinB, Voriconazole and Caspofungin.

TABLE 29

| Organism ID (# of isolates) | (Z)-14-(furan-2-yl)tetradeca-9-en-11,13-diynoic acid, potassium salt | Amphotericin B | Voriconazole | Caspofungin |
|---|---|---|---|---|
| *Coccidioides* spp. (n = 30)[1] | 30 | 500 | 125 | 500 |
| *B. dermatitidis* (n = 30)[2] | 30 | 250 | 250 | 4000 |
| *H. capsulatum* (n = 20)[3] | 30 | 125 | 125 | 2000 |

MIC read at
[1] 48 h,
[2] 96 h,
[3] 120 h

Example 25

Antifungal activity of single (Z)-14-(furan-2-yl)tetradeca-9-en-11,13-diynoic acid, sodium salt infusion in a rat model of systemic candidiasis The efficacy of (Z)-14-(furan-2-yl)tetradeca-9-en-11,13-diynoic acid, sodium salt was investigated in an in vivo rat model system for invasive candidiasis. The rats were infected systemically by injection of $1 \times 10^7$ *C. albicans* blastospores via a surgically implanted catheter in the jugular vein. A single 12 mg/kg infusion of (Z)-14-(furan-2-yl)tetradeca-9-en-11,13-diynoic acid, sodium salt was given as a 2 hour intravenous infusion through the same cannula starting 2 hours after infection. Livers were collected 24 hours after the end of the infusion and fungal burdens were determined in the tissues. (Z)-14-(furan-2-yl)tetradeca-9-en-11,13-diynoic acid, sodium salt reduced the tissue burden (cfu/g tissue) by 90% compared with vehicle treated animals at 24 hours. The comparator Fluconazole reduced the tissue burden (cfu/g tissue) by 93% compared with vehicle treated animals at 24 hours.

Figure 24:
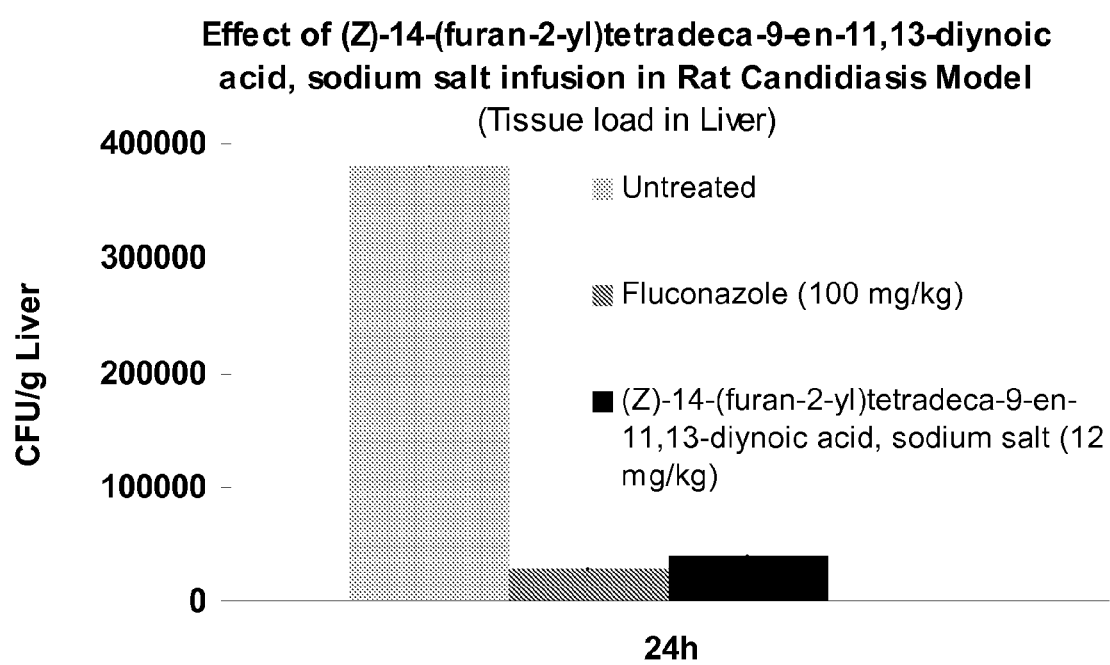
FIG. 24 shows the liver tissue fungal load of rats infected with *C. albicans* blastospores and treated with a single infusion of (Z)-14-(furan-2-yl)tetradeca-9-en-11,13-diynoic acid, sodium salt, Fluconazole or untreated.

FIG. 24 shows the liver tissue fungal load of rats infected with *C. albicans* blastospores and treated with a single infusion of (Z)-14-(furan-2-yl)tetradeca-9-en-11,13-diynoic acid, sodium salt, Fluconazole or untreated.

Antifungal activity of a single oral administration of (Z)-14-(furan-2-yl)tetradeca-9-en-11,13-diynoic acid, sodium in a rat model of systemic candidiasis The efficacy of (Z)-14-(furan-2-yl)tetradeca-9-en-11,13-diynoic acid, sodium salt was investigated in an in vivo rat model system for invasive candidiasis. The rats were infected systemically by injection of $1 \times 10^7$ *C. albicans* blastospores via a surgically implanted catheter in the jugular vein. A single 17 mg/kg infusion of (Z)-14-(furan-2-yl)tetradeca-9-en-11,13-diynoic acid, sodium salt was administered by oral gavage 2 hours after infection. Kidneys were collected 6 hours after the end of the infusion and fungal burdens were determined in the tissues. (Z)-14-(furan-2-yl)tetradeca-9-en-11,13-diynoic acid, sodium salt reduced the tissue burden (cfu/g tissue) by 57% compared with vehicle treated animals at 6 hours. The comparator Fluconazole reduced the tissue burden (cfu/g tissue) by 90% compared with vehicle treated animals at 24 hours.

Figure 25:
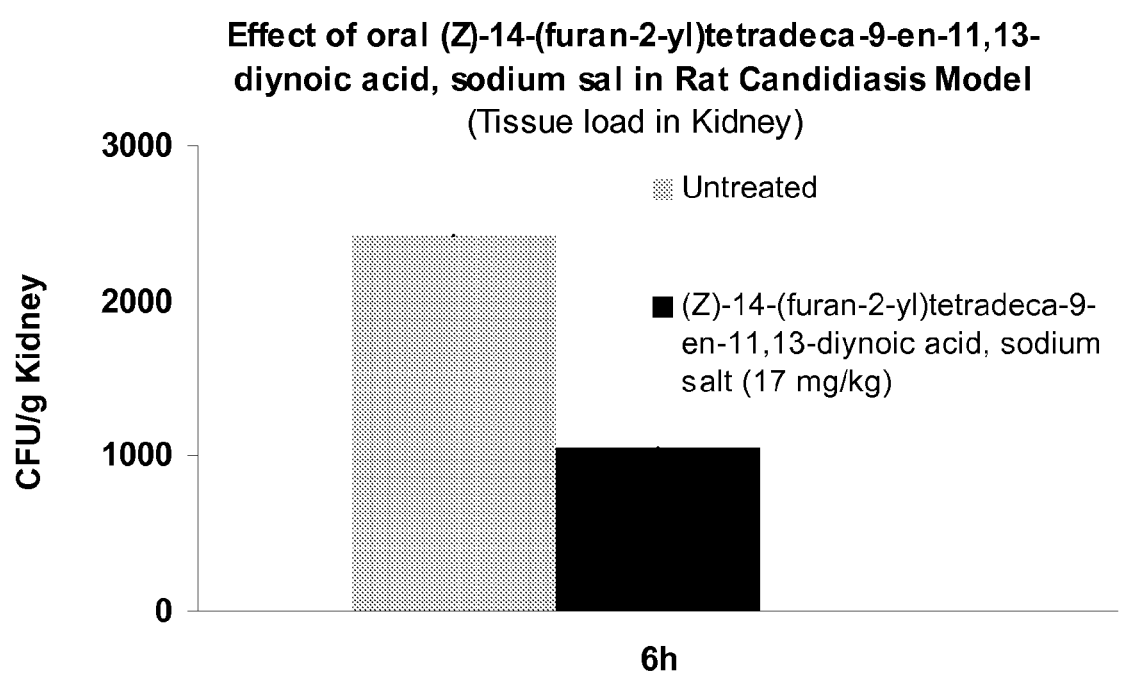
FIG. 25 compares the kidney tissue fungal load of rats infected with *C. albicans* blastospores and treated with a single oral administration of (Z)-14-(furan-2-yl)tetradeca-9-en-11,13-diynoic acid, sodium salt or untreated.

FIG. 25 compares the kidney tissue fungal load of rats infected with *C. albicans* blastospores and treated with a single oral administration of (Z)-14-(furan-2-yl)tetradeca-9-en-11,13-diynoic acid, sodium salt or untreated.

What we claim:

1. A crystalline diyne compound of the formula I:

wherein Z is a carbon chain substituted with —COO⁻ and is optionally substituted with one or more additional substituents; and $R_3$ is a heterocyclic ring, which optionally may be substituted at one or more positions.

2. The compound according to claim 1, wherein the compound has a solubility in water of at least 50 mg/ml.

3. The compound according to claim 1, wherein the melting point of said compound is at least 100° C.

4. A compound of structure IX",

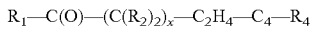

or a salt thereof, wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; R4 is a heterocyclic ring, optionally substituted at one or more positions with one or more substituents selected from the group consisting of a $C_{1-5}$ alkyl, a $C_{1-5}$ alkenyl, a $C_{1-5}$ alkoxy, a $C_{1-5}$ alcohol, a hydroxyl, an amine, a nitrate and a halogen; and x is an integer between 4 and 10, inclusive.

5. The compound according to claim 1, wherein the diyne is a diyne of formula IV:

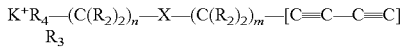

wherein $R_4$ is —COO⁻, and n is an integer in the range of 4 to 10, inclusive; and m is an integer in the range of 0 to 10; and each $R_2$ is, independently, —H, —OH or a hydrocarbon moiety containing between 1 and 6 carbon atoms, inclusive; and X is —CH₂—CH₂— or —CH=CH—; and $R_3$ is a heterocyclic ring, which optionally may be substituted at one or more positions.

6. The compound according to claim 1, wherein $R_3$ is furan.

7. The compound according to claim 5, wherein X is —CH=CH— in the cis configuration.

8. The compound according to claim 1, which is potassium (Z)-14-(furan-2-yl)tetradeca-9-en-11,13-diynoate.

9. The salt according to claim 4, which is potassium 14-(furan-2-yl)tetradeca-11,13-diynoate.

10. A pharmaceutical composition comprising the crystalline diyne compound according to claim 1, wherein the composition further comprises at least one antifungal polyene.

11. A compound according to claim 8 which is a crystalline form of potassium (Z)-14-(furan-2-yl)tetradeca-9-en-11,13-diynoate having an X-ray powder diffraction pattern as shown in FIG. 2(a), acquired using Cu Kα radiation.

12. A compound according to claim 8, which is a crystalline form of potassium (Z)-14-(furan-2-yl)tetradeca-9-en-11,13-diynoate having an X-ray powder diffraction pattern with peaks at about 7.1, 17.3, and 21.3, 23.9, and 27.0 degrees 2θ, acquired using Cu Kα radiation.

13. A compound according to claim 4, which is 14-(furan-2-yl)tetradeca-11,13-diynoic acid.

14. A crystalline diyne compound according to claim 1 of the formula

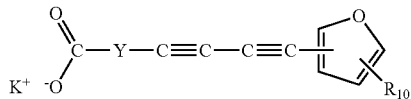

wherein

Y is a $C_9$-$C_{12}$ carbon chain optionally containing one double bond; and $R_{10}$ is hydrogen, methyl, methoxy, hydroxyl, amine or halogen.

15. A crystalline diyne compound according to claim 14, wherein Y is a carbon chain having 9 carbon atoms; and $R_{10}$ is hydrogen.

16. A crystalline diyne compound according to claim 14, where the compound has the formula

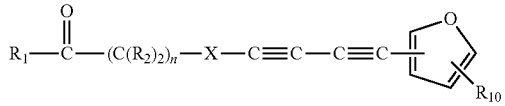

wherein $R_{10}$ is hydrogen;

each $R_2$ is hydrogen;

n is an integer of from 6-8; and

X represents —CH=CH—.

* * * * *